US010517889B2

(12) United States Patent
Freier et al.

(10) Patent No.: US 10,517,889 B2
(45) Date of Patent: Dec. 31, 2019

(54) MODULATORS OF SMAD7 EXPRESSION

(71) Applicant: Ionis Pharmaceuticals, Inc., Carlsbad, CA (US)

(72) Inventors: Susan M. Freier, San Diego, CA (US); Huynh-Hoa Bui, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/124,583

(22) Filed: Sep. 7, 2018

(65) Prior Publication Data

US 2019/0076465 A1 Mar. 14, 2019

Related U.S. Application Data

(60) Provisional application No. 62/556,214, filed on Sep. 8, 2017.

(51) Int. Cl.
*A61K 31/712* (2006.01)
*A61K 31/7125* (2006.01)
*A61K 31/713* (2006.01)
*A61K 31/7115* (2006.01)
*A61P 1/00* (2006.01)
*A61P 37/00* (2006.01)
*A61K 31/7042* (2006.01)
*A61P 35/00* (2006.01)
*A61P 37/06* (2006.01)

(52) U.S. Cl.
CPC ...... *A61K 31/7125* (2013.01); *A61K 31/7042* (2013.01); *A61P 1/00* (2018.01); *A61P 35/00* (2018.01); *A61P 37/06* (2018.01)

(58) Field of Classification Search
None
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |

(Continued)

FOREIGN PATENT DOCUMENTS

| | | | |
|---|---|---|---|
| WO | 2013037970 A1 | 3/2013 | |
| WO | 2015011694 A2 | 1/2015 | |
| WO | WO-2017059225 A1 * | 4/2017 | ........... C12N 15/113 |

OTHER PUBLICATIONS

Boirivant et al., "Inhibition of Smad7 With a Specific Antisense Oligonucleotide Facilitates TGF-?1-Mediated Suppression of Colitis" Gastroenterology (2006) 131: 1786-1798.
Bouma et al., "The immunological and genetic basis of inflammatory bowel disease" Nat. Rev. Immunol. (2003) 3: 521-533.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.

(Continued)

*Primary Examiner* — Tracy Vivlemore
(74) *Attorney, Agent, or Firm* — Panitch Schwarze Belisario & Nadel LLP

(57) ABSTRACT

The present embodiments provide methods, compounds, and compositions useful for inhibiting SMAD7 expression, which may be useful for treating, preventing, or ameliorating a disease associated with SMAD7.

26 Claims, No Drawings
Specification includes a Sequence Listing.

(56) References Cited

U.S. PATENT DOCUMENTS

| | | |
|---|---|---|
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o et al. |
| 6,005,087 A | 12/1999 | Cook et al. |
| 6,005,096 A | 12/1999 | Matteucci et al. |
| 6,159,697 A | 12/2000 | Monia et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,887,906 B1 | 5/2005 | Teng et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'O et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,576,067 B2 | 8/2009 | Weinbach et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Seth et al. |
| 7,750,131 B2 | 7/2010 | Seth et al. |
| 7,807,818 B2 | 10/2010 | Monteleone |
| 7,875,733 B2 | 1/2011 | Bhat et al. |
| 7,939,677 B2 | 5/2011 | Bhat et al. |
| 8,022,193 B2 | 9/2011 | Seth et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 8,912,154 B2 | 12/2014 | Baroni et al. |
| 9,005,906 B2 | 4/2015 | Swayze et al. |
| 9,012,421 B2 | 4/2015 | Migawa et al. |
| 9,127,276 B2 | 9/2015 | Prakash et al. |
| 9,290,760 B2 | 3/2016 | Rajeev et al. |
| 2001/0053519 A1 | 12/2001 | Fodor et al. |
| 2003/0049662 A1 | 3/2003 | Monia et al. |
| 2003/0082807 A1 | 5/2003 | Wengel |
| 2003/0158403 A1 | 8/2003 | Manoharan et al. |
| 2003/0175906 A1 | 9/2003 | Manoharan et al. |
| 2003/0207841 A1 | 11/2003 | Kaneko et al. |
| 2003/0224377 A1 | 12/2003 | Wengel et al. |
| 2003/0228597 A1 | 12/2003 | Cowsert et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2004/0229831 A1 | 11/2004 | Teng et al. |

(56) References Cited

U.S. PATENT DOCUMENTS

| | | | |
|---|---|---|---|
| 2005/0096284 A1* | 5/2005 | McSwiggen | A61K 49/0008 514/44 R |
| 2005/0130923 A1 | 6/2005 | Bhat et al. | |
| 2006/0148740 A1 | 7/2006 | Platenburg | |
| 2007/0031844 A1 | 2/2007 | Khvorova et al. | |
| 2008/0039618 A1 | 2/2008 | Allerson et al. | |
| 2010/0190837 A1 | 7/2010 | Migawa et al. | |
| 2010/0197762 A1 | 8/2010 | Swayze | |
| 2011/0123520 A1 | 5/2011 | Manoharan et al. | |
| 2011/0207795 A1 | 8/2011 | Steinbrecher et al. | |
| 2011/0288155 A1* | 11/2011 | Feinstein | C12N 15/1137 514/44 A |
| 2013/0053430 A1* | 2/2013 | Bell, III | C12N 15/113 514/44 A |
| 2013/0130378 A1 | 5/2013 | Manoharan et al. | |
| 2013/0203836 A1 | 8/2013 | Rajeev et al. | |
| 2014/0107330 A1 | 4/2014 | Freier et al. | |
| 2015/0018540 A1 | 1/2015 | Prakash et al. | |
| 2015/0184153 A1 | 7/2015 | Freier et al. | |
| 2015/0191727 A1 | 7/2015 | Migawa et al. | |
| 2015/0232836 A1 | 8/2015 | Krieg et al. | |
| 2015/0232854 A1 | 8/2015 | Baroni et al. | |
| 2015/0267195 A1 | 9/2015 | Seth et al. | |
| 2015/0275212 A1 | 10/2015 | Albaek et al. | |

OTHER PUBLICATIONS

Crooke, "Routes and Formulations for Delivery of Antisense" Antisense Drug Technology, Second Edition (2008) p. 225-233.

Kulkarni et al., "Transforming growth factor-beta 1 knockout mice. A mutation in one cytokine gene causes a dramatic inflammatory disease" Am. J. Pathol. (1993) 143: 3-9.

Marafini et al., "Smad7 Sustains Inflammation in the Gut: From Bench to Bedside" J Clin Cell Immunol (2014) 5: 1-5.

Monteleone et al., "Blocking Smad7 restores TGF-β1- signaling in chronic inflammatory bowel disease" The Journal of Clinical Investigation (2001) 108(4): 601-609.

Monteleone et al. "TGF-beta1 and Smad7 in the regulation of IBD" Mucosal Immunol. (2008) 1: S50-S53.

Monteleone et al., "Mongersen, an oral SMAD7 antisense oligonucleotide, and Crohn's disease" N Engl J Med (2015) 372(12): 1104-1113.

Nakao et al. "Identification of Smad7, a TGFbeta-inducible antagonist of TGF-beta signalling" Nature (1997) 389: 631-635.

New England Biolabs 1998/99 Catalog (cover page and pp. 121 and 284).

Raoof et al., "Oral Bioavailability and Multiple Dose Tolerability of an Antisense Oligonucleotide Tablet Formulated with Sodium Caprate" Journal of Pharmaceutical Sciences (2004) 93(6): 1431-1439.

Reynolds et al., "Rational siRNA design for RNA interference" Nature Biotechnology (2004) 22(3):326-330.

Sedda et al., "High Smad7 sustains inflammatory cytokine response in refractory coeliac disease" Immunology (2017) 150: 356-363.

Ulloa et al., "Inhibition of transforming growth factor-β/SMAD signalling by the interferon-γ/STAT pathway" Nature (1999) 397: 710-713.

Sanghvi et al., "Heterocyclic Base Modifications in Nucleic Acids and Their Applications in Antisense Oligonucleotides" Antisense Research and Applications (1993) pp. 273-288.

Wikberg et al., "Review article: Targeted drug delivery in treatment of intestinal diseases" Aliment Pharmacol Ther (1997) 11(3): 109-115.

Woolf et al., "Specificity of antisense oligonucleotides in vivo" Proc. Natl. Acad. Sci., vol. 89, pp. 7305-7309, Aug. 1992.

Gautschi et al., "Activity of a Novel bcl-2/bcl-xL-Bispecific Antisense Oligonucleotide Against Tumors of Diverse histologic Origins" Journal of the National cancer Institute, vol. 93, No. 6, Mar. 2001.

Maher et al., "Comparative hybrid arrest by tandem antisense oligodexyribonucleotides or oligodeoxy-ribonucleoside rnethylphosphonates in a cell-free system" Nucleic Acids Research, vol. 16, No. 8, 1988.

Seth et al., "Short Antisense Oligonucleotides with novel 2"-4" Conformationaly Restricted Nucleoside Analogues Show Improved Potency without Increased Toxicity in Animals" J. Med. Chem, vol. 52, pp. 10-13, 2009.

Egli et al., "Synthesis, Improved Antisense Activity and Structural Rationale for the Divergent RNA Affinities of 3'-Fluoro Hexitol Nucleic Acid (FHNA and Ara-FHNA) Modified Oligonucleotides", J Am Chem Soc. 133(41): pp. 16642-16649, Oct. 2011.

Crooke et al., "Mechanisms of Antisense Drug Action, an Introduction", Antisense Drug Technology, Chapters 1-28 (414 pages), 2008.

Int'l Search Report and Written Opinion dated Jan. 28, 2019 in Int'l Application PCT/US2018/49867.

* cited by examiner

MODULATORS OF SMAD7 EXPRESSION

CROSS-REFERENCE TO RELATED APPLICATION

This application claims the benefit of priority to U.S. Provisional Application No. 62/556,214, filed Sep. 8, 2017, the disclosure of which is incorporated herein by reference in its entirety.

SEQUENCE LISTING

The present application is being filed along with a Sequence Listing in electronic format. The Sequence Listing is provided as a file entitled BIOL0295USLSEQ_ST25.txt created Sep. 5, 2017, which is 601 kb in size. The information in the electronic format of the sequence listing is incorporated herein by reference in its entirety.

FIELD

The present embodiments provide methods, compounds, and compositions useful for inhibiting Mothers Against Decapenta-plegic, Drosophila, Homolog 7 (SMAD7; also known as MADH7, MADH8, MAD homolog 7) expression, and in certain instances, reducing the amount of SMAD7 protein in a cell or animal, which can be useful for treating, preventing, or ameliorating a disease, disorders, or syndromes associated with SMAD7.

BACKGROUND

Inflammatory bowel diseases (IBDs) are caused by an aberrant and excessive local immune response to components of bacterial microflora (Bouma G and Strober W. Nat. Rev. Immunol. 3: 521-533, 2003) and is controlled by regulatory molecules, including TGF-beta1 (Kulkarni A. B. and Karlsson, S. Am. J. Pathol. 143: 3-9, 1993). Disruption of TGF-beta1 signaling occurs in IBDs by the upregulation of the intracellular inhibitor of Smad signaling, Smad7 (Nakao A et al. Nature 389: 631-635, 1997); one of the main pathological processes involved in the tissue-destructive inflammatory response of IBDs in humans. Therefore, therapeutics that reduce Smad7 protein or function may restore TGF-beta1 signaling and reset immune homeostasis.

The current standard of medical care for Crohn's disease and ulcerative colitis, the two major forms of inflammatory bowel disease in humans, involves treatment with anti-inflammatory agents, corticosteroids, immunomodulators, including azathioprine, or its active metabolite 6-mercaptopurine, methotrexate, biologic agents, including tumor necrosis factor antagonist therapies, anti-integrin therapies, and anti-interleukin (IL) $12/23$ therapy. Recently, antisense inhibition of Smad7 by a morpholino oligonucleotide in animal models as well as in patients with Crohn's disease has been demonstrated (Monteleone et al. Mucosal Immunol. 1: S50-S53, 2008; Monteleone et al. N. Engl. J. Med. 372: 1104-1113, 2015). It is an object herein to provide compounds and compositions of high efficacy and tolerability for the treatment of diseases disclosed herein.

SUMMARY

Certain embodiments provided herein are compounds and methods for reducing the amount or activity of SMAD7 mRNA and, in certain embodiments, reducing the amount of SMAD7 protein in a cell or animal. In certain embodiments, the animal has a gastrointestinal disease. In certain embodiments, the disease is Crohn's disease. In certain embodiments, the disease is inflammatory bowel disease (IBD). In certain embodiments, the disease is ulcerative colitis. In certain embodiments, the disease is pouchitis. In certain embodiments, the disease is celiac disease. In certain embodiments, the disease is intestinal GVHD. In certain embodiments, the disease is cancer therapy-indiced colitis. Certain compounds provided herein are directed to compounds and compositions that reduce inflammation in an animal.

Certain embodiments provided herein are directed to potent and tolerable compounds and compositions useful for inhibiting SMAD7 expression, which can be useful for treating, preventing, ameliorating, or slowing progression of a gastrointestinal disease. Certain embodiments provided herein are directed to compounds and compositions that are more potent or have greater therapeutic value than compounds publicly disclosed. Certain embodiments provided herein are directed to compounds and compositions that exhibit higher stability leading to increased tissue resident time and uptake compared to compounds publicly disclosed.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ION number indicate a combination of nucleobase sequence, chemical modification, and motif.

DEFINITIONS

Unless otherwise indicated, the following terms have the following meanings:

"2'-deoxynucleoside" means a nucleoside comprising 2'-H(H) ribosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE) refers to a 2'-O (CH$_2$)$_2$—OCH$_3$ group in the place of the 2'-OH group of a ribosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of SMAD7", it is implied that SMAD7 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a ribosyl bicyclic sugar moiety wherein the second ring of the bicyclic sugar is formed via a bridge connecting the 4'-carbon and the 2'-carbon, wherein the bridge has the formula: 4'-CH($CH_3$)—O-2', and wherein the methyl group of the bridge is in the S configuration.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound.

Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating SMAD7 RNA can mean to increase or decrease the level of SMAD7 RNA and/or SMAD7 protein in a cell, tissue, organ or organism. A "modulator" effects the change in the cell, tissue, organ or organism. For example, a SMAD7 compound can be a modulator that decreases the amount of SMAD7 RNA and/or SMAD7 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"SMAD7" means any nucleic acid or protein of SMAD7. "SMAD7 nucleic acid" means any nucleic acid encoding SMAD7. For example, in certain embodiments, a SMAD7 nucleic acid includes a DNA sequence encoding SMAD7, an RNA sequence transcribed from DNA encoding SMAD7 (including genomic DNA comprising introns and exons), and an mRNA sequence encoding SMAD7. "SMAD7 mRNA" means an mRNA encoding a SMAD7 protein. The target may be referred to in either upper or lower case.

"SMAD7 specific inhibitor" refers to any agent capable of specifically inhibiting SMAD7 RNA and/or SMAD7 protein expression or activity at the molecular level. For example, SMAD7 specific inhibitors include nucleic acids (including antisense compounds), peptides, antibodies, small molecules, and other agents capable of inhibiting the expression of SMAD7 RNA and/or SMAD7 protein.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof "Standard in vivo experiment" means the procedure(s) described in the Example(s) and reasonable variations thereof.

"Stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

"Sugar moiety" means an unmodified sugar moiety or a modified sugar moiety. "Unmodified sugar moiety" or "unmodified sugar" means a 2'-OH(H) ribosyl moiety, as found in RNA (an "unmodified RNA sugar moiety"), or a 2'-H(H) moiety, as found in DNA (an "unmodified DNA sugar moiety"). "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen or hydroxyl of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"Synergy" or "synergize" refers to an effect of a combination that is greater than additive of the effects of each component alone at the same doses.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds and compositions for inhibiting Mothers Against Decapentaplegic, *Drosophila*, Homolog 7 (SMAD7) expression.

Certain embodiments provide compounds targeted to a SMAD7 nucleic acid. In certain embodiments, the SMAD7 nucleic acid has the sequence set forth in RefSeq or GENBANK Accession No. NM_005904.3 (incorporated by reference, disclosed herein as SEQ ID NO: 1), complement of NT_010966.15 truncated from nucleotides 28007000 to 28041000 (incorporated by reference, disclosed herein as SEQ ID NO: 2), NM_001190823.1 (incorporated by reference, disclosed herein as SEQ ID NO: 3), NM 001190822.1 (incorporated by reference, disclosed herein as SEQ ID NO: 4), NM_001190821.1 (incorporated by reference, disclosed herein as SEQ ID NO: 5), AF015261.1 (incorporated by reference, disclosed herein as SEQ ID NO: 6), and AF010193.1 (incorporated by reference, disclosed herein as SEQ ID NO: 7). In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 9 to 80 linked nucleosides in length and having a nucleobase sequence comprising at least 9 contiguous nucleobases of any of the nucleobase sequences of SEQ ID NOs: 14-2735. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 10 to 80 linked nucleosides in length and having a nucleobase sequence comprising at least 10 contiguous nucleobases of any of the nucleobase sequences of SEQ ID NOs: 14-2735. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 11 to 80 linked nucleosides in length and having a nucleobase sequence comprising at least 11 contiguous nucleobases of any of the nucleobase sequences of SEQ ID NOs: 14-2735. In certain embodiments, the compound is an antisense compound or oligomeric compound. In certain embodiments, the compound is single-stranded. In certain embodiments, the compound is double-stranded. In certain embodiments, the modified oligonucleotide is 11 to 30 linked nucleosides in length.

Certain embodiments provide a compound comprising a modified oligonucleotide 12 to 80 linked nucleosides in length and having a nucleobase sequence comprising at least 12 contiguous nucleobases of any of the nucleobase sequences of SEQ ID NOs: 14-2735. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

In certain embodiments, the compound comprises a modified oligonucleotide 16 linked nucleosides in length. In certain embodiments, the compound is an antisense compound or oligomeric compound.

Certain embodiments provide a compound comprising a modified oligonucleotide 16 to 80 linked nucleosides in length and having a nucleobase sequence comprising the nucleobase sequence of any one of SEQ ID NOs: 14-2735. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

Certain embodiments provide a compound comprising a modified oligonucleotide consisting of the nucleobase sequence of any one of SEQ ID NOs: 14-2735. In certain embodiments, the compound is an antisense compound or oligomeric compound. In certain embodiments, the compound is single-stranded. In certain embodiments, the compound is double-stranded.

In certain embodiments, compounds target nucleotides 1514-1539, 1632-1648, 1670-1686, 1713-1734, 1723-1739, 1728-1755, 1763-1813, 1911-1930, 1987-2022, 2069-2086, 2072-2089, 2115-2133, 2146-2162, 2224-2241, 2228-2245, 2234-2271, 2278-2294, 2281-2304, 2293-2313, 2296-2312, 2314-2334, 2314-2332, 2344-2362, 2494-2557, 2495-2554, 2498-2557, 2505-2546, 2508-2545, 2515-2556, 2904-2922, 3609-3627, 3641-3667, 3641-3657, 3666-3682, 3784-3801, 4142-4159, 4149-4169, 4199-4226, 4630-4655, 4866-4924, 4980-5038, 4996-5038, 5076-5093, 5248-5278, 5557-5581, 5558-5575, 5574-5593, 5581-5600, 5607-5625, 5956-5997, 6279-6301, 6416-6437, 6724-7041, 7022-7144, 7362-7436, 7766-7782, 8125-8141, 8750-8783, 9179-9231, 9407-9426, 9447-9464, 9452-9468, 9547-9571, 9644-9665, 9821-9870, 10020-10056, 10275-10290, 10277-10293, 10386-10417, 10811-10914, 10897-10914, 11124-11140, 11230-11246, 11759-11892, 11976-12008, 12019-12052, 12207-12261, 12501-12519, 12558-12574, 12619-12635, 12745-12788, 12942-12962, 13234-13259, 13243-13265, 13668-13714, 13778-13824, 13992-14043, 13995-14014, 14268-14387, 14518-14584, 14839-15040, 15647-15666, 15678-15777, 15847-15925, 16762-16810, 16898-16921, 16922-16960, 17155-17178, 17537-17581, 17588-17612, 17892-18007, 18021-18046, 18342-18396, 18456-18478, 19007-19027, 20650-20673, 20728-20758, 21139-21291, 22029-22116, 23268-23319, 24476-24499, 25501-25517, 26677-26698, 27028-27046, 27084-27101, 28191-28207, 28269-28312, 28301-28320, 28700-28768, 29276-29293, 29525-29541, 30320-30337, 30447-30464, 30584-30600, 30689-30727, 30753-30782, 30854-30872, 30864-30882, 30890-30908, 30993-31011, 31119-31137, 31141-31159, 31213-31238, 31294-31347, 31717-31738, 31739-31757, 31769-31787, 31819-31842, 31829-31845, 31887-31904, 31898-31914, 31913-31931, 31992-32008, 31998-32013, 32006-32022, 32026-32041 of a SMAD7 nucleic acid having the nucleobase sequence of SEQ ID NO: 2. In certain embodiments, the compound is at least 85%, at least 90%, at least 95%, or 100% complementary to SEQ ID NO: 2. In certain embodiments, the compound is an antisense compound or oligomeric compound. In certain embodiments, the compound is single-stranded. In certain embodiments, the compound is double-stranded.

In certain embodiments, compounds have at least an 8, 9, 10, 11, 12, 13, 14, 15, or 16 contiguous nucleobase portion complementary to an equal length portion within nucleotides 1514-1539, 1632-1648, 1670-1686, 1713-1734, 1723-1739, 1728-1755, 1763-1813, 1911-1930, 1987-2022, 2069-2086, 2072-2089, 2115-2133, 2146-2162, 2224-2241, 2228-2245, 2234-2271, 2278-2294, 2281-2304, 2293-2313, 2296-2312, 2314-2334, 2314-2332, 2344-2362, 2494-2557, 2495-2554, 2498-2557, 2505-2546, 2508-2545, 2515-2556, 2904-2922, 3609-3627, 3641-3667, 3641-3657, 3666-3682, 3784-3801, 4142-4159, 4149-4169, 4199-4226, 4630-4655, 4866-4924, 4980-5038, 4996-5038, 5076-5093, 5248-5278, 5557-5581, 5558-5575, 5574-5593, 5581-5600, 5607-5625, 5956-5997, 6279-6301, 6416-6437, 6724-7041, 7022-7144, 7362-7436, 7766-7782, 8125-8141, 8750-8783, 9179-9231, 9407-9426, 9447-9464, 9452-9468, 9547-9571, 9644-9665, 9821-9870, 10020-10056, 10275-10290, 10277-10293, 10386-10417, 10811-10914, 10897-10914, 11124-11140, 11230-11246, 11759-11892, 11976-12008, 12019-12052, 12207-12261, 12501-12519, 12558-12574, 12619-12635, 12745-12788, 12942-12962, 13234-13259, 13243-13265, 13668-13714, 13778-13824, 13992-14043, 13995-14014, 14268-14387, 14518-14584, 14839-15040, 15647-15666, 15678-15777, 15847-15925, 16762-16810, 16898-16921, 16922-16960, 17155-17178, 17537-17581, 17588-17612, 17892-18007, 18021-18046, 18342-18396, 18456-18478, 19007-19027, 20650-20673, 20728-20758, 21139-21291, 22029-22116, 23268-23319, 24476-24499, 25501-25517, 26677-26698, 27028-27046, 27084-27101, 28191-28207, 28269-28312, 28301-28320, 28700-28768, 29276-29293, 29525-29541, 30320-30337, 30447-30464, 30584-30600, 30689-30727, 30753-30782, 30854-30872, 30864-30882, 30890-30908, 30993-31011, 31119-31137, 31141-31159, 31213-31238, 31294-31347, 31717-31738, 31739-31757, 31769-31787, 31819-31842, 31829-31845, 31887-31904, 31898-31914, 31913-31931, 31992-32008, 31998-32013, 32006-32022, 32026-32041 of a SMAD7 nucleic acid having the nucleobase sequence of SEQ ID NO: 2. In certain embodiments, the compound is at least 85%, at least 90%, at least 95%, or 100% complementary to SEQ ID NO: 2. In certain embodiments, the compound is single-stranded. In certain embodiments, the compound is double-stranded. In certain embodiments, these compounds are antisense compounds, oligomeric compounds, or oligonucleotides.

In certain embodiments, compounds target a region of a SMAD7 nucleic acid having the nucleobase sequence of SEQ ID NO: 1 within nucleobases 19-44, 175-191, 218-239, 233-260, 268-318, 416-435, 496-431, 574-591, 577-594, 620-638, 651-667, 729-746, 733-750, 739-776, 783-799, 789-809, 798-818, 819-839, 849-867, 892-908, 977-1028, 1052-1069, 1192-1210, 1317-1333, 1440-1460, 1486-1515, 1597-1615, 1623-1641, 1726-1744, 1852-1870, 1874-1895, 1946-1971, 2027-2080, 2439-2459, 2450-2471, 2472-2490, 2502-2520, 2552-2575, 2562-2578, 2620-2637, 2631-2647, 2646-2664, 2725-2741, 2731-2746, or 2739-2755. In certain embodiments, compounds target at least an 8, 9, 10, 11, 12, 13, 14, 15, or 16 contiguous nucleobases within the aforementioned nucleobase regions. In certain embodiments, the compound is at least 85%, at least 90%, at least 95%, or 100% complementary to SEQ ID NO: 1. In certain embodiments, the compound is single-stranded. In certain embodiments, the compound is double-stranded. In certain embodiments, these compounds are antisense compounds, oligomeric compounds, or oligonucleotides.

In certain embodiments, a compound comprises a modified oligonucleotide 8 to 80 linked nucleosides in length and having at least an 8, 9, 10, 11, 12, 13, 14, 15, or 16 contiguous nucleobase portion complementary to an equal length portion within nucleotides 2317-2332, 3641-3656, 5023-5038, 5559-5574, 12558-12573, or 31998-32013 of SEQ ID NO: 2. In certain embodiments, the modified oligonucleotide is 10 to 30 linked nucleosides in length.

In certain embodiments, a compound comprises a modified oligonucleotide 8 to 80 linked nucleosides in length and complementary within nucleotides 2317-2332, 3641-3656, 5023-5038, 5559-5574, 12558-12573, or 31998-32013 of SEQ ID NO: 2. In certain embodiments, the modified oligonucleotide is 10 to 30 linked nucleosides in length.

In certain embodiments, a compound comprises a modified oligonucleotide 8 to 80 linked nucleosides in length and having a nucleobase sequence comprising at least an 8, 9, 10, 11, 12, 13, 14, 15, or 16 contiguous nucleobase portion any one of SEQ ID NOs: 1456, 2109, 2506, 2537, 2548, or 2633. In certain embodiments, the modified oligonucleotide is 10 to 30 linked nucleosides in length.

In certain embodiments, a compound comprises a modified oligonucleotide 8 to 80 linked nucleosides in length and having a nucleobase sequence comprising any one of SEQ ID NOs: 1456, 2109, 2506, 2537, 2548, or 2633. In certain embodiments, the modified oligonucleotide is 10 to 30 linked nucleosides in length.

In certain embodiments, a compound comprises a modified oligonucleotide having a nucleobase sequence consisting of any one of SEQ ID NOs: 1456, 2109, 2506, 2537, 2548, or 2633.

In certain embodiments, the compound is at least 85%, at least 90%, at least 95%, or 100% complementary to SEQ ID NO: 2. In certain embodiments, the compound is single-stranded. In certain embodiments, the compound is double-stranded. In certain embodiments, these compounds are antisense compounds, oligomeric compounds, or oligonucleotides.

In certain embodiments, a compound targeted to SMAD7 is ION 830025. Out of over 2,720 compounds that were screened as described in the Examples section below, ION 830121, ION 829994, ION 830037, ION 798781, ION 790615, and ION 830025 emerged as the top lead compounds. In particular, ION 830025 exhibited the best combination of properties in terms of potency and tolerability out of over 2,720 compounds.

In certain embodiments, any of the foregoing modified oligonucleotides comprises at least one modification selected from at least one modified internucleoside linkage, at least one modified sugar, and at least one modified nucleobase.

In certain embodiments, any of the foregoing modified oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH3)-O-2' group, a 4'-CH2-O-2' group, or a 4'-(CH2)2-O-2' group.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:
a gap segment consisting of linked deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar. In certain embodiments, the modified oligonucleotide is 16 to 80 linked nucleosides in length having a nucleobase sequence comprising the sequence recited in any one of SEQ ID NO: 1456, 2109, 2506, 2537, 2548, or 2633. In certain embodiments, the modified oligonucleotide is 16 to 30 linked nucleosides in length having a nucleobase sequence comprising the sequence recited in any one of SEQ ID NOs: 1456, 2109, 2506, 2537, 2548, or 2633. In certain embodiments, the modified oligonucleotide is 16 linked nucleosides in length having a nucleobase sequence consisting of the sequence recited in any one of SEQ ID NOs: 1456, 2109, 2506, 2537, 2548, or 2633.

In certain embodiments, a compound comprises or consists of a modified oligonucleotide 16-80 linked nucleobases in length having a nucleobase sequence comprising the sequence recited in any one of SEQ ID NOs: 1456, 2109, 2506, 2537, 2548, or 2633, wherein the modified oligonucleotide comprises a gap segment consisting often linked deoxynucleosides;
a 5' wing segment consisting of three linked nucleosides; and
a 3' wing segment consisting of three linked nucleosides;
wherein the gap segment is positioned between the 5' wing segment and the 3' wing segment; wherein each nucleoside of each wing segment comprises a cEt sugar; wherein at least one internucleoside linkage is a phosphorothioate linkage; and wherein each cytosine is a 5-methylcytosine. In certain embodiments, the modified oligonucleotide is 16-80 linked nucleosides in length. In certain embodiments, the modified oligonucleotide is 16-30 linked nucleosides in length.

In certain embodiments, a compound comprises or consists of ION 830025 or salt thereof, having the following chemical structure:

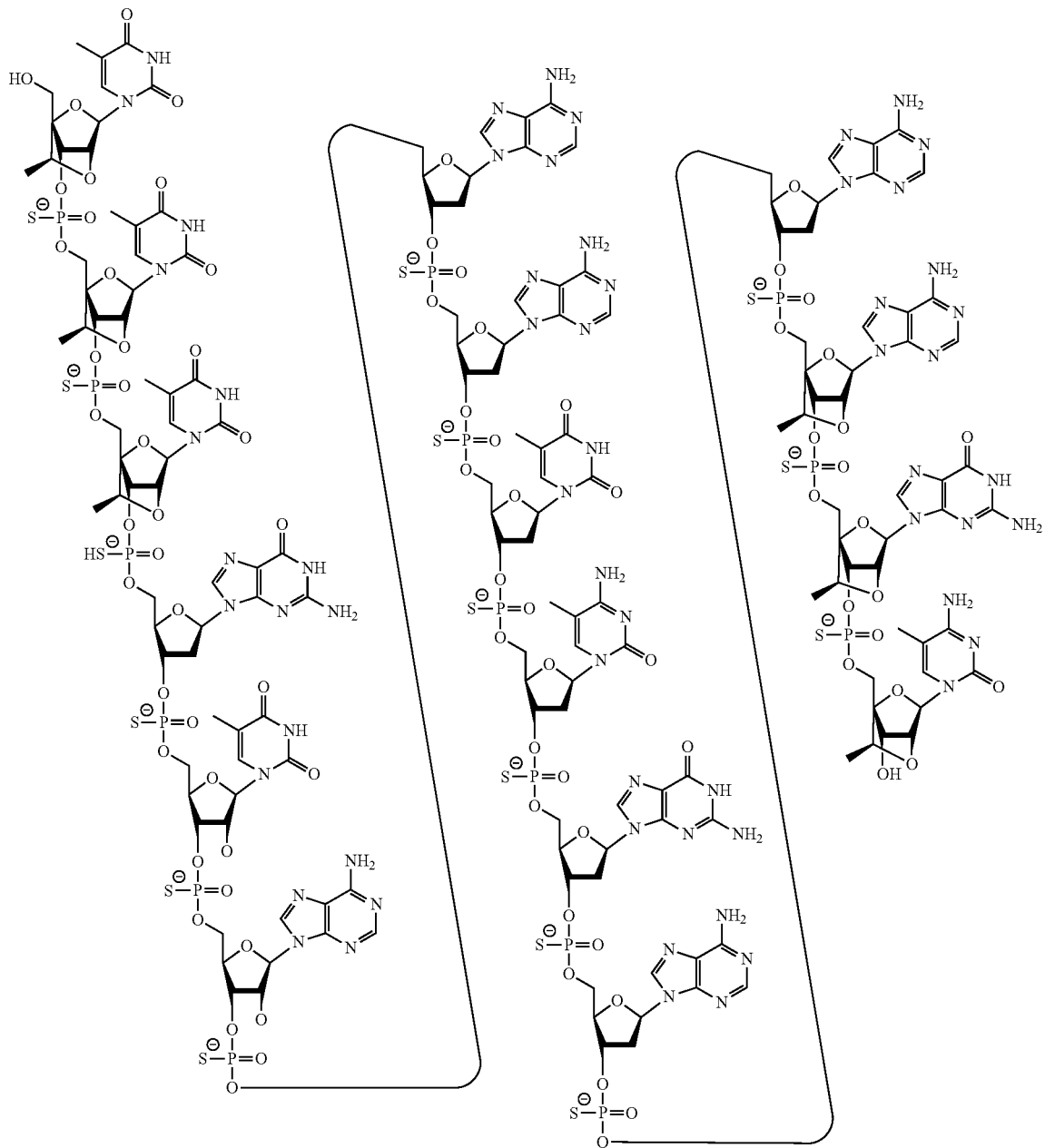

In certain embodiments, a compound comprises or consists of the sodium salt of ION 830025, having the following chemical structure:
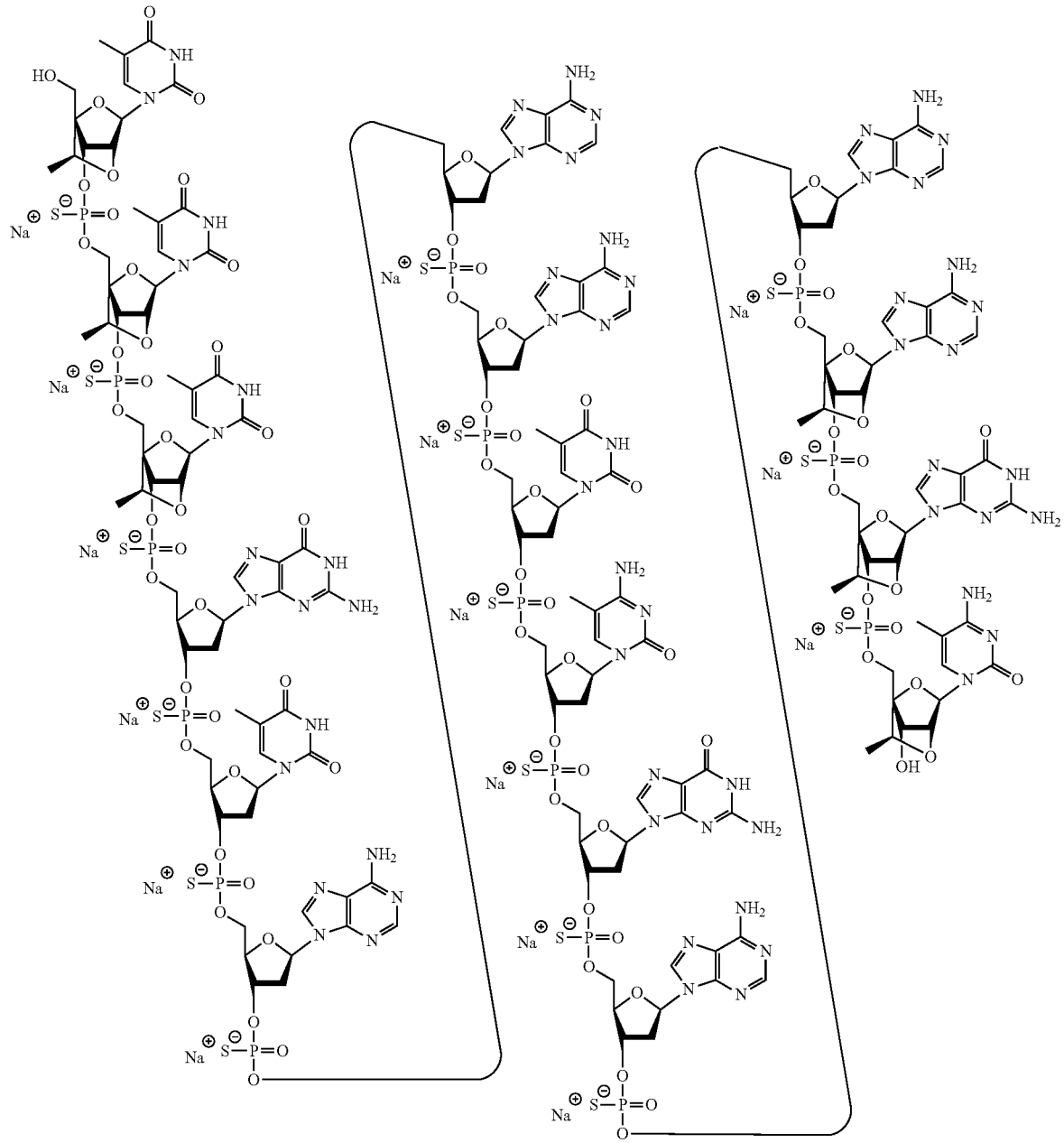

In certain embodiments, a compound comprises or consists of ION 798781 or salt thereof, having the following chemical structure:
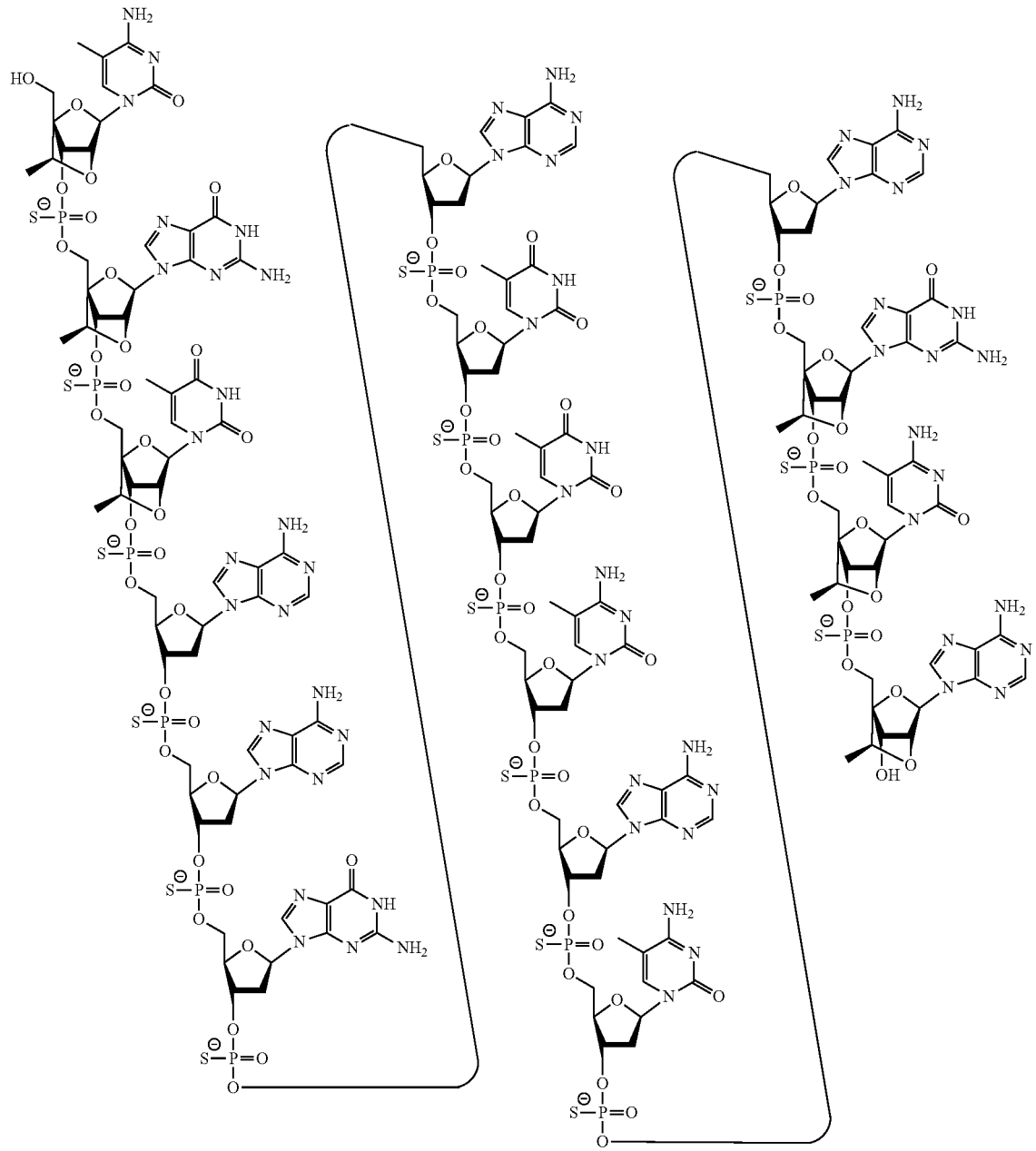

In certain embodiments, a compound comprises or consists of the sodium salt of ION 798781, having the following chemical structure:

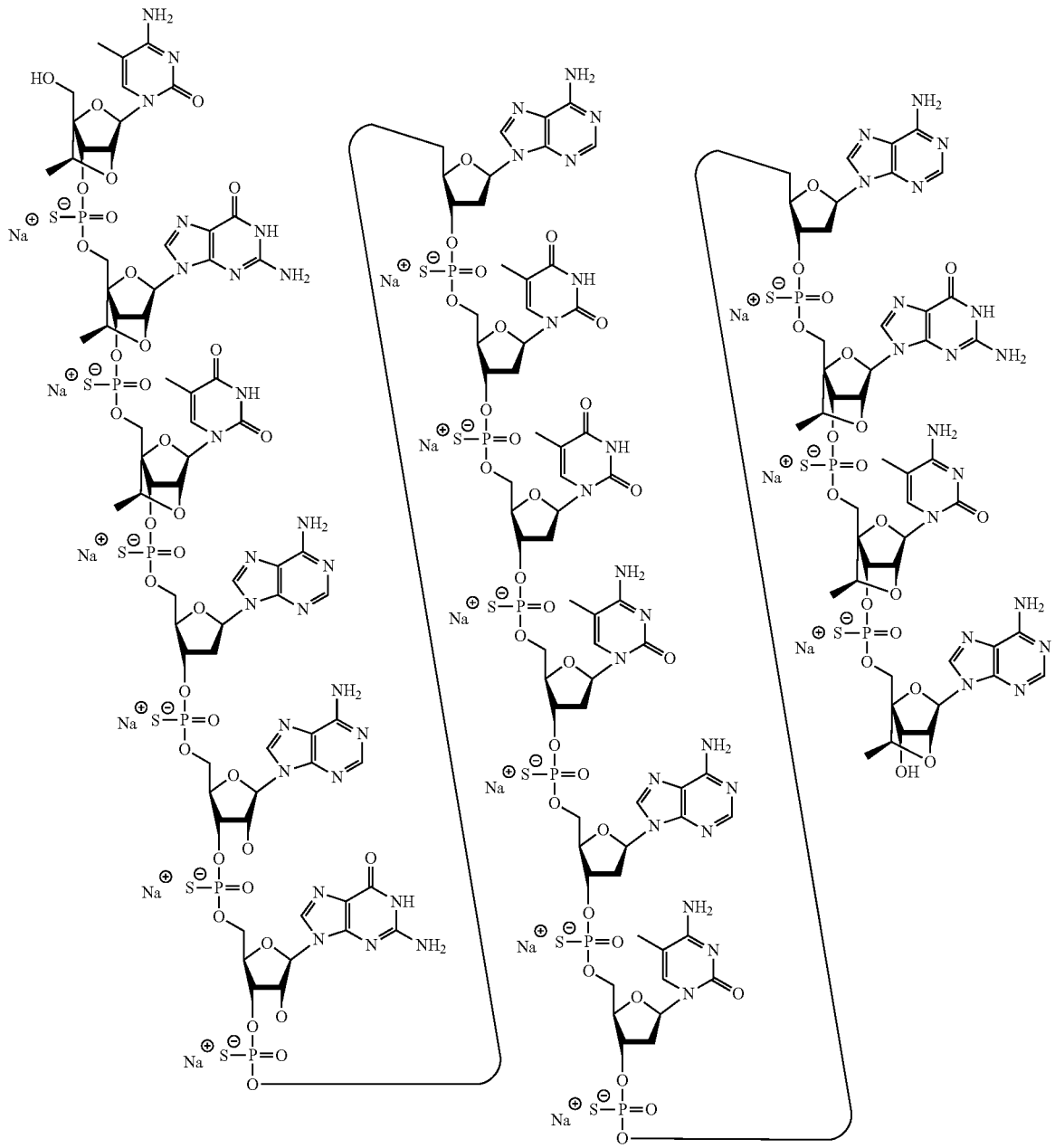

In any of the foregoing embodiments, the compound or oligonucleotide can be at least 85%, at least 90%, at least 95%, at least 98%, at least 99%, or 100% complementary to a nucleic acid encoding SMAD7.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

In certain embodiments, compounds or compositions provided herein comprise a salt of the modified oligonucleotide. In certain embodiments, the salt is a sodium salt. In certain embodiments, the salt is a potassium salt.

In certain embodiments, the compounds or compositions as described herein are active by virtue of having at least one of an in vitro $IC_{50}$ of less than 20 μM, less than 15 μM, less than 10 μM, less than 5 μM, less than 1 μM, less than 900 nM, less than 800 nM, less than 700 nM, less than 600 nM, less than 500 nM, less than 400 nM, less than 300 nM, less than 200 nM, less than 100 nM, or less than 50 nM.

In certain embodiments, the compounds or compositions as described herein are highly tolerable as demonstrated by having at least one of an increase an alanine transaminase (ALT) or aspartate transaminase (AST) value of no more than 4 fold, 3 fold, or 2 fold over saline treated animals or an increase in liver, spleen, or kidney weight of no more than 30%, 20%, 15%, 12%, 10%, 5%, or 2% compared to control treated animals. In certain embodiments, the compounds or compositions as described herein are highly tolerable as demonstrated by having no increase of ALT or AST over control treated animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

Certain Indications

Certain embodiments provided herein relate to methods comprising administering a compound or composition to an individual. Certain embodiments provided herein relate to methods of inhibiting SMAD7 expression, which can be useful for treating, preventing, or ameliorating a disease associated with SMAD7 in an individual, by administration of a compound that targets SMAD7. In certain embodiments, the compound can be a SMAD7 specific inhibitor. In certain embodiments, the compound can be an antisense compound, oligomeric compound, or oligonucleotide targeted to SMAD7.

Examples of diseases associated with SMAD7 treatable, preventable, and/or ameliorable with the methods provided herein include inflammatory bowel disease, pouchitis, celiac disease, intestinal graft-versus-host disease (GVHD) and cancer therapy-induced colitis.

Inflammatory bowel disease (IBD) is characterized by chronic inflammation in all or part of the digestive tract. It includes ulcerative colitis and Crohn's disease, both of which involve intestinal inflammation, disruption of the epithelial barrier, dysbiosis, severe diarrhea, pain, fatigue, abdominal cramping, reduced appetite, and weight loss. In certain embodiments, the diseases associated with SMAD7 are ulcerative colitis and Crohn's disease. Crohn's disease is an inflammatory bowel disease that causes inflammation in the lining of the digestive tract. The most common areas affected are the ileum and colon. Inflammation may be confined to the bowel wall, which can lead to narrowing from inflammation or scarring or both (fibrostenosis), or may tunnel through the bowel wall (fistula). Narrowing may lead to a blockage (obstruction). Ulcerative colitis is an inflammatory bowel disease that causes long-lasting inflammation and sores or ulcers in the innermost lining of the large intestine (colon) and rectum. Ulcerative colitis is classified according to location of the inflammation and severity of symptoms: (a) ulcerative proctitis, with inflammation confined to the area closest to the anus (rectum) and rectal bleeding may be the only sign of the disease; (b) proctosigmoiditis with inflammation in the rectum and sigmoid colon (lower end of the colon). Symptoms include bloody diarrhea, abdominal cramps and pain, and an inability to move the bowels inspite of the urge to do so (tenesmus); (c) Left-sided colitis, with inflammation extending from the rectum up through the sigmoid and descending colon. Symptoms include bloody diarrhea, abdominal cramping, and pain on the left side, and unintended weight loss; (d) Pancolitis, which affects the entire colon and causes bouts of bloody diarrhea that may be severe, abdominal cramps and pain, fatigue, and significant weight loss; and (e) Acute severe ulcerative colitis, previously called fulminant colitis. This rare form of colitis causes severe pain, profuse diarrhea, bleeding, fever, and inability to eat. In certain embodiments, the diseases associated with SMAD7 are ulcerative colitis and Crohn's disease.

Pouchitis is inflammation of the ileal pouch, an artificial rectum surgically created out of ileal gut tissue in patients that have undergone colectomy or proctocolectomy. The pouch is created in the management of patients with ulcerative colitis, indeterminate colitis, familial adenomatous polyposis, or other disorders. The inflammation can cause increased bowel frequency, abdominal cramping or bloating, lower abdominal pain, tenesmus or painful spasms of the anal sphincter, and/or blood in the stool. In certain embodiments, the disease associated with SMAD7 is pouchitis.

Celiac disease is a serious autoimmune disorder that can occur in genetically predisposed people where the ingestion of gluten leads to damage in the small intestine. Digestive symptoms common in patients include abdominal bloating and pain, chronic diarrhea, vomiting, constipation, weight loss, fatigue, unexplained iron-deficiency anemia, bone or joint pain, osteoporosis, liver and biliary tract disorders, or/and irritability. A recent study in patients with refractory celiac disease demonstrated the role of SMAD7 in the progression of the disease (Sedda S. et al., Immunology. 2017. 150: 356-363). In certain embodiments, the disease associated with SMAD7 is celiac disease.

In certain embodiments, a method of treating, preventing, or ameliorating a disease associated with SMAD7 in an individual comprises administering to the individual a compound comprising a SMAD7 specific inhibitor, thereby treating, preventing, or ameliorating the disease. In certain embodiments, the individual is identified as having or at risk of having a disease associated with SMAD7. In certain embodiments, the disease is a gastrointestinal disease. In certain embodiments, the compound comprises an antisense compound targeted to SMAD7. In certain embodiments, the compound comprises an oligonucleotide targeted to SMAD7. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, a compound comprises a modified oligonucleotide 12 to 80 linked nucleosides in length and having a nucleobase sequence comprising the nucleobase sequence of any one of SEQ ID NOs: 14-2735. In certain embodiments, a compound comprises a modified oligonucleotide consisting of the nucleobase sequence of any one of SEQ ID NOs: 14-2735. In certain embodiments, a compound comprises a modified oligonucleotide 12 to 80 linked nucleosides in length having a nucleobase sequence comprising any one of SEQ ID NOs: 1456, 2109, 2506, 2537, 2548, or 2633. In certain embodiments, a compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents inflammation in the gastrointestinal tract.

In certain embodiments, a method of treating, preventing, or ameliorating inflammation in the gastrointestinal tract, treating, preventing, or ameliorating diarrhea, treating, preventing, or ameliorating pain, treating, preventing, or ameliorating fatigue, treating, preventing, or ameliorating abdominal cramping, treating, preventing, or ameliorating blood in the stool, treating, preventing, or ameliorating intestinal inflammation, treating, preventing, or ameliorating disruption of the epithelial barrier of the gastrointestinal tract, treating, preventing, or ameliorating dysbiosis, treating, preventing, or ameliorating increased bowel frequency, treating, preventing, or ameliorating tenesmus or painful spasms of the anal sphincter, treating, preventing, or ameliorating constipation, or treating, preventing, or ameliorating unintended weight loss in an individual comprises administering to the individual a compound comprising a SMAD7 specific inhibitor. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having or at risk of having a disease associated with SMAD7.

In certain embodiments, a method of inhibiting expression of SMAD7 in an individual having, or at risk of having, a disease associated with SMAD7 comprises administering to the individual a compound comprising a SMAD7 specific inhibitor, thereby inhibiting expression of SMAD7 in the individual. In certain embodiments, administering the compound inhibits expression of SMAD7 in gastrointestinal tissue. In certain embodiments, administering the compound inhibits expression of SMAD7 in the ileum. In certain embodiments, administering the compound inhibits expression of SMAD7 in the rectum. In certain embodiments, administering the compound inhibits expression of SMAD7 in colon. In certain embodiments, administering the compound inhibits expression of SMAD7 in the sigmoid colon. In certain embodiments, administering the compound inhibits expression of SMAD7 in the descending colon. In certain embodiments, the individual has, or is at risk of having inflammatory bowel disease. In certain embodiments, the individual has, or is at risk of having ulcerative colitis. In certain embodiments, the individual has, or is at risk of having Crohn's disease. In certain embodiments, the individual has indeterminate colitis. In certain embodiments, the individual has familial adenomatous polyposis. In certain embodiments, the individual has intestinal GvHD. In certain embodiments, the individual has cancer therapy-induced colitis. In certain embodiments, the individual has, or is at risk of having diarrhea. In certain embodiments, the individual has, or is at risk of having pain and fatigue. In certain embodiments, the individual has, or is at risk of having abdominal cramping. In certain embodiments, the individual has, or is at risk of having blood in the stool. In certain embodiments, the individual has, or is at risk of having reduced appetite. In certain embodiments, the individual has, or is at risk of having unintended weight loss. In certain embodiments, the individual has, or is at risk of having intestinal inflammation. In certain embodiments, the individual has, or is at risk of having disruption of the epithelial barrier in the gastrointestinal tract. In certain embodiments, the individual has, or is at risk of having dysbiosis. In certain embodiments, the individual has, or is at risk of having increased bowel frequency. In certain embodiments, the individual has, or is at risk of having tenesmus or painful spasms of the anal sphincter. In certain embodiments, the individual has, or is at risk of having constipation. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound reduces or prevents inflammation in the gastrointestinal tract. In certain embodiments, administering the compound reduces or prevents diarrhea. In certain embodiments, administering the compound reduces or prevents pain. In certain embodiments, administering the compound reduces or prevents fatigue. In certain embodiments, administering the compound reduces or prevents abdominal cramping. In certain embodiments, administering the compound reduces or prevents blood in the stool. In certain embodiments, administering the compound improves, preserves, or prevents loss of appetite. In certain embodiments, administering the compound reduces or prevents unintended weight loss. In certain embodiments, administering the compound reduces or prevents fever. In certain embodiments, administering the compound reduces or prevents intestinal inflammation. In certain embodiments, administering the compound reduces or prevents disruption of the epithelial barrier of the gastrointestinal tract. In certain embodiments, administering the compound reduces or prevents dysbiosis. In certain embodiments, administering the compound reduces or prevents increased bowel frequency. In certain embodiments, administering the compound reduces or prevents tenesmus or painful spasms of the anal sphincter. In certain embodiments, administering the compound reduces or prevents constipation. In certain embodiments, the individual is identified as having or at risk of having a disease associated with SMAD7.

In certain embodiments, a method of inhibiting expression of SMAD7 in a cell comprises contacting the cell with a compound comprising a SMAD7 specific inhibitor, thereby inhibiting expression of SMAD7 in the cell. In certain embodiments, the cell is in the gastrointestinal tissue. In certain embodiments, the cell is in the rectum. In certain embodiments, the cell is in the ileum. In certain embodiments, the cell is in the colon. In certain embodiments, the cell is in the sigmoid colon. In certain embodiments, the cell is in the descending colon. In certain embodiments, the cell is in the gastrointestinal tissue of an individual who has, or is at risk of having inflammatory bowel disease. In certain embodiments, the inflammatory bowel disease is ulcerative colitis. In certain embodiments, the inflammatory bowel disease is Crohn's disease. In certain embodiments, the individual has indeterminate colitis. In certain embodiments, the individual has familial adenomatous polyposis. In certain embodiments, the individual has intestinal GvHD. In certain embodiments, the individual has cancer therapy-induced colitis. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound.

In certain embodiments, a method of reducing or inhibiting inflammation in the gastrointestinal tissue, reducing or inhibiting diarrhea, reducing or inhibiting pain, reducing or inhibiting fatigue, reducing of inhibiting abdominal cramping, reducing or inhibiting blood in the stool, reducing or inhibiting intestinal inflammation, reducing or inhibiting disruption of the epithelial barrier of the gastrointestinal tract, reducing or inhibiting dysbiosis, reducing or inhibiting increased bowel frequency, reducing or inhibiting tenesmus or painful spasms of the anal sphincter, reducing or inhibiting constipation, or reducing or inhibiting unintended weight loss in an individual having, or at risk of having, a disease associated with SMAD7 comprises administering to the individual a compound comprising a SMAD7 specific inhibitor. In certain embodiments, the individual has, or is at risk of having diarrhea. In certain embodiments, the individual has, or is at risk of having pain and fatigue. In certain embodiments, the individual has, or is at risk of having abdominal cramping. In certain embodiments, the individual has, or is at risk of having blood in the stool. In certain embodiments, the individual has, or is at risk of having reduced appetite. In certain embodiments, the individual has, or is at risk of having unintended weight loss. In certain embodiments, the individual has, or is at risk of having intestinal inflammation. In certain embodiments, the individual has, or is at risk of having disruption of the epithelial barrier of the gastrointestinal tract. In certain embodiments, the individual has, or is at risk of having dysbiosis. In certain embodiments, the individual has, or is at risk of having increased bowel frequency. In certain embodiments, the individual has, or is at risk of having tenesmus or painful spasms of the anal sphincter. In certain embodiments, the individual has, or is at risk of having constipation. In certain embodiments, the individual has, or is at risk of having, inflammatory bowel disease. In certain embodiments, the inflammatory bowel disease is ulcerative colitis. In certain embodiments, the inflammatory bowel disease is Crohn's disease. In certain embodiments, the individual has, or is at risk of having, indeterminate colitis. In certain embodiments, the individual has, or is at risk of having, familial adenomatous polyposis. In certain embodiments, the individual has, or is at risk of having, intestinal GvHD. In certain embodiments, the individual has, or is at risk of having, cancer therapy-induced colitis. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having or at risk of having a disease associated with SMAD7.

Certain embodiments are drawn to a compound comprising a SMAD7 specific inhibitor for use in treating a disease associated with SMAD7. In certain embodiments, the disease is inflammatory bowel disease. In certain embodiments, the disease is ulcerative colitis. In certain embodiments, the disease is Crohn's disease. In certain embodiments, the disease is indeterminate colitis. In certain embodiments, the disease is familial adenomatous polyposis. In certain embodiments, the disease is intestinal GvHD. In certain embodiments, the disease is cancer therapy-induced colitis. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound.

Certain embodiments are drawn to a compound comprising a SMAD7 specific inhibitor for use in reducing or inhibiting inflammation in the gastrointestinal tract, reducing or inhibiting diarrhea, reducing or inhibiting pain, reducing or inhibiting fatigue, reducing of inhibiting abdominal cramping, reducing or inhibiting blood in the stool, reducing or inhibiting intestinal inflammation, reducing or inhibiting disruption of the epithelial barrier of the gastrointestinal tract, reducing or inhibiting dysbiosis, reducing or inhibiting increased bowel frequency, reducing or inhibiting tenesmus or painful spasms of the anal sphincter, reducing or inhibiting constipation, or reducing or inhibiting unintended weight loss in an individual having or at risk of having inflammatory bowel disease. In certain embodiments, the inflammatory bowel disease is ulcerative colitis. the inflammatory bowel disease is Crohn's disease. In certain embodiments, the individual has indeterminate colitis. In certain embodiments, the individual has familial adenomatous polyposis. In certain embodiments, the individual has intestinal GvHD. In certain embodiments, the individual has cancer therapy-induced colitis. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound.

Certain embodiments are drawn to use of a compound comprising a SMAD7 specific inhibitor for the manufacture or preparation of a medicament for treating a disease associated with SMAD7. Certain embodiments are drawn to use of a compound comprising a SMAD7 specific inhibitor for the preparation of a medicament for treating a disease associated with SMAD7. In certain embodiments, the disease is a gastrointestinal disease. In certain embodiments, the individual has, or is at risk of having, inflammatory bowel disease. In certain embodiments, the inflammatory bowel disease is ulcerative colitis. In certain embodiments, the inflammatory bowel disease is Crohn's disease. In certain embodiments, the individual has indeterminate colitis. In certain embodiments, the individual has familial adenomatous polyposis. In certain embodiments, the individual has intestinal GvHD. In certain embodiments, the individual has cancer therapy-induced colitis. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound.

Certain embodiments are drawn to use of a compound comprising a SMAD7 specific inhibitor for the manufacture or preparation of a medicament for reducing or inhibiting inflammation in the gastrointestinal tract, reducing or inhibiting diarrhea, reducing or inhibiting pain, reducing or inhibiting fatigue, reducing or inhibiting abdominal cramping, reducing or inhibiting blood in the stool, reducing or inhibiting intestinal inflammation, reducing or inhibiting disruption of the epithelial barrier of the gastrointestinal tract, reducing or inhibiting dysbiosis, reducing or inhibiting increased bowel frequency, reducing or inhibiting tenesmus or painful spasms of the anal sphincter, reducing or inhibiting constipation, or reducing or inhibiting unintended weight loss in an individual having or at risk of having a gastrointestinal disease associated with SMAD7. In certain embodiments, the gastrointestinal disease is inflammatory bowel disease, ulcerative colitis, Crohn's disease. In certain embodiments, the gastrointestinal disease is indeterminate colitis. In certain embodiments, the gastrointestinal disease is familial adenomatous polyposis. In certain embodiments, the gastrointestinal disease is intestinal GvHD. In certain embodiments, the gastrointestinal disease is cancer therapy-induced colitis. Certain embodiments are drawn to use of a compound comprising a SMAD7 specific inhibitor for the preparation of a medicament for reducing or inhibiting inflammation in the gastrointestinal tract in an individual having or at risk of having inflammatory bowel disease. In certain embodiments, the inflammatory bowel disease is ulcerative colitis or Crohn's disease. In certain embodiments, the individual has indeterminate colitis. In certain embodiments, the individual has familial adenomatous polyposis. In certain embodiments, the individual has intestinal GvHD. In certain embodiments, the individual has cancer therapy-induced colitis. In certain embodiments, the compound comprises an antisense compound targeted to SMAD7. In certain embodiments, the compound comprises an oligonucleotide targeted to SMAD7. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 14-2735. In certain embodiments, the compound comprises a modified oligonucleotide 12 to 80 linked nucleosides in length and having a nucleobase sequence comprising the nucleobase sequence of any one of SEQ ID NOs: 14-2735. In certain embodiments, the compound comprises a modified oligonucleotide consisting of the nucleobase sequence of any one of SEQ ID NOs: 14-2735. In certain embodiments, the compound comprises a modified oligonucleotide of 12 to 80 linked nucleosides in length having a nucleobase sequence comprising any one of SEQ ID NOs: 1456, 2109, 2506, 2537, 2548, or 2633. In certain embodiments, the compound comprises a modified oligonucleotide having a nucleobase sequence consisting of any one of SEQ ID NOs: 1456, 2109, 2506, 2537, 2548, or 2633. In any of the foregoing embodiments, the modified oligonucleotide can be 10 to 30 linked nucleosides in length. In certain embodiments, the compound is ION 830121, ION 829994, ION 830037, ION 798781, ION 790615, or ION 830025. In any of the foregoing embodiments, the compound can be single-stranded or double-stranded. In any of the foregoing embodiments, the compound can be an antisense compound or oligomeric compound.

In any of the foregoing methods or uses, the compound can be targeted to SMAD7. In certain embodiments, the compound comprises or consists of a modified oligonucleotide, for example a modified oligonucleotide 8 to 80 linked nucleosides in length, 10 to 30 linked nucleosides in length, 12 to 30 linked nucleosides in length, or 20 linked nucleosides in length. In certain embodiments, the modified oligonucleotide is at least 80%, 85%, 90%, 95% or 100% complementary to any of the nucleobase sequences recited in SEQ ID NOs: 1-7. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide is 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides in length. In certain embodiments, the modified oligonucleotide is at least 80%, 85%, 90%, 95% or 100% complementary to any of the nucleobase sequences recited in SEQ ID NOs: 1-7. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound comprises or consists of a modified oligonucleotide 12 to 30 linked nucleosides in length and having a nucleobase sequence comprising any one of SEQ ID NOs: 14-2735, wherein the modified oligonucleotide comprises:

a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar.

In certain embodiments, a compound comprises or consists of a modified oligonucleotide 12-80 linked nucleobases in length having a nucleobase sequence comprising the sequence recited in any one of SEQ ID NOs: 1456, 2109, 2506, 2537, 2548, or 2633, wherein the modified oligonucleotide comprises a gap segment consisting of ten linked deoxynucleosides;
a 5' wing segment consisting of three linked nucleosides; and
a 3' wing segment consisting of three linked nucleosides;

wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine. In certain embodiments, the modified oligonucleotide is 16-80 linked nucleosides in length. In certain embodiments, the modified oligonucleotide is 10-30 linked nucleosides in length.

In certain embodiments a compound comprises or consists of ION 830025, designated as 2'-O,4'-C—[(S)-ethylidene]-5-methyl-P-thiouridylyl-(3'-O→5'-O)-2'-O,4'-C—[(S)-ethylidene]-5-methyl-Pthiouridylyl-(3'-O→5'-O)-2'-O,4'-C—[(S)-ethylidene]-5-methyl-P-thiouridylyl-(3'-O→5'-O)-2'-deoxy-Pthioguanylyl-(3'-O→5'-O)—P-thiothymidylyl-(3'-O→5'-O)-2'-deoxy-P-thioadenylyl-(3'-O→5'-O)-2'-deoxy-P-thioadenylyl-(3'-O→5'-O)-2'-deoxy-Pthioadenylyl-(3'-O→5'-O)—P-thiothymidylyl-(3'-O→5'-O)-2'-deoxy-5-methyl-P-thiocytidylyl-(3'-O→5'-O)-2'-deoxy-P-thioguanylyl-(3'-O→5'-O)-2'-deoxy-Pthioadenylyl-(3'-O→5'-O)-2'-deoxy-P-thioadenylyl-(3'-O→5'-O)-2'-O,4'-C—[(S)-ethylidene]-Pthioadenylyl-(3'-O→5'-O)-2'-O,4'-C—[(S)-ethylidene]-P-thioguanylyl-(3'-O→5'-O)-2'-O,4'-C—[(S)-ethylidene]-5-methylcytidine, sodium salt In certain embodiments, a compound comprises or consists of ION 830025 or salt thereof, having the following chemical structure:

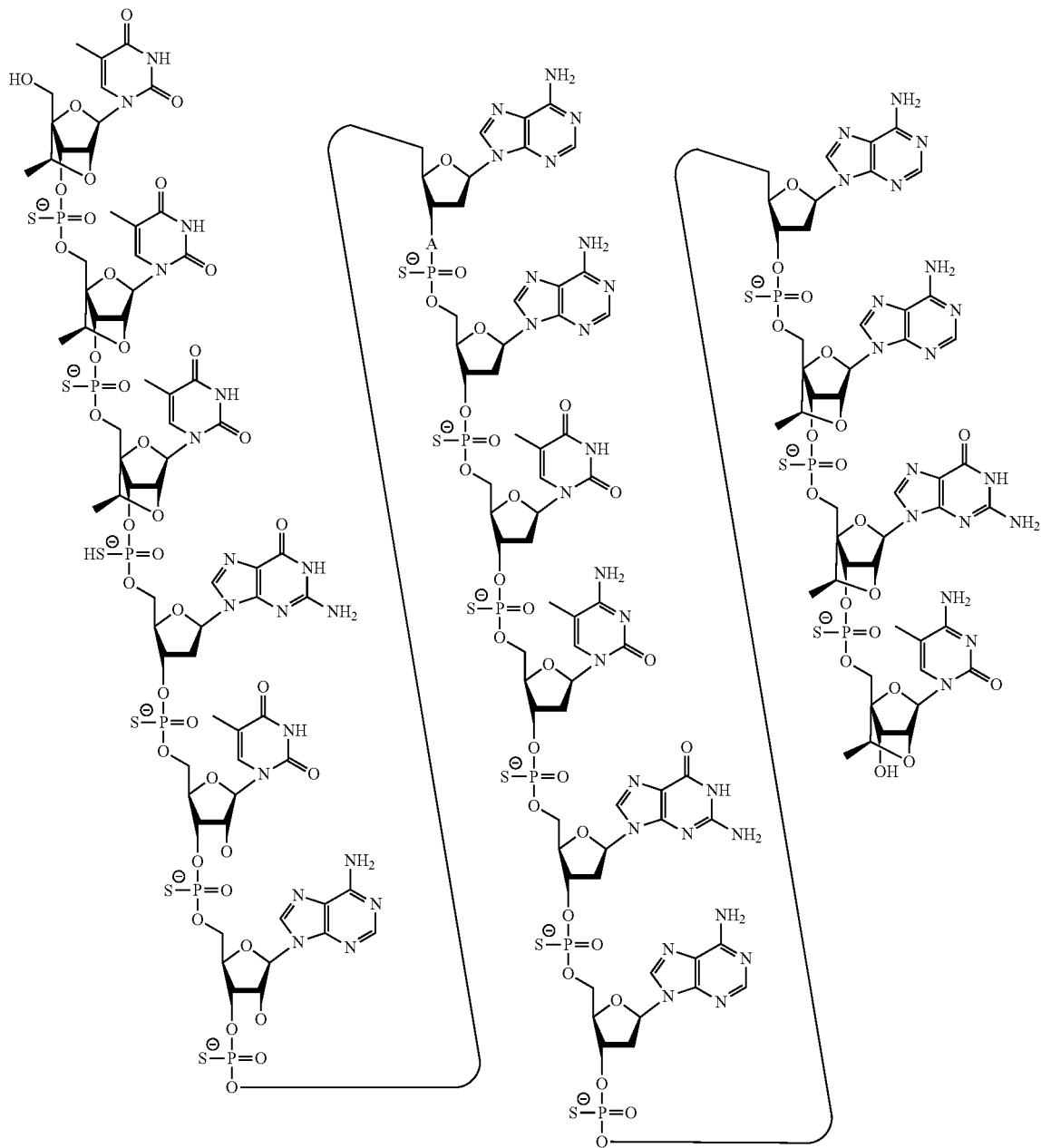

In certain embodiments, a compound comprises or consists of the sodium salt of ION 830025, having the following chemical structure:
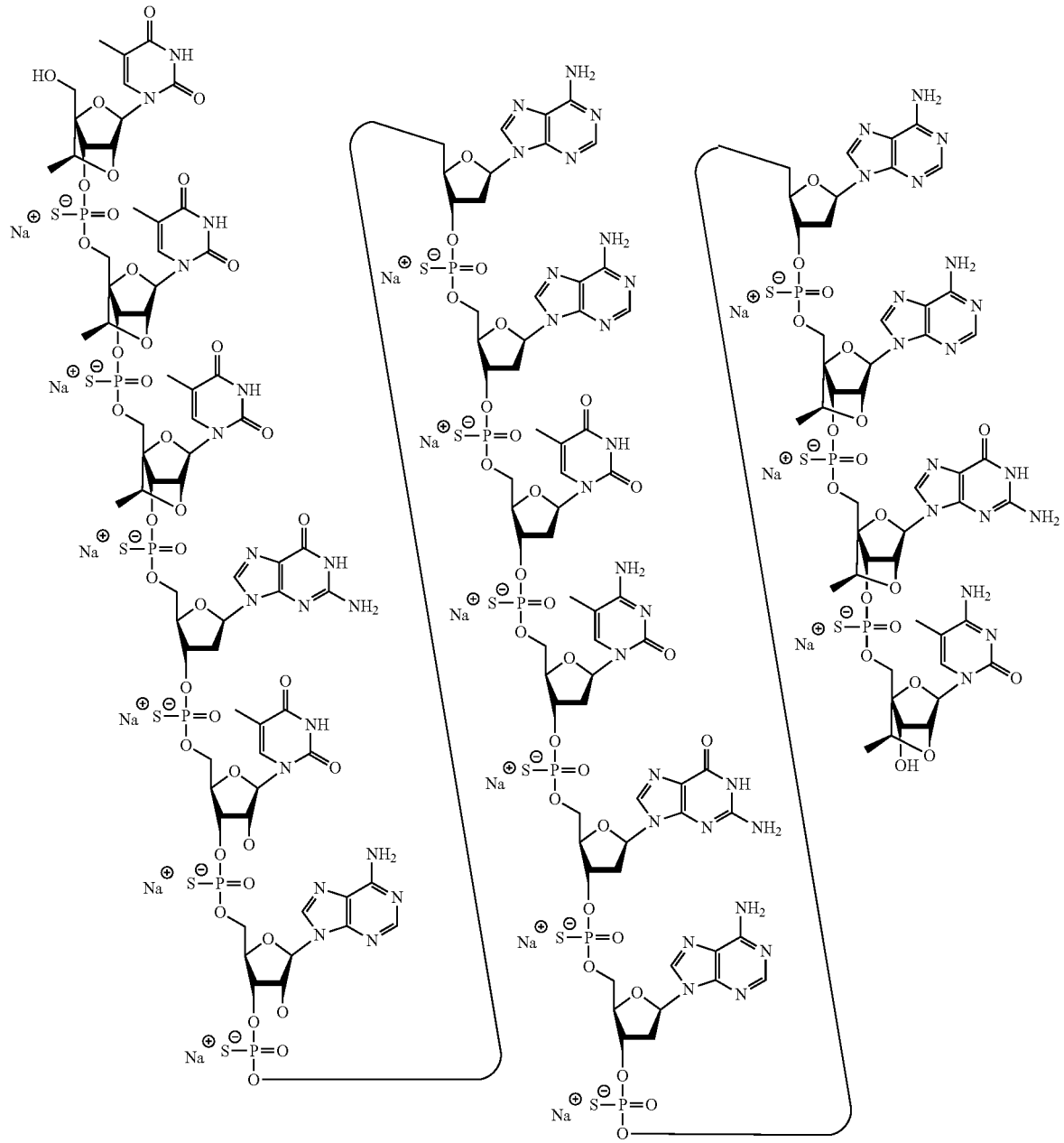

In certain embodiments, a compound comprises or consists of ION 798781 or salt thereof, having the following chemical structure:
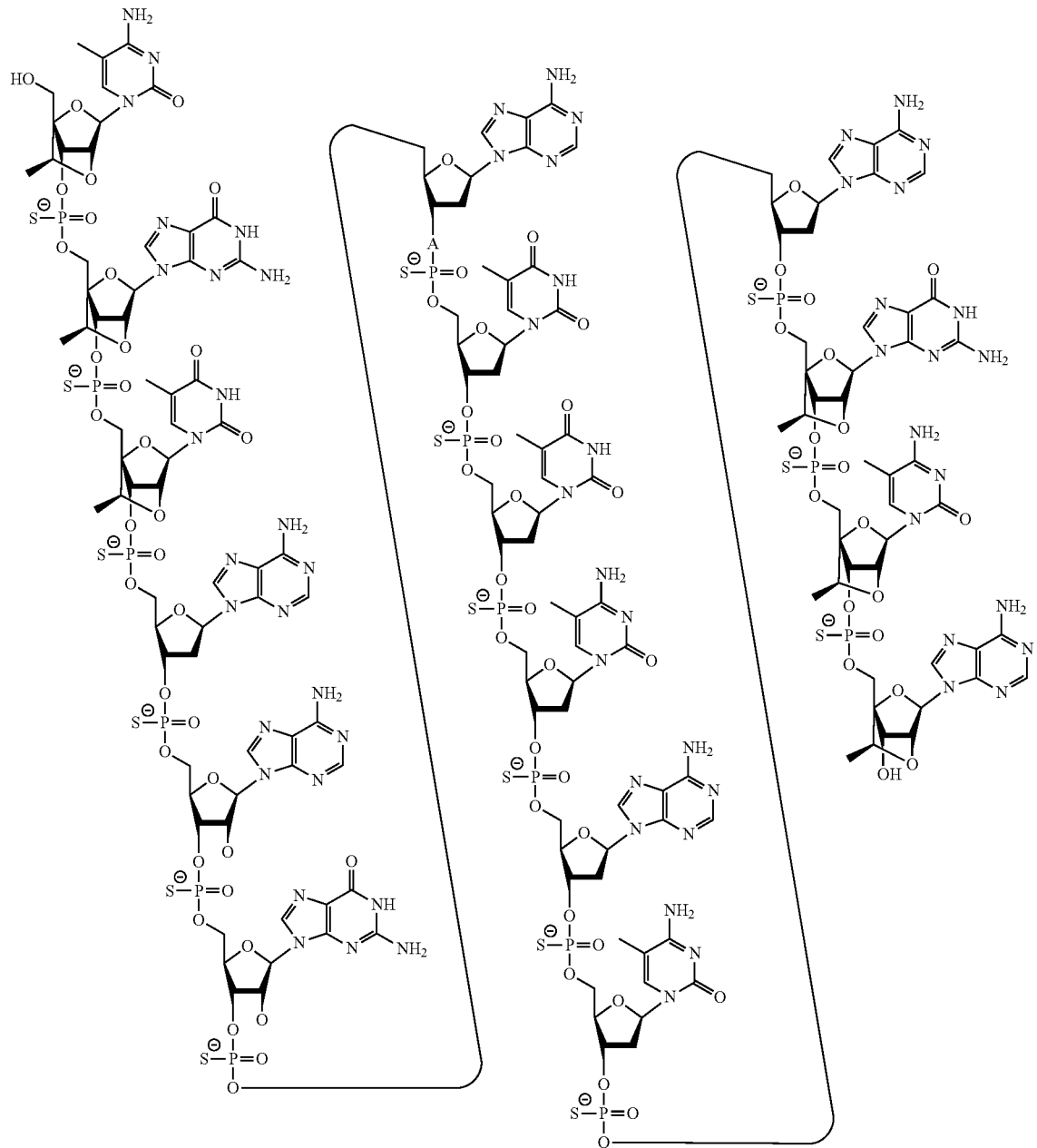

In certain embodiments, a compound comprises or consists of the sodium salt of ION 798781, having the following chemical structure:

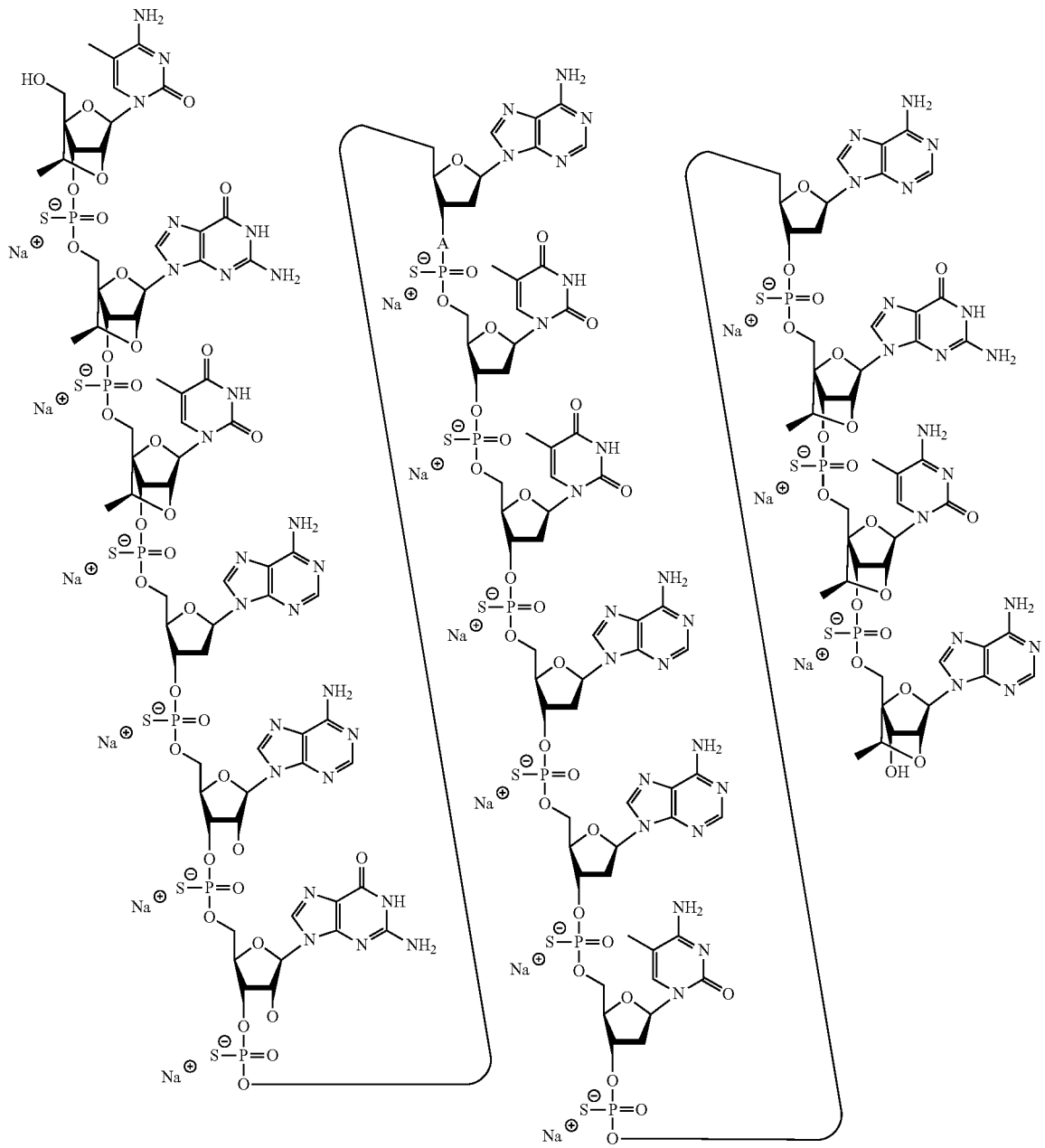

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 12-30 linked nucleosides in length and the second modified oligonucleotide is 12-30 linked nucleosides in length. In certain embodiments, one of the modified oligonucleotides has a nucleobase sequence comprising at least 8 contiguous nucleobases of any of SEQ ID NOs: 14-2735.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to an SMAD7 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. *Proc. Natl. Acad. Sci. USA* 1992, 89:7305-7309; Gautschi et al. *J. Natl. Cancer Inst.* March 2001, 93:463-471; Maher and Dolnick *Nuc. Acid. Res.* 1998, 16:3341-3358). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics.

In certain embodiments, a compound described herein can comprise any of the oligonucleotide sequences targeted to SMAD7 described herein. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 14-2735 and a second strand. In certain embodiments, the compound comprises a first strand comprising the nucleobase sequence of any one of SEQ ID NOs: 14-2735 and a second strand. In certain embodiments, the compound comprises ribonucleotides in which the first strand has uracil (U) in place of thymine (T) in any one of SEQ ID NOs: 14-2735. In certain embodiments, the compound comprises (i) a first strand comprising a nucleobase sequence complementary to the site on SMAD7 to which any of SEQ ID NOs: 14-2735 is targeted, and (ii) a second strand. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to SMAD7 described herein. In certain embodiments, the compound is single stranded. In certain embodiments, such a compound is a single-stranded RNAi (ssRNAi) compound. In certain embodiments, the compound comprises at least an 8, 9, 10, 11, 12, 13, 14, 15, 16, 17, 18, 19, or 20 contiguous nucleobase portion of any one of SEQ ID NOs: 14-2735. In certain embodiments, the compound comprises the nucleobase sequence of any one of SEQ ID NOs: 14-2735. In certain embodiments, the compound comprises ribonucleotides in which uracil (U) is in place of thymine (T) in any one of SEQ ID NOs: 14-2735. In certain embodiments, the compound comprises a nucleobase sequence complementary to the site on SMAD7 to which any of SEQ ID NOs: 14-2735 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ss-RNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode SMAD7 include, without limitation, the following: RefSeq or GENBANK Accession No. NM 005904.3 (incorporated by reference, disclosed herein as SEQ ID NO: 1), complement of NT_010966.15 truncated from nucleotides 28007000 to 28041000 (incorporated by reference, disclosed herein as SEQ ID NO: 2), NM_001190823.1 (incorporated by reference, disclosed herein as SEQ ID NO: 3), NM_001190822.1 (incorporated by reference, disclosed herein as SEQ ID NO: 4), NM_001190821.1 (incorporated by reference, disclosed herein as SEQ ID NO: 5), AF015261.1 (incorporated by reference, disclosed herein as SEQ ID NO: 6), and AF010193.1 (incorporated by reference, disclosed herein as SEQ ID NO: 7).

Hybridization

In some embodiments, hybridization occurs between a compound disclosed herein and a SMAD7 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a SMAD7 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a SMAD7 nucleic acid may be tolerated provided that the compound remains able to specifically hybridize to a target nucleic acid. Moreover, a compound may hybridize over one or more segments of a SMAD7 nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a SMAD7 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a SMAD7 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a SMAD7 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a SMAD7 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a SMAD7 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the—compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O- 2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem.,2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Wahlestedt et al., Proc. Natl. Acad. Sci. U S. A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 20017, 129, 8362-8379; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al. U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

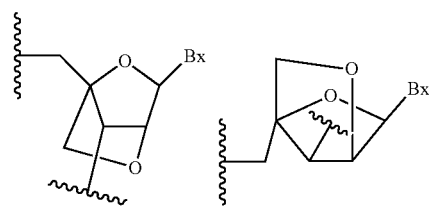

LNA (β-D-configuration) α-L-LNA (α-L-configuration)

bridge=4'-CH$_2$—O-2' bridge=4'-CH$_2$—O-2'

α-L-methyleneoxy (4'-CH$_2$—O-2') or α-L-LNA bicyclic nucleosides have been incorporated into oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. Bioorg. & Med. Chem. 2002, 10, 841-854), fluoro HNA:

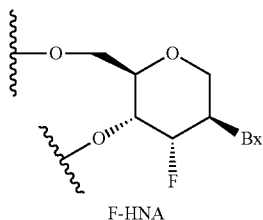

F-HNA ("F—HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F—HNA can also be referred to as a F-THP or 3'-fluoro tetrahydropyran), and nucleosides comprising additional modified THP compounds having the formula:

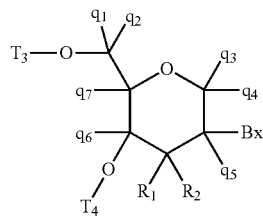

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

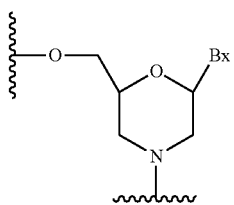

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds targeted to a SMAD7 nucleic acid comprise one or more modified nucleobases. In certain embodiments, the modified nucleobase is 5-methylcytosine. In certain embodiments, each cytosine is a 5-methylcytosine.

3. Modified Internucleoside Linkages

The naturally occurring internucleoside linkage of RNA and DNA is a 3' to 5' phosphodiester linkage In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

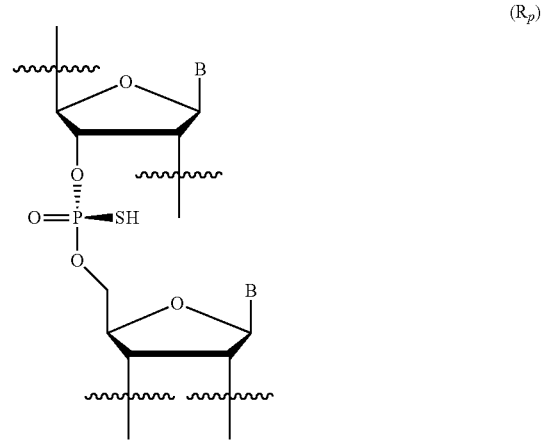

(R$_p$)

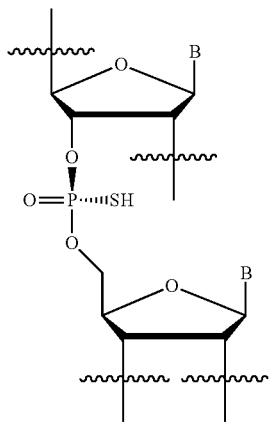
(S$_p$)

Unless otherwise indicated, chiral internucleoside linkages of modified oligonucleotides described herein can be stereorandom or in a particular stereochemical configuration.

In certain embodiments, compounds targeted to a SMAD7 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—CH2-N(CH3)-O—CH2-), thiodiester, thionocarbamate (—O—C(═O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(═O)—N(H)-5'), amide-4 (3'-CH2-N(H)—C(═O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

4. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

5. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., Ann. N.Y. Acad. Sci., 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic, a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 923-937), a tocopherol group (Nishina et al., *Molecular Therapy Nucleic Acids*, 2015, 4, e220; doi:10.1038/mtna.2014.72 and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to SMAD7 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to SMAD7 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

EXAMPLES

The Examples below describe the screening process to identify lead compounds targeted to human SMAD7. Out of over 2,720 oligonucleotides that were screened, ION 830025, ION 798781, and ION 790615 emerged as the top lead compounds. In particular, ION 830025 exhibited the best combination of properties in terms of potency and tolerability.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position.

Certain compounds described herein (e.g. modified oligonucleotides) have one or more asymmetric centers and thus give rise to enantiomers, diastereomers, and other stereoisomeric configurations that may be defined, in terms of absolute stereochemistry, as (R) or (S), as α or β, such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. Likewise, all tautomeric forms of the compounds provided herein are included unless otherwise indicated. Unless otherwise indicated, oligomeric compounds and modified oligonucleotides described herein are intended to include corresponding salt forms.

Compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human SMAD7 mRNA Expression in Hep3B Cells by 5-10-5 MOE Gapmers Antisense oligonucleotides were designed to target human SMAD7 mRNA and were tested for their effects on SMAD7 mRNA expression in vitro. Cultured Hep3B cells at a density of 20,000 cells per well were transfected using electroporation with antisense oligonucleotide ION 483663 (a 5-10-5 MOE gapmer), the sequence of which overlaps with ION 28453 (a 4-10-4 MOE gapmer) was included in these assays for comparison. ION 28453 has been previously disclosed in U.S. Pat. No. 6,159,697). After a treatment period of approximately 24 hours, RNA was isolated from the cells and SMAD7 mRNA levels were measured by quantitative real-time PCR. Primer probe set RTS5062 (forward sequence TTTCTCAAACCAACTGCAGACTGT, designated herein as SEQ ID NO: 11; reverse sequence CAGATAATTCGTTCCCCCTGTT, designated herein as SEQ ID NO: 12; probe sequence CAGATGCTGTGCCTTCCTCCGCTG, designated herein as SEQ ID NO: 13) was used to measure human SMAD7 mRNA levels. SMAD7 mRNA levels were adjusted according to total RNA content, as measured by RIBOGREEN®. Results are presented as percent inhibition of SMAD7 mRNA expression, relative to untreated control cells.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SMAD7 mRNA, designated herein as SEQ ID NO: 1 (GENBANK Accession No. NM_005904.3) or the human SMAD7 genomic sequence, designated herein as SEQ ID NO: 2 (complement of GENBANK Accession No. NT_010966.15 truncated from nucleotides 28007000 to 28041000). 'n/a' indicates that the antisense oligonucleotide does not target that particular gene sequence with 100% complementarity.

Study 1

Cultured Hep3B cells at a density of 20,000 cells per well were transfected using electroporation with 5,000 nM antisense oligonucleotide.

TABLE 1

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771390 | 25 | 44 | CGGCTGCCCCACCCCGCGCG | 32 | 1520 | 1539 | 14 |
| 771398 | 137 | 156 | GGCAGGAGCGGCGGCGGCCC | 53 | 1632 | 1651 | 15 |
| 483665 | 224 | 243 | GCGAACATGACCTCCGCACA | 10 | 1719 | 1738 | 16 |
| 771412 | 395 | 414 | TCGCCCCTTCTCCCCGCAGC | 52 | 1890 | 1909 | 17 |
| 771420 | 436 | 455 | GCCCGGGCCGCCGCCACCGG | 1 | 1931 | 1950 | 18 |
| 771428 | 476 | 495 | TGGCACCTCGCACCGCCTTG | 0 | 1971 | 1990 | 19 |
| 771436 | 604 | 623 | GAGCAGCAGCTCCAGCTGCC | 50 | 2099 | 2118 | 20 |
| 771444 | 798 | 817 | AGCCTCTTGACTTCCGAGGA | 65 | 2293 | 2312 | 21 |
| 483663 | 799 | 818 | CAGCCTCTTGACTTCCGAGG | 47 | 2294 | 2313 | 22 |
| 771350 | N/A | N/A | TTTGCCCCAAAACTCCAAAG | 68 | 2933 | 2952 | 23 |
| 771707 | N/A | N/A | TTGTTCCTCTGCACCCTGGG | 0 | 3007 | 3026 | 24 |
| 771452 | 911 | 930 | GGTATCTGGAGTAAGGAGGG | 25 | 3780 | 3799 | 25 |
| 771715 | N/A | N/A | AGTCTCCGAGTTATCCCCAT | 68 | 4142 | 4161 | 26 |
| 771723 | N/A | N/A | CCAAGGTTACATACAACCTG | 0 | 4657 | 4676 | 27 |
| 771731 | N/A | N/A | AAAACTTTGTGCCTGTTTCA | 44 | 5978 | 5997 | 28 |
| 771739 | N/A | N/A | TTTGAAAACCCAACCCTGGG | 22 | 7243 | 7262 | 29 |
| 771747 | N/A | N/A | GTGTGTTTCAAAGGAAAAGC | 2 | 7881 | 7900 | 30 |
| 771755 | N/A | N/A | AAACATTTGGCACCCAACAC | 44 | 8898 | 8917 | 31 |
| 771358 | N/A | N/A | AGTTAATCATTACTCGAGTC | 53 | 9415 | 9434 | 32 |
| 771366 | N/A | N/A | TGCTGATTATTAATGGTCTG | 49 | 9503 | 9522 | 33 |
| 771374 | N/A | N/A | AGCATGAAAGACAAACCACA | 44 | 9552 | 9571 | 34 |
| 771382 | N/A | N/A | AAATAAAAACACCAAGATCC | 55 | 9593 | 9612 | 35 |
| 771763 | N/A | N/A | CCCCGTCCACGGAACGGATC | 34 | 9930 | 9949 | 36 |
| 771771 | N/A | N/A | CAGCTCCTACTGTTGGCAGT | 63 | 10275 | 10294 | 37 |
| 771779 | N/A | N/A | ACACACTGCTGCCTTTCTC | 53 | 11011 | 11030 | 38 |
| 771787 | N/A | N/A | AAGAAGAAGGAGCTCAAACT | 0 | 11997 | 12016 | 39 |
| 771795 | N/A | N/A | CGTCTGCGGCAAAACCCACC | 53 | 13057 | 13076 | 40 |
| 771803 | N/A | N/A | ATGGATACTGACTCAAGGAC | 22 | 13937 | 13956 | 41 |
| 771811 | N/A | N/A | TGCCTCATTCTTTCCAGGAC | 48 | 14665 | 14684 | 42 |
| 771819 | N/A | N/A | AATAGTTTTCTCTCAAATGT | 56 | 15647 | 15666 | 43 |
| 771827 | N/A | N/A | AAGGACATCACAGGGACTGG | 31 | 16679 | 16698 | 44 |
| 771835 | N/A | N/A | AGTAAAATGGGAAATAAGGC | 17 | 17567 | 17586 | 45 |
| 771843 | N/A | N/A | CGCCGGCCCACCAACCTCTG | 19 | 18438 | 18457 | 46 |
| 771851 | N/A | N/A | GCTTTGAAAACATCCCACTT | 25 | 19314 | 19333 | 47 |
| 771859 | N/A | N/A | CCAGAAAATGCAGACAGCTA | 43 | 19898 | 19917 | 48 |
| 771867 | N/A | N/A | ACTGGGCTTCAGCAAAGATA | 39 | 20754 | 20773 | 49 |

TABLE 1-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771875 | N/A | N/A | CCCCGTGCACTCCCAGCCCT | 42 | 22089 | 22108 | 50 |
| 771883 | N/A | N/A | AGCTGGCACTGAATGCTGAT | 0 | 22695 | 22714 | 51 |
| 771891 | N/A | N/A | CTCCCAAGCCTACATATTTC | 65 | 23560 | 23579 | 52 |
| 771899 | N/A | N/A | CCTGATTGTCTCCACATCCC | 57 | 24447 | 24466 | 53 |
| 771691 | N/A | N/A | CCAGGAGGGTATGCACACTC | 17 | 2494 2516 2538 | 2513 2535 2557 | 54 |
| 771699 | N/A | N/A | TGCACACTCTCCCAGGAGGG | 49 | 2505 2527 | 2524 2546 | 55 |
| 771907 | N/A | N/A | TCTATTCTCACGCCAAACCA | 42 | 25268 | 25287 | 56 |
| 771915 | N/A | N/A | CTGGGCCCAGACACACAAAG | 10 | 25941 | 25960 | 57 |
| 771923 | N/A | N/A | CCCCAGAAAACTGTACAGGG | 29 | 26950 | 26969 | 58 |
| 771931 | N/A | N/A | CCCAGCCCAGAAAAACTGCA | 22 | 27602 | 27621 | 59 |
| 771939 | N/A | N/A | TTCCCTACAGACACCCCAAG | 45 | 28589 | 28608 | 60 |
| 771947 | N/A | N/A | TTAACCCGGGCTACCTTAAC | 61 | 29533 | 29552 | 61 |
| 771460 | 1081 | 1100 | CGTCTTCTCCTCCCAGTATG | 54 | 30348 | 30367 | 62 |
| 771468 | 1198 | 1217 | CACCAGCTGACTCTTGTTGT | 21 | 30465 | 30484 | 63 |
| 771476 | 1258 | 1277 | CACACCATCCACCTCCCGCG | 19 | 30525 | 30544 | 64 |
| 771484 | 1441 | 1460 | CGTCCACGGCTGCTGCATAA | 51 | 30708 | 30727 | 65 |
| 771492 | 1510 | 1529 | GCTGCTGATGAACTGGCGGG | 53 | 30777 | 30796 | 66 |
| 771500 | 1555 | 1574 | ACGCGGCTACCGGCTGTTGA | 38 | 30822 | 30841 | 67 |
| 771507 | 1584 | 1603 | CTGCTCAGCTCACGCTCTGT | 24 | 30851 | 30870 | 68 |
| 771515 | 1617 | 1636 | AAATATTAGCAGCAAAGTAG | 13 | 30884 | 30903 | 69 |
| 771523 | 1644 | 1663 | TGCATGAAAAGCAAGCACTC | 47 | 30911 | 30930 | 70 |
| 771531 | 1665 | 1684 | AAAAAAAACGACCAAAGAGT | 40 | 30932 | 30951 | 71 |
| 771539 | 1738 | 1757 | AGCTATTTCTCAAAGAGCGA | 24 | 31005 | 31024 | 72 |
| 771547 | 1798 | 1817 | GTGTCCTGCCGATCATACCT | 45 | 31065 | 31084 | 73 |
| 771555 | 1841 | 1860 | GTTTGGTGGTGCTTGGATTT | 0 | 31108 | 31127 | 74 |
| 771563 | 1893 | 1912 | TCACACACACTCCTGACAAG | 32 | 31160 | 31179 | 75 |
| 771571 | 2009 | 2028 | TTGGGACTGCAAACCTCTCT | 71 | 31276 | 31295 | 76 |
| 771579 | 2061 | 2080 | AGGTACTGCCTCTGCCCCAC | 58 | 31328 | 31347 | 77 |
| 771587 | 2160 | 2179 | CGTGTCCTTGATGAGGGAGA | 6 | 31427 | 31446 | 78 |
| 771595 | 2217 | 2236 | AATTGGTTCTGGTTCGGCCA | 36 | 31484 | 31503 | 79 |
| 771603 | 2306 | 2325 | CTCAGGGAGATCCAGGAGCA | 34 | 31573 | 31592 | 80 |
| 771611 | 2412 | 2431 | GAAAACCTGATGTCACCAG | 70 | 31679 | 31698 | 81 |
| 771619 | 2457 | 2476 | CACAGGATGGGAGCAGGCAG | 37 | 31724 | 31743 | 82 |
| 771627 | 2485 | 2504 | CTTGCTGGCCTAATAGCAGA | 0 | 31752 | 31771 | 83 |
| 771635 | 2556 | 2575 | GGTTATGACGGACCAAATCC | 48 | 31823 | 31842 | 84 |

TABLE 1-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771643 | 2596 | 2615 | ATGAAAGAAGAGTTAGGTGT | 2 | 31863 | 31882 | 85 |
| 771651 | 2645 | 2664 | GCTAAGAACAGTGTCGAAGT | 37 | 31912 | 31931 | 86 |
| 771659 | 2685 | 2704 | AGAAAAATAGCTTATGTTAA | 32 | 31952 | 31971 | 87 |
| 771667 | 2749 | 2768 | AAAGCACTACAATGCTAAAT | 44 | 32016 | 32035 | 88 |
| 771675 | 2793 | 2812 | CTTTAATAAATCTCAGGTTT | 44 | 32060 | 32079 | 89 |
| 771683 | 2950 | 2969 | GCATTTGTTATTTGCATTTA | 0 | 32217 | 32236 | 90 |

Study 2

Cultured Hep3B cells at a density of 20,000 cells per well were transfected using electroporation with 15,000 nM antisense oligonucleotide. The antisense oligonucleotides were tested in a series of experiments that had similar culture conditions as described below. The results for each experiment are presented in separate tables shown below.

Some of the oligonucleotides presented were complementary to SMAD7 mRNA sequences RefSeqNo. NM_001190821.1 (designated herein as SEQ ID NO: 3) or RefSeqNo. NM_001190822.1 (designated herein as SEQ ID NO: 4), and are presented in a separate table shown below.

TABLE 2

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771392 | 28 | 47 | CTCCGGCTGCCCCACCCCGC | 28 | 1523 | 1542 | 91 |
| 771400 | 162 | 181 | CGACAGCAGCAGCAGCAGGG | 52 | 1657 | 1676 | 92 |
| 771406 | 226 | 245 | GAGCGAACATGACCTCCGCA | 55 | 1721 | 1740 | 93 |
| 771414 | 406 | 425 | TCGGCTGTCCGTCGCCCCTT | 65 | 1901 | 1920 | 94 |
| 771422 | 446 | 465 | ATCCAGCCCTGCCCGGGCCG | 27 | 1941 | 1960 | 95 |
| 771430 | 512 | 531 | CGCCCGCGGCTGGCGGGTGG | 40 | 2007 | 2026 | 96 |
| 771438 | 614 | 633 | CCACGGCCTGGAGCAGCAGC | 26 | 2109 | 2128 | 97 |
| 483663 | 799 | 818 | CAGCCTCTTGACTTCCGAGG | 49 | 2294 | 2313 | 22 |
| 771446 | 801 | 820 | CACAGCCTCTTGACTTCCGA | 55 | 2296 | 2315 | 98 |
| 771352 | N/A | N/A | TCCAACTCTCTTTGCCCCAA | 54 | 2943 | 2962 | 99 |
| 771709 | N/A | N/A | TGAACCCTCACATCACACTC | 38 | 3233 | 3252 | 100 |
| 771717 | N/A | N/A | TCCCATCTATCGAATCACCC | 57 | 4199 | 4218 | 101 |
| 771725 | N/A | N/A | CTTGAGGGAGCTGGTAGAGT | 8 | 4937 | 4956 | 102 |
| 771733 | N/A | N/A | TGACAGCCACAAGTCACAAC | 75 | 6282 | 6301 | 103 |
| 771741 | N/A | N/A | GGTCTCACCTTAGGCCTGTG | 53 | 7417 | 7436 | 104 |
| 771749 | N/A | N/A | GAAATGGAGTTACTTGTTAA | 29 | 8081 | 8100 | 105 |
| 771757 | N/A | N/A | TCCCCTTTTTTAATTGAGGA | 48 | 9147 | 9166 | 106 |
| 771360 | N/A | N/A | ACCTTGTCACCCGTCTGGGC | 49 | 9446 | 9465 | 107 |
| 771368 | N/A | N/A | CGGCCTTGATGCTGATTATT | 27 | 9512 | 9531 | 108 |

TABLE 2-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771376 | N/A | N/A | ACGCTCTAAACAGCATGAAA | 17 | 9563 | 9582 | 109 |
| 771384 | N/A | N/A | TGCTGTGGATTTGAAAAGGG | 18 | 9634 | 9653 | 110 |
| 771765 | N/A | N/A | CCAAGCCAGGAGCTGCTTAA | 48 | 10004 | 10023 | 111 |
| 771773 | N/A | N/A | TCTTTTCGCATCCTCAGGAA | 57 | 10417 | 10436 | 112 |
| 771781 | N/A | N/A | AAAAAAAGCCCACCCATCGG | 10 | 11737 | 11756 | 113 |
| 771789 | N/A | N/A | CCCAAAACAGTGTACCCTCC | 30 | 12061 | 12080 | 114 |
| 771797 | N/A | N/A | GCACAGACTGCCAAATCACA | 62 | 13240 | 13259 | 115 |
| 771805 | N/A | N/A | GATTATATAGGTATTTTGA | 0 | 14032 | 14051 | 116 |
| 771813 | N/A | N/A | TCTTGTCTGGCCGGCAGAGC | 38 | 14745 | 14764 | 117 |
| 771821 | N/A | N/A | GTTCCTTATAGATTATCCAA | 60 | 15906 | 15925 | 118 |
| 771829 | N/A | N/A | TGTGCCTCAGCAGTTAATAA | 14 | 16914 | 16933 | 119 |
| 771837 | N/A | N/A | AGTGTTGAGGACTCCCCAGC | 48 | 17670 | 17689 | 120 |
| 771845 | N/A | N/A | TTCCAAGCACGGAGTCAGCC | 39 | 18578 | 18597 | 121 |
| 771853 | N/A | N/A | AGCTTGGAAGCCATCGGTTG | 36 | 19576 | 19595 | 122 |
| 771861 | N/A | N/A | AGAAAACAGCCCCCCCAGCA | 13 | 20217 | 20236 | 123 |
| 771869 | N/A | N/A | AGCCAAGTGTCCATCAAGCA | 62 | 21276 | 21295 | 124 |
| 771877 | N/A | N/A | TGCAGGATCCGATGGAAAAG | 24 | 22147 | 22166 | 125 |
| 771885 | N/A | N/A | CAAGTCTCTTACCTCACCCA | 60 | 22783 | 22802 | 126 |
| 771893 | N/A | N/A | GTCATCCGTCCACTGTCTGC | 35 | 23633 | 23652 | 127 |
| 771901 | N/A | N/A | AAAATGCCCACCAGTCTTCC | 41 | 24465 | 24484 | 128 |
| 771693 | N/A | N/A | TCCCAGGAGGGTATGCACAC | 45 | 2496 2518 2540 | 2515 2537 2559 | 129 |
| 771701 | N/A | N/A | GGTATGCACACTCTCCCAGG | 34 | 2509 2531 | 2528 2550 | 130 |
| 771909 | N/A | N/A | CAGGCTCCCTGTGCCAATCA | 52 | 25580 | 25599 | 131 |
| 771917 | N/A | N/A | CCAGACCCCTTCTTAAATTT | 22 | 26148 | 26167 | 132 |
| 771925 | N/A | N/A | GGCCTCTCGCTGATAGTTAA | 10 | 27055 | 27074 | 133 |
| 771933 | N/A | N/A | ATCGAGGTGCCCCCATGCCA | 31 | 27832 | 27851 | 134 |
| 771941 | N/A | N/A | TCAATGATGATGGGTTGCAC | 40 | 28878 | 28897 | 135 |
| 771949 | N/A | N/A | AGATCTTTCAACTGGATGGA | 26 | 29895 | 29914 | 136 |
| 771462 | 1108 | 1127 | CTGGACACAGTAGAGCCTCC | 31 | 30375 | 30394 | 137 |
| 771470 | 1208 | 1227 | GCACCTTCTGCACCAGCTGA | 56 | 30475 | 30494 | 138 |
| 771478 | 1348 | 1367 | CACCTTGTGTACCAACAGCG | 53 | 30615 | 30634 | 139 |
| 771486 | 1451 | 1470 | CGGTAAAGCCCGTCCACGGC | 52 | 30718 | 30737 | 140 |
| 771494 | 1521 | 1540 | CAGCACGGGCAGCTGCTGAT | 20 | 30788 | 30807 | 141 |
| 771502 | 1572 | 1591 | CGCTCTGTCCCCTCCGCACG | 48 | 30839 | 30858 | 142 |

TABLE 2-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771509 | 1587 | 1606 | GGCCTGCTCAGCTCACGCTC | 65 | 30854 | 30873 | 143 |
| 771517 | 1627 | 1646 | CTCAGGAGGAAAATATTAGC | 25 | 30894 | 30913 | 144 |
| 771525 | 1646 | 1665 | TTTGCATGAAAAGCAAGCAC | 28 | 30913 | 30932 | 145 |
| 771533 | 1704 | 1723 | CAAACGAGGACGAGAAGAAG | 2 | 30971 | 30990 | 146 |
| 771541 | 1748 | 1767 | TCTTTTCATAAGCTATTTCT | 35 | 31015 | 31034 | 147 |
| 771549 | 1813 | 1832 | CCTCTTCCTATCAGGGTGTC | 49 | 31080 | 31099 | 148 |
| 771557 | 1866 | 1885 | ATGACCGCCCCCCTTCATAC | 19 | 31133 | 31152 | 149 |
| 771565 | 1938 | 1957 | CTGCCGCTCCTGCACACGCG | 55 | 31205 | 31224 | 150 |
| 771573 | 2011 | 2030 | GCTTGGGACTGCAAACCTCT | 65 | 31278 | 31297 | 151 |
| 771581 | 2085 | 2104 | GGGACCCCAGCCGCCAGCTT | 58 | 31352 | 31371 | 152 |
| 771589 | 2170 | 2189 | TGGACAGGCCCGTGTCCTTG | 51 | 31437 | 31456 | 153 |
| 771597 | 2238 | 2257 | GAATAAGACAAGGATGAAAA | 0 | 31505 | 31524 | 154 |
| 771605 | 2336 | 2355 | GGCTGCCCCGGCAGCCCTTG | 26 | 31603 | 31622 | 155 |
| 771613 | 2422 | 2441 | CTAAGTCCGGGAAAAACCTG | 21 | 31689 | 31708 | 156 |
| 771621 | 2460 | 2479 | ACACACAGGATGGGAGCAGG | 36 | 31727 | 31746 | 157 |
| 771629 | 2512 | 2531 | AGCATGTCCCTCCCAGGGAC | 25 | 31779 | 31798 | 158 |
| 771637 | 2566 | 2585 | TGGTACCTTGGGTTATGACG | 23 | 31833 | 31852 | 159 |
| 771645 | 2608 | 2627 | GTTGTAGAAGAAATGAAAGA | 38 | 31875 | 31894 | 160 |
| 771653 | 2655 | 2674 | TGCTCATTGAGCTAAGAACA | 33 | 31922 | 31941 | 161 |
| 771661 | 2719 | 2738 | AATGCTTCTCTTGTTCATTT | 69 | 31986 | 32005 | 162 |
| 771669 | 2759 | 2778 | TTTCTCTCTCAAAGCACTAC | 55 | 32026 | 32045 | 163 |
| 771677 | 2900 | 2919 | TTTCTTGTTTATACACATTG | 21 | 32167 | 32186 | 164 |
| 771685 | 2963 | 2982 | CTTTTTTAATTTGGCATTTG | 17 | 32230 | 32249 | 165 |

TABLE 3

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771390 | 25 | 44 | CGGCTGCCCCACCCCGCGCG | 66 | 1520 | 1539 | 14 |
| 771391 | 27 | 46 | TCCGGCTGCCCCACCCCGCG | 16 | 1522 | 1541 | 166 |
| 771393 | 29 | 48 | GCTCCGGCTGCCCCACCCCG | 0 | 1524 | 1543 | 167 |
| 771394 | 30 | 49 | CGCTCCGGCTGCCCCACCCC | 10 | 1525 | 1544 | 168 |
| 771398 | 137 | 156 | GGCAGGAGCGGCGGCGGCCC | 48 | 1632 | 1651 | 15 |
| 771399 | 142 | 161 | GCCCGGGCAGGAGCGGCGGC | 33 | 1637 | 1656 | 169 |
| 771401 | 167 | 186 | GCAGGCGACAGCAGCAGCAG | 21 | 1662 | 1681 | 170 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771402 | 172 | 191 | CAGGCGCAGGCGACAGCAGC | 31 | 1667 | 1686 | 171 |
| 483665 | 224 | 243 | GCGAACATGACCTCCGCACA | 55 | 1719 | 1738 | 16 |
| 771405 | 225 | 244 | AGCGAACATGACCTCCGCAC | 25 | 1720 | 1739 | 172 |
| 771407 | 228 | 247 | AGGAGCGAACATGACCTCCG | 59 | 1723 | 1742 | 173 |
| 771408 | 233 | 252 | TGCTAAGGAGCGAACATGAC | 36 | 1728 | 1747 | 174 |
| 771412 | 395 | 414 | TCGCCCCTTCTCCCCGCAGC | 38 | 1890 | 1909 | 17 |
| 771413 | 401 | 420 | TGTCCGTCGCCCCTTCTCCC | 24 | 1896 | 1915 | 175 |
| 771415 | 411 | 430 | TGCGCTCGGCTGTCCGTCGC | 36 | 1906 | 1925 | 176 |
| 771416 | 416 | 435 | CCCCATGCGCTCGGCTGTCC | 58 | 1911 | 1930 | 177 |
| 771420 | 436 | 455 | GCCCGGGCCGCCGCCACCGG | 54 | 1931 | 1950 | 18 |
| 771421 | 441 | 460 | GCCCTGCCCGGGCCGCCGCC | 0 | 1936 | 1955 | 178 |
| 771423 | 451 | 470 | GCAGCATCCAGCCCTGCCCG | 39 | 1946 | 1965 | 179 |
| 771424 | 456 | 475 | CCCAGGCAGCATCCAGCCCT | 36 | 1951 | 1970 | 180 |
| 771428 | 476 | 495 | TGGCACCTCGCACCGCCTTG | 47 | 1971 | 1990 | 19 |
| 771429 | 481 | 500 | ACCTTTGGCACCTCGCACCG | 11 | 1976 | 1995 | 181 |
| 771431 | 529 | 548 | GCCCCCGGCCGCGCCGGCGC | 37 | 2024 | 2043 | 182 |
| 771432 | 577 | 596 | CAGTTTCTTGAGCACCGAGT | 28 | 2072 | 2091 | 183 |
| 771436 | 604 | 623 | GAGCAGCAGCTCCAGCTGCC | 27 | 2099 | 2118 | 20 |
| 771437 | 609 | 628 | GCCTGGAGCAGCAGCTCCAG | 0 | 2104 | 2123 | 184 |
| 771439 | 705 | 724 | GGCTGCGCGCCGGCGGGCGC | 48 | 2200 | 2219 | 185 |
| 771440 | 715 | 734 | CGGCTGCGCAGGCTGCGCGC | 48 | 2210 | 2229 | 186 |
| 771444 | 798 | 817 | AGCCTCTTGACTTCCGAGGA | 67 | 2293 | 2312 | 21 |
| 483663 | 799 | 818 | CAGCCTCTTGACTTCCGAGG | 56 | 2294 | 2313 | 22 |
| 771445 | 800 | 819 | ACAGCCTCTTGACTTCCGAG | 10 | 2295 | 2314 | 187 |
| 771447 | 803 | 822 | AACACAGCCTCTTGACTTCC | 19 | 2298 | 2317 | 188 |
| 771448 | 871 | 890 | GAGTCGGCTAAGGTGATGGG | 29 | 2366 | 2385 | 189 |
| 771691 | N/A | N/A | CCAGGAGGGTATGCACACTC | 71 | 2494<br>2516<br>2538 | 2513<br>2535<br>2557 | 66 |
| 771692 | N/A | N/A | CCCAGGAGGGTATGCACACT | 18 | 2495<br>2517<br>2539 | 2514<br>2536<br>2558 | 190 |
| 771694 | N/A | N/A | CTCCCAGGAGGGTATGCACA | 0 | 2497<br>2519 | 2516<br>2538 | 191 |
| 771695 | N/A | N/A | TCTCCCAGGAGGGTATGCAC | 22 | 2498<br>2520 | 2517<br>2539 | 192 |
| 771699 | N/A | N/A | TGCACACTCTCCCAGGAGGG | 84 | 2505<br>2527 | 2524<br>2546 | 86 |
| 771700 | N/A | N/A | TATGCACACTCTCCCAGGAG | 9 | 2507<br>2529 | 2526<br>2548 | 193 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771702 | N/A | N/A | AGGGTATGCACACTCTCCCA | 24 | 2511 2533 | 2530 2552 | 194 |
| 771703 | N/A | N/A | GGAGGGTATGCACACTCTCC | 31 | 2513 2535 | 2532 2554 | 195 |
| 771346 | N/A | N/A | CGTGATTCTCCGTATTTACT | 22 | 2874 | 2893 | 196 |
| 771350 | N/A | N/A | TTTGCCCCAAAACTCCAAAG | 28 | 2933 | 2952 | 23 |
| 771351 | N/A | N/A | CTCTCTTTGCCCCAAAACTC | 11 | 2938 | 2957 | 197 |
| 771353 | N/A | N/A | TTCCATCCAACTCTCTTTGC | 0 | 2948 | 2967 | 198 |
| 771354 | N/A | N/A | CGGCCTTCCATCCAACTCTC | 39 | 2953 | 2972 | 199 |
| 771707 | N/A | N/A | TTGTTCCTCTGCACCCTGGG | 42 | 3007 | 3026 | 24 |
| 771708 | N/A | N/A | GGATAAAAGGAAAGGAGTTT | 0 | 3167 | 3186 | 200 |
| 771710 | N/A | N/A | GGGCTGCCCATTCCTAGCGC | 40 | 3312 | 3331 | 201 |
| 771711 | N/A | N/A | CGCACTTCACAGTTCACAGG | 57 | 3476 | 3495 | 202 |
| 771452 | 911 | 930 | GGTATCTGGAGTAAGGAGGG | 55 | 3780 | 3799 | 25 |
| 771715 | N/A | N/A | AGTCTCCGAGTTATCCCCAT | 67 | 4142 | 4161 | 26 |
| 771716 | N/A | N/A | TCGAATCACCCTTTCCATTA | 24 | 4190 | 4209 | 203 |
| 771718 | N/A | N/A | AAAGTTCTAGTGTCTACTCC | 29 | 4255 | 4274 | 204 |
| 771719 | N/A | N/A | ACTGACTTGCAGGTGACTGG | 35 | 4330 | 4349 | 205 |
| 771723 | N/A | N/A | CCAAGGTTACATACAACCTG | 44 | 4657 | 4676 | 27 |
| 771724 | N/A | N/A | CCTTCTCCCAGAACCTTGGC | 27 | 4737 | 4756 | 206 |
| 771726 | N/A | N/A | AGCCAAAACCCAGTCAAGTT | 19 | 5137 | 5156 | 207 |
| 771727 | N/A | N/A | AACATGGCCTTTCTTTTCTA | 0 | 5337 | 5356 | 208 |
| 771731 | N/A | N/A | AAAACTTTGTGCCTGTTTCA | 54 | 5978 | 5997 | 28 |
| 771732 | N/A | N/A | GTCATGTGAACACTCTTTCA | 36 | 6244 | 6263 | 209 |
| 771734 | N/A | N/A | CTCAAACCTTTCAGACCATC | 64 | 6416 | 6435 | 210 |
| 771735 | N/A | N/A | TGGGTCCCTCAAGAGCTCAC | 38 | 6463 | 6482 | 211 |
| 771739 | N/A | N/A | TTTGAAAACCCAACCCTGGG | 33 | 7243 | 7262 | 29 |
| 771740 | N/A | N/A | GCCACTCCTGACTCACGCAA | 20 | 7350 | 7369 | 212 |
| 771742 | N/A | N/A | AGACAGATCTCTGAAGTCAG | 44 | 7437 | 7456 | 213 |
| 771743 | N/A | N/A | GCCATACCTCCATCTCTCAC | 0 | 7476 | 7495 | 214 |
| 771747 | N/A | N/A | GTGTGTTTCAAAGGAAAAGC | 10 | 7881 | 7900 | 30 |
| 771748 | N/A | N/A | ACCCCCACATTAAACATAAT | 0 | 7956 | 7975 | 215 |
| 771750 | N/A | N/A | GGACAACTTTTCAAGAACTC | 29 | 8281 | 8300 | 216 |
| 771751 | N/A | N/A | TGGCCATGCTGGCAAATAGG | 25 | 8465 | 8484 | 217 |
| 771755 | N/A | N/A | AAACATTTGGCACCCAACAC | 35 | 8898 | 8917 | 31 |
| 771756 | N/A | N/A | CCAGGCAACCCCAGACCTGC | 11 | 8945 | 8964 | 218 |
| 771758 | N/A | N/A | ATTACCAGTCCCCCATTACG | 0 | 9362 | 9381 | 219 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771759 | N/A | N/A | GCATTACCAGTCCCCCATTA | 26 | 9364 | 9383 | 220 |
| 771358 | N/A | N/A | AGTTAATCATTACTCGAGTC | 36 | 9415 | 9434 | 32 |
| 771359 | N/A | N/A | GTCACCCGTCTGGGCTCCGG | 15 | 9441 | 9460 | 221 |
| 771361 | N/A | N/A | ACAGCACCTTGTCACCCGTC | 27 | 9451 | 9470 | 222 |
| 771362 | N/A | N/A | GTAAGACAGACCACAGCACC | 15 | 9463 | 9482 | 223 |
| 771366 | N/A | N/A | TGCTGATTATTAATGGTCTG | 0 | 9503 | 9522 | 33 |
| 771367 | N/A | N/A | CTTGATGCTGATTATTAATG | 0 | 9508 | 9527 | 224 |
| 771369 | N/A | N/A | CAAAAGGCTGACTCGCGGCC | 22 | 9527 | 9546 | 225 |
| 771370 | N/A | N/A | CATTCCAAAAGGCTGACTCG | 18 | 9532 | 9551 | 226 |
| 771374 | N/A | N/A | AGCATGAAAGACAAACCACA | 51 | 9552 | 9571 | 34 |
| 771375 | N/A | N/A | CTAAACAGCATGAAAGACAA | 4 | 9558 | 9577 | 227 |
| 771377 | N/A | N/A | TAAGCACGCTCTAAACAGCA | 0 | 9568 | 9587 | 228 |
| 771378 | N/A | N/A | ATCTTTAAGCACGCTCTAAA | 22 | 9573 | 9592 | 229 |
| 771382 | N/A | N/A | AAATAAAAACACCAAGATCC | 0 | 9593 | 9612 | 35 |
| 771383 | N/A | N/A | TACACAAATAAAAACACCAA | 0 | 9598 | 9617 | 230 |
| 771385 | N/A | N/A | CAGTCTGCTGTGGATTTGAA | 25 | 9639 | 9658 | 231 |
| 771386 | N/A | N/A | CTGGACAGTCTGCTGTGGAT | 57 | 9644 | 9663 | 232 |
| 771763 | N/A | N/A | CCCCGTCCACGGAACGGATC | 45 | 9930 | 9949 | 36 |
| 771764 | N/A | N/A | ACACTTCACACACCAAAGCA | 20 | 9971 | 9990 | 233 |
| 771766 | N/A | N/A | CTGAAGCCCCCAAGCCAGG | 5 | 10014 | 10033 | 234 |
| 771767 | N/A | N/A | CCTAAAGGTGGGTCCATTCC | 16 | 10113 | 10132 | 235 |
| 771771 | N/A | N/A | CAGCTCCTACTGTTGGCAGT | 22 | 10275 | 10294 | 37 |
| 771772 | N/A | N/A | TCCTCAGGAACAACAATGCT | 27 | 10407 | 10426 | 236 |
| 771774 | N/A | N/A | GAAAAACAGGTAGAAATAGG | 14 | 10503 | 10522 | 237 |
| 771775 | N/A | N/A | AATGCCAAATGCCCAAAACT | 41 | 10607 | 10626 | 238 |
| 771779 | N/A | N/A | ACACACTGCTGCCTTTTCTC | 33 | 11011 | 11030 | 38 |
| 771780 | N/A | N/A | ACAAACCTTCCGAAAGGACC | 20 | 11230 | 11249 | 239 |
| 771782 | N/A | N/A | TAGGACTGGAAGAGCTTTGG | 50 | 11759 | 11778 | 240 |
| 771783 | N/A | N/A | CCCTTCAGAGAGTCACTGCT | 49 | 11873 | 11892 | 241 |
| 771787 | N/A | N/A | AAGAAGAAGGAGCTCAAACT | 27 | 11997 | 12016 | 39 |
| 771788 | N/A | N/A | CCAACTCTGAACGGAAAGAA | 30 | 12012 | 12031 | 242 |
| 771790 | N/A | N/A | CAAAACTCTCTGCCCTGGAC | 36 | 12196 | 12215 | 243 |
| 771791 | N/A | N/A | GAGGAGGGAGAAACTCCTCA | 22 | 12407 | 12426 | 244 |
| 771795 | N/A | N/A | CGTCTGCGGCAAAACCCACC | 59 | 13057 | 13076 | 40 |
| 771796 | N/A | N/A | GTTTGCGCACGGGATTGTCT | 16 | 13084 | 13103 | 245 |
| 771798 | N/A | N/A | GACACATCCATGTCCAAGCA | 17 | 13321 | 13340 | 246 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771799 | N/A | N/A | CTTCCAACACATGCTCTGCA | 57 | 13457 | 13476 | 247 |
| 771803 | N/A | N/A | ATGGATACTGACTCAAGGAC | 39 | 13937 | 13956 | 41 |
| 771804 | N/A | N/A | GACAGATGCCAGCAAGGATC | 17 | 13992 | 14011 | 248 |
| 771806 | N/A | N/A | ACAATGAATAATTGTTCACG | 0 | 14154 | 14173 | 249 |
| 771807 | N/A | N/A | GCCCTCACTCCACAATGGCA | 51 | 14298 | 14317 | 250 |
| 771811 | N/A | N/A | TGCCTCATTCTTTCCAGGAC | 50 | 14665 | 14684 | 42 |
| 771812 | N/A | N/A | TTAACCCCTGCCGGACTGCC | 26 | 14681 | 14700 | 251 |
| 771814 | N/A | N/A | TCCCTTTGCTGGCCCAGTTC | 39 | 14802 | 14821 | 252 |
| 771815 | N/A | N/A | CTCCCTTTTCACTGCTCCAC | 70 | 15021 | 15040 | 253 |
| 771819 | N/A | N/A | AATAGTTTTCTCTCAAATGT | 20 | 15647 | 15666 | 43 |
| 771820 | N/A | N/A | GGTCAAACTTGTGGTAAAAT | 29 | 15846 | 15865 | 254 |
| 771822 | N/A | N/A | CACCAAAACAAGTGTCTACC | 44 | 15984 | 16003 | 255 |
| 771823 | N/A | N/A | CTTCCCATGTGACCTCAGGG | 49 | 16008 | 16027 | 256 |
| 771827 | N/A | N/A | AAGGACATCACAGGGACTGG | 33 | 16679 | 16698 | 44 |
| 771828 | N/A | N/A | GCCCTAGAACTTGGGCAAGG | 8 | 16695 | 16714 | 257 |
| 771830 | N/A | N/A | TTTAGGTAGAGTGGCCGGGA | 40 | 16981 | 17000 | 258 |
| 771831 | N/A | N/A | CGATCATTTTCTACACCTTT | 66 | 17159 | 17178 | 259 |
| 771835 | N/A | N/A | AGTAAAATGGGAATAAGGC | 5 | 17567 | 17586 | 45 |
| 771836 | N/A | N/A | TGTTGAGGACTCCCCAGCCA | 28 | 17668 | 17687 | 260 |
| 771838 | N/A | N/A | GAACTCCTGCAGGATGAGGG | 53 | 17892 | 17911 | 261 |
| 771839 | N/A | N/A | CACAGCACCGTTACTGGACA | 21 | 17993 | 18012 | 262 |
| 771843 | N/A | N/A | CGCCGGCCCACCAACCTCTG | 17 | 18438 | 18457 | 46 |
| 771844 | N/A | N/A | GAAGGACCAAGTCCCTCTCC | 0 | 18557 | 18576 | 263 |
| 771846 | N/A | N/A | CATATTTGCTCCATAAACAA | 5 | 18699 | 18718 | 264 |
| 771847 | N/A | N/A | CATCACCTTCGGACAAGCCA | 53 | 18805 | 18824 | 265 |
| 771851 | N/A | N/A | GCTTTGAAAACATCCCACTT | 43 | 19314 | 19333 | 47 |
| 771852 | N/A | N/A | AGATTTAAAATTAAAAAGCA | 0 | 19411 | 19430 | 266 |
| 771854 | N/A | N/A | TCCCCGCCTTTTCTTCCTGG | 9 | 19647 | 19666 | 267 |
| 771855 | N/A | N/A | TCCCGACTTTGCAAGATGAA | 38 | 19729 | 19748 | 268 |
| 771859 | N/A | N/A | CCAGAAAATGCAGACAGCTA | 42 | 19898 | 19917 | 48 |
| 771860 | N/A | N/A | CTGGCTCAGAGGCTGCAGTG | 20 | 20058 | 20077 | 269 |
| 771862 | N/A | N/A | TCTTCCCCAGAAAACAGCCC | 10 | 20225 | 20244 | 270 |
| 771863 | N/A | N/A | CCAGCCCCTCCTGGGACTA | 9 | 20315 | 20334 | 271 |
| 771867 | N/A | N/A | ACTGGGCTTCAGCAAAGATA | 19 | 20754 | 20773 | 49 |
| 771868 | N/A | N/A | GGAGGCAAATTCATAGACAG | 16 | 21075 | 21094 | 272 |
| 771870 | N/A | N/A | AGGCACAAGTCAAGGAGGCC | 15 | 21460 | 21479 | 273 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771871 | N/A | N/A | CTCCCTCTGCCCCAGGATTC | 15 | 21546 | 21565 | 274 |
| 771875 | N/A | N/A | CCCCGTGCACTCCCAGCCCT | 51 | 22089 | 22108 | 50 |
| 771876 | N/A | N/A | CGAGCTCCCTCCCTGGCCCC | 0 | 22112 | 22131 | 275 |
| 771878 | N/A | N/A | CAGTTTCTAGAGGGTAGGAA | 22 | 22319 | 22338 | 276 |
| 771879 | N/A | N/A | AGGACCCAAAGGCAGACCCT | 23 | 22375 | 22394 | 277 |
| 771883 | N/A | N/A | AGCTGGCACTGAATGCTGAT | 26 | 22695 | 22714 | 51 |
| 771884 | N/A | N/A | CTGCCACCCTGAGAGTGTAG | 3 | 22754 | 22773 | 278 |
| 771886 | N/A | N/A | AACCAGGTTCCCACTGTTAC | 0 | 22999 | 23018 | 279 |
| 771887 | N/A | N/A | CAGCCACTGCTGTCTGAGGA | 14 | 23199 | 23218 | 280 |
| 771891 | N/A | N/A | CTCCCAAGCCTACATATTTC | 56 | 23560 | 23579 | 52 |
| 771892 | N/A | N/A | CTGAAGTTTCTCCTCCCATC | 2 | 23599 | 23618 | 281 |
| 771894 | N/A | N/A | CAAAAGGGAAAGGAGGTTTG | 17 | 23794 | 23813 | 282 |
| 771895 | N/A | N/A | ATTTGCAACAATAAAACAAA | 0 | 23821 | 23840 | 283 |
| 771899 | N/A | N/A | CCTGATTGTCTCCACATCCC | 47 | 24447 | 24466 | 53 |
| 771900 | N/A | N/A | ATGCCCACCAGTCTTCCTGA | 32 | 24462 | 24481 | 284 |
| 771902 | N/A | N/A | GGGTTCTCCAGCCGCTCAGA | 77 | 24484 | 24503 | 285 |
| 771903 | N/A | N/A | TGCCAACCCCAGAGGTGAGC | 20 | 24698 | 24717 | 286 |
| 771907 | N/A | N/A | TCTATTCTCACGCCAAACCA | 28 | 25268 | 25287 | 85 |
| 771908 | N/A | N/A | CAAACATCACCACGCCTCGC | 26 | 25500 | 25519 | 287 |
| 771910 | N/A | N/A | AGGCACGGCCGCCTCCTGCA | 4 | 25598 | 25617 | 288 |
| 771911 | N/A | N/A | ATGGTCCAGCAGAGCAGAAG | 20 | 25657 | 25676 | 289 |
| 771915 | N/A | N/A | CTGGGCCCAGACACACAAAG | 27 | 25941 | 25960 | 74 |
| 771916 | N/A | N/A | CCTTCTTAAATTTTTAATTT | 0 | 26141 | 26160 | 290 |
| 771918 | N/A | N/A | AAGGCCACATTTTAGGTTAA | 12 | 26487 | 26506 | 291 |
| 771919 | N/A | N/A | CAATGGCACAGGGTGACCAG | 29 | 26512 | 26531 | 292 |
| 771923 | N/A | N/A | CCCCAGAAAACTGTACAGGG | 46 | 26950 | 26969 | 68 |
| 771924 | N/A | N/A | TCGCTGATAGTTAACCTCTG | 9 | 27049 | 27068 | 293 |
| 771926 | N/A | N/A | ACAAAGGTCTGTGTGGACGC | 13 | 27153 | 27172 | 294 |
| 771927 | N/A | N/A | GCCCACAGCCCACACGAGTC | 0 | 27178 | 27197 | 295 |
| 771931 | N/A | N/A | CCCAGCCCAGAAAACTGCA | 36 | 27602 | 27621 | 67 |
| 771932 | N/A | N/A | CGAGGTGCCCCCATGCCAGG | 13 | 27830 | 27849 | 296 |
| 771934 | N/A | N/A | CTGGAAAGGAAGACTCGAGG | 15 | 28010 | 28029 | 297 |
| 771935 | N/A | N/A | GGAAGGACACATTGGCATCA | 23 | 28158 | 28177 | 298 |
| 771939 | N/A | N/A | TTCCCTACAGACACCCCAAG | 33 | 28589 | 28608 | 89 |
| 771940 | N/A | N/A | TCCTGCTGCCCCAGCAGGCT | 0 | 28823 | 28842 | 299 |
| 771942 | N/A | N/A | GTCGGTCAGGGCCTTGCCCT | 11 | 29013 | 29032 | 300 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771943 | N/A | N/A | GTATTTGTTAACAAAAATGG | 0 | 29072 | 29091 | 301 |
| 771947 | N/A | N/A | TTAACCCGGGCTACCTTAAC | 26 | 29533 | 29552 | 88 |
| 771948 | N/A | N/A | CACCCAGCTCTCAAATCAGT | 0 | 29718 | 29737 | 302 |
| 771950 | N/A | N/A | ATGCAAAGGGACCCTTAATA | 0 | 29971 | 29990 | 303 |
| 771951 | N/A | N/A | CTGCAGAGCACAGATGCAAA | 9 | 29984 | 30003 | 304 |
| 771460 | 1081 | 1100 | CGTCTTCTCCTCCCAGTATG | 36 | 30348 | 30367 | 70 |
| 771461 | 1099 | 1118 | GTAGAGCCTCCCCACTCTCG | 37 | 30366 | 30385 | 305 |
| 771463 | 1113 | 1132 | GGCTCCTGGACACAGTAGAG | 10 | 30380 | 30399 | 306 |
| 771464 | 1118 | 1137 | GAGAGGGCTCCTGGACACAG | 55 | 30385 | 30404 | 307 |
| 771468 | 1198 | 1217 | CACCAGCTGACTCTTGTTGT | 12 | 30465 | 30484 | 65 |
| 771469 | 1203 | 1222 | TTCTGCACCAGCTGACTCTT | 13 | 30470 | 30489 | 308 |
| 771471 | 1213 | 1232 | GCTCCGCACCTTCTGCACCA | 43 | 30480 | 30499 | 309 |
| 771472 | 1218 | 1237 | ATTTTGCTCCGCACCTTCTG | 0 | 30485 | 30504 | 310 |
| 771476 | 1258 | 1277 | CACACCATCCACCTCCCGCG | 39 | 30525 | 30544 | 63 |
| 771477 | 1274 | 1293 | TGCGGTTGTACACCCACACA | 20 | 30541 | 30560 | 311 |
| 771479 | 1353 | 1372 | GGGAACACCTTGTGTACCAA | 58 | 30620 | 30639 | 312 |
| 771480 | 1372 | 1391 | AGCCTTGATGGAGAAACCGG | 46 | 30639 | 30658 | 313 |
| 771484 | 1441 | 1460 | CGTCCACGGCTGCTGCATAA | 30 | 30708 | 30727 | 69 |
| 771485 | 1446 | 1465 | AAGCCCGTCCACGGCTGCTG | 15 | 30713 | 30732 | 314 |
| 771487 | 1456 | 1475 | CTGCACGGTAAAGCCCGTCC | 45 | 30723 | 30742 | 315 |
| 771488 | 1461 | 1480 | CTGATCTGCACGGTAAAGCC | 53 | 30728 | 30747 | 316 |
| 771492 | 1510 | 1529 | GCTGCTGATGAACTGGCGGG | 56 | 30777 | 30796 | 80 |
| 771493 | 1516 | 1535 | CGGGCAGCTGCTGATGAACT | 17 | 30783 | 30802 | 317 |
| 771495 | 1526 | 1545 | CTAGCCAGCACGGGCAGCTG | 18 | 30793 | 30812 | 318 |
| 771496 | 1532 | 1551 | TGACCTCTAGCCAGCACGGG | 20 | 30799 | 30818 | 319 |
| 771500 | 1555 | 1574 | ACGCGGCTACCGGCTGTTGA | 32 | 30822 | 30841 | 58 |
| 771501 | 1557 | 1576 | GCACGCGGCTACCGGCTGTT | 16 | 30824 | 30843 | 320 |
| 771503 | 1577 | 1596 | GCTCACGCTCTGTCCCCTCC | 27 | 30844 | 30863 | 321 |
| 771504 | 1579 | 1598 | CAGCTCACGCTCTGTCCCCT | 48 | 30846 | 30865 | 322 |
| 771507 | 1584 | 1603 | CTGCTCAGCTCACGCTCTGT | 47 | 30851 | 30870 | 73 |
| 771508 | 1585 | 1604 | CCTGCTCAGCTCACGCTCTG | 8 | 30852 | 30871 | 323 |
| 771510 | 1592 | 1611 | AGTGTGGCCTGCTCAGCTCA | 35 | 30859 | 30878 | 324 |
| 771511 | 1597 | 1616 | TTTGAAGTGTGGCCTGCTCA | 31 | 30864 | 30883 | 325 |
| 771515 | 1617 | 1636 | AAATATTAGCAGCAAAGTAG | 28 | 30884 | 30903 | 56 |
| 771516 | 1622 | 1641 | GAGGAAAATATTAGCAGCAA | 8 | 30889 | 30908 | 326 |
| 771518 | 1632 | 1651 | AAGCACTCAGGAGGAAAATA | 4 | 30899 | 30918 | 327 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 771519 | 1637 | 1656 | AAAGCAAGCACTCAGGAGGA | 25 | 30904 | 30923 | 328 |
| 771523 | 1644 | 1663 | TGCATGAAAAGCAAGCACTC | 43 | 30911 | 30930 | 87 |
| 771524 | 1645 | 1664 | TTGCATGAAAAGCAAGCACT | 19 | 30912 | 30931 | 329 |
| 771526 | 1647 | 1666 | GTTTGCATGAAAAGCAAGCA | 26 | 30914 | 30933 | 330 |
| 771527 | 1649 | 1668 | GAGTTTGCATGAAAAGCAAG | 0 | 30916 | 30935 | 331 |
| 771531 | 1665 | 1684 | AAAAAAAACGACCAAAGAGT | 32 | 30932 | 30951 | 54 |
| 771532 | 1689 | 1708 | AGAAGAAAACCAACCAACAA | 0 | 30956 | 30975 | 332 |
| 771534 | 1713 | 1732 | AACAGAACACAAACGAGGAC | 0 | 30980 | 30999 | 333 |
| 771535 | 1718 | 1737 | AACAAAACAGAACACAAACG | 17 | 30985 | 31004 | 334 |
| 771539 | 1738 | 1757 | AGCTATTTCTCAAAGAGCGA | 56 | 31005 | 31024 | 60 |
| 771540 | 1743 | 1762 | TCATAAGCTATTTCTCAAAG | 0 | 31010 | 31029 | 335 |
| 771542 | 1753 | 1772 | ACAATTCTTTTCATAAGCTA | 0 | 31020 | 31039 | 336 |
| 771543 | 1758 | 1777 | CCCCAACAATTCTTTTCATA | 36 | 31025 | 31044 | 337 |
| 771547 | 1798 | 1817 | GTGTCCTGCCGATCATACCT | 35 | 31065 | 31084 | 82 |
| 771548 | 1799 | 1818 | GGTGTCCTGCCGATCATACC | 19 | 31066 | 31085 | 338 |
| 771550 | 1820 | 1839 | TGCTTCCCCTCTTCCTATCA | 4 | 31087 | 31106 | 339 |
| 771551 | 1825 | 1844 | ATTTCTGCTTCCCTCTTCC | 18 | 31092 | 31111 | 340 |
| 771555 | 1841 | 1860 | GTTTGGTGGTGCTTGGATTT | 56 | 31108 | 31127 | 83 |
| 771556 | 1856 | 1875 | CCCTTCATACACTGTGTTTG | 30 | 31123 | 31142 | 341 |
| 771558 | 1871 | 1890 | AAATGATGACCGCCCCCCTT | 7 | 31138 | 31157 | 342 |
| 771559 | 1876 | 1895 | AAGTGAAATGATGACCGCCC | 49 | 31143 | 31162 | 343 |
| 771563 | 1893 | 1912 | TCACACACACTCCTGACAAG | 23 | 31160 | 31179 | 84 |
| 771564 | 1908 | 1927 | GCCGCACACTCACACTCACA | 28 | 31175 | 31194 | 344 |
| 771566 | 1970 | 1989 | GACACAAAACAAAGAGCACG | 28 | 31237 | 31256 | 345 |
| 771567 | 1985 | 2004 | GGGACATCCATAAGAGACAC | 39 | 31252 | 31271 | 346 |
| 771571 | 2009 | 2028 | TTGGGACTGCAAACCTCTCT | 42 | 31276 | 31295 | 90 |
| 771572 | 2010 | 2029 | CTTGGGACTGCAAACCTCTC | 37 | 31277 | 31296 | 347 |
| 771574 | 2012 | 2031 | CGCTTGGGACTGCAAACCTC | 66 | 31279 | 31298 | 348 |
| 771575 | 2014 | 2033 | ACCGCTTGGGACTGCAAACC | 47 | 31281 | 31300 | 349 |
| 771579 | 2061 | 2080 | AGGTACTGCCTCTGCCCCAC | 62 | 31328 | 31347 | 61 |
| 771580 | 2070 | 2089 | AGCTTGCCCAGGTACTGCCT | 25 | 31337 | 31356 | 350 |
| 771582 | 2097 | 2116 | CTGGCAGCTGCTGGGACCCC | 37 | 31364 | 31383 | 351 |
| 771583 | 2102 | 2121 | TGCTCCTGGCAGCTGCTGGG | 57 | 31369 | 31388 | 352 |
| 771587 | 2160 | 2179 | CGTGTCCTTGATGAGGGAGA | 42 | 31427 | 31446 | 71 |
| 771588 | 2165 | 2184 | AGGCCCGTGTCCTTGATGAG | 13 | 31432 | 31451 | 353 |
| 771590 | 2175 | 2194 | GCCTGTGGACAGGCCCGTGT | 14 | 31442 | 31461 | 354 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771591 | 2180 | 2199 | CAGAAGCCTGTGGACAGGCC | 50 | 31447 | 31466 | 355 |
| 771595 | 2217 | 2236 | AATTGGTTCTGGTTCGGCCA | 36 | 31484 | 31503 | 57 |
| 771596 | 2232 | 2251 | GACAAGGATGAAAATAATTG | 0 | 31499 | 31518 | 356 |
| 771598 | 2243 | 2262 | GAAGGGAATAAGACAAGGAT | 34 | 31510 | 31529 | 357 |
| 771599 | 2247 | 2266 | GCAGGAAGGGAATAAGACAA | 39 | 31514 | 31533 | 358 |
| 771603 | 2306 | 2325 | CTCAGGGAGATCCAGGAGCA | 26 | 31573 | 31592 | 72 |
| 771604 | 2321 | 2340 | CCTTGGGAAGCCCATCTCAG | 12 | 31588 | 31607 | 359 |
| 771606 | 2337 | 2356 | GGGCTGCCCCGGCAGCCCTT | 0 | 31604 | 31623 | 360 |
| 771607 | 2356 | 2375 | GGTGAGCAATACTGTGAGGG | 34 | 31623 | 31642 | 361 |
| 771611 | 2412 | 2431 | GAAAAACCTGATGTCACCAG | 69 | 31679 | 31698 | 77 |
| 771612 | 2417 | 2436 | TCCGGGAAAACCTGATGTC | 3 | 31684 | 31703 | 362 |
| 771614 | 2427 | 2446 | GTTTTCTAAGTCCGGGAAAA | 25 | 31694 | 31713 | 363 |
| 771615 | 2432 | 2451 | AGCTGGTTTTCTAAGTCCGG | 45 | 31699 | 31718 | 364 |
| 771619 | 2457 | 2476 | CACAGGATGGGAGCAGGCAG | 48 | 31724 | 31743 | 64 |
| 771620 | 2459 | 2478 | CACACAGGATGGGAGCAGGC | 12 | 31726 | 31745 | 365 |
| 771622 | 2461 | 2480 | AACACACAGGATGGGAGCAG | 34 | 31728 | 31747 | 366 |
| 771623 | 2462 | 2481 | TAACACACAGGATGGGAGCA | 51 | 31729 | 31748 | 367 |
| 771627 | 2485 | 2504 | CTTGCTGGCCTAATAGCAGA | 27 | 31752 | 31771 | 75 |
| 771628 | 2500 | 2519 | CCAGGGACATCCCCGCTTGC | 12 | 31767 | 31786 | 368 |
| 771630 | 2517 | 2536 | TGCTAAGCATGTCCCTCCCA | 37 | 31784 | 31803 | 369 |
| 771631 | 2522 | 2541 | GGGACTGCTAAGCATGTCCC | 0 | 31789 | 31808 | 370 |
| 771635 | 2556 | 2575 | GGTTATGACGGACCAAATCC | 55 | 31823 | 31842 | 81 |
| 771636 | 2561 | 2580 | CCTTGGGTTATGACGGACCA | 0 | 31828 | 31847 | 371 |
| 771638 | 2571 | 2590 | TAGGATGGTACCTTGGGTTA | 41 | 31838 | 31857 | 372 |
| 771639 | 2576 | 2595 | CAGCCTAGGATGGTACCTTG | 51 | 31843 | 31862 | 373 |
| 771643 | 2596 | 2615 | ATGAAAGAAGAGTTAGGTGT | 22 | 31863 | 31882 | 62 |
| 771644 | 2602 | 2621 | GAAGAAATGAAAGAAGAGTT | 0 | 31869 | 31888 | 374 |
| 771646 | 2613 | 2632 | TATGAGTTGTAGAAGAAATG | 0 | 31880 | 31899 | 375 |
| 771647 | 2618 | 2637 | GAGTGTATGAGTTGTAGAAG | 6 | 31885 | 31904 | 376 |
| 771651 | 2645 | 2664 | GCTAAGAACAGTGTCGAAGT | 33 | 31912 | 31931 | 79 |
| 771652 | 2650 | 2669 | ATTGAGCTAAGAACAGTGTC | 0 | 31917 | 31936 | 377 |
| 771654 | 2660 | 2679 | AAACATGCTCATTGAGCTAA | 32 | 31927 | 31946 | 378 |
| 771655 | 2665 | 2684 | AGTCTAAACATGCTCATTGA | 14 | 31932 | 31951 | 379 |
| 771659 | 2685 | 2704 | AGAAAAATAGCTTATGTTAA | 0 | 31952 | 31971 | 59 |
| 771660 | 2714 | 2733 | TTCTCTTGTTCATTTAAACC | 0 | 31981 | 32000 | 380 |
| 771662 | 2724 | 2743 | ATGAGAATGCTTCTCTTGTT | 29 | 31991 | 32010 | 381 |

TABLE 3-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771663 | 2729 | 2748 | TTCCAATGAGAATGCTTCTC | 56 | 31996 | 32015 | 382 |
| 771667 | 2749 | 2768 | AAAGCACTACAATGCTAAAT | 29 | 32016 | 32035 | 55 |
| 771668 | 2754 | 2773 | CTCTCAAAGCACTACAATGC | 9 | 32021 | 32040 | 383 |
| 771670 | 2764 | 2783 | AGTCCTTTCTCTCTCAAAGC | 46 | 32031 | 32050 | 384 |
| 771671 | 2769 | 2788 | TCAGGAGTCCTTTCTCTCTC | 69 | 32036 | 32055 | 385 |
| 771675 | 2793 | 2812 | CTTTAATAAATCTCAGGTTT | 24 | 32060 | 32079 | 89 |
| 771676 | 2895 | 2914 | TGTTTATACACATTGCACAA | 2 | 32162 | 32181 | 386 |
| 771678 | 2905 | 2924 | TTATTTTCTTGTTTATACA | 0 | 32172 | 32191 | 387 |
| 771679 | 2916 | 2935 | GCATCTTTTCTTTATTTTC | 0 | 32183 | 32202 | 388 |
| 771683 | 2950 | 2969 | GCATTTGTTATTTGCATTTA | 0 | 32217 | 32236 | 78 |
| 771684 | 2955 | 2974 | ATTTGGCATTTGTTATTTGC | 0 | 32222 | 32241 | 389 |
| 771686 | 2969 | 2988 | GTTTATCTTTTTAATTTGG | 0 | 32236 | 32255 | 390 |
| 771687 | 2974 | 2993 | CTTGTGTTTATCTTTTTAA | 13 | 32241 | 32260 | 391 |
| 582468 | N/A | N/A | GCCAATATCATAACCCAAGC | 4 | N/A | N/A | 392 |
| 771453 | 949 | 968 | ATCTGGACAGTCTGCAGTTG | 38 | N/A | N/A | 393 |

TABLE 4

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771388 | 1 | 20 | GCGCCCTGCGCGGCTCTCCG | 31 | 1496 | 1515 | 394 |
| 771389 | 16 | 35 | CACCCCGCGCGGCCCGCGCC | 18 | 1511 | 1530 | 395 |
| 771395 | 31 | 50 | GCGCTCCGGCTGCCCCACCC | 0 | 1526 | 1545 | 396 |
| 771396 | 33 | 52 | CTGCGCTCCGGCTGCCCCAC | 48 | 1528 | 1547 | 397 |
| 771397 | 132 | 151 | GAGCGGCGGCGGCCCGAGGG | 55 | 1627 | 1646 | 398 |
| 278478 | 220 | 239 | ACATGACCTCCGCACACCAT | 18 | 1715 | 1734 | 399 |
| 771403 | 222 | 241 | GAACATGACCTCCGCACACC | 62 | 1717 | 1736 | 400 |
| 771404 | 223 | 242 | CGAACATGACCTCCGCACAC | 51 | 1718 | 1737 | 401 |
| 771409 | 356 | 375 | CCCCTGCGCCCTCCTCCTCG | 19 | 1851 | 1870 | 402 |
| 771410 | 377 | 396 | GCTCGCCTCCTCCTCCACCT | 37 | 1872 | 1891 | 403 |
| 771411 | 390 | 409 | CCTTCTCCCCGCAGCTCGCC | 33 | 1885 | 1904 | 404 |
| 771417 | 421 | 440 | ACCGGCCCCATGCGCTCGGC | 16 | 1916 | 1935 | 405 |
| 771418 | 426 | 445 | CCGCCACCGGCCCCATGCGC | 60 | 1921 | 1940 | 406 |
| 771419 | 431 | 450 | GGCCGCCGCCACCGGCCCCA | 37 | 1926 | 1945 | 407 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771425 | 461 | 480 | CCTTGCCCAGGCAGCATCCA | 1 | 1956 | 1975 | 408 |
| 771426 | 466 | 485 | CACCGCCTTGCCCAGGCAGC | 28 | 1961 | 1980 | 409 |
| 771427 | 471 | 490 | CCTCGCACCGCCTTGCCCAG | 36 | 1966 | 1985 | 410 |
| 771433 | 582 | 601 | TCCTTCAGTTTCTTGAGCAC | 0 | 2077 | 2096 | 411 |
| 771434 | 587 | 606 | GCCGCTCCTTCAGTTTCTTG | 27 | 2082 | 2101 | 412 |
| 771435 | 592 | 611 | CAGCTGCCGCTCCTTCAGTT | 29 | 2087 | 2106 | 413 |
| 771441 | 721 | 740 | CGAGGGCGGCTGCGCAGGCT | 10 | 2216 | 2235 | 414 |
| 771442 | 795 | 814 | CTCTTGACTTCCGAGGAATG | 22 | 2290 | 2309 | 415 |
| 771443 | 797 | 816 | GCCTCTTGACTTCCGAGGAA | 30 | 2292 | 2311 | 416 |
| 483663 | 799 | 818 | CAGCCTCTTGACTTCCGAGG | 41 | 2294 | 2313 | 22 |
| 771449 | 876 | 895 | TCGCAGAGTCGGCTAAGGTG | 0 | 2371 | 2390 | 417 |
| 771450 | 881 | 900 | CTAGTTCGCAGAGTCGGCTA | 45 | 2376 | 2395 | 418 |
| 771690 | N/A | N/A | CCTAGTTCGCAGAGTCGGCT | 43 | 2377 | 2396 | 419 |
| 771696 | N/A | N/A | CTCTCCCAGGAGGGTATGCA | 0 | 2499 2521 | 2518 2540 | 420 |
| 771697 | N/A | N/A | CACTCTCCCAGGAGGGTATG | 5 | 2501 2523 | 2520 2542 | 421 |
| 771698 | N/A | N/A | CACACTCTCCCAGGAGGGTA | 43 | 2503 2525 | 2522 2544 | 422 |
| 771704 | N/A | N/A | CAGGAGGGTATGCACACTCT | 32 | 2515 2537 | 2534 2556 | 423 |
| 771705 | N/A | N/A | AATGCCCTTTGAGTTTCCCC | 52 | 2593 | 2612 | 424 |
| 771706 | N/A | N/A | GGGCCTGGACCAAATCCAAC | 22 | 2793 | 2812 | 425 |
| 771347 | N/A | N/A | TGGGCCACTGGTGTTCGACG | 0 | 2892 | 2911 | 426 |
| 771348 | N/A | N/A | GGCCACGACAGTATCTGGGC | 42 | 2907 | 2926 | 427 |
| 771349 | N/A | N/A | ACTCCAAAGGTGCGCGGCCA | 26 | 2922 | 2941 | 428 |
| 771355 | N/A | N/A | CAGTTCGGCCTTCCATCCAA | 0 | 2958 | 2977 | 429 |
| 771712 | N/A | N/A | ATTCTTTTAGCCCAACTGTT | 3 | 3676 | 3695 | 430 |
| 771713 | N/A | N/A | TGCCTACACACAAAAAGCCA | 15 | 3886 | 3905 | 431 |
| 771714 | N/A | N/A | TCTGGACTAAAGCTTCCACG | 44 | 4088 | 4107 | 432 |
| 771720 | N/A | N/A | CAGGCAGAGCTATGCTTCAA | 20 | 4396 | 4415 | 433 |
| 771721 | N/A | N/A | CCCAGCACTGTGATGTCCAG | 43 | 4537 | 4556 | 434 |
| 771722 | N/A | N/A | AGAGGGAGCTCCAGGAATTT | 10 | 4604 | 4623 | 435 |
| 771728 | N/A | N/A | AACTTTTCTCCCCCTTGGAA | 1 | 5537 | 5556 | 436 |
| 771729 | N/A | N/A | TGCTCCAGCTCCAGACCTGG | 35 | 5747 | 5766 | 437 |
| 771730 | N/A | N/A | AATGCCCCCGGCCACAGCAG | 27 | 5811 | 5830 | 438 |
| 771736 | N/A | N/A | TGCCAGATCTCAGGTCAAGA | 0 | 6539 | 6558 | 439 |
| 771737 | N/A | N/A | TCAAATGAACCCTGGTTATA | 57 | 7043 | 7062 | 440 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771738 | N/A | N/A | GAGCTTCCTAAGTACTGTTA | 14 | 7140 | 7159 | 441 |
| 771744 | N/A | N/A | GGCTATTCCCAAGAGTCCAG | 23 | 7595 | 7614 | 442 |
| 771745 | N/A | N/A | GTGAAGAAGCAAAGTATACC | 24 | 7681 | 7700 | 443 |
| 771746 | N/A | N/A | AAGCCGGGCATCTCAGAGCA | 22 | 7865 | 7884 | 444 |
| 771752 | N/A | N/A | AATGTCCCTGTGGGTTTCCA | 0 | 8497 | 8516 | 445 |
| 771753 | N/A | N/A | GTCCATGAACCACAACTCAT | 50 | 8697 | 8716 | 446 |
| 771754 | N/A | N/A | CCCTCAGGTACTCTGCACAG | 45 | 8805 | 8824 | 447 |
| 771357 | N/A | N/A | GAGTCAGGCTCAATGAGACT | 16 | 9400 | 9419 | 448 |
| 771363 | N/A | N/A | TCAGGCTTCACTGCCCATCG | 12 | 9482 | 9501 | 449 |
| 771364 | N/A | N/A | TAATGGTCTGCTCAGGCTTC | 23 | 9493 | 9512 | 450 |
| 771365 | N/A | N/A | ATTATTAATGGTCTGCTCAG | 5 | 9498 | 9517 | 451 |
| 771371 | N/A | N/A | CCACACATTCCAAAAGGCTG | 0 | 9537 | 9556 | 452 |
| 771372 | N/A | N/A | ACAAACCACACATTCCAAAA | 37 | 9542 | 9561 | 453 |
| 771373 | N/A | N/A | GAAAGACAAACCACACATTC | 32 | 9547 | 9566 | 454 |
| 771379 | N/A | N/A | GATCCATCTTTAAGCACGCT | 0 | 9578 | 9597 | 455 |
| 771380 | N/A | N/A | ACCAAGATCCATCTTTAAGC | 0 | 9583 | 9602 | 456 |
| 771381 | N/A | N/A | AAAACACCAAGATCCATCTT | 0 | 9588 | 9607 | 457 |
| 771387 | N/A | N/A | AGCATCTGGACAGTCTGCTG | 6 | 9649 | 9668 | 458 |
| 771760 | N/A | N/A | ATCTTACCTGAAAGCCCCCC | 3 | 9714 | 9733 | 459 |
| 771761 | N/A | N/A | CCCCATTCCTCCAGTCTTTA | 33 | 9779 | 9798 | 460 |
| 771762 | N/A | N/A | GTCACCACCGATGCATCCAA | 72 | 9857 | 9876 | 461 |
| 771768 | N/A | N/A | GTATGCTTGGGATCTGTCTT | 11 | 10143 | 10162 | 462 |
| 771769 | N/A | N/A | GGCTGGGAATCAGAACTTGG | 71 | 10197 | 10216 | 463 |
| 771770 | N/A | N/A | CTGTTGGCAGTGCTCCCACC | 61 | 10266 | 10285 | 464 |
| 771776 | N/A | N/A | CTCAGCAAGCTCAGTTCCTG | 38 | 10811 | 10830 | 465 |
| 771777 | N/A | N/A | CCCTCAGTCTCAGATAACAG | 50 | 10882 | 10901 | 466 |
| 771778 | N/A | N/A | TGAGTAAACAATACCCTCAG | 66 | 10895 | 10914 | 467 |
| 771784 | N/A | N/A | TAAATCAAGAGCTGAAATTC | 0 | 11958 | 11977 | 468 |
| 771785 | N/A | N/A | ACTTTGAAGCCTTTGGAATT | 12 | 11980 | 11999 | 469 |
| 771786 | N/A | N/A | AGCTCAAACTTTGAAGCCTT | 56 | 11987 | 12006 | 470 |
| 771792 | N/A | N/A | AGCACACCCCACCCCCACCT | 2 | 12632 | 12651 | 471 |
| 771793 | N/A | N/A | AAGTCCCTAACGACCAGGCC | 58 | 12845 | 12864 | 472 |
| 771794 | N/A | N/A | GAAGCAAGTCACTGCCTTCT | 68 | 12924 | 12943 | 473 |
| 771800 | N/A | N/A | GACAGCAGACAGGCAAAATG | 12 | 13523 | 13542 | 474 |
| 771801 | N/A | N/A | ACCTACAACTCACAAGGGAG | 31 | 13572 | 13591 | 475 |
| 771802 | N/A | N/A | CCTTGAGATCCATGGGAGCA | 40 | 13737 | 13756 | 476 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771808 | N/A | N/A | CCCCAAAGTCCACGCTCATG | 32 | 14368 | 14387 | 477 |
| 771809 | N/A | N/A | ACCTGAGTCCCCCAAAGTCC | 7 | 14377 | 14396 | 478 |
| 771810 | N/A | N/A | GGCACTGCAGAAGAGGCGGG | 46 | 14594 | 14613 | 479 |
| 771816 | N/A | N/A | ATCCAACTACTCAGAGGCTG | 27 | 15227 | 15246 | 480 |
| 771817 | N/A | N/A | GGAATTATGACACAGTAACA | 19 | 15431 | 15450 | 481 |
| 771818 | N/A | N/A | TGAAGACAACTGCTTTGAGA | 38 | 15519 | 15538 | 482 |
| 771824 | N/A | N/A | TTCTACTAGAAAAAAATTAG | 0 | 16278 | 16297 | 483 |
| 771825 | N/A | N/A | CTCTCATTTCTGGAACCCAC | 76 | 16478 | 16497 | 484 |
| 771826 | N/A | N/A | CACCATCCTGGTTCGCAGTC | 31 | 16604 | 16623 | 485 |
| 771832 | N/A | N/A | ACCTTTCACGAACCACTTTT | 11 | 17364 | 17383 | 486 |
| 771833 | N/A | N/A | TTAAAGAAAATGGCCTACAT | 21 | 17456 | 17475 | 487 |
| 771834 | N/A | N/A | AACATAAAGTTCTCAAACAG | 25 | 17484 | 17503 | 488 |
| 771840 | N/A | N/A | AGATGCTTCTAGGTGAACCA | 16 | 18033 | 18052 | 489 |
| 771841 | N/A | N/A | TTTAGAAACCCAGAGACAAA | 36 | 18111 | 18130 | 490 |
| 771842 | N/A | N/A | TTGTGTTATGAAAACAAAAC | 6 | 18311 | 18330 | 491 |
| 771848 | N/A | N/A | CCACACAACCAAAGCAGAAG | 36 | 19011 | 19030 | 492 |
| 771849 | N/A | N/A | CTAGGCTGGTCACTTCCACT | 66 | 19211 | 19230 | 493 |
| 771850 | N/A | N/A | TCCCACTTCTCCTCTGGCTG | 58 | 19302 | 19321 | 494 |
| 771856 | N/A | N/A | CTGAAAGAAAGTCCCGACTT | 34 | 19740 | 19759 | 495 |
| 771857 | N/A | N/A | CGTCTTATTGTTTTGTTCC | 29 | 19850 | 19869 | 496 |
| 771858 | N/A | N/A | CTGCCAACGGCACAGTCATA | 31 | 19876 | 19895 | 497 |
| 771864 | N/A | N/A | AGACAAAGATCACAGATCAC | 0 | 20528 | 20547 | 498 |
| 771865 | N/A | N/A | ATAGGGATATCTCATCAATA | 38 | 20580 | 20599 | 499 |
| 771866 | N/A | N/A | GCATTTTCTGAACAGAGTC | 34 | 20695 | 20714 | 500 |
| 771872 | N/A | N/A | TCCCCACCGCGCAGGGACA | 0 | 21590 | 21609 | 501 |
| 771873 | N/A | N/A | AGCTGCTGTCACAAGGCCCT | 31 | 21746 | 21765 | 502 |
| 771874 | N/A | N/A | ATTACTTCTGTCTGCCTCCG | 34 | 21946 | 21965 | 503 |
| 771880 | N/A | N/A | TCCCTGGTTTTGCAGGTGGT | 29 | 22497 | 22516 | 504 |
| 771881 | N/A | N/A | ATTTTCCAAAAGGACAAAAC | 0 | 22540 | 22559 | 505 |
| 771882 | N/A | N/A | GCATCATGAAAATCTTAATA | 35 | 22583 | 22602 | 506 |
| 771888 | N/A | N/A | TCGCCATGGAGAATGTAATT | 0 | 23351 | 23370 | 507 |
| 771889 | N/A | N/A | TAAGAGCATTTATCTCGCCA | 29 | 23365 | 23384 | 508 |
| 771890 | N/A | N/A | AGTCTGAAGCCCCCAACCTG | 14 | 23399 | 23418 | 509 |
| 771896 | N/A | N/A | GGGCCCCCTTCTGCCTTCAT | 0 | 23956 | 23975 | 510 |
| 771897 | N/A | N/A | CTCTCAGGGTCTCAGTTTGA | 44 | 24021 | 24040 | 511 |
| 771898 | N/A | N/A | GGTGTGAGCTGTGGACACAG | 27 | 24221 | 24240 | 512 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771904 | N/A | N/A | CCCAACCCATCTCCACCACC | 0 | 24966 | 24985 | 513 |
| 771905 | N/A | N/A | TAGGCGAATCCCTCCCCCAA | 0 | 25208 | 25227 | 514 |
| 771906 | N/A | N/A | ACCCTTGCTGGTCTCTTGTT | 0 | 25233 | 25252 | 515 |
| 771912 | N/A | N/A | ATATTCCTCTGCCAAAGTCC | 19 | 25710 | 25729 | 516 |
| 771913 | N/A | N/A | AAAAAAGCCAGTAAAGACAT | 11 | 25860 | 25879 | 517 |
| 771914 | N/A | N/A | ATTTAGGAACAAGGGCAAGC | 34 | 25886 | 25905 | 518 |
| 771920 | N/A | N/A | TTATTTAATTACCCTGCTCA | 13 | 26598 | 26617 | 519 |
| 771921 | N/A | N/A | TCCTCCCTTTAAAGGGAAGG | 14 | 26716 | 26735 | 520 |
| 771922 | N/A | N/A | AAATTCCTTTAAGGTGTTGC | 29 | 26774 | 26793 | 521 |
| 771928 | N/A | N/A | CCCCATTGCCACTACAGAGA | 0 | 27288 | 27307 | 522 |
| 771929 | N/A | N/A | CTTTCCAGCAAAACCATTCG | 0 | 27380 | 27399 | 523 |
| 771930 | N/A | N/A | CCAGCCCAGAAAAACTGCAA | 26 | 27601 | 27620 | 524 |
| 771936 | N/A | N/A | TGTTTCTGTGTGCACATACG | 36 | 28358 | 28377 | 525 |
| 771937 | N/A | N/A | TCCAGTGCTTGTGCATGTGC | 52 | 28429 | 28448 | 526 |
| 771938 | N/A | N/A | CCTTCCCAAATGCCTGCCCC | 29 | 28565 | 28584 | 527 |
| 771944 | N/A | N/A | GGTAATTTTCCTCAACAGGC | 8 | 29276 | 29295 | 528 |
| 771945 | N/A | N/A | TTATGTGTCTCAAATAGATG | 0 | 29486 | 29505 | 529 |
| 771946 | N/A | N/A | GGGCTACCTTAACAAAGCTT | 47 | 29526 | 29545 | 530 |
| 771952 | N/A | N/A | TCTTCTCTGCAGAGCACAGA | 0 | 29990 | 30009 | 531 |
| 771953 | N/A | N/A | TCACCAGCTCATCTCTCAGG | 42 | 30190 | 30209 | 532 |
| 771954 | N/A | N/A | CTAGAATGAAGACACCCGCC | 0 | 30226 | 30245 | 533 |
| 771465 | 1123 | 1142 | ATCCAGAGAGGGCTCCTGGA | 0 | 30390 | 30409 | 534 |
| 771466 | 1128 | 1147 | AAGATATCCAGAGAGGGCTC | 38 | 30395 | 30414 | 535 |
| 771467 | 1133 | 1152 | CATAGAAGATATCCAGAGAG | 11 | 30400 | 30419 | 536 |
| 771473 | 1223 | 1242 | AGCCGATTTTGCTCCGCACC | 9 | 30490 | 30509 | 537 |
| 771474 | 1225 | 1244 | GCAGCCGATTTTGCTCCGCA | 56 | 30492 | 30511 | 538 |
| 771475 | 1240 | 1259 | CGTCAGCTGGATGCCGCAGC | 26 | 30507 | 30526 | 539 |
| 771481 | 1400 | 1419 | GCAGGCTGTACGCCTTCTCG | 0 | 30667 | 30686 | 540 |
| 771482 | 1405 | 1424 | CCGCTGCAGGCTGTACGCCT | 38 | 30672 | 30691 | 541 |
| 771483 | 1436 | 1455 | ACGGCTGCTGCATAAACTCG | 22 | 30703 | 30722 | 542 |
| 771489 | 1466 | 1485 | CAAAGCTGATCTGCACGGTA | 27 | 30733 | 30752 | 543 |
| 771490 | 1471 | 1490 | CTTCACAAAGCTGATCTGCA | 44 | 30738 | 30757 | 544 |
| 771491 | 1481 | 1500 | GGCCCCAGCCCTTCACAAAG | 39 | 30748 | 30767 | 545 |
| 771497 | 1537 | 1556 | GAAGATGACCTCTAGCCAGC | 0 | 30804 | 30823 | 546 |
| 771498 | 1542 | 1561 | CTGTTGAAGATGACCTCTAG | 48 | 30809 | 30828 | 547 |
| 771499 | 1550 | 1569 | GCTACCGGCTGTTGAAGATG | 1 | 30817 | 30836 | 548 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771505 | 1581 | 1600 | CTCAGCTCACGCTCTGTCCC | 0 | 30848 | 30867 | 549 |
| 771506 | 1582 | 1601 | GCTCAGCTCACGCTCTGTCC | 53 | 30849 | 30868 | 550 |
| 483664 | 1583 | 1602 | TGCTCAGCTCACGCTCTGTC | 36 | 30850 | 30869 | 551 |
| 771512 | 1602 | 1621 | AGTAGTTTGAAGTGTGGCCT | 0 | 30869 | 30888 | 552 |
| 771513 | 1607 | 1626 | AGCAAAGTAGTTTGAAGTGT | 34 | 30874 | 30893 | 553 |
| 771514 | 1612 | 1631 | TTAGCAGCAAAGTAGTTTGA | 19 | 30879 | 30898 | 554 |
| 771520 | 1641 | 1660 | ATGAAAAGCAAGCACTCAGG | 12 | 30908 | 30927 | 555 |
| 771521 | 1642 | 1661 | CATGAAAAGCAAGCACTCAG | 33 | 30909 | 30928 | 556 |
| 771522 | 1643 | 1662 | GCATGAAAAGCAAGCACTCA | 29 | 30910 | 30929 | 557 |
| 771528 | 1652 | 1671 | AAAGAGTTTGCATGAAAAGC | 4 | 30919 | 30938 | 558 |
| 771529 | 1657 | 1676 | CGACCAAAGAGTTTGCATGA | 0 | 30924 | 30943 | 559 |
| 771530 | 1662 | 1681 | AAAAACGACCAAAGAGTTTG | 16 | 30929 | 30948 | 560 |
| 771536 | 1723 | 1742 | AGCGAAACAAAACAGAACAC | 0 | 30990 | 31009 | 561 |
| 771537 | 1728 | 1747 | CAAAGAGCGAAACAAAACAG | 16 | 30995 | 31014 | 562 |
| 771538 | 1733 | 1752 | TTTCTCAAAGAGCGAAACAA | 24 | 31000 | 31019 | 563 |
| 771544 | 1763 | 1782 | AAAACCCCCAACAATTCTTT | 0 | 31030 | 31049 | 564 |
| 771545 | 1768 | 1787 | CCAAAAAAACCCCCAACAAT | 21 | 31035 | 31054 | 565 |
| 771546 | 1783 | 1802 | TACCTGCCCCTTCTTCCAAA | 26 | 31050 | 31069 | 566 |
| 771552 | 1830 | 1849 | CTTGGATTTCTGCTTCCCCT | 28 | 31097 | 31116 | 567 |
| 771553 | 1835 | 1854 | TGGTGCTTGGATTTCTGCTT | 38 | 31102 | 31121 | 568 |
| 771554 | 1840 | 1859 | TTTGGTGGTGCTTGGATTTC | 20 | 31107 | 31126 | 569 |
| 771560 | 1881 | 1900 | CTGACAAGTGAAATGATGAC | 0 | 31148 | 31167 | 570 |
| 771561 | 1886 | 1905 | CACTCCTGACAAGTGAAATG | 30 | 31153 | 31172 | 571 |
| 771562 | 1891 | 1910 | ACACACACTCCTGACAAGTG | 30 | 31158 | 31177 | 572 |
| 771568 | 2003 | 2022 | CTGCAAACCTCTCTGCTGGG | 17 | 31270 | 31289 | 573 |
| 771569 | 2006 | 2025 | GGACTGCAAACCTCTCTGCT | 30 | 31273 | 31292 | 574 |
| 771570 | 2008 | 2027 | TGGGACTGCAAACCTCTCTG | 60 | 31275 | 31294 | 575 |
| 771576 | 2027 | 2046 | GGGCAGGAGAGACACCGCTT | 28 | 31294 | 31313 | 576 |
| 771577 | 2055 | 2074 | TGCCTCTGCCCCACTGAGCG | 21 | 31322 | 31341 | 577 |
| 771578 | 2056 | 2075 | CTGCCTCTGCCCCACTGAGC | 50 | 31323 | 31342 | 578 |
| 771584 | 2107 | 2126 | AGCCGTGCTCCTGGCAGCTG | 7 | 31374 | 31393 | 579 |
| 771585 | 2108 | 2127 | GAGCCGTGCTCCTGGCAGCT | 49 | 31375 | 31394 | 580 |
| 771586 | 2155 | 2174 | CCTTGATGAGGGAGAGGAGG | 48 | 31422 | 31441 | 581 |
| 771592 | 2185 | 2204 | CTGCTCAGAAGCCTGTGGAC | 0 | 31452 | 31471 | 582 |
| 771593 | 2187 | 2206 | CGCTGCTCAGAAGCCTGTGG | 41 | 31454 | 31473 | 583 |
| 771594 | 2202 | 2221 | GGCCACTAGCAGGCTCGCTG | 37 | 31469 | 31488 | 584 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771600 | 2284 | 2303 | TGGCCAAAAAGAAAGACGC | 0 | 31551 | 31570 | 585 |
| 771601 | 2286 | 2305 | GATGGCCAAAAAGAAAGAC | 13 | 31553 | 31572 | 586 |
| 771602 | 2301 | 2320 | GGAGATCCAGGAGCAGATGG | 39 | 31568 | 31587 | 587 |
| 771608 | 2359 | 2378 | CTGGGTGAGCAATACTGTGA | 34 | 31626 | 31645 | 588 |
| 771609 | 2402 | 2421 | ATGTCACCAGGGCAGGCAGG | 47 | 31669 | 31688 | 589 |
| 771610 | 2407 | 2426 | ACCTGATGTCACCAGGGCAG | 52 | 31674 | 31693 | 590 |
| 771616 | 2437 | 2456 | TGCTGAGCTGGTTTTCTAAG | 0 | 31704 | 31723 | 591 |
| 771617 | 2440 | 2459 | CAGTGCTGAGCTGGTTTTCT | 10 | 31707 | 31726 | 592 |
| 771618 | 2455 | 2474 | CAGGATGGGAGCAGGCAGTG | 30 | 31722 | 31741 | 593 |
| 771624 | 2463 | 2482 | TTAACACACAGGATGGGAGC | 0 | 31730 | 31749 | 594 |
| 771625 | 2465 | 2484 | GCTTAACACACAGGATGGGA | 48 | 31732 | 31751 | 595 |
| 771626 | 2470 | 2489 | GCAGAGCTTAACACACAGGA | 35 | 31737 | 31756 | 596 |
| 771632 | 2541 | 2560 | AATCCTTCTTGGAGGGAAGG | 31 | 31808 | 31827 | 597 |
| 771633 | 2546 | 2565 | GACCAAATCCTTCTTGGAGG | 40 | 31813 | 31832 | 598 |
| 771634 | 2551 | 2570 | TGACGGACCAAATCCTTCTT | 53 | 31818 | 31837 | 599 |
| 771640 | 2581 | 2600 | GGTGTCAGCCTAGGATGGTA | 0 | 31848 | 31867 | 600 |
| 771641 | 2586 | 2605 | AGTTAGGTGTCAGCCTAGGA | 71 | 31853 | 31872 | 601 |
| 771642 | 2591 | 2610 | AGAAGAGTTAGGTGTCAGCC | 36 | 31858 | 31877 | 602 |
| 771648 | 2623 | 2642 | CATACGAGTGTATGAGTTGT | 0 | 31890 | 31909 | 603 |
| 771649 | 2629 | 2648 | AAGTATCATACGAGTGTATG | 0 | 31896 | 31915 | 604 |
| 771650 | 2630 | 2649 | GAAGTATCATACGAGTGTAT | 24 | 31897 | 31916 | 605 |
| 771656 | 2670 | 2689 | GTTAAAGTCTAAACATGCTC | 0 | 31937 | 31956 | 606 |
| 771657 | 2675 | 2694 | CTTATGTTAAAGTCTAAACA | 6 | 31942 | 31961 | 607 |
| 771658 | 2680 | 2699 | AATAGCTTATGTTAAAGTCT | 33 | 31947 | 31966 | 608 |
| 771664 | 2734 | 2753 | TAAATTTCCAATGAGAATGC | 5 | 32001 | 32020 | 609 |
| 771665 | 2739 | 2758 | AATGCTAAATTTCCAATGAG | 24 | 32006 | 32025 | 610 |
| 771666 | 2744 | 2763 | ACTACAATGCTAAATTTCCA | 39 | 32011 | 32030 | 611 |
| 771672 | 2774 | 2793 | TTTTTTCAGGAGTCCTTTCT | 2 | 32041 | 32060 | 612 |
| 771673 | 2779 | 2798 | AGGTTTTTTTCAGGAGTCC | 44 | 32046 | 32065 | 613 |
| 771674 | 2788 | 2807 | ATAAATCTCAGGTTTTTTTT | 0 | 32055 | 32074 | 614 |
| 771680 | 2935 | 2954 | ATTTATATTAAAGCAAAGTG | 0 | 32202 | 32221 | 615 |
| 771681 | 2940 | 2959 | TTTGCATTTATATTAAAGCA | 0 | 32207 | 32226 | 616 |
| 771682 | 2945 | 2964 | TGTTATTTGCATTTATATTA | 18 | 32212 | 32231 | 617 |
| 771688 | 3047 | 3066 | CGTTTAATGGAACATAAACT | 0 | 32314 | 32333 | 618 |
| 771689 | 3065 | 3084 | AGTGTACATTTTAAAAATCG | 30 | 32332 | 32351 | 619 |

TABLE 4-continued

Inhibition of SMAD7 mRNA expression by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 582468 | N/A | N/A | GCCAATATCATAACCCAAGC | 0 | N/A | N/A | 392 |
| 771451 | 886 | 905 | AGACTCTAGTTCGCAGAGTC | 15 | N/A | N/A | 620 |

TABLE 5

Inhibition of SMAD7 mRNA by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 278478 | 220 | 239 | ACATGACCTCCGCACACCAT | 54 | 1715 | 1734 | 399 |
| 483663 | 799 | 818 | CAGCCTCTTGACTTCCGAGG | 35 | 2294 | 2313 | 22 |
| 771347 | N/A | N/A | TGGGCCACTGGTGTTCGACG | 32 | 2892 | 2911 | 426 |
| 771355 | N/A | N/A | CAGTTCGGCCTTCCATCCAA | 13 | 2958 | 2977 | 429 |
| 771363 | N/A | N/A | TCAGGCTTCACTGCCCATCG | 35 | 9482 | 9501 | 449 |
| 771371 | N/A | N/A | CCACACATTCCAAAAGGCTG | 14 | 9537 | 9556 | 626 |
| 771379 | N/A | N/A | GATCCATCTTTAAGCACGCT | 21 | 9578 | 9597 | 455 |
| 771387 | N/A | N/A | AGCATCTGGACAGTCTGCTG | 59 | 9649 | 9668 | 458 |
| 771395 | 31 | 50 | GCGCTCCGGCTGCCCCACCC | 34 | 1526 | 1545 | 396 |
| 771409 | 356 | 375 | CCCCTGCGCCCTCCTCCTCG | 33 | 1851 | 1870 | 402 |
| 771417 | 421 | 440 | ACCGGCCCCATGCGCTCGGC | 24 | 1916 | 1935 | 405 |
| 771425 | 461 | 480 | CCTTGCCCAGGCAGCATCCA | 15 | 1956 | 1975 | 408 |
| 771433 | 582 | 601 | TCCTTCAGTTTCTTGAGCAC | 28 | 2077 | 2096 | 411 |
| 771441 | 721 | 740 | CGAGGGCGGCTGCGCAGGCT | 60 | 2216 | 2235 | 414 |
| 771449 | 876 | 895 | TCGCAGAGTCGGCTAAGGTG | 4 | 2371 | 2390 | 417 |
| 771696 | N/A | N/A | CTCTCCCAGGAGGGTATGCA | 0 | 2499 2521 | 2518 2540 | 420 |
| 771704 | N/A | N/A | CAGGAGGGTATGCACACTCT | 55 | 2515 2537 | 2534 2556 | 423 |
| 771465 | 1123 | 1142 | ATCCAGAGAGGGCTCCTGGA | 16 | 30390 | 30409 | 534 |
| 771473 | 1223 | 1242 | AGCCGATTTTGCTCCGCACC | 37 | 30490 | 30509 | 537 |
| 771481 | 1400 | 1419 | GCAGGCTGTACGCCTTCTCG | 26 | 30667 | 30686 | 540 |
| 771489 | 1466 | 1485 | CAAAGCTGATCTGCACGGTA | 34 | 30733 | 30752 | 543 |
| 771497 | 1537 | 1556 | GAAGATGACCTCTAGCCAGC | 25 | 30804 | 30823 | 546 |
| 771505 | 1581 | 1600 | CTCAGCTCACGCTCTGTCCC | 29 | 30848 | 30867 | 549 |
| 771512 | 1602 | 1621 | AGTAGTTTGAAGTGTGGCCT | 34 | 30869 | 30888 | 552 |
| 771520 | 1641 | 1660 | ATGAAAAGCAAGCACTCAGG | 37 | 30908 | 30927 | 555 |
| 771528 | 1652 | 1671 | AAAGAGTTTGCATGAAAAGC | 12 | 30919 | 30938 | 558 |

TABLE 5-continued

Inhibition of SMAD7 mRNA by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771536 | 1723 | 1742 | AGCGAAACAAAACAGAACAC | 25 | 30990 | 31009 | 561 |
| 771544 | 1763 | 1782 | AAAACCCCCAACAATTCTTT | 16 | 31030 | 31049 | 564 |
| 771552 | 1830 | 1849 | CTTGGATTTCTGCTTCCCCT | 53 | 31097 | 31116 | 567 |
| 771560 | 1881 | 1900 | CTGACAAGTGAAATGATGAC | 0 | 31148 | 31167 | 570 |
| 771568 | 2003 | 2022 | CTGCAAACCTCTCTGCTGGG | 26 | 31270 | 31289 | 573 |
| 771576 | 2027 | 2046 | GGGCAGGAGAGACACCGCTT | 64 | 31294 | 31313 | 576 |
| 771584 | 2107 | 2126 | AGCCGTGCTCCTGGCAGCTG | 26 | 31374 | 31393 | 579 |
| 771592 | 2185 | 2204 | CTGCTCAGAAGCCTGTGGAC | 16 | 31452 | 31471 | 582 |
| 771600 | 2284 | 2303 | TGGCCAAAAAGAAAGACGC | 11 | 31551 | 31570 | 585 |
| 771608 | 2359 | 2378 | CTGGGTGAGCAATACTGTGA | 45 | 31626 | 31645 | 588 |
| 771616 | 2437 | 2456 | TGCTGAGCTGGTTTTCTAAG | 33 | 31704 | 31723 | 591 |
| 771624 | 2463 | 2482 | TTAACACACAGGATGGGAGC | 27 | 31730 | 31749 | 594 |
| 771632 | 2541 | 2560 | AATCCTTCTTGGAGGGAAGG | 54 | 31808 | 31827 | 597 |
| 771640 | 2581 | 2600 | GGTGTCAGCCTAGGATGGTA | 35 | 31848 | 31867 | 600 |
| 771648 | 2623 | 2642 | CATACGAGTGTATGAGTTGT | 17 | 31890 | 31909 | 603 |
| 771656 | 2670 | 2689 | GTTAAAGTCTAAACATGCTC | 35 | 31937 | 31956 | 606 |
| 771664 | 2734 | 2753 | TAAATTTCCAATGAGAATGC | 25 | 32001 | 32020 | 609 |
| 771672 | 2774 | 2793 | TTTTTTCAGGAGTCCTTTCT | 30 | 32041 | 32060 | 612 |
| 771680 | 2935 | 2954 | ATTTATATTAAAGCAAAGTG | 0 | 32202 | 32221 | 615 |
| 771688 | 3047 | 3066 | CGTTTAATGGAACATAAACT | 13 | 32314 | 32333 | 618 |
| 771712 | N/A | N/A | ATTCTTTTAGCCCAACTGTT | 27 | 3676 | 3695 | 430 |
| 771720 | N/A | N/A | CAGGCAGAGCTATGCTTCAA | 37 | 4396 | 4415 | 433 |
| 771728 | N/A | N/A | AACTTTTCTCCCCCTTGGAA | 7 | 5537 | 5556 | 436 |
| 771736 | N/A | N/A | TGCCAGATCTCAGGTCAAGA | 34 | 6539 | 6558 | 439 |
| 771744 | N/A | N/A | GGCTATTCCCAAGAGTCCAG | 40 | 7595 | 7614 | 442 |
| 771752 | N/A | N/A | AATGTCCCTGTGGGTTTCCA | 3 | 8497 | 8516 | 445 |
| 771760 | N/A | N/A | ATCTTACCTGAAAGCCCCCC | 25 | 9714 | 9733 | 459 |
| 771768 | N/A | N/A | GTATGCTTGGGATCTGTCTT | 24 | 10143 | 10162 | 462 |
| 771776 | N/A | N/A | CTCAGCAAGCTCAGTTCCTG | 54 | 10811 | 10830 | 465 |
| 771784 | N/A | N/A | TAAATCAAGAGCTGAAATTC | 1 | 11958 | 11977 | 468 |
| 771792 | N/A | N/A | AGCACACCCCACCCCCACCT | 33 | 12632 | 12651 | 471 |
| 771800 | N/A | N/A | GACAGCAGACAGGCAAAATG | 32 | 13523 | 13542 | 474 |
| 771808 | N/A | N/A | CCCCAAAGTCCACGCTCATG | 54 | 14368 | 14387 | 477 |
| 771816 | N/A | N/A | ATCCAACTACTCAGAGGCTG | 28 | 15227 | 15246 | 480 |
| 771824 | N/A | N/A | TTCTACTAGAAAAAAATTAG | 3 | 16278 | 16297 | 483 |
| 771832 | N/A | N/A | ACCTTTCACGAACCACTTTT | 31 | 17364 | 17383 | 486 |

TABLE 5-continued

Inhibition of SMAD7 mRNA by 5-10-5 MOE gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 771840 | N/A | N/A | AGATGCTTCTAGGTGAACCA | 30 | 18033 | 18052 | 489 |
| 771848 | N/A | N/A | CCACACAACCAAAGCAGAAG | 47 | 19011 | 19030 | 492 |
| 771856 | N/A | N/A | CTGAAAGAAAGTCCCGACTT | 35 | 19740 | 19759 | 495 |
| 771864 | N/A | N/A | AGACAAAGATCACAGATCAC | 27 | 20528 | 20547 | 498 |
| 771872 | N/A | N/A | TCCCCCACCGCGCAGGGACA | 11 | 21590 | 21609 | 501 |
| 771880 | N/A | N/A | TCCCTGGTTTTGCAGGTGGT | 41 | 22497 | 22516 | 504 |
| 771888 | N/A | N/A | TCGCCATGGAGAATGTAATT | 21 | 23351 | 23370 | 507 |
| 771896 | N/A | N/A | GGGCCCCCTTCTGCCTTCAT | 17 | 23956 | 23975 | 510 |
| 771904 | N/A | N/A | CCCAACCCATCTCCACCACC | 0 | 24966 | 24985 | 513 |
| 771912 | N/A | N/A | ATATTCCTCTGCCAAAGTCC | 44 | 25710 | 25729 | 516 |
| 771920 | N/A | N/A | TTATTTAATTACCCTGCTCA | 33 | 26598 | 26617 | 519 |
| 771928 | N/A | N/A | CCCCATTGCCACTACAGAGA | 27 | 27288 | 27307 | 522 |
| 771936 | N/A | N/A | TGTTTCTGTGTGCACATACG | 32 | 28358 | 28377 | 525 |
| 771944 | N/A | N/A | GGTAATTTTCCTCAACAGGC | 50 | 29276 | 29295 | 528 |
| 771952 | N/A | N/A | TCTTCTCTGCAGAGCACAGA | 26 | 29990 | 30009 | 531 |

TABLE 6

Inhibition of SMAD7 mRNA expression by 5-10-5 MOE gapmers targeting SEQ ID NO: 3 and 4

| IONIS NO. | SEQ ID: 3 Start Site | SEQ ID: 3 Stop Site | Sequence | % Inhibition | SEQ ID: 4 Start Site | SEQ ID 4: Stop Site | SEQ ID NO. |
|---|---|---|---|---|---|---|---|
| 771342 | 936 | 955 | TCAGTTGGTTTGAGAAAATC | 35 | N/A | N/A | 621 |
| 771343 | 941 | 960 | GACAGTCAGTTGGTTTGAGA | 0 | N/A | N/A | 622 |
| 771344 | 946 | 965 | ATCTGGACAGTCAGTTGGTT | 17 | N/A | N/A | 623 |
| 771345 | 951 | 970 | ACAGCATCTGGACAGTCAGT | 54 | N/A | N/A | 624 |
| 771356 | N/A | N/A | TCCAGTTCGGCCTTCCATCC | 40 | 87 | 102 | 625 |

Example 2: Antisense Inhibition of Human SMAD7 mRNA Expression in Hep3B Cells by 3-10-3 cEt Gapmers Antisense oligonucleotides were designed to target human SMAD7 mRNA and were tested for their effects on SMAD7 mRNA expression in vitro. The antisense oligonucleotides were tested in a series of experiments that had similar culture conditions, as described below. The results for each experiment are presented in separate tables shown below. ION 771576, described in the studies above and which is a 5-10-5 MOE gapmer, was also included in these assays. Cultured Hep3B cells at a density of 20,000 cells per well were transfected using electroporation with 10,000 nM antisense oligonucleotide. After a treatment period of approximately 24 hours, RNA was isolated from the cells and SMAD7 mRNA levels were measured by quantitative real-time PCR. Primer probe set RTS5062 was used to measure human SMAD7 mRNA levels. SMAD7 mRNA levels were adjusted according to total RNA content, as measured by RIBOGREEN®. Results are presented as percent inhibition of SMAD7 mRNA expression, relative to untreated control cells.

The newly designed chimeric antisense oligonucleotides in the Tables below were designed as 3-10-3 cEt gapmers. The gapmers are 16 nucleosides in length, wherein the central gap segment comprises often 2'-deoxynucleosides and is flanked by wing segments on the 5' direction and the 3' direction comprising three nucleosides each. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either SEQ ID NO: 1 or SEQ ID NO: 2. 'n/a' indicates that the antisense oligonucleotide does not target that particular gene sequence with 100% complementarity. Some of the oligonucleotides presented were complementary to SMAD7 mRNA sequences RefSeqNo. NM_001190821.1 (designated herein as SEQ ID NO: 3) or RefSeqNo. NM_001190822.1 (designated herein as SEQ ID NO: 4), and are presented in a separate table shown below.

TABLE 7

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798654 | 2 | 17 | CCCTGCGCGGCTCTCC | 23 | 1497 | 1512 | 626 |
| 798655 | 10 | 25 | GGCCCGCGCCCTGCGC | 21 | 1505 | 1520 | 627 |
| 798656 | 13 | 28 | CGCGGCCCGCGCCCTG | 10 | 1508 | 1523 | 628 |
| 798657 | 16 | 31 | CCGCGCGGCCCGCGCC | 0 | 1511 | 1526 | 629 |
| 798658 | 19 | 34 | ACCCCGCGCGGCCCGC | 71 | 1514 | 1529 | 630 |
| 798659 | 22 | 37 | CCCACCCCGCGCGGCC | 58 | 1517 | 1532 | 631 |
| 798660 | 25 | 40 | TGCCCACCCCGCGCG | 38 | 1520 | 1535 | 632 |
| 798661 | 28 | 43 | GGCTGCCCCACCCCGC | 52 | 1523 | 1538 | 633 |
| 798662 | 33 | 48 | GCTCCGGCTGCCCCAC | 62 | 1528 | 1543 | 634 |
| 798663 | 36 | 51 | TGCGCTCCGGCTGCCC | 41 | 1531 | 1546 | 635 |
| 798672 | 141 | 156 | GGCAGGAGCGGCGGCG | 6 | 1636 | 1651 | 636 |
| 790461 | 144 | 159 | CCGGGCAGGAGCGGCG | 42 | 1639 | 1654 | 637 |
| 798673 | 147 | 162 | GGCCCGGGCAGGAGCG | 15 | 1642 | 1657 | 638 |
| 798674 | 170 | 185 | CAGGCGACAGCAGCAG | 39 | 1665 | 1680 | 639 |
| 790462 | 173 | 188 | GCGCAGGCGACAGCAG | 43 | 1668 | 1683 | 640 |
| 798675 | 176 | 191 | CAGGCGCAGGCGACAG | 51 | 1671 | 1686 | 641 |
| 772532 | 179 | 194 | CAGCAGGCGCAGGCGA | 21 | 1674 | 1689 | 642 |
| 772533 | 205 | 220 | TGAAGAAGTCGGGCGC | 31 | 1700 | 1715 | 643 |
| 798676 | 208 | 223 | CCATGAAGAAGTCGGG | 21 | 1703 | 1718 | 644 |
| 798677 | 211 | 226 | ACACCATGAAGAAGTC | 36 | 1706 | 1721 | 645 |
| 790468 | 259 | 274 | GCGAGGAGAAAAGTCG | 0 | 1754 | 1769 | 646 |
| 798685 | 262 | 277 | GAGGCGAGGAGAAAAG | 58 | 1757 | 1772 | 647 |
| 798686 | 265 | 280 | GAGGAGGCGAGGAGAA | 59 | 1760 | 1775 | 648 |
| 798687 | 268 | 283 | GGCGAGGAGGCGAGGA | 64 | 1763 | 1778 | 649 |
| 798688 | 283 | 298 | GTCCTGAACATGCGGG | 68 | 1778 | 1793 | 650 |
| 772543 | 303 | 318 | GGACGAGCGCAGATCG | 58 | 1798 | 1813 | 651 |
| 798689 | 306 | 321 | GCCGGACGAGCGCAGA | 33 | 1801 | 1816 | 652 |
| 798690 | 321 | 336 | GGCTCCTCCAGAGACG | 29 | 1816 | 1831 | 653 |
| 798691 | 326 | 341 | CGCACGGCTCCTCCAG | 42 | 1821 | 1836 | 654 |
| 798692 | 329 | 344 | GGGCGCACGGCTCCTC | 48 | 1824 | 1839 | 655 |
| 798703 | 404 | 419 | GTCCGTCGCCCCTTCT | 68 | 1899 | 1914 | 656 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798704 | 406 | 421 | CTGTCCGTCGCCCCTT | 61 | 1901 | 1916 | 657 |
| 798705 | 408 | 423 | GGCTGTCCGTCGCCCC | 41 | 1903 | 1918 | 658 |
| 798706 | 409 | 424 | CGGCTGTCCGTCGCCC | 1 | 1904 | 1919 | 659 |
| 798707 | 412 | 427 | GCTCGGCTGTCCGTCG | 74 | 1907 | 1922 | 660 |
| 798708 | 413 | 428 | CGCTCGGCTGTCCGTC | 45 | 1908 | 1923 | 661 |
| 798709 | 415 | 430 | TGCGCTCGGCTGTCCG | 2 | 1910 | 1925 | 662 |
| 798710 | 420 | 435 | CCCCATGCGCTCGGCT | 54 | 1915 | 1930 | 663 |
| 798711 | 423 | 438 | CGGCCCCATGCGCTCG | 59 | 1918 | 1933 | 664 |
| 798712 | 428 | 443 | GCCACCGGCCCCATGC | 6 | 1923 | 1938 | 665 |
| 798723 | 467 | 482 | CGCCTTGCCCAGGCAG | 0 | 1962 | 1977 | 666 |
| 798724 | 470 | 485 | CACCGCCTTGCCCAGG | 19 | 1965 | 1980 | 667 |
| 798725 | 473 | 488 | TCGCACCGCCTTGCCC | 29 | 1968 | 1983 | 668 |
| 798726 | 477 | 492 | CACCTCGCACCGCCTT | 7 | 1972 | 1987 | 669 |
| 798727 | 480 | 495 | TGGCACCTCGCACCGC | 51 | 1975 | 1990 | 670 |
| 798728 | 483 | 498 | CTTTGGCACCTCGCAC | 41 | 1978 | 1993 | 671 |
| 798729 | 486 | 501 | GACCTTTGGCACCTCG | 51 | 1981 | 1996 | 672 |
| 798730 | 489 | 504 | GGTGACCTTTGGCACC | 0 | 1984 | 1999 | 673 |
| 798731 | 492 | 507 | GGTGGTGACCTTTGGC | 43 | 1987 | 2002 | 674 |
| 798732 | 496 | 511 | GGATGGTGGTGACCTT | 51 | 1991 | 2006 | 675 |
| 798742 | 587 | 602 | CTCCTTCAGTTTCTTG | 30 | 2082 | 2097 | 676 |
| 798743 | 592 | 607 | TGCCGCTCCTTCAGTT | 19 | 2087 | 2102 | 677 |
| 798744 | 595 | 610 | AGCTGCCGCTCCTTCA | 12 | 2090 | 2105 | 678 |
| 798745 | 603 | 618 | GCAGCTCCAGCTGCCG | 0 | 2098 | 2113 | 679 |
| 798746 | 610 | 625 | TGGAGCAGCAGCTCCA | 30 | 2105 | 2120 | 680 |
| 798747 | 615 | 630 | CGGCCTGGAGCAGCAG | 14 | 2110 | 2125 | 681 |
| 798748 | 620 | 635 | CTCCACGGCCTGGAGC | 58 | 2115 | 2130 | 682 |
| 798749 | 623 | 638 | GGACTCCACGGCCTGG | 63 | 2118 | 2133 | 683 |
| 772555 | 649 | 664 | AGGCACGCGGTGCGCG | 23 | 2144 | 2159 | 684 |
| 798750 | 652 | 667 | AGGAGGCACGCGGTGC | 54 | 2147 | 2162 | 685 |
| 798758 | 717 | 732 | GCTGCGCAGGCTGCGC | 0 | 2212 | 2227 | 686 |
| 798759 | 721 | 736 | GGCGGCTGCGCAGGCT | 40 | 2216 | 2231 | 687 |
| 798760 | 724 | 739 | GAGGGCGGCTGCGCAG | 47 | 2219 | 2234 | 688 |
| 798761 | 727 | 742 | GACGAGGGCGGCTGCG | 39 | 2222 | 2237 | 689 |
| 798762 | 730 | 745 | TAGGACGAGGGCGGCT | 56 | 2225 | 2240 | 690 |
| 798763 | 733 | 748 | GAGTAGGACGAGGGCG | 53 | 2228 | 2243 | 691 |
| 772559 | 736 | 751 | AGCGAGTAGGACGAGG | 14 | 2231 | 2246 | 692 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 772560 | 754 | 769 | TTGCACAGCAGGAGGG | 66 | 2249 | 2264 | 693 |
| 798764 | 757 | 772 | ACTTTGCACAGCAGGA | 69 | 2252 | 2267 | 694 |
| 798765 | 760 | 775 | AACACTTTGCACAGCA | 63 | 2255 | 2270 | 695 |
| 798773 | 795 | 810 | TGACTTCCGAGGAATG | 40 | 2290 | 2305 | 696 |
| 798774 | 796 | 811 | TTGACTTCCGAGGAAT | 12 | 2291 | 2306 | 697 |
| 790489 | 799 | 814 | CTCTTGACTTCCGAGG | 0 | 2294 | 2309 | 698 |
| 798775 | 800 | 815 | CCTCTTGACTTCCGAG | 0 | 2295 | 2310 | 699 |
| 772568 | 802 | 817 | AGCCTCTTGACTTCCG | 82 | 2297 | 2312 | 700 |
| 798776 | 806 | 821 | ACACAGCCTCTTGACT | 34 | 2301 | 2316 | 701 |
| 798777 | 809 | 824 | GCAACACAGCCTCTTG | 20 | 2304 | 2319 | 702 |
| 798778 | 813 | 828 | CACAGCAACACAGCCT | 64 | 2308 | 2323 | 703 |
| 798779 | 816 | 831 | ATTCACAGCAACACAG | 31 | 2311 | 2326 | 704 |
| 798780 | 819 | 834 | AAGATTCACAGCAACA | 58 | 2314 | 2329 | 705 |
| 798785 | 885 | 900 | CTAGTTCGCAGAGTCG | 0 | 2380 | 2395 | 706 |
| 799322 | N/A | N/A | GGAGGGTATGCACACT | 83 | 2495 2517 2539 | 2510 2532 2554 | 707 |
| 799323 | N/A | N/A | CCAGGAGGGTATGCAC | 60 | 2498 2520 2542 | 2513 2535 2557 | 708 |
| 799324 | N/A | N/A | TCCCAGGAGGGTATGC | 6 | 2500 2522 2544 | 2515 2537 2559 | 709 |
| 799325 | N/A | N/A | TCTCCCAGGAGGGTAT | 2 | 2502 2524 | 2517 2539 | 710 |
| 799326 | N/A | N/A | ACACTCTCCCAGGAGG | 31 | 2506 2528 | 2521 2543 | 711 |
| 799327 | N/A | N/A | GCACACTCTCCCAGGA | 52 | 2508 2530 | 2523 2545 | 712 |
| 799338 | N/A | N/A | TTATAGCACGCCTCTC | 0 | 2828 | 2843 | 713 |
| 799242 | N/A | N/A | CGTGATTCTCCGTATT | 0 | 2878 | 2893 | 714 |
| 799243 | N/A | N/A | CCACTGGTGTTCGACG | 19 | 2892 | 2907 | 715 |
| 799244 | N/A | N/A | GGGCCACTGGTGTTCG | 8 | 2895 | 2910 | 716 |
| 799245 | N/A | N/A | GTATCTGGGCCACTGG | 18 | 2901 | 2916 | 717 |
| 799246 | N/A | N/A | ACAGTATCTGGGCCAC | 74 | 2904 | 2919 | 718 |
| 799247 | N/A | N/A | ACGACAGTATCTGGGC | 61 | 2907 | 2922 | 719 |
| 799248 | N/A | N/A | GCCACGACAGTATCTG | 40 | 2910 | 2925 | 720 |
| 799249 | N/A | N/A | GCGGCCACGACAGTAT | 26 | 2913 | 2928 | 721 |
| 799250 | N/A | N/A | TGCGCGGCCACGACAG | 21 | 2916 | 2931 | 722 |
| 799251 | N/A | N/A | AGGTGCGCGGCCACGA | 37 | 2919 | 2934 | 723 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799262 | N/A | N/A | CTCTTTGCCCCAAAAC | 0 | 2940 | 2955 | 724 |
| 799263 | N/A | N/A | TCCAACTCTCTTTGCC | 0 | 2947 | 2962 | 725 |
| 799264 | N/A | N/A | CCATCCAACTCTCTTT | 16 | 2950 | 2965 | 726 |
| 799265 | N/A | N/A | CTTCCATCCAACTCTC | 3 | 2953 | 2968 | 727 |
| 799266 | N/A | N/A | GGCCTTCCATCCAACT | 37 | 2956 | 2971 | 728 |
| 799267 | N/A | N/A | GTTCGGCCTTCCATCC | 62 | 2960 | 2975 | 729 |
| 799339 | N/A | N/A | GATACCCAGTTCGGCC | 18 | 2968 | 2983 | 730 |
| 799340 | N/A | N/A | AGATACCCAGTTCGGC | 0 | 2969 | 2984 | 731 |
| 799341 | N/A | N/A | GAAGGAAAAAGTAGGG | 8 | 3050 | 3065 | 732 |
| 799342 | N/A | N/A | CTTATCTGTGCGGAAG | 44 | 3066 | 3081 | 733 |
| 799343 | N/A | N/A | ACTAATCTACAGACTT | 53 | 3079 | 3094 | 734 |
| 799344 | N/A | N/A | CCCACTAATCTACAGA | 34 | 3082 | 3097 | 735 |
| 799345 | N/A | N/A | CGAGAAGCCCAGGCCC | 20 | 3139 | 3154 | 736 |
| 799346 | N/A | N/A | TCTCAGCCGAGAAGCC | 26 | 3146 | 3161 | 737 |
| 799347 | N/A | N/A | AAGGAGTTTCAGGGTC | 59 | 3160 | 3175 | 738 |
| 798788 | 911 | 926 | TCTGGAGTAAGGAGGG | 31 | 3780 | 3795 | 739 |
| 798789 | 914 | 929 | GTATCTGGAGTAAGGA | 44 | 3783 | 3798 | 740 |
| 798790 | 917 | 932 | CGGGTATCTGGAGTAA | 49 | 3786 | 3801 | 741 |
| 798791 | 920 | 935 | CATCGGGTATCTGGAG | 25 | 3789 | 3804 | 742 |
| 799358 | N/A | N/A | AGCACAAATACATGAA | 52 | 4045 | 4060 | 743 |
| 799359 | N/A | N/A | TGTTAAAGCTGAGCCC | 22 | 4072 | 4087 | 744 |
| 790655 | N/A | N/A | CGTGTTAAAGCTGAGC | 42 | 4074 | 4089 | 745 |
| 799360 | N/A | N/A | CCAAGACACTTCTCTC | 42 | 4106 | 4121 | 746 |
| 799361 | N/A | N/A | GTCCTATTTGGTTCCC | 77 | 4120 | 4135 | 747 |
| 799362 | N/A | N/A | CATCAACCAGTCCTAT | 39 | 4129 | 4144 | 748 |
| 799363 | N/A | N/A | GAGTTATCCCCATCAA | 49 | 4139 | 4154 | 749 |
| 799364 | N/A | N/A | TCCGAGTTATCCCCAT | 73 | 4142 | 4157 | 750 |
| 799365 | N/A | N/A | CTCCGAGTTATCCCCA | 61 | 4143 | 4158 | 751 |
| 799366 | N/A | N/A | TCTCCGAGTTATCCCC | 70 | 4144 | 4159 | 752 |
| 799377 | N/A | N/A | TTGCAGGTGACTGGAG | 15 | 4328 | 4343 | 753 |
| 799378 | N/A | N/A | GAATACTGAGAAAACC | 46 | 4360 | 4375 | 754 |
| 799379 | N/A | N/A | TTTGATAGTCCCTATG | 0 | 4378 | 4393 | 755 |
| 799380 | N/A | N/A | CTCCTACTGTAAGAGG | 1 | 4619 | 4634 | 756 |
| 799381 | N/A | N/A | AACAGATCTATCTCCT | 54 | 4630 | 4645 | 757 |
| 799382 | N/A | N/A | ACTTTTAGCAAACAGA | 82 | 4640 | 4655 | 758 |
| 799383 | N/A | N/A | CACAAAAACCAAGGTT | 40 | 4669 | 4684 | 759 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799384 | N/A | N/A | GGCACAAAAACCAAGG | 40 | 4671 | 4686 | 760 |
| 799385 | N/A | N/A | TGCCCAACCCTTCACT | 31 | 4760 | 4775 | 761 |
| 799386 | N/A | N/A | AGGAGCTAAATGGTGC | 12 | 4773 | 4788 | 762 |
| 799397 | N/A | N/A | AAAACAGAGCTTGGTA | 27 | 5109 | 5124 | 763 |
| 799398 | N/A | N/A | CTTGGAAAATGAACTT | 48 | 5181 | 5196 | 764 |
| 799399 | N/A | N/A | TCCAAATTTGAAGAAT | 0 | 5232 | 5247 | 765 |
| 799400 | N/A | N/A | GGAAAACCTCCAAATT | 0 | 5240 | 5255 | 766 |
| 799401 | N/A | N/A | TCTTTTAAGGAAAACC | 53 | 5248 | 5263 | 767 |
| 799402 | N/A | N/A | GGTCACTGTTCTCTCT | 66 | 5263 | 5278 | 768 |
| 799403 | N/A | N/A | GCTAAGGTCACTGTTC | 0 | 5268 | 5283 | 769 |
| 799404 | N/A | N/A | GGAACATTTACCCCTG | 68 | 5302 | 5317 | 770 |
| 799405 | N/A | N/A | CTGGGAACATTTACCC | 28 | 5305 | 5320 | 771 |
| 799406 | N/A | N/A | GGGAACATGGCCTTTC | 65 | 5344 | 5359 | 772 |
| 799416 | N/A | N/A | AAGACCTGGGTCAGCG | 41 | 5851 | 5866 | 773 |
| 799417 | N/A | N/A | GGCCAAACATTCTCCC | 26 | 5885 | 5900 | 774 |
| 799418 | N/A | N/A | GTAAATGGTCCATGTA | 12 | 5909 | 5924 | 775 |
| 799419 | N/A | N/A | AAAAATTCAACCTAAG | 0 | 5945 | 5960 | 776 |
| 799420 | N/A | N/A | CAAGACCAAAAATTCA | 32 | 5952 | 5967 | 777 |
| 799421 | N/A | N/A | AACCCAAGACCAAAAA | 63 | 5956 | 5971 | 778 |
| 799422 | N/A | N/A | GATTTTAACAGTTGTC | 33 | 6004 | 6019 | 779 |
| 799423 | N/A | N/A | TACCAGGCCCCAGCCC | 14 | 6089 | 6104 | 780 |
| 799424 | N/A | N/A | CTCCAAAGGCTGCAGG | 34 | 6106 | 6121 | 781 |
| 799425 | N/A | N/A | ATTATAGCAAAATGGA | 23 | 6147 | 6162 | 782 |
| 800109 | N/A | N/A | ACAGCCACAAGTCACA | 75 | 6284 | 6299 | 783 |
| 799436 | N/A | N/A | AGCCATTCCTCAAACC | 4 | 6428 | 6443 | 784 |
| 799437 | N/A | N/A | CCAGATCTCAGGTCAA | 26 | 6541 | 6556 | 785 |
| 799438 | N/A | N/A | AAGAGAGAAACGCAGT | 32 | 6558 | 6573 | 786 |
| 799439 | N/A | N/A | AAGAGGGACCTCGGTT | 0 | 6574 | 6589 | 787 |
| 799440 | N/A | N/A | TAGAAAAGTTAAGAGG | 41 | 6584 | 6599 | 788 |
| 799441 | N/A | N/A | CTAGAAAAGTTAAGAG | 22 | 6585 | 6600 | 789 |
| 799442 | N/A | N/A | GATTTTAAAAGAGGCC | 0 | 6600 | 6615 | 790 |
| 799443 | N/A | N/A | TCATGCTGATTTTAAA | 24 | 6607 | 6622 | 791 |
| 799444 | N/A | N/A | CATCATGCTGATTTTA | 45 | 6609 | 6624 | 792 |
| 799445 | N/A | N/A | CCTAATCTCTTTCATC | 28 | 6621 | 6636 | 793 |
| 799456 | N/A | N/A | TCCTAAGTACTGTTAA | 0 | 7139 | 7154 | 794 |
| 799457 | N/A | N/A | CACGATAGTCTCAGCA | 62 | 7170 | 7185 | 795 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799458 | N/A | N/A | TTGAAAACCCAACCCT | 3 | 7246 | 7261 | 796 |
| 799459 | N/A | N/A | ACAGAGTCTTTGAAAA | 0 | 7255 | 7270 | 797 |
| 799460 | N/A | N/A | CAACAGAGTCTTTGAA | 29 | 7257 | 7272 | 798 |
| 799461 | N/A | N/A | CTGCGAGAGAAAAAGA | 62 | 7297 | 7312 | 799 |
| 799462 | N/A | N/A | AAGCACTAGGTTCTGC | 43 | 7309 | 7324 | 800 |
| 799463 | N/A | N/A | TGGTAAGCACTAGGTT | 33 | 7313 | 7328 | 801 |
| 799464 | N/A | N/A | AAGCACTTGGTAAGCA | 40 | 7320 | 7335 | 802 |
| 799465 | N/A | N/A | AGCTCTAGGCCACTCC | 64 | 7362 | 7377 | 803 |
| 799476 | N/A | N/A | GCTCAAAGGGCCACCC | 0 | 7624 | 7639 | 804 |
| 799477 | N/A | N/A | GTTCCATAGGCAGCCA | 4 | 7664 | 7679 | 805 |
| 799478 | N/A | N/A | CCCTACCACCCCTGTG | 17 | 7698 | 7713 | 806 |
| 799479 | N/A | N/A | TGCCCTTCTGCAGTGG | 24 | 7754 | 7769 | 807 |
| 790695 | N/A | N/A | TGAAATGGTGCTCTGC | 62 | 7767 | 7782 | 808 |
| 799480 | N/A | N/A | CACACAGGCAACCACA | 45 | 7793 | 7808 | 809 |
| 799481 | N/A | N/A | CTCCACACAGGCAACC | 34 | 7796 | 7811 | 810 |
| 799482 | N/A | N/A | GAAAAGCCGGGCATCT | 30 | 7872 | 7887 | 811 |
| 799483 | N/A | N/A | CAAAGGAAAAGCCGGG | 35 | 7877 | 7892 | 812 |
| 799484 | N/A | N/A | CGCCACCTTTGGCTGG | 0 | 7919 | 7934 | 813 |
| 799495 | N/A | N/A | CTAACAGGAATATACA | 25 | 8149 | 8164 | 814 |
| 799496 | N/A | N/A | GGGTGAGGTGGCTGCG | 72 | 8226 | 8241 | 815 |
| 799497 | N/A | N/A | AAGAACTCTCCTAAGC | 0 | 8273 | 8288 | 816 |
| 799498 | N/A | N/A | TCAAGAACTCTCCTAA | 31 | 8275 | 8290 | 817 |
| 799499 | N/A | N/A | TCCTTTAGTGGCCTAC | 54 | 8406 | 8421 | 818 |
| 799500 | N/A | N/A | GAGCAGACGGGCAAGT | 28 | 8434 | 8449 | 819 |
| 799501 | N/A | N/A | AAAAGAGCAGACGGGC | 0 | 8438 | 8453 | 820 |
| 799502 | N/A | N/A | CAAATAGGAAAGCCAA | 31 | 8457 | 8472 | 821 |
| 799503 | N/A | N/A | GGCCACCAGGACAATG | 0 | 8513 | 8528 | 822 |
| 799504 | N/A | N/A | AGGAAAGGTGCTGCCC | 15 | 8585 | 8600 | 823 |
| 799515 | N/A | N/A | CCCCAGACCTGCTAAG | 38 | 8941 | 8956 | 824 |
| 790710 | N/A | N/A | GGGAAATGTTCTACCT | 15 | 9005 | 9020 | 825 |
| 799516 | N/A | N/A | CACCAGATCAAGACAG | 0 | 9052 | 9067 | 826 |
| 799517 | N/A | N/A | CTTAAGTAGAGCAAAG | 0 | 9127 | 9142 | 827 |
| 799518 | N/A | N/A | ACTTAAGTAGAGCAAA | 38 | 9128 | 9143 | 828 |
| 799519 | N/A | N/A | AACTTAAGTAGAGCAA | 44 | 9129 | 9144 | 829 |
| 799520 | N/A | N/A | GATTGATGTTGGGCTG | 51 | 9179 | 9194 | 830 |
| 799521 | N/A | N/A | TAAAGACAGGTTTCCC | 57 | 9216 | 9231 | 831 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799522 | N/A | N/A | TTTAAAGACAGGTTTC | 32 | 9218 | 9233 | 832 |
| 799523 | N/A | N/A | GGCAGAAGGCTCTCTC | 28 | 9266 | 9281 | 833 |
| 799270 | N/A | N/A | AGTCAGGCTCAATGAG | 16 | 9403 | 9418 | 834 |
| 799271 | N/A | N/A | CTCGAGTCAGGCTCAA | 60 | 9407 | 9422 | 835 |
| 799280 | N/A | N/A | AGCACCTTGTCACCCG | 44 | 9453 | 9468 | 836 |
| 799281 | N/A | N/A | CACAGCACCTTGTCAC | 25 | 9456 | 9471 | 837 |
| 772786 | N/A | N/A | GACCACAGCACCTTGT | 19 | 9459 | 9474 | 838 |
| 799282 | N/A | N/A | ACAGACCACAGCACCT | 16 | 9462 | 9477 | 839 |
| 799283 | N/A | N/A | AAGACAGACCACAGCA | 34 | 9465 | 9480 | 840 |
| 799284 | N/A | N/A | CGTAAGACAGACCACA | 51 | 9468 | 9483 | 841 |
| 799285 | N/A | N/A | GGCTTCACTGCCCATC | 36 | 9483 | 9498 | 842 |
| 799286 | N/A | N/A | GCTCAGGCTTCACTGC | 0 | 9488 | 9503 | 843 |
| 799287 | N/A | N/A | TCTGCTCAGGCTTCAC | 15 | 9491 | 9506 | 844 |
| 799288 | N/A | N/A | TAATGGTCTGCTCAGG | 23 | 9497 | 9512 | 845 |
| 799299 | N/A | N/A | ATTCCAAAAGGCTGAC | 42 | 9535 | 9550 | 846 |
| 799300 | N/A | N/A | CACATTCCAAAAGGCT | 28 | 9538 | 9553 | 847 |
| 799301 | N/A | N/A | CCACACATTCCAAAAG | 37 | 9541 | 9556 | 848 |
| 799302 | N/A | N/A | AAACCACACATTCCAA | 39 | 9544 | 9559 | 849 |
| 799303 | N/A | N/A | GACAAACCACACATTC | 73 | 9547 | 9562 | 850 |
| 799304 | N/A | N/A | GAAAGACAAACCACAC | 54 | 9551 | 9566 | 851 |
| 799305 | N/A | N/A | CATGAAAGACAAACCA | 0 | 9554 | 9569 | 852 |
| 799306 | N/A | N/A | AAACAGCATGAAAGAC | 27 | 9560 | 9575 | 853 |
| 799307 | N/A | N/A | TCTAAACAGCATGAAA | 10 | 9563 | 9578 | 854 |
| 799308 | N/A | N/A | CGCTCTAAACAGCATG | 47 | 9566 | 9581 | 855 |
| 799319 | N/A | N/A | TGCTGTGGATTTGAAA | 0 | 9638 | 9653 | 856 |
| 799320 | N/A | N/A | GTCTGCTGTGGATTTG | 0 | 9641 | 9656 | 857 |
| 790719 | N/A | N/A | GGACAGTCTGCTGTGG | 86 | 9646 | 9661 | 858 |
| 799321 | N/A | N/A | ATCTGGACAGTCTGCT | 93 | 9650 | 9665 | 859 |
| 798806 | 1013 | 1028 | TGAAAGCCCCCAGGG | 50 | 9710 | 9725 | 860 |
| 799534 | N/A | N/A | GAGAATGAAGTCCAGA | 68 | 9823 | 9838 | 861 |
| 799535 | N/A | N/A | AACTTAAGGCATATAA | 42 | 9843 | 9858 | 862 |
| 799536 | N/A | N/A | ACCGATGCATCCAACT | 50 | 9855 | 9870 | 863 |
| 799537 | N/A | N/A | GGGCACCACAATGTCA | 3 | 9873 | 9888 | 864 |
| 799538 | N/A | N/A | TGCAGGATGAGGAGCT | 29 | 9892 | 9907 | 865 |
| 799539 | N/A | N/A | CCCGTCCACGGAACGG | 41 | 9933 | 9948 | 866 |
| 799540 | N/A | N/A | AGCTGAAGCCCCCAA | 76 | 10020 | 10035 | 867 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799541 | N/A | N/A | TTAATGACACCAAAGT | 55 | 10041 | 10056 | 868 |
| 799542 | N/A | N/A | GTTAATGACACCAAAG | 30 | 10042 | 10057 | 869 |
| 799543 | N/A | N/A | TCAAATGCATGAGTTA | 65 | 10054 | 10069 | 870 |
| 799554 | N/A | N/A | TACCTGTGAGCCCTGA | 0 | 10324 | 10339 | 871 |
| 799555 | N/A | N/A | TACCCCGTGCCTGTCA | 51 | 10386 | 10401 | 872 |
| 799556 | N/A | N/A | ACAACAATGCTCTGGC | 68 | 10402 | 10417 | 873 |
| 799557 | N/A | N/A | AGCCAGTTCTTAGAAA | 28 | 10548 | 10563 | 874 |
| 799558 | N/A | N/A | CTTCTATTCGAGCTGC | 47 | 10652 | 10667 | 875 |
| 799559 | N/A | N/A | AGCTTCTATTCGAGCT | 37 | 10654 | 10669 | 876 |
| 799560 | N/A | N/A | GGCACAGCTTCTATTC | 18 | 10659 | 10674 | 877 |
| 799561 | N/A | N/A | GGAATGAACTTTGCCT | 45 | 10766 | 10781 | 878 |
| 799562 | N/A | N/A | GAAGAGGAGAGCCGGG | 39 | 10796 | 10811 | 879 |
| 799563 | N/A | N/A | AAAACAAACAAGGGTC | 68 | 10845 | 10860 | 880 |
| 799574 | N/A | N/A | CATTCAGGGTTTAAAA | 7 | 11147 | 11162 | 881 |
| 799575 | N/A | N/A | CACATTCAGGGTTTAA | 38 | 11149 | 11164 | 882 |
| 799576 | N/A | N/A | GAAAGGACCCTTTCAA | 25 | 11223 | 11238 | 883 |
| 799577 | N/A | N/A | TTCCGAAAGGACCCTT | 55 | 11227 | 11242 | 884 |
| 799578 | N/A | N/A | ACCTTCCGAAAGGACC | 76 | 11230 | 11245 | 885 |
| 799579 | N/A | N/A | AACCTTCCGAAAGGAC | 51 | 11231 | 11246 | 886 |
| 799580 | N/A | N/A | AAACCTTCCGAAAGGA | 33 | 11232 | 11247 | 887 |
| 799581 | N/A | N/A | CAAACCTTCCGAAAGG | 0 | 11233 | 11248 | 888 |
| 799582 | N/A | N/A | ACAAACCTTCCGAAAG | 19 | 11234 | 11249 | 889 |
| 772801 | N/A | N/A | GACAAACCTTCCGAAA | 34 | 11235 | 11250 | 890 |
| 799593 | N/A | N/A | GAAGGAGCTCAAACTT | 0 | 11996 | 12011 | 891 |
| 799594 | N/A | N/A | TGAACGGAAAGAAGAA | 35 | 12009 | 12024 | 892 |
| 799595 | N/A | N/A | CTCTGAACGGAAAGAA | 35 | 12012 | 12027 | 893 |
| 799596 | N/A | N/A | ACTCTGAACGGAAAGA | 49 | 12013 | 12028 | 894 |
| 799597 | N/A | N/A | AACTCTGAACGGAAAG | 46 | 12014 | 12029 | 895 |
| 799598 | N/A | N/A | CAACTCTGAACGGAAA | 39 | 12015 | 12030 | 896 |
| 799599 | N/A | N/A | CCAACTCTGAACGGAA | 12 | 12016 | 12031 | 897 |
| 799600 | N/A | N/A | GCACCAACTCTGAACG | 63 | 12019 | 12034 | 898 |
| 799601 | N/A | N/A | GAATACACTGCACCAA | 48 | 12028 | 12043 | 899 |
| 799602 | N/A | N/A | CCATTATGAATACACT | 51 | 12035 | 12050 | 900 |
| 799613 | N/A | N/A | TCACATTCGGCTGTTT | 17 | 12600 | 12615 | 901 |
| 799614 | N/A | N/A | GGCCTTTGAGCACACC | 37 | 12644 | 12659 | 902 |
| 799615 | N/A | N/A | GGAGAGGACCGGCCTT | 24 | 12654 | 12669 | 903 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 772813 | N/A | N/A | AAGGGCGCAGGAAAGG | 43 | 12704 | 12719 | 904 |
| 799616 | N/A | N/A | GGCTCCTACCCGCCCA | 80 | 12745 | 12760 | 905 |
| 799617 | N/A | N/A | CAACCTGCAGCCAGCA | 50 | 12773 | 12788 | 906 |
| 799618 | N/A | N/A | AACAAAGCTGCAATGC | 0 | 12797 | 12812 | 907 |
| 799619 | N/A | N/A | ACGACCAGGCCTGTCG | 9 | 12840 | 12855 | 908 |
| 799620 | N/A | N/A | TAACGACCAGGCCTGT | 31 | 12842 | 12857 | 909 |
| 799621 | N/A | N/A | TTTCACTGCAAGTCCC | 49 | 12858 | 12873 | 910 |
| 799632 | N/A | N/A | CTGCCAAATCACAAAG | 48 | 13237 | 13252 | 911 |
| 799633 | N/A | N/A | AGACTGCCAAATCACA | 25 | 13240 | 13255 | 912 |
| 799634 | N/A | N/A | CAGACTGCCAAATCAC | 23 | 13241 | 13256 | 913 |
| 799635 | N/A | N/A | ACAGACTGCCAAATCA | 28 | 13242 | 13257 | 914 |
| 799636 | N/A | N/A | CACAGACTGCCAAATC | 55 | 13243 | 13258 | 915 |
| 799637 | N/A | N/A | GCACAGACTGCCAAAT | 48 | 13244 | 13259 | 916 |
| 799638 | N/A | N/A | AGTCAGGCACAGACTG | 53 | 13250 | 13265 | 917 |
| 799639 | N/A | N/A | CCAGAGAGTCAGGCAC | 34 | 13256 | 13271 | 918 |
| 799640 | N/A | N/A | CAAGGACCTGTTCTGG | 40 | 13301 | 13316 | 919 |
| 799641 | N/A | N/A | CATCAGACCTCTCCCA | 33 | 13360 | 13375 | 920 |
| 799652 | N/A | N/A | ACTCAAACCAGGACAG | 0 | 13538 | 13553 | 921 |
| 799653 | N/A | N/A | ACCCACTCAAACCAGG | 51 | 13542 | 13557 | 922 |
| 799654 | N/A | N/A | GCTGAATAACCTACAA | 22 | 13584 | 13599 | 923 |
| 799655 | N/A | N/A | TGCAGCTGAATAACCT | 47 | 13588 | 13603 | 924 |
| 799656 | N/A | N/A | CTAACTGGGCAGGTCC | 60 | 13668 | 13683 | 925 |
| 799657 | N/A | N/A | TACAAGTGGTTGCTGG | 62 | 13699 | 13714 | 926 |
| 799658 | N/A | N/A | AACTACAAGTGGTTGC | 22 | 13702 | 13717 | 927 |
| 799659 | N/A | N/A | AAATAACTACAAGTGG | 57 | 13706 | 13721 | 928 |
| 799660 | N/A | N/A | TGGGAGCACTTCTTTT | 35 | 13729 | 13744 | 929 |
| 799661 | N/A | N/A | CTCCACTGCCTCCTAC | 44 | 13763 | 13778 | 930 |
| 799672 | N/A | N/A | ACAGGATGGAGCAATG | 41 | 14114 | 14129 | 931 |
| 799673 | N/A | N/A | CTGATTAACTTTCCTT | 64 | 14133 | 14148 | 932 |
| 799674 | N/A | N/A | GATCACAATTCCAAGC | 48 | 14177 | 14192 | 933 |
| 799675 | N/A | N/A | TCCCAGTTCATGATCA | 0 | 14188 | 14203 | 934 |
| 799676 | N/A | N/A | GAAACCATGAGCTGTT | 64 | 14268 | 14283 | 935 |
| 799677 | N/A | N/A | GCTCATGAGCATTTGG | 68 | 14359 | 14374 | 936 |
| 799678 | N/A | N/A | CACAAGCACCTGTCCA | 0 | 14396 | 14411 | 937 |
| 799679 | N/A | N/A | CTGCAGGGTACTAAGG | 0 | 14441 | 14456 | 938 |
| 799680 | N/A | N/A | GAGTTCTAGGCCGTCA | 33 | 14471 | 14486 | 939 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799681 | N/A | N/A | ACTCATCCTGTTGGCA | 53 | 14518 | 14533 | 940 |
| 799692 | N/A | N/A | ACACAGTAACAACAAT | 0 | 15426 | 15441 | 941 |
| 799693 | N/A | N/A | TTATGACACAGTAACA | 17 | 15431 | 15446 | 942 |
| 799694 | N/A | N/A | AAGGAATTATGACACA | 7 | 15437 | 15452 | 943 |
| 799695 | N/A | N/A | CCAGGAACCAGCACTT | 6 | 15564 | 15579 | 944 |
| 799696 | N/A | N/A | AAGTTATCTGGGAAGC | 43 | 15613 | 15628 | 945 |
| 799697 | N/A | N/A | AATAGTTTTCTCTCAA | 59 | 15651 | 15666 | 946 |
| 799698 | N/A | N/A | TAATAGTTTTCTCTCA | 33 | 15652 | 15667 | 947 |
| 799699 | N/A | N/A | CAAAACAGTGGACCAT | 57 | 15678 | 15693 | 948 |
| 799700 | N/A | N/A | CATGACAGCAAAGCAA | 49 | 15691 | 15706 | 949 |
| 799701 | N/A | N/A | CTACAGTTCCAGAACA | 46 | 15762 | 15777 | 950 |
| 799712 | N/A | N/A | ATAGATTATCCAAGTA | 70 | 15903 | 15918 | 951 |
| 799713 | N/A | N/A | CACAATCACTGTTCCT | 0 | 15920 | 15935 | 952 |
| 799714 | N/A | N/A | CACCAAAACAAGTGTC | 33 | 15988 | 16003 | 953 |
| 799715 | N/A | N/A | CCTCAGGGCTGCCACC | 32 | 16000 | 16015 | 954 |
| 799716 | N/A | N/A | GGCTACCAGCCTTGCT | 32 | 16046 | 16061 | 955 |
| 799717 | N/A | N/A | GCAGGCTACCAGCCTT | 0 | 16049 | 16064 | 956 |
| 799718 | N/A | N/A | CTGCTAGGGATACTGA | 65 | 16230 | 16245 | 957 |
| 799719 | N/A | N/A | CCTTTCTACTAGAAAA | 19 | 16285 | 16300 | 958 |
| 799720 | N/A | N/A | ACACACAGCAGAAGGC | 40 | 16408 | 16423 | 959 |
| 799721 | N/A | N/A | GTAACACACAGCAGAA | 42 | 16411 | 16426 | 960 |
| 799731 | N/A | N/A | CTTTCTTGGTGTGTTA | 37 | 16951 | 16966 | 961 |
| 799732 | N/A | N/A | GGGATCAGGTGAGTGT | 48 | 16969 | 16984 | 962 |
| 799733 | N/A | N/A | GTTTAGGTAGAGTGGC | 27 | 16986 | 17001 | 963 |
| 799734 | N/A | N/A | TCCCAGGTGAACCCAC | 45 | 17055 | 17070 | 964 |
| 799735 | N/A | N/A | TCCACGGGAGTGGAAG | 0 | 17079 | 17094 | 965 |
| 799736 | N/A | N/A | TTCTACACCTTTTAAG | 56 | 17155 | 17170 | 966 |
| 799737 | N/A | N/A | CTTAGAGTATAAATAC | 5 | 17178 | 17193 | 967 |
| 799738 | N/A | N/A | TCAAAAAATGTCCCCA | 50 | 17195 | 17210 | 968 |
| 799739 | N/A | N/A | CACCCCTATCAAAAAA | 0 | 17203 | 17218 | 969 |
| 799740 | N/A | N/A | TTAAATAACTGTCCTC | 48 | 17254 | 17269 | 970 |
| 799751 | N/A | N/A | GAGCTAATGACACTGG | 60 | 17699 | 17714 | 971 |
| 799752 | N/A | N/A | TTAAAACTGAGCTAAT | 0 | 17707 | 17722 | 972 |
| 799753 | N/A | N/A | CGTGAGTAAATTCTTA | 69 | 17767 | 17782 | 973 |
| 799754 | N/A | N/A | GGCTAAGTGCCAGGTG | 0 | 17831 | 17846 | 974 |
| 799755 | N/A | N/A | GAAAGTTACAGAACTC | 77 | 17906 | 17921 | 975 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799756 | N/A | N/A | CAGGGCAGCTCCGAGA | 44 | 17968 | 17983 | 976 |
| 799757 | N/A | N/A | CCGTTACTGGACACAG | 41 | 17990 | 18005 | 977 |
| 799758 | N/A | N/A | CACCGTTACTGGACAC | 57 | 17992 | 18007 | 978 |
| 799759 | N/A | N/A | ACCATATCACTCCTTC | 66 | 18021 | 18036 | 979 |
| 799760 | N/A | N/A | TTCTAGGTGAACCATA | 58 | 18031 | 18046 | 980 |
| 799771 | N/A | N/A | GCATATGCCACTGAGA | 0 | 18475 | 18490 | 981 |
| 799772 | N/A | N/A | CGCCGCGGCATATGCC | 30 | 18482 | 18497 | 982 |
| 799773 | N/A | N/A | CGCTAGGTCACACTCA | 43 | 18500 | 18515 | 983 |
| 799774 | N/A | N/A | GCCCTGTTCTGCGCTA | 0 | 18511 | 18526 | 984 |
| 799775 | N/A | N/A | ACACAAGAGGGAAGCC | 22 | 18524 | 18539 | 985 |
| 799776 | N/A | N/A | CAGAAGGACCAAGTCC | 11 | 18563 | 18578 | 986 |
| 799777 | N/A | N/A | AGTCAGCCAGAAGGAC | 34 | 18570 | 18585 | 987 |
| 799778 | N/A | N/A | GCACACCTTCCAAGCA | 10 | 18589 | 18604 | 988 |
| 799779 | N/A | N/A | TAAACAAACCACAGGG | 19 | 18690 | 18705 | 989 |
| 799780 | N/A | N/A | CCATAAACAAACCACA | 28 | 18693 | 18708 | 990 |
| 799791 | N/A | N/A | GGGAGACCTACCTCTG | 56 | 19070 | 19085 | 991 |
| 799792 | N/A | N/A | ACCAAAACCCGGGAGA | 31 | 19080 | 19095 | 992 |
| 799793 | N/A | N/A | GTTCTTCCTGCTGTCA | 30 | 19137 | 19152 | 993 |
| 799794 | N/A | N/A | AACCACAGCTCCTGTT | 0 | 19150 | 19165 | 994 |
| 799795 | N/A | N/A | CCAGATGTTTCCCCAC | 66 | 19263 | 19278 | 995 |
| 799796 | N/A | N/A | CATTAGATACTGTCTT | 43 | 19280 | 19295 | 996 |
| 799797 | N/A | N/A | GACATTAGATACTGTC | 27 | 19282 | 19297 | 997 |
| 799798 | N/A | N/A | TCCCACTTCTCCTCTG | 50 | 19306 | 19321 | 998 |
| 799799 | N/A | N/A | AAAACATCCCACTTCT | 28 | 19312 | 19327 | 999 |
| 799800 | N/A | N/A | TTACAAAGGGAAAGTC | 28 | 19342 | 19357 | 1000 |
| 799811 | N/A | N/A | CTGCCAACGGCACAGT | 0 | 19880 | 19895 | 1001 |
| 799812 | N/A | N/A | CAGACAGCTAATCTGC | 39 | 19892 | 19907 | 1002 |
| 799813 | N/A | N/A | ATGCAGACAGCTAATC | 16 | 19895 | 19910 | 1003 |
| 799814 | N/A | N/A | CCTCACTTAGCCTGCA | 0 | 20006 | 20021 | 1004 |
| 799815 | N/A | N/A | CTCTTGATGATCCTCA | 68 | 20017 | 20032 | 1005 |
| 799816 | N/A | N/A | TGACAAGGTCCCCAGG | 19 | 20038 | 20053 | 1006 |
| 799817 | N/A | N/A | TACTGATTCATGAGGG | 45 | 20090 | 20105 | 1007 |
| 799818 | N/A | N/A | CACTGATAACTAACTT | 24 | 20125 | 20140 | 1008 |
| 799819 | N/A | N/A | CCCCACTGAGCAGGAG | 26 | 20186 | 20201 | 1009 |
| 799820 | N/A | N/A | CCCCAGCAGGGTTTTG | 0 | 20209 | 20224 | 1010 |
| 799831 | N/A | N/A | TACTTGGAAGAGTTTG | 18 | 20664 | 20679 | 1011 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799832 | N/A | N/A | CACCCATACTTGGAAG | 14 | 20670 | 20685 | 1012 |
| 799833 | N/A | N/A | TTTCTGAACAGAGTCC | 39 | 20694 | 20709 | 1013 |
| 799834 | N/A | N/A | GTGGTATAGCATGCAT | 0 | 20711 | 20726 | 1014 |
| 799835 | N/A | N/A | GCAGATGTATACAAAT | 70 | 20728 | 20743 | 1015 |
| 799836 | N/A | N/A | AGATATCGGCCCCCTG | 61 | 20743 | 20758 | 1016 |
| 799837 | N/A | N/A | TCATAAGCATAGATTT | 38 | 20800 | 20815 | 1017 |
| 799838 | N/A | N/A | TTGCACCCCCATAACT | 2 | 20821 | 20836 | 1018 |
| 799839 | N/A | N/A | AGCACAATATGAATGT | 36 | 20943 | 20958 | 1019 |
| 799840 | N/A | N/A | AGGGAAGTTAGTGTTT | 22 | 21022 | 21037 | 1020 |
| 799851 | N/A | N/A | AAGTGTCCATCAAGCA | 70 | 21276 | 21291 | 1021 |
| 799852 | N/A | N/A | CAAGTGTCCATCAAGC | 11 | 21277 | 21292 | 1022 |
| 799853 | N/A | N/A | CCAAGTGTCCATCAAG | 42 | 21278 | 21293 | 1023 |
| 799854 | N/A | N/A | GCCAAGTGTCCATCAA | 45 | 21279 | 21294 | 1024 |
| 799855 | N/A | N/A | AGCCAAGTGTCCATCA | 52 | 21280 | 21295 | 1025 |
| 799856 | N/A | N/A | GCAAGCCAAGTGTCCA | 43 | 21283 | 21298 | 1026 |
| 799857 | N/A | N/A | AGAACTGAAAGCGGCG | 31 | 21363 | 21378 | 1027 |
| 799858 | N/A | N/A | GTAATTTAGCAATTCC | 64 | 21400 | 21415 | 1028 |
| 799859 | N/A | N/A | TGTAATTTAGCAATTC | 32 | 21401 | 21416 | 1029 |
| 799860 | N/A | N/A | TGCCGACACATGAGGC | 0 | 21476 | 21491 | 1030 |
| 799871 | N/A | N/A | TTGGACACACTCACTG | 0 | 21912 | 21927 | 1031 |
| 799872 | N/A | N/A | AAGTTAATCATTACTT | 0 | 21959 | 21974 | 1032 |
| 799873 | N/A | N/A | AAAAGTTAATCATTAC | 0 | 21961 | 21976 | 1033 |
| 799874 | N/A | N/A | CAGACTGGAAAAGTTA | 0 | 21969 | 21984 | 1034 |
| 799875 | N/A | N/A | GTGCAGACTGGAAAAG | 41 | 21972 | 21987 | 1035 |
| 799876 | N/A | N/A | GCCAGGGCCGCACTGT | 55 | 22029 | 22044 | 1036 |
| 799877 | N/A | N/A | ACTTTACAACCCAATA | 52 | 22060 | 22075 | 1037 |
| 799878 | N/A | N/A | GCCCCCCTCCCCGTGC | 70 | 22101 | 22116 | 1038 |
| 799879 | N/A | N/A | TGGAAAAGCTCCTTCT | 3 | 22139 | 22154 | 1039 |
| 799880 | N/A | N/A | TCCGATGGAAAAGCTC | 39 | 22144 | 22159 | 1040 |
| 799891 | N/A | N/A | ATCATTAAGCCAATTT | 0 | 22556 | 22571 | 1041 |
| 799892 | N/A | N/A | GCATCATTAAGCCAAT | 54 | 22558 | 22573 | 1042 |
| 799893 | N/A | N/A | ATACAAACCACTGCAT | 0 | 22570 | 22585 | 1043 |
| 799894 | N/A | N/A | TCCCAACTGGGCAGCT | 2 | 22711 | 22726 | 1044 |
| 799895 | N/A | N/A | CTGAGAGTGTAGGAGA | 50 | 22750 | 22765 | 1045 |
| 799896 | N/A | N/A | CTTACCTCACCCACCT | 36 | 22780 | 22795 | 1046 |
| 799897 | N/A | N/A | TCTCTTACCTCACCCA | 27 | 22783 | 22798 | 1047 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 799898 | N/A | N/A | GTCTCTTACCTCACCC | 37 | 22784 | 22799 | 1048 |
| 799899 | N/A | N/A | AAGTCTCTTACCTCAC | 33 | 22786 | 22801 | 1049 |
| 799900 | N/A | N/A | CAAGTCTCTTACCTCA | 51 | 22787 | 22802 | 1050 |
| 799910 | N/A | N/A | CCAACTCCATTCATAA | 36 | 23119 | 23134 | 1051 |
| 799911 | N/A | N/A | AGCCAACTCCATTCAT | 0 | 23121 | 23136 | 1052 |
| 799912 | N/A | N/A | CTCAGAGGAAGGGTGG | 22 | 23150 | 23165 | 1053 |
| 799913 | N/A | N/A | GGCCTCAGAGGAAGGG | 18 | 23153 | 23168 | 1054 |
| 799914 | N/A | N/A | CTGAGAGAGGCCTCAG | 24 | 23161 | 23176 | 1055 |
| 799915 | N/A | N/A | GCTGACGCGGCTTCCT | 52 | 23268 | 23283 | 1056 |
| 799916 | N/A | N/A | CACAAATCAAAAGCTC | 47 | 23304 | 23319 | 1057 |
| 799917 | N/A | N/A | TGGAGAATGTAATTGA | 17 | 23349 | 23364 | 1058 |
| 799918 | N/A | N/A | CATTTATCTCGCCATG | 16 | 23363 | 23378 | 1059 |
| 799919 | N/A | N/A | TCCTAAGAGCATTTAT | 0 | 23372 | 23387 | 1060 |
| 799930 | N/A | N/A | TCTTTTATCACTGTCA | 8 | 23649 | 23664 | 1061 |
| 799932 | N/A | N/A | TCAAGAGACGGTGAGC | 0 | 23680 | 23695 | 1062 |
| 799933 | N/A | N/A | TACTATTCATCACCCT | 22 | 23695 | 23710 | 1063 |
| 799934 | N/A | N/A | ACTTTTTACTCTGTCT | 61 | 23711 | 23726 | 1064 |
| 799935 | N/A | N/A | AGAAATGACTTTTTAC | 42 | 23718 | 23733 | 1065 |
| 799936 | N/A | N/A | CTTTAATTTCAGAGTC | 44 | 23734 | 23749 | 1066 |
| 799937 | N/A | N/A | TCTTTAATTTCAGAGT | 24 | 23735 | 23750 | 1067 |
| 799938 | N/A | N/A | CTCTAAACCAACTTTT | 17 | 23756 | 23771 | 1068 |
| 799939 | N/A | N/A | GCATTTAATTTGCAAC | 38 | 23832 | 23847 | 1069 |
| 799950 | N/A | N/A | GCACAAGTCACTGGCC | 0 | 24279 | 24294 | 1070 |
| 799951 | N/A | N/A | TCTTAAAAAAGGGAG | 0 | 24308 | 24323 | 1071 |
| 799952 | N/A | N/A | CTCTAAGTGGCTCATG | 30 | 24359 | 24374 | 1072 |
| 799953 | N/A | N/A | AGAAAATGCCCACCAG | 0 | 24471 | 24486 | 1073 |
| 799954 | N/A | N/A | CAGAAAATGCCCACCA | 42 | 24472 | 24487 | 1074 |
| 799955 | N/A | N/A | CGCTCAGAAAATGCCC | 50 | 24476 | 24491 | 1075 |
| 799956 | N/A | N/A | TCTCCAGCCGCTCAGA | 57 | 24484 | 24499 | 1076 |
| 799957 | N/A | N/A | TCTGAGGCTCCTGGGT | 11 | 24500 | 24515 | 1077 |
| 799958 | N/A | N/A | GTGGAGAGTGCTGCAC | 23 | 24532 | 24547 | 1078 |
| 799959 | N/A | N/A | AGCTTGTGGAGAGTGC | 1 | 24537 | 24552 | 1079 |
| 799970 | N/A | N/A | TCCTCAGGAAACACAG | 43 | 25075 | 25090 | 1080 |
| 799971 | N/A | N/A | GTAAAACTTGCTGAGA | 31 | 25182 | 25197 | 1081 |
| 799972 | N/A | N/A | CACAAGGACCCTTGCT | 0 | 25244 | 25259 | 1082 |
| 799973 | N/A | N/A | ATAATTCACAAGGACC | 0 | 25250 | 25265 | 1083 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799974 | N/A | N/A | GACTCCAGTGCCAATC | 23 | 25295 | 25310 | 1084 |
| 799975 | N/A | N/A | TCTTCAGGGACAAGCC | 38 | 25324 | 25339 | 1085 |
| 799976 | N/A | N/A | TCAAAGGTTAACAGCA | 34 | 25397 | 25412 | 1086 |
| 799977 | N/A | N/A | GGACATCTCAAAGGTT | 36 | 25404 | 25419 | 1087 |
| 799978 | N/A | N/A | CTCCACAACGGACATC | 24 | 25413 | 25428 | 1088 |
| 799979 | N/A | N/A | AACGGTTGCCTCATCC | 38 | 25438 | 25453 | 1089 |
| 799990 | N/A | N/A | TTGCACCTGGCAACCT | 0 | 25527 | 25542 | 1090 |
| 799991 | N/A | N/A | GGCCGCCTCCTGCAGG | 19 | 25596 | 25611 | 1091 |
| 799992 | N/A | N/A | GGCACGGCCGCCTCCT | 9 | 25601 | 25616 | 1092 |
| 799993 | N/A | N/A | ATAATGAAGTGATATT | 0 | 25725 | 25740 | 1093 |
| 799994 | N/A | N/A | ACTTGGATAATGAAGT | 2 | 25731 | 25746 | 1094 |
| 799995 | N/A | N/A | CTGTGAGGCACTTGGA | 63 | 25740 | 25755 | 1095 |
| 799996 | N/A | N/A | GACCCACGGTTAAATG | 36 | 25827 | 25842 | 1096 |
| 799997 | N/A | N/A | ATGACCCACGGTTAAA | 14 | 25829 | 25844 | 1097 |
| 799998 | N/A | N/A | CAGTAAAGACATGAGC | 45 | 25856 | 25871 | 1098 |
| 799999 | N/A | N/A | TTAGGAACAAGGGCAA | 23 | 25888 | 25903 | 1099 |
| 800010 | N/A | N/A | GTTATTTAATTACCCT | 69 | 26603 | 26618 | 1100 |
| 790847 | N/A | N/A | TCTTACAAAGAGTTAT | 24 | 26614 | 26629 | 1101 |
| 800011 | N/A | N/A | CTTCAGCCTGTGTTTG | 21 | 26672 | 26687 | 1102 |
| 800012 | N/A | N/A | GAGGACTTCAGCCTGT | 49 | 26677 | 26692 | 1103 |
| 800013 | N/A | N/A | AAAGGAGAGGACTTCA | 56 | 26683 | 26698 | 1104 |
| 800014 | N/A | N/A | TAAAGCATAAAATCCT | 21 | 26732 | 26747 | 1105 |
| 800015 | N/A | N/A | CTTTAAGGTGTTGCCC | 26 | 26772 | 26787 | 1106 |
| 800016 | N/A | N/A | GTTCATTTTAAAGCAT | 32 | 26913 | 26928 | 1107 |
| 800017 | N/A | N/A | TAAAACAGTATGTGTT | 11 | 26926 | 26941 | 1108 |
| 800018 | N/A | N/A | AAAACTCACAGTCCTT | 51 | 27028 | 27043 | 1109 |
| 800029 | N/A | N/A | CCTGAATCGGGCCCAC | 0 | 27192 | 27207 | 1110 |
| 800030 | N/A | N/A | AAACACAGTTCCCTGA | 0 | 27203 | 27218 | 1111 |
| 800031 | N/A | N/A | AGAAACACAGTTCCCT | 52 | 27205 | 27220 | 1112 |
| 800032 | N/A | N/A | GAATTCCCCGCCATTT | 0 | 27258 | 27273 | 1113 |
| 800033 | N/A | N/A | CACTACAGAGATTCCC | 52 | 27283 | 27298 | 1114 |
| 800034 | N/A | N/A | CCGCACGACATCCCCC | 47 | 27304 | 27319 | 1115 |
| 800035 | N/A | N/A | CAAAGGCCCCTCGAAC | 34 | 27357 | 27372 | 1116 |
| 800036 | N/A | N/A | GTTAGGACAGCTCCAG | 38 | 27444 | 27459 | 1117 |
| 800037 | N/A | N/A | CACCAGCAGCCTCTGT | 0 | 27466 | 27481 | 1118 |
| 800038 | N/A | N/A | TGCTCCTCCCTCGCTG | 2 | 27498 | 27513 | 1119 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 800049 | N/A | N/A | AACAAACCTGGCCTGG | 7 | 28026 | 28041 | 1120 |
| 800050 | N/A | N/A | GCTTATTTTCCCAATT | 10 | 28048 | 28063 | 1121 |
| 800051 | N/A | N/A | CAGCACATCCACCCTT | 20 | 28104 | 28119 | 1122 |
| 800052 | N/A | N/A | CCCTCTTCCGGGAGGC | 0 | 28121 | 28136 | 1123 |
| 800053 | N/A | N/A | CTACACCAAAGACCTG | 63 | 28191 | 28206 | 1124 |
| 800054 | N/A | N/A | GCTACACCAAAGACCT | 62 | 28192 | 28207 | 1125 |
| 800055 | N/A | N/A | ATAAACTTGTGAGCGC | 8 | 28252 | 28267 | 1126 |
| 800056 | N/A | N/A | TGCTAATAAACTTGTG | 7 | 28257 | 28272 | 1127 |
| 800057 | N/A | N/A | TTCACTTGTTTCTGCA | 46 | 28287 | 28302 | 1128 |
| 800058 | N/A | N/A | TCATCAGGCATTCACT | 51 | 28297 | 28312 | 1129 |
| 800069 | N/A | N/A | CATGGCGGAAGATGGG | 25 | 28849 | 28864 | 1130 |
| 800070 | N/A | N/A | CCATGGCGGAAGATGG | 9 | 28850 | 28865 | 1131 |
| 800071 | N/A | N/A | TGTATTTGTTAACAAA | 2 | 29077 | 29092 | 1132 |
| 800072 | N/A | N/A | GACTTGGGACCATAAA | 0 | 29160 | 29175 | 1133 |
| 800073 | N/A | N/A | TAAGTAGGAGCCAGCG | 39 | 29187 | 29202 | 1134 |
| 800074 | N/A | N/A | GGGCATTCTGACTCCT | 33 | 29206 | 29221 | 1135 |
| 800075 | N/A | N/A | TAATTTTCCTCAACAG | 55 | 29278 | 29293 | 1136 |
| 800076 | N/A | N/A | CGCTTCCCTACACAGT | 25 | 29336 | 29351 | 1137 |
| 800077 | N/A | N/A | CCTTAACAAAGCTTCC | 36 | 29524 | 29539 | 1138 |
| 800078 | N/A | N/A | ACCTTAACAAAGCTTC | 51 | 29525 | 29540 | 1139 |
| 800089 | N/A | N/A | AGGAACCTATCTGGTA | 0 | 29690 | 29705 | 1140 |
| 800090 | N/A | N/A | CACCTATGCGATGGTC | 0 | 29751 | 29766 | 1141 |
| 800091 | N/A | N/A | TGACACAGCCAGAGCT | 0 | 29794 | 29809 | 1142 |
| 800092 | N/A | N/A | ATCCTGATGAGAAAAC | 0 | 29847 | 29862 | 1143 |
| 800093 | N/A | N/A | TTGAAGGCCAGCTCCT | 48 | 29876 | 29891 | 1144 |
| 800094 | N/A | N/A | ATGGAACCTTGAAGGC | 49 | 29884 | 29899 | 1145 |
| 800095 | N/A | N/A | AGTTACAGATCTTTCA | 47 | 29905 | 29920 | 1146 |
| 800096 | N/A | N/A | TGGAGTTACAGATCTT | 32 | 29908 | 29923 | 1147 |
| 800097 | N/A | N/A | GCCTCAAAAAGCCTCA | 1 | 29933 | 29948 | 1148 |
| 800098 | N/A | N/A | TTTTAGGGCCTCAAAA | 1 | 29940 | 29955 | 1149 |
| 790507 | 1028 | 1043 | AAGAAGTTGGGAATCT | 0 | 30295 | 30310 | 1150 |
| 772597 | 1072 | 1087 | CAGTATGCCACCACGC | 0 | 30339 | 30354 | 1151 |
| 798819 | 1075 | 1090 | TCCCAGTATGCCACCA | 0 | 30342 | 30357 | 1152 |
| 798820 | 1080 | 1095 | TCTCCTCCCAGTATGC | 24 | 30347 | 30362 | 1153 |
| 798821 | 1099 | 1114 | AGCCTCCCCACTCTCG | 32 | 30366 | 30381 | 1154 |
| 798822 | 1103 | 1118 | GTAGAGCCTCCCCACT | 56 | 30370 | 30385 | 1155 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798823 | 1106 | 1121 | ACAGTAGAGCCTCCCC | 74 | 30373 | 30388 | 1156 |
| 798824 | 1109 | 1124 | GACACAGTAGAGCCTC | 74 | 30376 | 30391 | 1157 |
| 798825 | 1112 | 1127 | CTGGACACAGTAGAGC | 24 | 30379 | 30394 | 1158 |
| 798826 | 1115 | 1130 | CTCCTGGACACAGTAG | 14 | 30382 | 30397 | 1159 |
| 798827 | 1123 | 1138 | AGAGAGGGCTCCTGGA | 21 | 30390 | 30405 | 1160 |
| 798835 | 1167 | 1182 | CGAGGCAAAAGCCATT | 22 | 30434 | 30449 | 1161 |
| 798836 | 1170 | 1185 | GTCCGAGGCAAAAGCC | 56 | 30437 | 30452 | 1162 |
| 798837 | 1173 | 1188 | GCTGTCCGAGGCAAAA | 33 | 30440 | 30455 | 1163 |
| 772613 | 1178 | 1193 | ATTGAGCTGTCCGAGG | 7 | 30445 | 30460 | 1164 |
| 798838 | 1182 | 1197 | CCGAATTGAGCTGTCC | 58 | 30449 | 30464 | 1165 |
| 798839 | 1187 | 1202 | GTTGTCCGAATTGAGC | 47 | 30454 | 30469 | 1166 |
| 798840 | 1192 | 1207 | CTCTTGTTGTCCGAAT | 56 | 30459 | 30474 | 1167 |
| 798841 | 1196 | 1211 | CTGACTCTTGTTGTCC | 0 | 30463 | 30478 | 1168 |
| 798842 | 1199 | 1214 | CAGCTGACTCTTGTTG | 0 | 30466 | 30481 | 1169 |
| 790513 | 1202 | 1217 | CACCAGCTGACTCTTG | 10 | 30469 | 30484 | 1170 |
| 798853 | 1265 | 1280 | CCACACACCATCCACC | 7 | 30532 | 30547 | 1171 |
| 798854 | 1270 | 1285 | TACACCCACACACCAT | 25 | 30537 | 30552 | 1172 |
| 798855 | 1273 | 1288 | TTGTACACCCACACAC | 11 | 30540 | 30555 | 1173 |
| 798856 | 1278 | 1293 | TGCGGTTGTACACCCA | 67 | 30545 | 30560 | 1174 |
| 798857 | 1281 | 1296 | TGCTGCGGTTGTACAC | 11 | 30548 | 30563 | 1175 |
| 772621 | 1284 | 1299 | AACTGCTGCGGTTGTA | 38 | 30551 | 30566 | 1176 |
| 798858 | 1287 | 1302 | GGTAACTGCTGCGGTT | 46 | 30554 | 30569 | 1177 |
| 798859 | 1305 | 1320 | CGGACTTGATGAAGAT | 14 | 30572 | 30587 | 1178 |
| 798860 | 1308 | 1323 | TGGCGGACTTGATGAA | 22 | 30575 | 30590 | 1179 |
| 772628 | 1375 | 1390 | GCCTTGATGGAGAAAC | 33 | 30642 | 30657 | 1180 |
| 798871 | 1378 | 1393 | AAAGCCTTGATGGAGA | 20 | 30645 | 30660 | 1181 |
| 798872 | 1384 | 1399 | TAGTCGAAAGCCTTGA | 2 | 30651 | 30666 | 1182 |
| 798873 | 1400 | 1415 | GCTGTACGCCTTCTCG | 27 | 30667 | 30682 | 1183 |
| 798874 | 1404 | 1419 | GCAGGCTGTACGCCTT | 27 | 30671 | 30686 | 1184 |
| 798875 | 1408 | 1423 | CGCTGCAGGCTGTACG | 58 | 30675 | 30690 | 1185 |
| 798876 | 1411 | 1426 | GGCCGCTGCAGGCTGT | 50 | 30678 | 30693 | 1186 |
| 798877 | 1416 | 1431 | CATTGGGCCGCTGCAG | 24 | 30683 | 30698 | 1187 |
| 772633 | 1419 | 1434 | GGTCATTGGGCCGCTG | 37 | 30686 | 30701 | 1188 |
| 798878 | 1436 | 1451 | CTGCTGCATAAACTCG | 49 | 30703 | 30718 | 1189 |
| 798889 | 1472 | 1487 | CACAAAGCTGATCTGC | 0 | 30739 | 30754 | 1190 |
| 798890 | 1475 | 1490 | CTTCACAAAGCTGATC | 40 | 30742 | 30757 | 1191 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 798891 | 1478 | 1493 | GCCCTTCACAAAGCTG | 58 | 30745 | 30760 | 1192 |
| 798892 | 1483 | 1498 | CCCCAGCCCTTCACAA | 39 | 30750 | 30765 | 1193 |
| 798893 | 1486 | 1501 | TGGCCCCAGCCCTTCA | 77 | 30753 | 30768 | 1194 |
| 798894 | 1491 | 1506 | AGCACTGGCCCCAGCC | 55 | 30758 | 30773 | 1195 |
| 798895 | 1494 | 1509 | TGTAGCACTGGCCCCA | 53 | 30761 | 30776 | 1196 |
| 798896 | 1497 | 1512 | GGGTGTAGCACTGGCC | 46 | 30764 | 30779 | 1197 |
| 798897 | 1500 | 1515 | GGCGGGTGTAGCACTG | 60 | 30767 | 30782 | 1198 |
| 790531 | 1512 | 1527 | TGCTGATGAACTGGCG | 8 | 30779 | 30794 | 1199 |
| 798906 | 1554 | 1569 | GCTACCGGCTGTTGAA | 0 | 30821 | 30836 | 1200 |
| 790533 | 1555 | 1570 | GGCTACCGGCTGTTGA | 16 | 30822 | 30837 | 1201 |
| 798907 | 1557 | 1572 | GCGGCTACCGGCTGTT | 0 | 30824 | 30839 | 1202 |
| 798908 | 1558 | 1573 | CGCGGCTACCGGCTGT | 0 | 30825 | 30840 | 1203 |
| 798909 | 1559 | 1574 | ACGCGGCTACCGGCTG | 42 | 30826 | 30841 | 1204 |
| 798910 | 1560 | 1575 | CACGCGGCTACCGGCT | 42 | 30827 | 30842 | 1205 |
| 798911 | 1561 | 1576 | GCACGCGGCTACCGGC | 0 | 30828 | 30843 | 1206 |
| 798912 | 1564 | 1579 | TCCGCACGCGGCTACC | 22 | 30831 | 30846 | 1207 |
| 798913 | 1567 | 1582 | CCCTCCGCACGCGGCT | 21 | 30834 | 30849 | 1208 |
| 798914 | 1570 | 1585 | GTCCCTCCGCACGCG | 56 | 30837 | 30852 | 1209 |
| 798925 | 1606 | 1621 | AGTAGTTTGAAGTGTG | 0 | 30873 | 30888 | 1210 |
| 798926 | 1609 | 1624 | CAAAGTAGTTTGAAGT | 17 | 30876 | 30891 | 1211 |
| 798927 | 1612 | 1627 | CAGCAAAGTAGTTTGA | 0 | 30879 | 30894 | 1212 |
| 798928 | 1615 | 1630 | TAGCAGCAAAGTAGTT | 6 | 30882 | 30897 | 1213 |
| 798929 | 1618 | 1633 | TATTAGCAGCAAAGTA | 41 | 30885 | 30900 | 1214 |
| 798930 | 1623 | 1638 | GAAAATATTAGCAGCA | 62 | 30890 | 30905 | 1215 |
| 798931 | 1626 | 1641 | GAGGAAAATATTAGCA | 69 | 30893 | 30908 | 1216 |
| 798932 | 1631 | 1646 | CTCAGGAGGAAAATAT | 0 | 30898 | 30913 | 1217 |
| 798933 | 1634 | 1649 | GCACTCAGGAGGAAAA | 52 | 30901 | 30916 | 1218 |
| 798934 | 1638 | 1653 | GCAAGCACTCAGGAGG | 40 | 30905 | 30920 | 1219 |
| 798943 | 1704 | 1719 | CGAGGACGAGAAGAAG | 13 | 30971 | 30986 | 1220 |
| 798944 | 1707 | 1722 | AAACGAGGACGAGAAG | 3 | 30974 | 30989 | 1221 |
| 798945 | 1710 | 1725 | CACAAACGAGGACGAG | 19 | 30977 | 30992 | 1222 |
| 798946 | 1713 | 1728 | GAACACAAACGAGGAC | 4 | 30980 | 30995 | 1223 |
| 798947 | 1716 | 1731 | ACAGAACACAAACGAG | 52 | 30983 | 30998 | 1224 |
| 798948 | 1726 | 1741 | GCGAAACAAAACAGAA | 56 | 30993 | 31008 | 1225 |
| 798949 | 1729 | 1744 | AGAGCGAAACAAAACA | 55 | 30996 | 31011 | 1226 |
| 798950 | 1732 | 1747 | CAAAGAGCGAAACAAA | 0 | 30999 | 31014 | 1227 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798951 | 1735 | 1750 | TCTCAAAGAGCGAAAC | 37 | 31002 | 31017 | 1228 |
| 798952 | 1739 | 1754 | TATTTCTCAAAGAGCG | 61 | 31006 | 31021 | 1229 |
| 798963 | 1777 | 1792 | TTCTTCCAAAAAACC | 13 | 31044 | 31059 | 1230 |
| 798964 | 1780 | 1795 | CCCTTCTTCCAAAAAA | 32 | 31047 | 31062 | 1231 |
| 798965 | 1783 | 1798 | TGCCCCTTCTTCCAAA | 43 | 31050 | 31065 | 1232 |
| 798966 | 1787 | 1802 | TACCTGCCCCTTCTTC | 35 | 31054 | 31069 | 1233 |
| 798967 | 1790 | 1805 | TCATACCTGCCCCTTC | 40 | 31057 | 31072 | 1234 |
| 798968 | 1793 | 1808 | CGATCATACCTGCCCC | 62 | 31060 | 31075 | 1235 |
| 798969 | 1796 | 1811 | TGCCGATCATACCTGC | 48 | 31063 | 31078 | 1236 |
| 798970 | 1799 | 1814 | TCCTGCCGATCATACC | 41 | 31066 | 31081 | 1237 |
| 798971 | 1803 | 1818 | GGTGTCCTGCCGATCA | 53 | 31070 | 31085 | 1238 |
| 798972 | 1809 | 1824 | TATCAGGGTGTCCTGC | 18 | 31076 | 31091 | 1239 |
| 798983 | 1861 | 1876 | CCCCTTCATACACTGT | 0 | 31128 | 31143 | 1240 |
| 798984 | 1864 | 1879 | GCCCCCCTTCATACAC | 64 | 31131 | 31146 | 1241 |
| 798985 | 1868 | 1883 | GACCGCCCCCCTTCAT | 41 | 31135 | 31150 | 1242 |
| 798986 | 1871 | 1886 | GATGACCGCCCCCCTT | 34 | 31138 | 31153 | 1243 |
| 798987 | 1874 | 1889 | AATGATGACCGCCCCC | 84 | 31141 | 31156 | 1244 |
| 798988 | 1877 | 1892 | TGAAATGATGACCGCC | 69 | 31144 | 31159 | 1245 |
| 798989 | 1880 | 1895 | AAGTGAAATGATGACC | 8 | 31147 | 31162 | 1246 |
| 798990 | 1883 | 1898 | GACAAGTGAAATGATG | 39 | 31150 | 31165 | 1247 |
| 798991 | 1886 | 1901 | CCTGACAAGTGAAATG | 23 | 31153 | 31168 | 1248 |
| 798992 | 1889 | 1904 | ACTCCTGACAAGTGAA | 29 | 31156 | 31171 | 1249 |
| 799003 | 1917 | 1932 | ACACAGCCGCACACTC | 0 | 31184 | 31199 | 1250 |
| 799004 | 1921 | 1936 | GCACACACAGCCGCAC | 0 | 31188 | 31203 | 1251 |
| 799005 | 1924 | 1939 | CGTGCACACACAGCCG | 0 | 31191 | 31206 | 1252 |
| 799006 | 1938 | 1953 | CGCTCCTGCACACGCG | 0 | 31205 | 31220 | 1253 |
| 799007 | 1941 | 1956 | TGCCGCTCCTGCACAC | 47 | 31208 | 31223 | 1254 |
| 799008 | 1946 | 1961 | CCATCTGCCGCTCCTG | 60 | 31213 | 31228 | 1255 |
| 799009 | 1949 | 1964 | TCCCCATCTGCCGCTC | 62 | 31216 | 31231 | 1256 |
| 799010 | 1956 | 1971 | CGTTGTCTCCCCATCT | 57 | 31223 | 31238 | 1257 |
| 799011 | 1970 | 1985 | CAAAACAAAGAGCACG | 35 | 31237 | 31252 | 1258 |
| 799012 | 1980 | 1995 | ATAAGAGACACAAAAC | 43 | 31247 | 31262 | 1259 |
| 799023 | 2012 | 2027 | TGGGACTGCAAACCTC | 42 | 31279 | 31294 | 1260 |
| 799024 | 2014 | 2029 | CTTGGGACTGCAAACC | 0 | 31281 | 31296 | 1261 |
| 799025 | 2016 | 2031 | CGCTTGGGACTGCAAA | 10 | 31283 | 31298 | 1262 |
| 799026 | 2017 | 2032 | CCGCTTGGGACTGCAA | 1 | 31284 | 31299 | 1263 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799027 | 2018 | 2033 | ACCGCTTGGGACTGCA | 46 | 31285 | 31300 | 1264 |
| 799028 | 2022 | 2037 | AGACACCGCTTGGGAC | 37 | 31289 | 31304 | 1265 |
| 799029 | 2026 | 2041 | GGAGAGACACCGCTTG | 0 | 31293 | 31308 | 1266 |
| 771576 | 2027 | 2046 | GGGCAGGAGAGACACCGCTT | 50 | 31294 | 31313 | 576 |
| 799030 | 2029 | 2044 | GCAGGAGAGACACCGC | 52 | 31296 | 31311 | 1267 |
| 799031 | 2059 | 2074 | TGCCTCTGCCCCACTG | 46 | 31326 | 31341 | 1268 |
| 799032 | 2065 | 2080 | AGGTACTGCCTCTGCC | 42 | 31332 | 31347 | 1269 |
| 799043 | 2111 | 2126 | AGCCGTGCTCCTGGCA | 0 | 31378 | 31393 | 1270 |
| 799043 | 2111 | 2126 | AGCCGTGCTCCTGGCA | 10 | 31378 | 31393 | 1270 |
| 799044 | 2114 | 2129 | CAGAGCCGTGCTCCTG | 0 | 31381 | 31396 | 1271 |
| 799045 | 2117 | 2132 | GGACAGAGCCGTGCTC | 37 | 31384 | 31399 | 1272 |
| 799046 | 2133 | 2148 | GGCTTTCCCAGGCTGG | 0 | 31400 | 31415 | 1273 |
| 799047 | 2157 | 2172 | TTGATGAGGGAGAGGA | 63 | 31424 | 31439 | 1274 |
| 799048 | 2160 | 2175 | TCCTTGATGAGGGAGA | 60 | 31427 | 31442 | 1275 |
| 799049 | 2167 | 2182 | GCCCGTGTCCTTGATG | 44 | 31434 | 31449 | 1276 |
| 799050 | 2171 | 2186 | ACAGGCCCGTGTCCTT | 36 | 31438 | 31453 | 1277 |
| 799051 | 2174 | 2189 | TGGACAGGCCCGTGTC | 32 | 31441 | 31456 | 1278 |
| 799052 | 2177 | 2192 | CTGTGGACAGGCCCGT | 40 | 31444 | 31459 | 1279 |
| 799063 | 2218 | 2233 | TGGTTCTGGTTCGGCC | 9 | 31485 | 31500 | 1280 |
| 799064 | 2222 | 2237 | TAATTGGTTCTGGTTC | 47 | 31489 | 31504 | 1281 |
| 799065 | 2225 | 2240 | AAATAATTGGTTCTGG | 35 | 31492 | 31507 | 1282 |
| 799066 | 2228 | 2243 | TGAAAATAATTGGTTC | 0 | 31495 | 31510 | 1283 |
| 799067 | 2231 | 2246 | GGATGAAAATAATTGG | 74 | 31498 | 31513 | 1284 |
| 799068 | 2236 | 2251 | GACAAGGATGAAAATA | 49 | 31503 | 31518 | 1285 |
| 799069 | 2240 | 2255 | ATAAGACAAGGATGAA | 18 | 31507 | 31522 | 1286 |
| 799070 | 2245 | 2260 | AGGGAATAAGACAAGG | 67 | 31512 | 31527 | 1287 |
| 799071 | 2248 | 2263 | GGAAGGGAATAAGACA | 44 | 31515 | 31530 | 1288 |
| 799072 | 2251 | 2266 | GCAGGAAGGGAATAAG | 55 | 31518 | 31533 | 1289 |
| 799083 | 2320 | 2335 | GGAAGCCCATCTCAGG | 0 | 31587 | 31602 | 1290 |
| 799084 | 2324 | 2339 | CTTGGGAAGCCCATCT | 0 | 31591 | 31606 | 1291 |
| 799085 | 2327 | 2342 | GCCCTTGGGAAGCCCA | 10 | 31594 | 31609 | 1292 |
| 799086 | 2331 | 2346 | GGCAGCCCTTGGGAAG | 0 | 31598 | 31613 | 1293 |
| 799087 | 2335 | 2350 | CCCCGGCAGCCCTTGG | 69 | 31602 | 31617 | 1294 |
| 799088 | 2339 | 2354 | GCTGCCCCGGCAGCCC | 24 | 31606 | 31621 | 1295 |
| 799089 | 2356 | 2371 | AGCAATACTGTGAGGG | 60 | 31623 | 31638 | 1296 |
| 799090 | 2359 | 2374 | GTGAGCAATACTGTGA | 49 | 31626 | 31641 | 1297 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799091 | 2364 | 2379 | ACTGGGTGAGCAATAC | 42 | 31631 | 31646 | 1298 |
| 799092 | 2367 | 2382 | GGCACTGGGTGAGCAA | 30 | 31634 | 31649 | 1299 |
| 799103 | 2420 | 2435 | CCGGGAAAAACCTGAT | 12 | 31687 | 31702 | 1300 |
| 799104 | 2423 | 2438 | AGTCCGGGAAAAACCT | 40 | 31690 | 31705 | 1301 |
| 799105 | 2426 | 2441 | CTAAGTCCGGGAAAAA | 12 | 31693 | 31708 | 1302 |
| 799106 | 2430 | 2445 | TTTTCTAAGTCCGGGA | 34 | 31697 | 31712 | 1303 |
| 799107 | 2434 | 2449 | CTGGTTTTCTAAGTCC | 51 | 31701 | 31716 | 1304 |
| 799108 | 2439 | 2454 | CTGAGCTGGTTTTCTA | 64 | 31706 | 31721 | 1305 |
| 799109 | 2444 | 2459 | CAGTGCTGAGCTGGTT | 48 | 31711 | 31726 | 1306 |
| 799110 | 2447 | 2462 | AGGCAGTGCTGAGCTG | 33 | 31714 | 31729 | 1307 |
| 799111 | 2450 | 2465 | AGCAGGCAGTGCTGAG | 50 | 31717 | 31732 | 1308 |
| 799112 | 2453 | 2468 | GGGAGCAGGCAGTGCT | 58 | 31720 | 31735 | 1309 |
| 799123 | 2489 | 2504 | CTTGCTGGCCTAATAG | 23 | 31756 | 31771 | 1310 |
| 799124 | 2492 | 2507 | CCGCTTGCTGGCCTAA | 17 | 31759 | 31774 | 1311 |
| 799125 | 2495 | 2510 | TCCCCGCTTGCTGGCC | 62 | 31762 | 31777 | 1312 |
| 799126 | 2499 | 2514 | GACATCCCCGCTTGCT | 4 | 31766 | 31781 | 1313 |
| 799127 | 2502 | 2517 | AGGGACATCCCCGCTT | 67 | 31769 | 31784 | 1314 |
| 799128 | 2505 | 2520 | CCCAGGGACATCCCCG | 63 | 31772 | 31787 | 1315 |
| 799129 | 2508 | 2523 | CCTCCCAGGGACATCC | 37 | 31775 | 31790 | 1316 |
| 799130 | 2511 | 2526 | GTCCCTCCCAGGGACA | 1 | 31778 | 31793 | 1317 |
| 799131 | 2514 | 2529 | CATGTCCCTCCCAGGG | 6 | 31781 | 31796 | 1318 |
| 799132 | 2517 | 2532 | AAGCATGTCCCTCCCA | 38 | 31784 | 31799 | 1319 |
| 799143 | 2562 | 2577 | TGGGTTATGACGGACC | 66 | 31829 | 31844 | 1320 |
| 799144 | 2563 | 2578 | TTGGGTTATGACGGAC | 72 | 31830 | 31845 | 1321 |
| 799145 | 2564 | 2579 | CTTGGGTTATGACGGA | 46 | 31831 | 31846 | 1322 |
| 799146 | 2567 | 2582 | TACCTTGGGTTATGAC | 0 | 31834 | 31849 | 1323 |
| 799147 | 2568 | 2583 | GTACCTTGGGTTATGA | 28 | 31835 | 31850 | 1324 |
| 799148 | 2570 | 2585 | TGGTACCTTGGGTTAT | 29 | 31837 | 31852 | 1325 |
| 799149 | 2573 | 2588 | GGATGGTACCTTGGGT | 46 | 31840 | 31855 | 1326 |
| 799150 | 2576 | 2591 | CTAGGATGGTACCTTG | 22 | 31843 | 31858 | 1327 |
| 799151 | 2579 | 2594 | AGCCTAGGATGGTACC | 39 | 31846 | 31861 | 1328 |
| 799152 | 2583 | 2598 | TGTCAGCCTAGGATGG | 33 | 31850 | 31865 | 1329 |
| 799163 | 2633 | 2648 | AAGTATCATACGAGTG | 45 | 31900 | 31915 | 1330 |
| 799164 | 2636 | 2651 | TCGAAGTATCATACGA | 37 | 31903 | 31918 | 1331 |
| 799165 | 2639 | 2654 | GTGTCGAAGTATCATA | 42 | 31906 | 31921 | 1332 |
| 799166 | 2643 | 2658 | AACAGTGTCGAAGTAT | 21 | 31910 | 31925 | 1333 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799167 | 2646 | 2661 | AAGAACAGTGTCGAAG | 58 | 31913 | 31928 | 1334 |
| 799168 | 2649 | 2664 | GCTAAGAACAGTGTCG | 75 | 31916 | 31931 | 1335 |
| 799169 | 2653 | 2668 | TTGAGCTAAGAACAGT | 0 | 31920 | 31935 | 1336 |
| 799170 | 2656 | 2671 | TCATTGAGCTAAGAAC | 17 | 31923 | 31938 | 1337 |
| 799171 | 2659 | 2674 | TGCTCATTGAGCTAAG | 30 | 31926 | 31941 | 1338 |
| 799172 | 2663 | 2678 | AACATGCTCATTGAGC | 4 | 31930 | 31945 | 1339 |
| 799183 | 2699 | 2714 | CTTTGTAGTTAGAAAA | 0 | 31966 | 31981 | 1340 |
| 799184 | 2702 | 2717 | AACCTTTGTAGTTAGA | 58 | 31969 | 31984 | 1341 |
| 799185 | 2705 | 2720 | TTAAACCTTTGTAGTT | 0 | 31972 | 31987 | 1342 |
| 790613 | 2708 | 2723 | CATTTAAACCTTTGTA | 0 | 31975 | 31990 | 1343 |
| 772689 | 2711 | 2726 | GTTCATTTAAACCTTT | 26 | 31978 | 31993 | 1344 |
| 799186 | 2714 | 2729 | CTTGTTCATTTAAACC | 31 | 31981 | 31996 | 1345 |
| 799187 | 2719 | 2734 | CTTCTCTTGTTCATTT | 17 | 31986 | 32001 | 1346 |
| 799188 | 2721 | 2736 | TGCTTCTCTTGTTCAT | 43 | 31988 | 32003 | 1347 |
| 799189 | 2723 | 2738 | AATGCTTCTCTTGTTC | 33 | 31990 | 32005 | 1348 |
| 799190 | 2725 | 2740 | AGAATGCTTCTCTTGT | 61 | 31992 | 32007 | 1349 |
| 799197 | 2756 | 2771 | CTCAAAGCACTACAAT | 34 | 32023 | 32038 | 1350 |
| 772696 | 2759 | 2774 | TCTCTCAAAGCACTAC | 56 | 32026 | 32041 | 1351 |
| 799198 | 2767 | 2782 | GTCCTTTCTCTCTCAA | 17 | 32034 | 32049 | 1352 |
| 799199 | 2770 | 2785 | GGAGTCCTTTCTCTCT | 24 | 32037 | 32052 | 1353 |
| 799200 | 2773 | 2788 | TCAGGAGTCCTTTCTC | 69 | 32040 | 32055 | 1354 |
| 799201 | 2776 | 2791 | TTTTCAGGAGTCCTTT | 38 | 32043 | 32058 | 1355 |
| 799202 | 2779 | 2794 | TTTTTTTCAGGAGTCC | 33 | 32046 | 32061 | 1356 |
| 799203 | 2782 | 2797 | GGTTTTTTTTCAGGAG | 56 | 32049 | 32064 | 1357 |
| 799204 | 2786 | 2801 | CTCAGGTTTTTTTCA | 36 | 32053 | 32068 | 1358 |
| 799205 | 2791 | 2806 | TAAATCTCAGGTTTTT | 54 | 32058 | 32073 | 1359 |
| 799213 | 2899 | 2914 | TGTTTATACACATTGC | 42 | 32166 | 32181 | 1360 |
| 799214 | 2903 | 2918 | TTCTTGTTTATACACA | 46 | 32170 | 32185 | 1361 |
| 790621 | 2922 | 2937 | GTGCATCTTTTCTTTA | 0 | 32189 | 32204 | 1362 |
| 772708 | 2925 | 2940 | AAAGTGCATCTTTTCT | 0 | 32192 | 32207 | 1363 |
| 799215 | 2928 | 2943 | AGCAAAGTGCATCTTT | 0 | 32195 | 32210 | 1364 |
| 772709 | 2931 | 2946 | TAAAGCAAAGTGCATC | 0 | 32198 | 32213 | 1365 |
| 799216 | 2934 | 2949 | TATTAAAGCAAAGTGC | 49 | 32201 | 32216 | 1366 |
| 790623 | 2941 | 2956 | GCATTTATATTAAAGC | 0 | 32208 | 32223 | 1367 |
| 799217 | 2948 | 2963 | GTTATTTGCATTTATA | 0 | 32215 | 32230 | 1368 |
| 799218 | 2953 | 2968 | CATTTGTTATTTGCAT | 0 | 32220 | 32235 | 1369 |

TABLE 7-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 772712 | 3000 | 3015 | ACCCATAGAAAAAAAC | 0 | 32267 | 32282 | 1370 |
| 799229 | 3003 | 3018 | AACACCCATAGAAAAA | 22 | 32270 | 32285 | 1371 |
| 790626 | 3006 | 3021 | GATAACACCCATAGAA | 0 | 32273 | 32288 | 1372 |
| 799230 | 3009 | 3024 | GGTGATAACACCCATA | 14 | 32276 | 32291 | 1373 |
| 799231 | 3013 | 3028 | GCTAGGTGATAACACC | 8 | 32280 | 32295 | 1374 |
| 799232 | 3016 | 3031 | TCAGCTAGGTGATAAC | 13 | 32283 | 32298 | 1375 |
| 799233 | 3019 | 3034 | CATTCAGCTAGGTGAT | 28 | 32286 | 32301 | 1376 |
| 799234 | 3022 | 3037 | AAACATTCAGCTAGGT | 13 | 32289 | 32304 | 1377 |
| 799235 | 3025 | 3040 | GAAAACATTCAGCTA | 24 | 32292 | 32307 | 1378 |
| 772717 | 3034 | 3049 | ACTCCTTTAGAAAAAC | 28 | 32301 | 32316 | 1379 |
| 798786 | 888 | 903 | ACTCTAGTTCGCAGAG | 11 | N/A | N/A | 1380 |
| 798787 | 891 | 906 | GAGACTCTAGTTCGCA | 20 | N/A | N/A | 1381 |
| 798807 | 1016 | 1031 | ATCTGAAAGCCCCCCA | 64 | N/A | N/A | 1382 |
| 798808 | 1019 | 1034 | GGAATCTGAAAGCCCC | 44 | N/A | N/A | 1383 |
| 798809 | 1022 | 1037 | TTGGGAATCTGAAAGC | 2 | N/A | N/A | 1384 |
| 798810 | 1025 | 1040 | AAGTTGGGAATCTGAA | 0 | N/A | N/A | 1385 |

TABLE 8

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 798664 | 40 | 55 | GGCCTGCGCTCCGGCT | 7 | 1535 | 1550 | 1386 |
| 798665 | 98 | 113 | CAGTCTCCCGGAGGCC | 7 | 1593 | 1608 | 1387 |
| 790458 | 101 | 116 | CGCCAGTCTCCCGGAG | 0 | 1596 | 1611 | 1388 |
| 798666 | 105 | 120 | CATGCGCCAGTCTCCC | 33 | 1600 | 1615 | 1389 |
| 798667 | 108 | 123 | TGGCATGCGCCAGTCT | 21 | 1603 | 1618 | 1390 |
| 798668 | 112 | 127 | TCCGTGGCATGCGCCA | 45 | 1607 | 1622 | 1391 |
| 798669 | 115 | 130 | CGCTCCGTGGCATGCG | 0 | 1610 | 1625 | 1392 |
| 798670 | 132 | 147 | GGCGGCGGCCCGAGGG | 44 | 1627 | 1642 | 1393 |
| 798671 | 135 | 150 | AGCGGCGGCGGCCCGA | 61 | 1630 | 1645 | 1394 |
| 790460 | 138 | 153 | AGGAGCGGCGGCGGCC | 58 | 1633 | 1648 | 1395 |
| 798678 | 214 | 229 | CGCACACCATGAAGAA | 45 | 1709 | 1724 | 1396 |
| 798679 | 217 | 232 | CTCCGCACACCATGAA | 32 | 1712 | 1727 | 1397 |
| 772536 | 220 | 235 | GACCTCCGCACACCAT | 22 | 1715 | 1730 | 1398 |
| 798680 | 223 | 238 | CATGACCTCCGCACAC | 31 | 1718 | 1733 | 1399 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 798681 | 226 | 241 | GAACATGACCTCCGCA | 29 | 1721 | 1736 | 1400 |
| 790464 | 229 | 244 | AGCGAACATGACCTCC | 58 | 1724 | 1739 | 1401 |
| 790465 | 233 | 248 | AAGGAGCGAACATGAC | 54 | 1728 | 1743 | 1402 |
| 798682 | 236 | 251 | GCTAAGGAGCGAACAT | 60 | 1731 | 1746 | 1403 |
| 798683 | 240 | 255 | GCCTGCTAAGGAGCGA | 51 | 1735 | 1750 | 1404 |
| 798684 | 245 | 260 | CGTTTGCCTGCTAAGG | 51 | 1740 | 1755 | 1405 |
| 798693 | 332 | 347 | GCCGGGCGCACGGCTC | 0 | 1827 | 1842 | 1406 |
| 798694 | 341 | 356 | GTCCTCGCCGCCGGGC | 0 | 1836 | 1851 | 1407 |
| 798695 | 356 | 371 | TGCGCCCTCCTCCTCG | 35 | 1851 | 1866 | 1408 |
| 798696 | 362 | 377 | TCCCCCTGCGCCCTCC | 82 | 1857 | 1872 | 1409 |
| 798697 | 365 | 380 | ACCTCCCCCTGCGCCC | 23 | 1860 | 1875 | 1410 |
| 798698 | 382 | 397 | AGCTCGCCTCCTCCTC | 57 | 1877 | 1892 | 1411 |
| 798699 | 385 | 400 | CGCAGCTCGCCTCCTC | 51 | 1880 | 1895 | 1412 |
| 798700 | 388 | 403 | CCCCGCAGCTCGCCTC | 52 | 1883 | 1898 | 1413 |
| 798701 | 393 | 408 | CTTCTCCCCGCAGCTC | 23 | 1888 | 1903 | 1414 |
| 798702 | 396 | 411 | CCCCTTCTCCCCGCAG | 45 | 1891 | 1906 | 1415 |
| 798713 | 431 | 446 | GCCGCCACCGGCCCCA | 45 | 1926 | 1941 | 1416 |
| 798714 | 435 | 450 | GGCCGCCGCCACCGGC | 0 | 1930 | 1945 | 1417 |
| 798715 | 440 | 455 | GCCCGGGCCGCCGCCA | 0 | 1935 | 1950 | 1418 |
| 798716 | 443 | 458 | CCTGCCCGGGCCGCCG | 0 | 1938 | 1953 | 1419 |
| 798717 | 446 | 461 | AGCCCTGCCCGGGCCG | 18 | 1941 | 1956 | 1420 |
| 798718 | 450 | 465 | ATCCAGCCCTGCCCGG | 37 | 1945 | 1960 | 1421 |
| 798719 | 453 | 468 | AGCATCCAGCCCTGCC | 34 | 1948 | 1963 | 1422 |
| 798720 | 456 | 471 | GGCAGCATCCAGCCCT | 25 | 1951 | 1966 | 1423 |
| 798721 | 461 | 476 | GCCCAGGCAGCATCCA | 41 | 1956 | 1971 | 1424 |
| 798722 | 464 | 479 | CTTGCCCAGGCAGCAT | 0 | 1959 | 1974 | 1425 |
| 798733 | 512 | 527 | CGCGGCTGGCGGGTGG | 72 | 2007 | 2022 | 1426 |
| 798734 | 515 | 530 | GCCCGCGGCTGGCGGG | 0 | 2010 | 2025 | 1427 |
| 798735 | 532 | 547 | CCCCCGGCCGCGCCGG | 0 | 2027 | 2042 | 1428 |
| 798736 | 535 | 550 | GCGCCCCGGCCGCGC | 0 | 2030 | 2045 | 1429 |
| 798737 | 548 | 563 | CAGATCCGCCTCGGCG | 2 | 2043 | 2058 | 1430 |
| 798738 | 551 | 566 | CTTCAGATCCGCCTCG | 25 | 2046 | 2061 | 1431 |
| 798739 | 554 | 569 | CGCCTTCAGATCCGCC | 37 | 2049 | 2064 | 1432 |
| 798740 | 574 | 589 | TTGAGCACCGAGTGCG | 56 | 2069 | 2084 | 1433 |
| 790476 | 577 | 592 | TTCTTGAGCACCGAGT | 67 | 2072 | 2087 | 1434 |
| 798741 | 584 | 599 | CTTCAGTTTCTTGAGC | 17 | 2079 | 2094 | 1435 |

TABLE 8-continued

Inhibition of SMAD7 mRNA expression by 3-10-3 cEt
gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 772556 | 655 | 670 | AGCAGGAGGCACGCGG | 43 | 2150 | 2165 | 1436 |
| 790479 | 658 | 673 | GGCAGCAGGAGGCACG | 43 | 2153 | 2168 | 1437 |
| 798751 | 661 | 676 | CCGGGCAGCAGGAGGC | 0 | 2156 | 2171 | 1438 |
| 798752 | 664 | 679 | CGGCCGGGCAGCAGGA | 0 | 2159 | 2174 | 1439 |
| 772557 | 671 | 686 | GTCCAGGCGGCCGGGC | 2 | 2166 | 2181 | 1440 |
| 798753 | 675 | 690 | TGCAGTCCAGGCGGCC | 0 | 2170 | 2185 | 1441 |
| 798754 | 679 | 694 | AGCCTGCAGTCCAGGC | 16 | 2174 | 2189 | 1442 |
| 798755 | 683 | 698 | GCCCAGCCTGCAGTCC | 46 | 2178 | 2193 | 1443 |
| 798756 | 692 | 707 | CGCCCCGGGCCCAGC | 16 | 2187 | 2202 | 1444 |
| 798757 | 714 | 729 | GCGCAGGCTGCGCGCC | 0 | 2209 | 2224 | 1445 |
| 798766 | 763 | 778 | CTGAACACTTTGCACA | 34 | 2258 | 2273 | 1446 |
| 790485 | 766 | 781 | CACCTGAACACTTTGC | 26 | 2261 | 2276 | 1447 |
| 772563 | 769 | 784 | GGCCACCTGAACACTT | 0 | 2264 | 2279 | 1448 |
| 798767 | 772 | 787 | TCCGGCCACCTGAACA | 0 | 2267 | 2282 | 1449 |
| 798768 | 776 | 791 | GAGATCCGGCCACCTG | 42 | 2271 | 2286 | 1450 |
| 798769 | 779 | 794 | CCTGAGATCCGGCCAC | 58 | 2274 | 2289 | 1451 |
| 772565 | 783 | 798 | AATGCCTGAGATCCGG | 64 | 2278 | 2293 | 1452 |
| 798770 | 786 | 801 | AGGAATGCCTGAGATC | 47 | 2281 | 2296 | 1453 |
| 798771 | 789 | 804 | CCGAGGAATGCCTGAG | 62 | 2284 | 2299 | 1454 |
| 798772 | 792 | 807 | CTTCCGAGGAATGCCT | 48 | 2287 | 2302 | 1455 |
| 798781 | 822 | 837 | CGTAAGATTCACAGCA | 52 | 2317 | 2332 | 1456 |
| 790492 | 825 | 840 | TCCCGTAAGATTCACA | 38 | 2320 | 2335 | 1457 |
| 772572 | 829 | 844 | ATCTTCCCGTAAGATT | 0 | 2324 | 2339 | 1458 |
| 790493 | 833 | 848 | GTTGATCTTCCCGTAA | 0 | 2328 | 2343 | 1459 |
| 772573 | 849 | 864 | AGCACACCAGCTCGGG | 57 | 2344 | 2359 | 1460 |
| 798782 | 852 | 867 | TGCAGCACACCAGCTC | 51 | 2347 | 2362 | 1461 |
| 798783 | 871 | 886 | CGGCTAAGGTGATGGG | 45 | 2366 | 2381 | 1462 |
| 798784 | 875 | 890 | GAGTCGGCTAAGGTGA | 35 | 2370 | 2385 | 1463 |
| 790496 | 878 | 893 | GCAGAGTCGGCTAAGG | 42 | 2373 | 2388 | 1464 |
| 790497 | 882 | 897 | GTTCGCAGAGTCGGCT | 23 | 2377 | 2392 | 1465 |
| 799328 | N/A | N/A | ATGCACACTCTCCCAG | 0 | 2510 2532 | 2525 2547 | 1466 |
| 799329 | N/A | N/A | GTATGCACACTCTCCC | 0 | 2512 2534 | 2527 2549 | 1467 |
| 799330 | N/A | N/A | GGTATGCACACTCTCC | 45 | 2513 2535 | 2528 2550 | 1468 |
| 799331 | N/A | N/A | AGGGTATGCACACTCT | 1 | 2515 2537 | 2530 2552 | 1469 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799332 | N/A | N/A | GGGAATGCCCTTTGAG | 45 | 2600 | 2615 | 1470 |
| 799333 | N/A | N/A | AGAAAACCTGGAAGGG | 24 | 2624 | 2639 | 1471 |
| 799334 | N/A | N/A | CCGTAGACCCCTTCGG | 21 | 2651 | 2666 | 1472 |
| 799335 | N/A | N/A | TGCAGGAGCAGTGCCC | 31 | 2665 | 2680 | 1473 |
| 799336 | N/A | N/A | ACTGCAGGAGCAGTGC | 25 | 2667 | 2682 | 1474 |
| 799337 | N/A | N/A | GTCTTTCCGGGTGCGG | 30 | 2759 | 2774 | 1475 |
| 799241 | N/A | N/A | ATTCTCCGTATTTACT | 16 | 2874 | 2889 | 1476 |
| 799252 | N/A | N/A | CAAAGGTGCGCGGCCA | 41 | 2922 | 2937 | 1477 |
| 799253 | N/A | N/A | CTCCAAAGGTGCGCGG | 0 | 2925 | 2940 | 1478 |
| 799254 | N/A | N/A | AAACTCCAAAGGTGCG | 11 | 2928 | 2943 | 1479 |
| 799255 | N/A | N/A | CAAAACTCCAAAGGTG | 0 | 2930 | 2945 | 1480 |
| 799256 | N/A | N/A | CCAAAACTCCAAAGGT | 0 | 2931 | 2946 | 1481 |
| 799257 | N/A | N/A | CCCCAAAACTCCAAAG | 27 | 2933 | 2948 | 1482 |
| 799258 | N/A | N/A | GCCCCAAAACTCCAAA | 4 | 2934 | 2949 | 1483 |
| 799259 | N/A | N/A | TGCCCCAAAACTCCAA | 45 | 2935 | 2950 | 1484 |
| 799260 | N/A | N/A | TTGCCCCAAAACTCCA | 27 | 2936 | 2951 | 1485 |
| 799261 | N/A | N/A | TTTGCCCCAAAACTCC | 52 | 2937 | 2952 | 1486 |
| 799348 | N/A | N/A | ATAAAAGGAAAGGAGT | 21 | 3169 | 3184 | 1487 |
| 799349 | N/A | N/A | AGCGCACTCGGGAGAT | 0 | 3301 | 3316 | 1488 |
| 799349 | N/A | N/A | AGCGCACTCGGGAGAT | 0 | 3301 | 3316 | 1488 |
| 799350 | N/A | N/A | ATTCCTAGCGCACTCG | 31 | 3307 | 3322 | 1489 |
| 799351 | N/A | N/A | TTTAGCTGTCAGATAA | 31 | 3606 | 3621 | 1490 |
| 799352 | N/A | N/A | GCGGTGATTGCCTTGA | 24 | 3624 | 3639 | 1491 |
| 799353 | N/A | N/A | TCTTTTAGCCCAACTG | 45 | 3678 | 3693 | 1492 |
| 799354 | N/A | N/A | ATCTACTCACCAGTTG | 0 | 3818 | 3833 | 1493 |
| 799355 | N/A | N/A | AGGAAACCTAGAACCA | 23 | 3935 | 3950 | 1494 |
| 799356 | N/A | N/A | GAAAAATTCACCAAAC | 23 | 3960 | 3975 | 1495 |
| 799357 | N/A | N/A | CACAACAGAAAAATTC | 41 | 3967 | 3982 | 1496 |
| 799367 | N/A | N/A | AGTCTCCGAGTTATCC | 41 | 4146 | 4161 | 1497 |
| 799368 | N/A | N/A | CTAAGTCTCCGAGTTA | 68 | 4149 | 4164 | 1498 |
| 799369 | N/A | N/A | ACTCACTAAGTCTCCG | 50 | 4154 | 4169 | 1499 |
| 799370 | N/A | N/A | GGCACTCACTAAGTCT | 13 | 4157 | 4172 | 1500 |
| 799371 | N/A | N/A | CCCTTTCCATTATTCC | 28 | 4186 | 4201 | 1501 |
| 799372 | N/A | N/A | CCCATCTATCGAATCA | 67 | 4202 | 4217 | 1502 |
| 799373 | N/A | N/A | AACCGTCTTCCCATCT | 56 | 4211 | 4226 | 1503 |
| 799374 | N/A | N/A | TTGCACCTTTTTAAAC | 30 | 4224 | 4239 | 1504 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 799375 | N/A | N/A | GCCTATACTTCTGAAA | 10 | 4273 | 4288 | 1505 |
| 799376 | N/A | N/A | GCAGGAGGAACCTACC | 45 | 4313 | 4328 | 1506 |
| 799387 | N/A | N/A | CCAGGAGCTAAATGGT | 22 | 4775 | 4790 | 1507 |
| 799388 | N/A | N/A | TTGCAGAATTCCAGGA | 41 | 4785 | 4800 | 1508 |
| 799389 | N/A | N/A | AAAACGCAGGAGGCGG | 27 | 4807 | 4822 | 1509 |
| 799390 | N/A | N/A | CAAAACTTTTAATTAG | 0 | 4845 | 4860 | 1510 |
| 799391 | N/A | N/A | CGCCCCAGCAAAACTT | 0 | 4853 | 4868 | 1511 |
| 799392 | N/A | N/A | TATTAGACCGGCACCA | 46 | 4980 | 4995 | 1512 |
| 799393 | N/A | N/A | TGCTTTGCGGGCCACT | 56 | 4996 | 5011 | 1513 |
| 799394 | N/A | N/A | ACAGAGAGCTGGGTAT | 33 | 5068 | 5083 | 1514 |
| 799395 | N/A | N/A | TTACAAATACAGAGAG | 62 | 5076 | 5091 | 1515 |
| 799396 | N/A | N/A | TGTTACAAATACAGAG | 69 | 5078 | 5093 | 1516 |
| 799407 | N/A | N/A | TGCAGGAAACCCAAGG | 33 | 5358 | 5373 | 1517 |
| 799408 | N/A | N/A | TTAAATCCTGAGAACA | 27 | 5392 | 5407 | 1518 |
| 799409 | N/A | N/A | CTACCTAATGTCAACA | 34 | 5475 | 5490 | 1519 |
| 799410 | N/A | N/A | TCTGTTTACACACATT | 79 | 5494 | 5509 | 1520 |
| 799411 | N/A | N/A | TGGAGAACTTTTCTCC | 0 | 5546 | 5561 | 1521 |
| 790680 | N/A | N/A | GGTGAGTAACCAGCTG | 56 | 5607 | 5622 | 1522 |
| 799412 | N/A | N/A | TTCTTACACAGCAGCG | 60 | 5669 | 5684 | 1523 |
| 799413 | N/A | N/A | ATTACTGATGCTAAAT | 34 | 5684 | 5699 | 1524 |
| 799414 | N/A | N/A | CAAAACCAGCCCCAGA | 34 | 5791 | 5806 | 1525 |
| 799415 | N/A | N/A | GCCACAGCAGCTGGCA | 0 | 5805 | 5820 | 1526 |
| 799426 | N/A | N/A | GCTTAAATTATAGCAA | 7 | 6153 | 6168 | 1527 |
| 799427 | N/A | N/A | GTCCAGGCCTCCCAGA | 20 | 6183 | 6198 | 1528 |
| 799428 | N/A | N/A | GACCACACAGTACCTA | 47 | 6209 | 6224 | 1529 |
| 799429 | N/A | N/A | CACAAGTCACAACTGG | 74 | 6279 | 6294 | 1530 |
| 799430 | N/A | N/A | AGCCACAAGTCACAAC | 29 | 6282 | 6297 | 1531 |
| 800109 | N/A | N/A | ACAGCCACAAGTCACA | 86 | 6284 | 6299 | 783 |
| 799431 | N/A | N/A | GACAGCCACAAGTCAC | 39 | 6285 | 6300 | 1532 |
| 799432 | N/A | N/A | TGACAGCCACAAGTCA | 7 | 6286 | 6301 | 1533 |
| 799433 | N/A | N/A | TTCTTGTGGGATGTGG | 56 | 6326 | 6341 | 1534 |
| 799434 | N/A | N/A | TGAAACACGGGAAGCA | 37 | 6392 | 6407 | 1535 |
| 799435 | N/A | N/A | TCCTCAAACCTTTCAG | 60 | 6422 | 6437 | 1536 |
| 799446 | N/A | N/A | GACCTAATCTCTTTCA | 48 | 6623 | 6638 | 1537 |
| 799447 | N/A | N/A | ATGAATGACCTAATCT | 30 | 6629 | 6644 | 1538 |
| 799448 | N/A | N/A | GTAAAATGAATGACTG | 41 | 6666 | 6681 | 1539 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799449 | N/A | N/A | CAGCACTGCATCGGAA | 37 | 6717 | 6732 | 1540 |
| 799450 | N/A | N/A | AAGAACACAGCACTGC | 53 | 6724 7026 | 6739 7041 | 1541 |
| 799451 | N/A | N/A | AAAGAACACAGCACTG | 41 | 6725 7027 | 6740 7042 | 1542 |
| 799452 | N/A | N/A | AAAAGAACACAGCACT | 44 | 6726 7028 | 6741 7043 | 1543 |
| 799453 | N/A | N/A | ACACAGCACTGCCAGG | 58 | 7022 | 7037 | 1544 |
| 799454 | N/A | N/A | TTAAAGACAGAGGAGC | 55 | 7127 | 7142 | 1545 |
| 799455 | N/A | N/A | TGTTAAAGACAGAGGA | 55 | 7129 | 7144 | 1546 |
| 799466 | N/A | N/A | GACAGAAGCTCTAGGC | 53 | 7368 | 7383 | 1547 |
| 799467 | N/A | N/A | GCAGACAGAAGCTCTA | 69 | 7371 | 7386 | 1548 |
| 799468 | N/A | N/A | TCACCTTAGGCCTGTG | 22 | 7417 | 7432 | 1549 |
| 799469 | N/A | N/A | CTCCGCATAGACAGAT | 69 | 7449 | 7464 | 1550 |
| 799470 | N/A | N/A | AAAAGCTCCGCATAGA | 10 | 7454 | 7469 | 1551 |
| 799471 | N/A | N/A | CACAGAAAAGCTCCGC | 71 | 7459 | 7474 | 1552 |
| 799472 | N/A | N/A | AGCCATACCTCCATCT | 31 | 7481 | 7496 | 1553 |
| 799473 | N/A | N/A | TATCCCATGGCTCTCA | 63 | 7576 | 7591 | 1554 |
| 799474 | N/A | N/A | CAAGAGTCCAGCCCTA | 39 | 7590 | 7605 | 1555 |
| 799475 | N/A | N/A | GTGAGCTGGGCTATTC | 51 | 7607 | 7622 | 1556 |
| 799485 | N/A | N/A | AGCCACTCCCCGCCAC | 0 | 7929 | 7944 | 1557 |
| 799486 | N/A | N/A | CATAATGACTTATCCA | 52 | 7946 | 7961 | 1558 |
| 799487 | N/A | N/A | AAACATAATGACTTAT | 0 | 7949 | 7964 | 1559 |
| 799488 | N/A | N/A | TGGAAGACACCCCCAC | 42 | 7968 | 7983 | 1560 |
| 799489 | N/A | N/A | TCTAAACCATTTTGAT | 0 | 8045 | 8060 | 1561 |
| 799490 | N/A | N/A | TTAAATGGTGTATACC | 0 | 8069 | 8084 | 1562 |
| 799491 | N/A | N/A | GGCAGGCAGGAAATGG | 38 | 8094 | 8109 | 1563 |
| 799492 | N/A | N/A | AAACAATAGAGGCAGG | 58 | 8104 | 8119 | 1564 |
| 799493 | N/A | N/A | ATACACTTAATCAAAC | 1 | 8123 | 8138 | 1565 |
| 799494 | N/A | N/A | AGGATACACTTAATCA | 45 | 8126 | 8141 | 1566 |
| 799505 | N/A | N/A | CCCGGCTAAGGAAAGG | 31 | 8593 | 8608 | 1567 |
| 799506 | N/A | N/A | GGAGAGCCCGGCTAAG | 4 | 8599 | 8614 | 1568 |
| 799507 | N/A | N/A | ACTCATTAGTCCCATG | 34 | 8687 | 8702 | 1569 |
| 799508 | N/A | N/A | GCAATTAAAGCAAAAC | 0 | 8722 | 8737 | 1570 |
| 799509 | N/A | N/A | AGAAACAGTCTCCACA | 57 | 8750 | 8765 | 1571 |
| 799510 | N/A | N/A | GAGAAACAGTCTCCAC | 57 | 8751 | 8766 | 1572 |
| 799511 | N/A | N/A | TAATGACAATTCCAGC | 65 | 8768 | 8783 | 1573 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799512 | N/A | N/A | GTTAATGAGGATAATG | 16 | 8779 | 8794 | 1574 |
| 799513 | N/A | N/A | TACCTTTAGATTGCAT | 66 | 8860 | 8875 | 1575 |
| 799514 | N/A | N/A | TCGGAGTTTCCTCACT | 40 | 8882 | 8897 | 1576 |
| 799524 | N/A | N/A | ATCAAGGGCAGAAGGC | 23 | 9272 | 9287 | 1577 |
| 799525 | N/A | N/A | AGGTTTGGGTTGGACT | 8 | 9318 | 9333 | 1578 |
| 799526 | N/A | N/A | AAGGAGGTTTGGGTTG | 12 | 9322 | 9337 | 1579 |
| 799527 | N/A | N/A | GTCAAAGGAGGTTTGG | 4 | 9326 | 9341 | 1580 |
| 799528 | N/A | N/A | CGGATACCAGGTGGTT | 17 | 9348 | 9363 | 1581 |
| 799529 | N/A | N/A | GAATTTCTCTTGCATT | 27 | 9379 | 9394 | 1582 |
| 799530 | N/A | N/A | GCTCAATGAGACTGGC | 34 | 9397 | 9412 | 1583 |
| 799272 | N/A | N/A | ATTACTCGAGTCAGGC | 55 | 9411 | 9426 | 1584 |
| 799273 | N/A | N/A | ATCATTACTCGAGTCA | 41 | 9414 | 9429 | 1585 |
| 799274 | N/A | N/A | TTAATCATTACTCGAG | 24 | 9417 | 9432 | 1586 |
| 799275 | N/A | N/A | CAGTTAATCATTACTC | 0 | 9420 | 9435 | 1587 |
| 790714 | N/A | N/A | AGCCAGTTAATCATTA | 11 | 9423 | 9438 | 1588 |
| 799276 | N/A | N/A | GGCAGCCAGTTAATCA | 29 | 9426 | 9441 | 1589 |
| 799277 | N/A | N/A | CTCCGGGCAGCCAGTT | 21 | 9431 | 9446 | 1590 |
| 799278 | N/A | N/A | CCCGTCTGGGCTCCGG | 14 | 9441 | 9456 | 1591 |
| 790715 | N/A | N/A | TGTCACCCGTCTGGGC | 16 | 9446 | 9461 | 1592 |
| 799279 | N/A | N/A | ACCTTGTCACCCGTCT | 48 | 9450 | 9465 | 1593 |
| 799289 | N/A | N/A | TATTAATGGTCTGCTC | 61 | 9500 | 9515 | 1594 |
| 799290 | N/A | N/A | GATTATTAATGGTCTG | 16 | 9503 | 9518 | 1595 |
| 799291 | N/A | N/A | GCTGATTATTAATGGT | 0 | 9506 | 9521 | 1596 |
| 799292 | N/A | N/A | TGATGCTGATTATTAA | 19 | 9510 | 9525 | 1597 |
| 799293 | N/A | N/A | CCTTGATGCTGATTAT | 5 | 9513 | 9528 | 1598 |
| 799294 | N/A | N/A | CGCGGCCTTGATGCTG | 13 | 9518 | 9533 | 1599 |
| 799295 | N/A | N/A | GACTCGCGGCCTTGAT | 30 | 9522 | 9537 | 1600 |
| 799296 | N/A | N/A | GCTGACTCGCGGCCTT | 45 | 9525 | 9540 | 1601 |
| 799297 | N/A | N/A | AAAGGCTGACTCGCGG | 62 | 9529 | 9544 | 1602 |
| 799298 | N/A | N/A | CCAAAAGGCTGACTCG | 54 | 9532 | 9547 | 1603 |
| 799309 | N/A | N/A | GCACGCTCTAAACAGC | 42 | 9569 | 9584 | 1604 |
| 799310 | N/A | N/A | TAAGCACGCTCTAAAC | 18 | 9572 | 9587 | 1605 |
| 799311 | N/A | N/A | CTTTAAGCACGCTCTA | 27 | 9575 | 9590 | 1606 |
| 799312 | N/A | N/A | CATCTTTAAGCACGCT | 66 | 9578 | 9593 | 1607 |
| 799313 | N/A | N/A | ATCCATCTTTAAGCAC | 0 | 9581 | 9596 | 1608 |
| 799314 | N/A | N/A | CAAGATCCATCTTTAA | 0 | 9585 | 9600 | 1609 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799315 | N/A | N/A | CACCAAGATCCATCTT | 15 | 9588 | 9603 | 1610 |
| 799316 | N/A | N/A | AAACACCAAGATCCAT | 0 | 9591 | 9606 | 1611 |
| 799317 | N/A | N/A | TAAAACACCAAGATC | 0 | 9594 | 9609 | 1612 |
| 799318 | N/A | N/A | GTGGATTTGAAAAGGG | 58 | 9634 | 9649 | 1613 |
| 799531 | N/A | N/A | CTTTAGCAATTTCAAA | 32 | 9768 | 9783 | 1614 |
| 799532 | N/A | N/A | GCAGAAGGCCACCCCC | 21 | 9795 | 9810 | 1615 |
| 799533 | N/A | N/A | GAATGAAGTCCAGACC | 50 | 9821 | 9836 | 1616 |
| 799544 | N/A | N/A | TTCAACAAGTTCCCTA | 72 | 10129 | 10144 | 1617 |
| 799545 | N/A | N/A | TCCCACCCTGGTGCTC | 9 | 10257 | 10272 | 1618 |
| 799546 | N/A | N/A | TACTGTTGGCAGTGCT | 48 | 10272 | 10287 | 1619 |
| 799547 | N/A | N/A | TCCTACTGTTGGCAGT | 50 | 10275 | 10290 | 1620 |
| 799548 | N/A | N/A | CTCCTACTGTTGGCAG | 39 | 10276 | 10291 | 1621 |
| 799549 | N/A | N/A | GCTCCTACTGTTGGCA | 53 | 10277 | 10292 | 1622 |
| 799550 | N/A | N/A | AGCTCCTACTGTTGGC | 50 | 10278 | 10293 | 1623 |
| 799551 | N/A | N/A | TTACAGCTCCTACTGT | 12 | 10282 | 10297 | 1624 |
| 799552 | N/A | N/A | AGGGAACAATTACAGC | 58 | 10291 | 10306 | 1625 |
| 799553 | N/A | N/A | CCCCGCTAGGGAACAA | 46 | 10298 | 10313 | 1626 |
| 799564 | N/A | N/A | CAGATAACAGAGTATA | 70 | 10876 | 10891 | 1627 |
| 799565 | N/A | N/A | AGTAAACAATACCCTC | 79 | 10897 | 10912 | 1628 |
| 799566 | N/A | N/A | GAGTAAACAATACCCT | 74 | 10898 | 10913 | 1629 |
| 799567 | N/A | N/A | CTTTGAGTAAACAATA | 15 | 10902 | 10917 | 1630 |
| 799568 | N/A | N/A | CATTAGAAGCTTTGAG | 62 | 10911 | 10926 | 1631 |
| 799569 | N/A | N/A | CTCTAGGTCCCTCTTT | 24 | 10942 | 10957 | 1632 |
| 799570 | N/A | N/A | AAAAGATGCAGTTCAC | 39 | 11029 | 11044 | 1633 |
| 799571 | N/A | N/A | CAGAAAAGATGCAGTT | 46 | 11032 | 11047 | 1634 |
| 799572 | N/A | N/A | ACCATCTAACAACATC | 79 | 11125 | 11140 | 1635 |
| 799573 | N/A | N/A | AATAAAACCATCTAAC | 0 | 11131 | 11146 | 1636 |
| 799583 | N/A | N/A | AAGACAAACCTTCCGA | 74 | 11237 | 11252 | 1637 |
| 799584 | N/A | N/A | TATCAAGAAGACAAAC | 39 | 11244 | 11259 | 1638 |
| 799585 | N/A | N/A | AGACAAGATGTTATCA | 34 | 11255 | 11270 | 1639 |
| 799586 | N/A | N/A | GAGGAGGCACTCAGGC | 50 | 11315 | 11330 | 1640 |
| 799587 | N/A | N/A | TTCACAGGTCACATGG | 42 | 11342 | 11357 | 1641 |
| 799588 | N/A | N/A | AAAAAGCCCACCCATC | 44 | 11368 11739 | 11383 11754 | 1642 |
| 799589 | N/A | N/A | AATATCTGTGTCTACA | 65 | 11836 | 11851 | 1643 |
| 799590 | N/A | N/A | CTGCAGTCTTCTGAAG | 9 | 11901 | 11916 | 1644 |
| 799591 | N/A | N/A | ATTAGTAAATCAAGAG | 56 | 11967 | 11982 | 1645 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799592 | N/A | N/A | GGAATTAGTAAATCAA | 47 | 11970 | 11985 | 1646 |
| 799603 | N/A | N/A | GCCCATTATGAATACA | 52 | 12037 | 12052 | 1647 |
| 799604 | N/A | N/A | CATCACCTCCCCTCCA | 0 | 12108 | 12123 | 1648 |
| 799605 | N/A | N/A | CCAATAAAGTTCCCTT | 56 | 12175 | 12190 | 1649 |
| 799606 | N/A | N/A | TTTACAAAACTCTCTG | 50 | 12204 | 12219 | 1650 |
| 799607 | N/A | N/A | CCATTTACAAAACTCT | 71 | 12207 | 12222 | 1651 |
| 799608 | N/A | N/A | ACGATCAACTTCTTGA | 70 | 12246 | 12261 | 1652 |
| 799609 | N/A | N/A | CCCCATGGAACGATCA | 41 | 12255 | 12270 | 1653 |
| 799610 | N/A | N/A | GGGAGAAACTCCTCAG | 45 | 12406 | 12421 | 1654 |
| 799611 | N/A | N/A | TGTGAAAGAGGCTCAG | 37 | 12445 | 12460 | 1655 |
| 799612 | N/A | N/A | AAACAGCACACAGGGC | 50 | 12462 | 12477 | 1656 |
| 799622 | N/A | N/A | TTCTAAAAATGTCCCA | 45 | 12912 | 12927 | 1657 |
| 799623 | N/A | N/A | TACAATCTCCTGGAAG | 45 | 12940 | 12955 | 1658 |
| 799624 | N/A | N/A | TGAAAGTACAATCTCC | 58 | 12946 | 12961 | 1659 |
| 799625 | N/A | N/A | AATGAAAGTACAATCT | 31 | 12948 | 12963 | 1660 |
| 799626 | N/A | N/A | AGCTTGCACCCAGCAA | 41 | 12994 | 13009 | 1661 |
| 799627 | N/A | N/A | CACAAGCTTGCACCCA | 48 | 12998 | 13013 | 1662 |
| 799628 | N/A | N/A | ACACACACAAGCTTGC | 38 | 13003 | 13018 | 1663 |
| 799629 | N/A | N/A | TACACACACAAGCTTG | 24 | 13004 | 13019 | 1664 |
| 799630 | N/A | N/A | CCCTATCCCAGAGCCT | 43 | 13132 | 13147 | 1665 |
| 799631 | N/A | N/A | CCAAATCACAAAGCAG | 82 | 13234 | 13249 | 1666 |
| 799642 | N/A | N/A | GCAAATCCTTTCCATC | 53 | 13412 | 13427 | 1667 |
| 799643 | N/A | N/A | GTGATCCCCGGAAAGC | 26 | 13435 | 13450 | 1668 |
| 799644 | N/A | N/A | TTCCAACACATGCTCT | 31 | 13460 | 13475 | 1669 |
| 799645 | N/A | N/A | CAAAGATGATAGCTTC | 45 | 13473 | 13488 | 1670 |
| 799646 | N/A | N/A | CAGAAACTCCAGATGG | 18 | 13495 | 13510 | 1671 |
| 799647 | N/A | N/A | ACAGAAACTCCAGATG | 0 | 13496 | 13511 | 1672 |
| 799648 | N/A | N/A | ATGAAAGCCCCCAGAC | 9 | 13510 | 13525 | 1673 |
| 799649 | N/A | N/A | AAATGAAAGCCCCCAG | 53 | 13512 | 13527 | 1674 |
| 799650 | N/A | N/A | CAGCAGACAGGCAAAA | 46 | 13525 | 13540 | 1675 |
| 799651 | N/A | N/A | AGGACAGCAGACAGGC | 55 | 13529 | 13544 | 1676 |
| 799662 | N/A | N/A | CGTGAGCACTTCTGTC | 55 | 13778 | 13793 | 1677 |
| 799663 | N/A | N/A | GCACAGCCAAGAGATG | 57 | 13809 | 13824 | 1678 |
| 799664 | N/A | N/A | GCCAGCAAGGATCAAA | 8 | 13989 | 14004 | 1679 |
| 799665 | N/A | N/A | GATGCCAGCAAGGATC | 57 | 13992 | 14007 | 1680 |
| 799666 | N/A | N/A | CAGATGCCAGCAAGGA | 51 | 13994 | 14009 | 1681 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 799667 | N/A | N/A | ACAGATGCCAGCAAGG | 79 | 13995 | 14010 | 1682 |
| 799668 | N/A | N/A | GACAGATGCCAGCAAG | 75 | 13996 | 14011 | 1683 |
| 799669 | N/A | N/A | TATGACAGATGCCAGC | 81 | 13999 | 14014 | 1684 |
| 799670 | N/A | N/A | TCTGAGACTATGACAG | 51 | 14007 | 14022 | 1685 |
| 799671 | N/A | N/A | AGGTATTTTTGAAGGC | 59 | 14028 | 14043 | 1686 |
| 799682 | N/A | N/A | GGTCCAGGACTGGTCT | 55 | 14579 | 14594 | 1687 |
| 799683 | N/A | N/A | CTGCAGAAGAGGCGGG | 32 | 14594 | 14609 | 1688 |
| 799684 | N/A | N/A | AATGCTGTCACCCTGT | 52 | 14703 | 14718 | 1689 |
| 799685 | N/A | N/A | GATTTTAAATGCTGTC | 25 | 14710 | 14725 | 1690 |
| 799686 | N/A | N/A | GAGATTTTAAATGCTG | 62 | 14712 | 14727 | 1691 |
| 799687 | N/A | N/A | GGCAGCAGACCATCTT | 35 | 14761 | 14776 | 1692 |
| 799688 | N/A | N/A | CACCACCCAAAGCCTG | 50 | 14839 | 14854 | 1693 |
| 799689 | N/A | N/A | TGCTACAGTGTCACCA | 63 | 14862 | 14877 | 1694 |
| 799690 | N/A | N/A | AGCTACAGTCAGGCTT | 51 | 14958 | 14973 | 1695 |
| 799691 | N/A | N/A | TCCCATAGGTGTACAA | 49 | 14982 | 14997 | 1696 |
| 799702 | N/A | N/A | CATCACCACTCTACAG | 43 | 15772 | 15787 | 1697 |
| 799703 | N/A | N/A | CCAATGGCATTGAATA | 45 | 15808 | 15823 | 1698 |
| 799704 | N/A | N/A | ACCAATGGCATTGAAT | 12 | 15809 | 15824 | 1699 |
| 799705 | N/A | N/A | AACTTAAAATGTGCCA | 26 | 15824 | 15839 | 1700 |
| 799706 | N/A | N/A | CTTGTGGTAAAATACA | 47 | 15843 | 15858 | 1701 |
| 799707 | N/A | N/A | AAACTTGTGGTAAAAT | 38 | 15846 | 15861 | 1702 |
| 799708 | N/A | N/A | CAAACTTGTGGTAAAA | 60 | 15847 | 15862 | 1703 |
| 799709 | N/A | N/A | TCAAACTTGTGGTAAA | 60 | 15848 | 15863 | 1704 |
| 799710 | N/A | N/A | GTCAAACTTGTGGTAA | 48 | 15849 | 15864 | 1705 |
| 799711 | N/A | N/A | GGTCAAACTTGTGGTA | 60 | 15850 | 15865 | 1706 |
| 799722 | N/A | N/A | GCAGAGTGAGAACAAG | 67 | 16560 | 16575 | 1707 |
| 799723 | N/A | N/A | AGCCAACCCTGGCACC | 0 | 16620 | 16635 | 1708 |
| 799724 | N/A | N/A | AACTTGGGCAAGGACA | 24 | 16692 | 16707 | 1709 |
| 799725 | N/A | N/A | GGCCACTGCAGCCCTA | 0 | 16709 | 16724 | 1710 |
| 799726 | N/A | N/A | GTATCCTTTCACGAGG | 49 | 16762 | 16777 | 1711 |
| 799727 | N/A | N/A | TGACAGTAGGCAGGCA | 22 | 16857 | 16872 | 1712 |
| 799728 | N/A | N/A | CGGAGAGGAAGCCTCT | 37 | 16876 | 16891 | 1713 |
| 799729 | N/A | N/A | TATCTTCCCGCTGAAA | 52 | 16898 | 16913 | 1714 |
| 772842 | N/A | N/A | GTTAATAATATCTTCC | 79 | 16906 | 16921 | 1715 |
| 799730 | N/A | N/A | TAAATTGAGAACTGTG | 60 | 16930 | 16945 | 1716 |
| 799741 | N/A | N/A | AGTTATCACCCTGTTT | 32 | 17269 | 17284 | 1717 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799742 | N/A | N/A | ATATTTCCTGTTAACT | 23 | 17296 | 17311 | 1718 |
| 799743 | N/A | N/A | CTGGAGTTATTCTCAA | 51 | 17346 | 17361 | 1719 |
| 799744 | N/A | N/A | AAAGAAAATGGCCTAC | 1 | 17458 | 17473 | 1720 |
| 799745 | N/A | N/A | GGCAGTTAACATTTCA | 43 | 17551 | 17566 | 1721 |
| 799746 | N/A | N/A | AATGGGAAATAAGGCG | 59 | 17566 | 17581 | 1722 |
| 799747 | N/A | N/A | AAATGGGAAATAAGGC | 43 | 17567 | 17582 | 1723 |
| 799748 | N/A | N/A | GCTGAAAAGTCATGA | 51 | 17597 | 17612 | 1724 |
| 799749 | N/A | N/A | TGCTTGGCCTTACCAT | 17 | 17625 | 17640 | 1725 |
| 799750 | N/A | N/A | AGCCAAGAGCTGCTTG | 0 | 17635 | 17650 | 1726 |
| 799761 | N/A | N/A | TGTCATTAGAACAATG | 35 | 18149 | 18164 | 1727 |
| 799762 | N/A | N/A | GTCCTAAAGACGGCTC | 21 | 18202 | 18217 | 1728 |
| 799763 | N/A | N/A | TGTCCTAAAGACGGCT | 50 | 18203 | 18218 | 1729 |
| 799764 | N/A | N/A | ACGCTAAGGAAAAAGC | 19 | 18290 | 18305 | 1730 |
| 799765 | N/A | N/A | AAGCACGCTAAGGAAA | 23 | 18294 | 18309 | 1731 |
| 799766 | N/A | N/A | AAACAAAGCACGCTAA | 35 | 18299 | 18314 | 1732 |
| 799767 | N/A | N/A | TCTGTTTGGACAAGTT | 47 | 18379 | 18394 | 1733 |
| 799768 | N/A | N/A | CACCAACCTCTGTGGG | 0 | 18434 | 18449 | 1734 |
| 799769 | N/A | N/A | CCACCAACCTCTGTGG | 0 | 18435 | 18450 | 1735 |
| 799770 | N/A | N/A | GTTTCCAAGGCCGGCG | 50 | 18456 | 18471 | 1736 |
| 799781 | N/A | N/A | GTCAATACATATTTGC | 66 | 18710 | 18725 | 1737 |
| 799782 | N/A | N/A | CATAATAGGTGTCAAT | 4 | 18720 | 18735 | 1738 |
| 799783 | N/A | N/A | GCACATAATAGGTGTC | 24 | 18723 | 18738 | 1739 |
| 799784 | N/A | N/A | CAGGAACTGGTCCTCT | 19 | 18756 | 18771 | 1740 |
| 799785 | N/A | N/A | CTCCAGGTAGAGGCAA | 0 | 18872 | 18887 | 1741 |
| 799786 | N/A | N/A | ACAGAAGCTGCCCCTG | 0 | 18893 | 18908 | 1742 |
| 799787 | N/A | N/A | CCAAAGCAGAAGTAGA | 58 | 19007 | 19022 | 1743 |
| 799788 | N/A | N/A | CACAACCAAAGCAGAA | 59 | 19012 | 19027 | 1744 |
| 799789 | N/A | N/A | ACACAACCAAAGCAGA | 44 | 19013 | 19028 | 1745 |
| 799790 | N/A | N/A | GAGACCTACCTCTGTT | 33 | 19068 | 19083 | 1746 |
| 799801 | N/A | N/A | AATCAAGTCCTCTGGA | 18 | 19359 | 19374 | 1747 |
| 799802 | N/A | N/A | CCAGACAGGCCAGGGC | 20 | 19473 | 19488 | 1748 |
| 799803 | N/A | N/A | AGAAGGATGAATGTGA | 10 | 19541 | 19556 | 1749 |
| 799804 | N/A | N/A | ACAGACAGAGAAGGAT | 38 | 19549 | 19564 | 1750 |
| 799805 | N/A | N/A | CGAGAAGAGTAATTCA | 1 | 19613 | 19628 | 1751 |
| 799806 | N/A | N/A | GAGGAGCGAGAAGAGT | 6 | 19619 | 19634 | 1752 |
| 799807 | N/A | N/A | AAATTGGAATTGAGAC | 37 | 19715 | 19730 | 1753 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID: 2 Stop Site | SEQ ID NO. |
|---|---|---|---|---|---|---|---|
| 799808 | N/A | N/A | GCTGAAAGAAAGTCCC | 70 | 19745 | 19760 | 1754 |
| 799809 | N/A | N/A | CAATACTGAAATGAGC | 43 | 19798 | 19813 | 1755 |
| 799810 | N/A | N/A | CTTATTGTTTTTGTTC | 14 | 19851 | 19866 | 1756 |
| 799821 | N/A | N/A | CCCCAGAAAACAGCCC | 17 | 20225 | 20240 | 1757 |
| 799822 | N/A | N/A | CACGATCCTGGGCTCT | 0 | 20242 | 20257 | 1758 |
| 799823 | N/A | N/A | ACAGGAAAGTGGAGGA | 46 | 20362 | 20377 | 1759 |
| 799824 | N/A | N/A | GAAATGGCTCCTGCAA | 9 | 20445 | 20460 | 1760 |
| 799825 | N/A | N/A | GACTTGGCAGCCAAGC | 0 | 20506 | 20521 | 1761 |
| 799826 | N/A | N/A | GATCATTCCCACACCC | 33 | 20560 | 20575 | 1762 |
| 799827 | N/A | N/A | AACTACAACCTTTTTA | 26 | 20629 | 20644 | 1763 |
| 799828 | N/A | N/A | TGCGAGCCAAGAGACA | 54 | 20650 | 20665 | 1764 |
| 799829 | N/A | N/A | GAGTTTGCGAGCCAAG | 75 | 20655 | 20670 | 1765 |
| 799830 | N/A | N/A | GAAGAGTTTGCGAGCC | 55 | 20658 | 20673 | 1766 |
| 799841 | N/A | N/A | AAAGAATGGTGGGTGC | 37 | 21059 | 21074 | 1767 |
| 799842 | N/A | N/A | GAAAGAATGGTGGGTG | 16 | 21060 | 21075 | 1768 |
| 799843 | N/A | N/A | GGAGGAGGCAAATTCA | 42 | 21082 | 21097 | 1769 |
| 799844 | N/A | N/A | AGAGGAGGAGGCAAAT | 11 | 21085 | 21100 | 1770 |
| 799845 | N/A | N/A | GAAGTACCTAGAGGAG | 31 | 21094 | 21109 | 1771 |
| 799846 | N/A | N/A | TCCACTATTCTATGAA | 25 | 21107 | 21122 | 1772 |
| 799847 | N/A | N/A | TTCCACTATTCTATGA | 30 | 21108 | 21123 | 1773 |
| 799848 | N/A | N/A | AGCCGATCACAAAAGG | 59 | 21139 | 21154 | 1774 |
| 799849 | N/A | N/A | ATAAGCCGATCACAAA | 41 | 21142 | 21157 | 1775 |
| 799850 | N/A | N/A | GCAATAAATCAACCAG | 49 | 21263 | 21278 | 1776 |
| 799861 | N/A | N/A | ACCGCATGCGATCGGT | 15 | 21495 | 21510 | 1777 |
| 799862 | N/A | N/A | CCCACCGCATGCGATC | 14 | 21498 | 21513 | 1778 |
| 799863 | N/A | N/A | GGCTCCCCCACCGCAT | 16 | 21504 | 21519 | 1779 |
| 799864 | N/A | N/A | CTCAAGCCCACCCCGG | 42 | 21527 | 21542 | 1780 |
| 799865 | N/A | N/A | GGGACAGACTGTCCCC | 0 | 21580 | 21595 | 1781 |
| 799866 | N/A | N/A | CACCGCGCAGGGACAG | 0 | 21589 | 21604 | 1782 |
| 799867 | N/A | N/A | CTCCAATCTGGCTGGT | 24 | 21635 | 21650 | 1783 |
| 799868 | N/A | N/A | CATAAACATGGGCTCC | 34 | 21663 | 21678 | 1784 |
| 799869 | N/A | N/A | CCATAAACATGGGCTC | 16 | 21664 | 21679 | 1785 |
| 799870 | N/A | N/A | ACCCAGAAGCTGCTGT | 18 | 21757 | 21772 | 1786 |
| 799881 | N/A | N/A | AATAAATTCCAATGCA | 0 | 22163 | 22178 | 1787 |
| 799882 | N/A | N/A | TTTGAACATTTACTGC | 41 | 22188 | 22203 | 1788 |
| 799883 | N/A | N/A | TCTAGAGGGTAGGAAA | 9 | 22318 | 22333 | 1789 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799884 | N/A | N/A | CTCCAGTTTCTAGAGG | 0 | 22326 | 22341 | 1790 |
| 799885 | N/A | N/A | CCCCACAGATCCAACT | 0 | 22345 | 22360 | 1791 |
| 799886 | N/A | N/A | ACCAAGCTACTTTTGC | 25 | 22457 | 22472 | 1792 |
| 799887 | N/A | N/A | CAGGACAGTTTTTCCC | 29 | 22513 | 22528 | 1793 |
| 799888 | N/A | N/A | GGACAAAACCCCTAGA | 22 | 22533 | 22548 | 1794 |
| 799889 | N/A | N/A | AAAGGACAAAACCCC | 45 | 22537 | 22552 | 1795 |
| 799890 | N/A | N/A | CATTAAGCCAATTTTC | 41 | 22554 | 22569 | 1796 |
| 799901 | N/A | N/A | AGTCAAGTCTCTTACC | 31 | 22790 | 22805 | 1797 |
| 799902 | N/A | N/A | GGAAGACACAAGGGCT | 34 | 22854 | 22869 | 1798 |
| 799903 | N/A | N/A | TGCATGGCATTGTCTG | 34 | 22910 | 22925 | 1799 |
| 799904 | N/A | N/A | ACTCAGAGCAGCTCTC | 61 | 22973 | 22988 | 1800 |
| 799905 | N/A | N/A | AGTCGAATCATTTCTC | 53 | 23058 | 23073 | 1801 |
| 799906 | N/A | N/A | CATGCAGTCGAATCAT | 11 | 23063 | 23078 | 1802 |
| 799907 | N/A | N/A | AGTAAAGGGCCTCTCT | 10 | 23096 | 23111 | 1803 |
| 799908 | N/A | N/A | CATAATATTGACAGTA | 41 | 23108 | 23123 | 1804 |
| 799909 | N/A | N/A | ATTCATAATATTGACA | 36 | 23111 | 23126 | 1805 |
| 772889 | N/A | N/A | CTCCATTCATAATATT | 7 | 23115 | 23130 | 1806 |
| 799920 | N/A | N/A | GATGAATGCTCCTAAG | 0 | 23381 | 23396 | 1807 |
| 799921 | N/A | N/A | CTAATTAGTGACTGTG | 75 | 23521 | 23536 | 1808 |
| 799922 | N/A | N/A | ACACTAATTAGTGACT | 15 | 23524 | 23539 | 1809 |
| 799923 | N/A | N/A | GCCTACATATTTCGCA | 15 | 23557 | 23572 | 1810 |
| 799924 | N/A | N/A | CAAGCCTACATATTTC | 22 | 23560 | 23575 | 1811 |
| 799925 | N/A | N/A | CCAAGCCTACATATTT | 10 | 23561 | 23576 | 1812 |
| 799926 | N/A | N/A | CCCAAGCCTACATATT | 17 | 23562 | 23577 | 1813 |
| 799927 | N/A | N/A | TCCCAAGCCTACATAT | 0 | 23563 | 23578 | 1814 |
| 799928 | N/A | N/A | CTCCCAAGCCTACATA | 7 | 23564 | 23579 | 1815 |
| 799929 | N/A | N/A | TGCCCAGGCTTGGTTC | 9 | 23620 | 23635 | 1816 |
| 799940 | N/A | N/A | CTTTGAGGAGCAGGGT | 50 | 23856 | 23871 | 1817 |
| 799941 | N/A | N/A | TTTACTACCTTCCAGA | 44 | 23886 | 23901 | 1818 |
| 799942 | N/A | N/A | AACACTGGTTCCATTT | 0 | 23905 | 23920 | 1819 |
| 799943 | N/A | N/A | TGCCCTCTCAGGGTCT | 0 | 24029 | 24044 | 1820 |
| 799944 | N/A | N/A | CTGCAGCAAGAAGTGG | 5 | 24100 | 24115 | 1821 |
| 799945 | N/A | N/A | AGCTTTTAGAGCTGCG | 5 | 24133 | 24148 | 1822 |
| 799946 | N/A | N/A | TCAGAACACACTTTGG | 2 | 24161 | 24176 | 1823 |
| 799947 | N/A | N/A | TCTAAAGCCACCAAGC | 28 | 24202 | 24217 | 1824 |
| 799948 | N/A | N/A | ATATTGCCTGGTGTGA | 48 | 24234 | 24249 | 1825 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799949 | N/A | N/A | ACTGGCCGAAGTGCAG | 10 | 24270 | 24285 | 1826 |
| 799960 | N/A | N/A | AAACAGGGTTCCCCCA | 8 | 24606 | 24621 | 1827 |
| 799961 | N/A | N/A | CCTAAAACAGGGTTCC | 20 | 24610 | 24625 | 1828 |
| 799962 | N/A | N/A | CCAACCCCAGAGGTGA | 0 | 24700 | 24715 | 1829 |
| 799963 | N/A | N/A | AGCCATGGCAGAACCC | 6 | 24727 | 24742 | 1830 |
| 799964 | N/A | N/A | CCCCTTAGCGCATTCT | 55 | 24743 | 24758 | 1831 |
| 799965 | N/A | N/A | CTCCAGTGAAGTGAGA | 0 | 24853 | 24868 | 1832 |
| 799966 | N/A | N/A | GTGGAAGGCTGACCTG | 35 | 24907 | 24922 | 1833 |
| 799967 | N/A | N/A | GACGATGAATCCTGGC | 72 | 24925 | 24940 | 1834 |
| 799968 | N/A | N/A | CTGCGAGTTAATCAGA | 27 | 24997 | 25012 | 1835 |
| 799969 | N/A | N/A | TTAGAGTGAGTTCCTC | 46 | 25046 | 25061 | 1836 |
| 799980 | N/A | N/A | CCAACGGTTGCCTCAT | 78 | 25440 | 25455 | 1837 |
| 799981 | N/A | N/A | ACCAACGGTTGCCTCA | 14 | 25441 | 25456 | 1838 |
| 799982 | N/A | N/A | CACCACGCCTCGCTAA | 0 | 25497 | 25512 | 1839 |
| 799983 | N/A | N/A | CATCACCACGCCTCGC | 15 | 25500 | 25515 | 1840 |
| 799984 | N/A | N/A | ACATCACCACGCCTCG | 61 | 25501 | 25516 | 1841 |
| 799985 | N/A | N/A | AACATCACCACGCCTC | 53 | 25502 | 25517 | 1842 |
| 799986 | N/A | N/A | AAACATCACCACGCCT | 44 | 25503 | 25518 | 1843 |
| 799987 | N/A | N/A | CAAACATCACCACGCC | 57 | 25504 | 25519 | 1844 |
| 799988 | N/A | N/A | GCGCAAACATCACCAC | 32 | 25507 | 25522 | 1845 |
| 799989 | N/A | N/A | TGCACCTGGCAACCTG | 57 | 25526 | 25541 | 1846 |
| 800000 | N/A | N/A | CATTTAGGAACAAGGG | 37 | 25891 | 25906 | 1847 |
| 800001 | N/A | N/A | CAAGATTCCATTTAGG | 2 | 25899 | 25914 | 1848 |
| 800002 | N/A | N/A | CCCCAAGATTCCATTT | 0 | 25902 | 25917 | 1849 |
| 800003 | N/A | N/A | AGAACACGGGCACGCG | 24 | 25986 | 26001 | 1850 |
| 800004 | N/A | N/A | TTTTAATTTGAAGGCG | 8 | 26134 | 26149 | 1851 |
| 800005 | N/A | N/A | CCGCACCCAGACCCCT | 27 | 26158 | 26173 | 1852 |
| 800006 | N/A | N/A | CAAGGAATTTTCCCCT | 41 | 26470 | 26485 | 1853 |
| 800007 | N/A | N/A | CTCAAGGCCACATTTT | 23 | 26494 | 26509 | 1854 |
| 800008 | N/A | N/A | GAACAGACCAGACCCT | 40 | 26577 | 26592 | 1855 |
| 800009 | N/A | N/A | TGCTCATGAATGAACA | 51 | 26588 | 26603 | 1856 |
| 800019 | N/A | N/A | GGCAAAACTCACAGTC | 61 | 27031 | 27046 | 1857 |
| 800020 | N/A | N/A | AACCTCTGAAGGCAAA | 21 | 27041 | 27056 | 1858 |
| 800021 | N/A | N/A | GGCCTCTCGCTGATAG | 0 | 27059 | 27074 | 1859 |
| 800022 | N/A | N/A | GGAAGAGCCTTGGCCT | 30 | 27070 | 27085 | 1860 |
| 800023 | N/A | N/A | AGGAAGAGCCTTGGCC | 0 | 27071 | 27086 | 1861 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 800024 | N/A | N/A | CAAGGACTAAGGAAGA | 18 | 27080 | 27095 | 1862 |
| 800025 | N/A | N/A | AGTACAAGGACTAAGG | 65 | 27084 | 27099 | 1863 |
| 800026 | N/A | N/A | TCAGTACAAGGACTAA | 50 | 27086 | 27101 | 1864 |
| 800027 | N/A | N/A | CGCTTTGCTCCCAGGG | 0 | 27140 | 27155 | 1865 |
| 800028 | N/A | N/A | CACAGCCCACACGAGT | 10 | 27179 | 27194 | 1866 |
| 800039 | N/A | N/A | GGTTAATGGCCCAGCC | 27 | 27615 | 27630 | 1867 |
| 800040 | N/A | N/A | CGCCAGCAATGTGCTG | 15 | 27666 | 27681 | 1868 |
| 800041 | N/A | N/A | GCCACCTAGGCAAGGG | 0 | 27807 | 27822 | 1869 |
| 800042 | N/A | N/A | TGTCAGCCACCTAGGC | 0 | 27812 | 27827 | 1870 |
| 800043 | N/A | N/A | TGCCAGGCCTGTCAGC | 31 | 27821 | 27836 | 1871 |
| 800044 | N/A | N/A | CCTGAGATCGAGGTGC | 18 | 27842 | 27857 | 1872 |
| 800045 | N/A | N/A | GAGGAGCAAGGGAGTG | 59 | 27871 | 27886 | 1873 |
| 800046 | N/A | N/A | GGCCAACAGGAGGAGG | 42 | 27892 | 27907 | 1874 |
| 800047 | N/A | N/A | ACCCACTGAAACCTGG | 28 | 27912 | 27927 | 1875 |
| 800048 | N/A | N/A | TGGAAAGGAAGACTCG | 64 | 28013 | 28028 | 1876 |
| 800059 | N/A | N/A | AAAACAAGACAGGGAC | 31 | 28327 | 28342 | 1877 |
| 800060 | N/A | N/A | CCCCAAAAGCTCCACA | 5 | 28553 | 28568 | 1878 |
| 800061 | N/A | N/A | CCCAAATGCCTGCCCC | 44 | 28565 | 28580 | 1879 |
| 800062 | N/A | N/A | CCCCAAGCTGGCCTTC | 25 | 28580 | 28595 | 1880 |
| 800063 | N/A | N/A | GCCATACAAATGTGCA | 0 | 28658 | 28673 | 1881 |
| 800064 | N/A | N/A | ATGGAGGTGCCCGTCA | 0 | 28679 | 28694 | 1882 |
| 800065 | N/A | N/A | TTAAGTAGCAGCCAGT | 55 | 28700 | 28715 | 1883 |
| 800066 | N/A | N/A | TGTTTTAAGTAGCAGC | 63 | 28704 | 28719 | 1884 |
| 800067 | N/A | N/A | AGGACCTGGGAACCCA | 51 | 28753 | 28768 | 1885 |
| 800068 | N/A | N/A | ACACTAACTGGCTCCA | 34 | 28786 | 28801 | 1886 |
| 800079 | N/A | N/A | TACCTTAACAAAGCTT | 61 | 29526 | 29541 | 1887 |
| 800080 | N/A | N/A | GGGCTACCTTAACAAA | 14 | 29530 | 29545 | 1888 |
| 800081 | N/A | N/A | CGGTATTAACCCGGGC | 0 | 29542 | 29557 | 1889 |
| 800082 | N/A | N/A | GCAGACCGGTATTAAC | 12 | 29548 | 29563 | 1890 |
| 800083 | N/A | N/A | TGCAGACCGGTATTAA | 11 | 29549 | 29564 | 1891 |
| 800084 | N/A | N/A | GCCAAATCACAACATG | 57 | 29563 | 29578 | 1892 |
| 800085 | N/A | N/A | AGCAGCCCTGTACACA | 37 | 29601 | 29616 | 1893 |
| 800086 | N/A | N/A | AGCAGCAGCCCTGTAC | 40 | 29604 | 29619 | 1894 |
| 800087 | N/A | N/A | TAATAGGAAAACAGTC | 0 | 29630 | 29645 | 1895 |
| 800088 | N/A | N/A | AATGAGGGTGGCTTGG | 54 | 29666 | 29681 | 1896 |
| 800099 | N/A | N/A | TGCAAAGGGACCCTTA | 6 | 29974 | 29989 | 1897 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 800100 | N/A | N/A | TGCAGAGCACAGATGC | 16 | 29987 | 30002 | 1898 |
| 800101 | N/A | N/A | AACAAAGCCTCTTCTC | 0 | 30003 | 30018 | 1899 |
| 800102 | N/A | N/A | ACGAGACAGAAAGAAG | 21 | 30174 | 30189 | 1900 |
| 800103 | N/A | N/A | GGACGAGACAGAAAGA | 4 | 30176 | 30191 | 1901 |
| 800104 | N/A | N/A | AGGACGAGACAGAAAG | 17 | 30177 | 30192 | 1902 |
| 800105 | N/A | N/A | TCCTAGAATGAAGACA | 17 | 30232 | 30247 | 1903 |
| 800106 | N/A | N/A | CAGAGAGGGTTAGTGG | 12 | 30265 | 30280 | 1904 |
| 800107 | N/A | N/A | AATCTAGAAAACACAT | 0 | 30284 | 30299 | 1905 |
| 800108 | N/A | N/A | GGAATCTAGAAAACAC | 12 | 30286 | 30301 | 1906 |
| 798811 | 1031 | 1046 | CAGAAGAAGTTGGGAA | 1 | 30298 | 30313 | 1907 |
| 798812 | 1034 | 1049 | CTCCAGAAGAAGTTGG | 0 | 30301 | 30316 | 1908 |
| 772587 | 1043 | 1058 | ATCCCCAGGCTCCAGA | 39 | 30310 | 30325 | 1909 |
| 798813 | 1046 | 1061 | CCGATCCCCAGGCTCC | 23 | 30313 | 30328 | 1910 |
| 772590 | 1051 | 1066 | TGTGACCGATCCCCAG | 37 | 30318 | 30333 | 1911 |
| 798814 | 1056 | 1071 | ACCAGTGTGACCGATC | 25 | 30323 | 30338 | 1912 |
| 798815 | 1059 | 1074 | CGCACCAGTGTGACCG | 45 | 30326 | 30341 | 1913 |
| 798816 | 1062 | 1077 | CCACGCACCAGTGTGA | 24 | 30329 | 30344 | 1914 |
| 798817 | 1066 | 1081 | GCCACCACGCACCAGT | 26 | 30333 | 30348 | 1915 |
| 798818 | 1069 | 1084 | TATGCCACCACGCACC | 63 | 30336 | 30351 | 1916 |
| 798828 | 1127 | 1142 | ATCCAGAGAGGGCTCC | 18 | 30394 | 30409 | 1917 |
| 798829 | 1130 | 1145 | GATATCCAGAGAGGGC | 0 | 30397 | 30412 | 1918 |
| 798830 | 1133 | 1148 | GAAGATATCCAGAGAG | 17 | 30400 | 30415 | 1919 |
| 798831 | 1136 | 1151 | ATAGAAGATATCCAGA | 0 | 30403 | 30418 | 1920 |
| 798832 | 1139 | 1154 | ATCATAGAAGATATCC | 41 | 30406 | 30421 | 1921 |
| 798833 | 1142 | 1157 | TAGATCATAGAAGATA | 48 | 30409 | 30424 | 1922 |
| 790510 | 1151 | 1166 | CCCCTGAGGTAGATCA | 33 | 30418 | 30433 | 1923 |
| 772606 | 1158 | 1173 | AGCCATTCCCCTGAGG | 41 | 30425 | 30440 | 1924 |
| 798834 | 1161 | 1176 | AAAGCCATTCCCCTG | 55 | 30428 | 30443 | 1925 |
| 772610 | 1164 | 1179 | GGCAAAAGCCATTCCC | 34 | 30431 | 30446 | 1926 |
| 798843 | 1205 | 1220 | CTGCACCAGCTGACTC | 37 | 30472 | 30487 | 1927 |
| 798844 | 1210 | 1225 | ACCTTCTGCACCAGCT | 30 | 30477 | 30492 | 1928 |
| 798845 | 1213 | 1228 | CGCACCTTCTGCACCA | 18 | 30480 | 30495 | 1929 |
| 798846 | 1216 | 1231 | CTCCGCACCTTCTGCA | 40 | 30483 | 30498 | 1930 |
| 798847 | 1219 | 1234 | TTGCTCCGCACCTTCT | 24 | 30486 | 30501 | 1931 |
| 798848 | 1223 | 1238 | GATTTTGCTCCGCACC | 40 | 30490 | 30505 | 1932 |
| 798849 | 1228 | 1243 | CAGCCGATTTTGCTCC | 21 | 30495 | 30510 | 1933 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798850 | 1241 | 1256 | CAGCTGGATGCCGCAG | 12 | 30508 | 30523 | 1934 |
| 790515 | 1244 | 1259 | CGTCAGCTGGATGCCG | 26 | 30511 | 30526 | 1935 |
| 798851 | 1259 | 1274 | ACCATCCACCTCCCGC | 21 | 30526 | 30541 | 1936 |
| 798861 | 1311 | 1326 | GTGTGGCGGACTTGAT | 24 | 30578 | 30593 | 1937 |
| 798862 | 1315 | 1330 | TCCAGTGTGGCGGACT | 20 | 30582 | 30597 | 1938 |
| 798863 | 1321 | 1336 | GGGTTGTCCAGTGTGG | 41 | 30588 | 30603 | 1939 |
| 798864 | 1325 | 1340 | GTCCGGGTTGTCCAGT | 33 | 30592 | 30607 | 1940 |
| 798865 | 1328 | 1343 | GGAGTCCGGGTTGTCC | 8 | 30595 | 30610 | 1941 |
| 798866 | 1333 | 1348 | GTCCTGGAGTCCGGGT | 20 | 30600 | 30615 | 1942 |
| 798867 | 1348 | 1363 | TTGTGTACCAACAGCG | 29 | 30615 | 30630 | 1943 |
| 798868 | 1351 | 1366 | ACCTTGTGTACCAACA | 48 | 30618 | 30633 | 1944 |
| 798869 | 1354 | 1369 | AACACCTTGTGTACCA | 41 | 30621 | 30636 | 1945 |
| 798870 | 1357 | 1372 | GGGAACACCTTGTGTA | 14 | 30624 | 30639 | 1946 |
| 798879 | 1440 | 1455 | ACGGCTGCTGCATAAA | 57 | 30707 | 30722 | 1947 |
| 798880 | 1443 | 1458 | TCCACGGCTGCTGCAT | 37 | 30710 | 30725 | 1948 |
| 798881 | 1446 | 1461 | CCGTCCACGGCTGCTG | 14 | 30713 | 30728 | 1949 |
| 798882 | 1449 | 1464 | AGCCCGTCCACGGCTG | 0 | 30716 | 30731 | 1950 |
| 798883 | 1452 | 1467 | TAAAGCCCGTCCACGG | 0 | 30719 | 30734 | 1951 |
| 798884 | 1455 | 1470 | CGGTAAAGCCCGTCCA | 15 | 30722 | 30737 | 1952 |
| 798885 | 1458 | 1473 | GCACGGTAAAGCCCGT | 43 | 30725 | 30740 | 1953 |
| 798886 | 1461 | 1476 | TCTGCACGGTAAAGCC | 29 | 30728 | 30743 | 1954 |
| 798887 | 1465 | 1480 | CTGATCTGCACGGTAA | 26 | 30732 | 30747 | 1955 |
| 798888 | 1469 | 1484 | AAAGCTGATCTGCACG | 40 | 30736 | 30751 | 1956 |
| 798898 | 1515 | 1530 | AGCTGCTGATGAACTG | 2 | 30782 | 30797 | 1957 |
| 798899 | 1518 | 1533 | GGCAGCTGCTGATGAA | 13 | 30785 | 30800 | 1958 |
| 790532 | 1523 | 1538 | GCACGGGCAGCTGCTG | 0 | 30790 | 30805 | 1959 |
| 798900 | 1526 | 1541 | CCAGCACGGGCAGCTG | 0 | 30793 | 30808 | 1960 |
| 798901 | 1533 | 1548 | CCTCTAGCCAGCACGG | 30 | 30800 | 30815 | 1961 |
| 798902 | 1536 | 1551 | TGACCTCTAGCCAGCA | 54 | 30803 | 30818 | 1962 |
| 798903 | 1540 | 1555 | AAGATGACCTCTAGCC | 48 | 30807 | 30822 | 1963 |
| 798904 | 1543 | 1558 | TTGAAGATGACCTCTA | 23 | 30810 | 30825 | 1964 |
| 798905 | 1548 | 1563 | GGCTGTTGAAGATGAC | 35 | 30815 | 30830 | 1965 |
| 772642 | 1552 | 1567 | TACCGGCTGTTGAAGA | 0 | 30819 | 30834 | 1966 |
| 798915 | 1573 | 1588 | TCTGTCCCTCCGCAC | 7 | 30840 | 30855 | 1967 |
| 798916 | 1576 | 1591 | CGCTCTGTCCCCTCCG | 13 | 30843 | 30858 | 1968 |
| 798917 | 1581 | 1596 | GCTCACGCTCTGTCCC | 0 | 30848 | 30863 | 1969 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798918 | 1584 | 1599 | TCAGCTCACGCTCTGT | 44 | 30851 | 30866 | 1970 |
| 798919 | 1587 | 1602 | TGCTCAGCTCACGCTC | 45 | 30854 | 30869 | 1971 |
| 798920 | 1590 | 1605 | GCCTGCTCAGCTCACG | 58 | 30857 | 30872 | 1972 |
| 798921 | 1591 | 1606 | GGCCTGCTCAGCTCAC | 42 | 30858 | 30873 | 1973 |
| 798922 | 1597 | 1612 | AAGTGTGGCCTGCTCA | 59 | 30864 | 30879 | 1974 |
| 798923 | 1600 | 1615 | TTGAAGTGTGGCCTGC | 54 | 30867 | 30882 | 1975 |
| 798924 | 1603 | 1618 | AGTTTGAAGTGTGGCC | 43 | 30870 | 30885 | 1976 |
| 798935 | 1641 | 1656 | AAAGCAAGCACTCAGG | 48 | 30908 | 30923 | 1977 |
| 790543 | 1644 | 1659 | TGAAAAGCAAGCACTC | 23 | 30911 | 30926 | 1978 |
| 798936 | 1647 | 1662 | GCATGAAAAGCAAGCA | 14 | 30914 | 30929 | 1979 |
| 798937 | 1651 | 1666 | GTTTGCATGAAAAGCA | 35 | 30918 | 30933 | 1980 |
| 790545 | 1656 | 1671 | AAAGAGTTTGCATGAA | 24 | 30923 | 30938 | 1981 |
| 798938 | 1659 | 1674 | ACCAAAGAGTTTGCAT | 15 | 30926 | 30941 | 1982 |
| 798939 | 1662 | 1677 | ACGACCAAAGAGTTTG | 46 | 30929 | 30944 | 1983 |
| 798940 | 1665 | 1680 | AAAACGACCAAAGAGT | 29 | 30932 | 30947 | 1984 |
| 798941 | 1668 | 1683 | AAAAAAACGACCAAAG | 40 | 30935 | 30950 | 1985 |
| 798942 | 1698 | 1713 | CGAGAAGAAGAAAACC | 35 | 30965 | 30980 | 1986 |
| 798953 | 1742 | 1757 | AGCTATTTCTCAAAGA | 17 | 31009 | 31024 | 1987 |
| 798954 | 1745 | 1760 | ATAAGCTATTTCTCAA | 54 | 31012 | 31027 | 1988 |
| 798955 | 1748 | 1763 | TTCATAAGCTATTTCT | 15 | 31015 | 31030 | 1989 |
| 798956 | 1751 | 1766 | CTTTTCATAAGCTATT | 22 | 31018 | 31033 | 1990 |
| 798957 | 1754 | 1769 | ATTCTTTTCATAAGCT | 28 | 31021 | 31036 | 1991 |
| 798958 | 1758 | 1773 | AACAATTCTTTTCATA | 0 | 31025 | 31040 | 1992 |
| 798959 | 1761 | 1776 | CCCAACAATTCTTTTC | 36 | 31028 | 31043 | 1993 |
| 798960 | 1764 | 1779 | ACCCCCAACAATTCTT | 39 | 31031 | 31046 | 1994 |
| 798961 | 1767 | 1782 | AAAACCCCCAACAATT | 0 | 31034 | 31049 | 1995 |
| 798962 | 1774 | 1789 | TTCCAAAAAAACCCCC | 2 | 31041 | 31056 | 1996 |
| 798973 | 1812 | 1827 | TCCTATCAGGGTGTCC | 30 | 31079 | 31094 | 1997 |
| 798974 | 1816 | 1831 | CTCTTCCTATCAGGGT | 12 | 31083 | 31098 | 1998 |
| 798975 | 1820 | 1835 | TCCCCTCTTCCTATCA | 47 | 31087 | 31102 | 1999 |
| 798976 | 1832 | 1847 | TGGATTTCTGCTTCCC | 19 | 31099 | 31114 | 2000 |
| 798977 | 1836 | 1851 | TGCTTGGATTTCTGCT | 43 | 31103 | 31118 | 2001 |
| 798978 | 1844 | 1859 | TTTGGTGGTGCTTGGA | 25 | 31111 | 31126 | 2002 |
| 798979 | 1847 | 1862 | GTGTTTGGTGGTGCTT | 19 | 31114 | 31129 | 2003 |
| 798980 | 1852 | 1867 | ACACTGTGTTTGGTGG | 50 | 31119 | 31134 | 2004 |
| 798981 | 1855 | 1870 | CATACACTGTGTTTGG | 58 | 31122 | 31137 | 2005 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 798982 | 1858 | 1873 | CTTCATACACTGTGTT | 45 | 31125 | 31140 | 2006 |
| 798993 | 1892 | 1907 | CACACTCCTGACAAGT | 37 | 31159 | 31174 | 2007 |
| 798994 | 1895 | 1910 | ACACACACTCCTGACA | 0 | 31162 | 31177 | 2008 |
| 798995 | 1905 | 1920 | ACTCACACTCACACAC | 0 | 31172 | 31187 | 2009 |
| 798996 | 1908 | 1923 | CACACTCACACTCACA | 49 | 31175 | 31190 | 2010 |
| 798997 | 1909 | 1924 | GCACACTCACACTCAC | 12 | 31176 | 31191 | 2011 |
| 798998 | 1910 | 1925 | CGCACACTCACACTCA | 13 | 31177 | 31192 | 2012 |
| 798999 | 1911 | 1926 | CCGCACACTCACACTC | 17 | 31178 | 31193 | 2013 |
| 799000 | 1912 | 1927 | GCCGCACACTCACACT | 42 | 31179 | 31194 | 2014 |
| 799001 | 1914 | 1929 | CAGCCGCACACTCACA | 37 | 31181 | 31196 | 2015 |
| 799002 | 1915 | 1930 | ACAGCCGCACACTCAC | 15 | 31182 | 31197 | 2016 |
| 799013 | 1983 | 1998 | TCCATAAGAGACACAA | 37 | 31250 | 31265 | 2017 |
| 799014 | 1986 | 2001 | ACATCCATAAGAGACA | 29 | 31253 | 31268 | 2018 |
| 799015 | 1989 | 2004 | GGGACATCCATAAGAG | 25 | 31256 | 31271 | 2019 |
| 799016 | 2004 | 2019 | CAAACCTCTCTGCTGG | 30 | 31271 | 31286 | 2020 |
| 799017 | 2006 | 2021 | TGCAAACCTCTCTGCT | 0 | 31273 | 31288 | 2021 |
| 799018 | 2007 | 2022 | CTGCAAACCTCTCTGC | 29 | 31274 | 31289 | 2022 |
| 799019 | 2008 | 2023 | ACTGCAAACCTCTCTG | 36 | 31275 | 31290 | 2023 |
| 799020 | 2009 | 2024 | GACTGCAAACCTCTCT | 48 | 31276 | 31291 | 2024 |
| 799021 | 2010 | 2025 | GGACTGCAAACCTCTC | 62 | 31277 | 31292 | 2025 |
| 799022 | 2011 | 2026 | GGGACTGCAAACCTCT | 61 | 31278 | 31293 | 2026 |
| 771576 | 2027 | 2046 | GGGCAGGAGAGACACCGCTT | 49 | 31294 | 31313 | 576 |
| 799033 | 2068 | 2083 | CCCAGGTACTGCCTCT | 35 | 31335 | 31350 | 2027 |
| 799034 | 2072 | 2087 | CTTGCCCAGGTACTGC | 12 | 31339 | 31354 | 2028 |
| 799035 | 2078 | 2093 | CGCCAGCTTGCCCAGG | 0 | 31345 | 31360 | 2029 |
| 799036 | 2081 | 2096 | AGCCGCCAGCTTGCCC | 8 | 31348 | 31363 | 2030 |
| 799037 | 2085 | 2100 | CCCCAGCCGCCAGCTT | 9 | 31352 | 31367 | 2031 |
| 799038 | 2088 | 2103 | GGACCCCAGCCGCCAG | 19 | 31355 | 31370 | 2032 |
| 799039 | 2093 | 2108 | TGCTGGGACCCCAGCC | 19 | 31360 | 31375 | 2033 |
| 799040 | 2096 | 2111 | AGCTGCTGGGACCCCA | 51 | 31363 | 31378 | 2034 |
| 799041 | 2099 | 2114 | GGCAGCTGCTGGGACC | 22 | 31366 | 31381 | 2035 |
| 799042 | 2106 | 2121 | TGCTCCTGGCAGCTGC | 33 | 31373 | 31388 | 2036 |
| 799053 | 2180 | 2195 | AGCCTGTGGACAGGCC | 0 | 31447 | 31462 | 2037 |
| 799054 | 2184 | 2199 | CAGAAGCCTGTGGACA | 15 | 31451 | 31466 | 2038 |
| 799055 | 2187 | 2202 | GCTCAGAAGCCTGTGG | 19 | 31454 | 31469 | 2039 |
| 799056 | 2191 | 2206 | CGCTGCTCAGAAGCCT | 28 | 31458 | 31473 | 2040 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799057 | 2195 | 2210 | GGCTCGCTGCTCAGAA | 0 | 31462 | 31477 | 2041 |
| 799058 | 2199 | 2214 | AGCAGGCTCGCTGCTC | 0 | 31466 | 31481 | 2042 |
| 799059 | 2202 | 2217 | ACTAGCAGGCTCGCTG | 18 | 31469 | 31484 | 2043 |
| 799060 | 2205 | 2220 | GCCACTAGCAGGCTCG | 37 | 31472 | 31487 | 2044 |
| 799061 | 2209 | 2224 | TTCGGCCACTAGCAGG | 45 | 31476 | 31491 | 2045 |
| 799062 | 2213 | 2228 | CTGGTTCGGCCACTAG | 45 | 31480 | 31495 | 2046 |
| 799073 | 2271 | 2286 | CGCTACAATGGCAGGG | 34 | 31538 | 31553 | 2047 |
| 799074 | 2284 | 2299 | CAAAAAGAAAGACGC | 9 | 31551 | 31566 | 2048 |
| 799075 | 2291 | 2306 | AGATGGCCAAAAAGA | 0 | 31558 | 31573 | 2049 |
| 799076 | 2294 | 2309 | AGCAGATGGCCAAAAA | 34 | 31561 | 31576 | 2050 |
| 799077 | 2298 | 2313 | CAGGAGCAGATGGCCA | 28 | 31565 | 31580 | 2051 |
| 799078 | 2301 | 2316 | ATCCAGGAGCAGATGG | 19 | 31568 | 31583 | 2052 |
| 799079 | 2304 | 2319 | GAGATCCAGGAGCAGA | 46 | 31571 | 31586 | 2053 |
| 799080 | 2307 | 2322 | AGGGAGATCCAGGAGC | 56 | 31574 | 31589 | 2054 |
| 799081 | 2311 | 2326 | TCTCAGGGAGATCCAG | 28 | 31578 | 31593 | 2055 |
| 799082 | 2316 | 2331 | GCCCATCTCAGGGAGA | 27 | 31583 | 31598 | 2056 |
| 799093 | 2404 | 2419 | GTCACCAGGGCAGGCA | 47 | 31671 | 31686 | 2057 |
| 799094 | 2408 | 2423 | TGATGTCACCAGGGCA | 57 | 31675 | 31690 | 2058 |
| 799095 | 2411 | 2426 | ACCTGATGTCACCAGG | 0 | 31678 | 31693 | 2059 |
| 799096 | 2412 | 2427 | AACCTGATGTCACCAG | 30 | 31679 | 31694 | 2060 |
| 799097 | 2413 | 2428 | AAACCTGATGTCACCA | 39 | 31680 | 31695 | 2061 |
| 799098 | 2414 | 2429 | AAAACCTGATGTCACC | 38 | 31681 | 31696 | 2062 |
| 799099 | 2415 | 2430 | AAAAACCTGATGTCAC | 44 | 31682 | 31697 | 2063 |
| 799100 | 2416 | 2431 | GAAAAACCTGATGTCA | 38 | 31683 | 31698 | 2064 |
| 799101 | 2417 | 2432 | GGAAAAACCTGATGTC | 55 | 31684 | 31699 | 2065 |
| 799102 | 2419 | 2434 | CGGGAAAAACCTGATG | 34 | 31686 | 31701 | 2066 |
| 799113 | 2456 | 2471 | GATGGGAGCAGGCAGT | 57 | 31723 | 31738 | 2067 |
| 799114 | 2459 | 2474 | CAGGATGGGAGCAGGC | 35 | 31726 | 31741 | 2068 |
| 799115 | 2462 | 2477 | ACACAGGATGGGAGCA | 40 | 31729 | 31744 | 2069 |
| 799116 | 2466 | 2481 | TAACACACAGGATGGG | 34 | 31733 | 31748 | 2070 |
| 799117 | 2469 | 2484 | GCTTAACACACAGGAT | 46 | 31736 | 31751 | 2071 |
| 799118 | 2472 | 2487 | AGAGCTTAACACACAG | 71 | 31739 | 31754 | 2072 |
| 799119 | 2475 | 2490 | AGCAGAGCTTAACACA | 50 | 31742 | 31757 | 2073 |
| 799120 | 2478 | 2493 | AATAGCAGAGCTTAAC | 45 | 31745 | 31760 | 2074 |
| 799121 | 2481 | 2496 | CCTAATAGCAGAGCTT | 25 | 31748 | 31763 | 2075 |
| 799122 | 2485 | 2500 | CTGGCCTAATAGCAGA | 29 | 31752 | 31767 | 2076 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799133 | 2520 | 2535 | GCTAAGCATGTCCCTC | 17 | 31787 | 31802 | 2077 |
| 799134 | 2523 | 2538 | ACTGCTAAGCATGTCC | 17 | 31790 | 31805 | 2078 |
| 799135 | 2526 | 2541 | GGGACTGCTAAGCATG | 38 | 31793 | 31808 | 2079 |
| 799136 | 2541 | 2556 | CTTCTTGGAGGGAAGG | 3 | 31808 | 31823 | 2080 |
| 799137 | 2545 | 2560 | AATCCTTCTTGGAGGG | 49 | 31812 | 31827 | 2081 |
| 799138 | 2548 | 2563 | CCAAATCCTTCTTGGA | 7 | 31815 | 31830 | 2082 |
| 799139 | 2552 | 2567 | CGGACCAAATCCTTCT | 56 | 31819 | 31834 | 2083 |
| 799140 | 2555 | 2570 | TGACGGACCAAATCCT | 60 | 31822 | 31837 | 2084 |
| 799141 | 2558 | 2573 | TTATGACGGACCAAAT | 47 | 31825 | 31840 | 2085 |
| 799142 | 2561 | 2576 | GGGTTATGACGGACCA | 38 | 31828 | 31843 | 2086 |
| 799153 | 2589 | 2604 | GTTAGGTGTCAGCCTA | 68 | 31856 | 31871 | 2087 |
| 799154 | 2592 | 2607 | AGAGTTAGGTGTCAGC | 39 | 31859 | 31874 | 2088 |
| 799155 | 2595 | 2610 | AGAAGAGTTAGGTGTC | 32 | 31862 | 31877 | 2089 |
| 799156 | 2598 | 2613 | GAAAGAAGAGTTAGGT | 37 | 31865 | 31880 | 2090 |
| 799157 | 2612 | 2627 | GTTGTAGAAGAAATGA | 39 | 31879 | 31894 | 2091 |
| 799158 | 2617 | 2632 | TATGAGTTGTAGAAGA | 33 | 31884 | 31899 | 2092 |
| 799159 | 2620 | 2635 | GTGTATGAGTTGTAGA | 56 | 31887 | 31902 | 2093 |
| 799160 | 2624 | 2639 | ACGAGTGTATGAGTTG | 61 | 31891 | 31906 | 2094 |
| 799161 | 2627 | 2642 | CATACGAGTGTATGAG | 29 | 31894 | 31909 | 2095 |
| 799162 | 2630 | 2645 | TATCATACGAGTGTAT | 36 | 31897 | 31912 | 2096 |
| 799173 | 2666 | 2681 | CTAAACATGCTCATTG | 18 | 31933 | 31948 | 2097 |
| 799174 | 2669 | 2684 | AGTCTAAACATGCTCA | 42 | 31936 | 31951 | 2098 |
| 799175 | 2672 | 2687 | TAAAGTCTAAACATGC | 0 | 31939 | 31954 | 2099 |
| 799176 | 2675 | 2690 | TGTTAAAGTCTAAACA | 0 | 31942 | 31957 | 2100 |
| 799177 | 2678 | 2693 | TTATGTTAAAGTCTAA | 0 | 31945 | 31960 | 2101 |
| 799178 | 2681 | 2696 | AGCTTATGTTAAAGTC | 34 | 31948 | 31963 | 2102 |
| 799179 | 2684 | 2699 | AATAGCTTATGTTAAA | 0 | 31951 | 31966 | 2103 |
| 799180 | 2688 | 2703 | GAAAATAGCTTATGT | 20 | 31955 | 31970 | 2104 |
| 799181 | 2692 | 2707 | GTTAGAAAATAGCTT | 37 | 31959 | 31974 | 2105 |
| 799182 | 2695 | 2710 | GTAGTTAGAAAATAG | 20 | 31962 | 31977 | 2106 |
| 790614 | 2726 | 2741 | GAGAATGCTTCTCTTG | 70 | 31993 | 32008 | 2107 |
| 799191 | 2728 | 2743 | ATGAGAATGCTTCTCT | 26 | 31995 | 32010 | 2108 |
| 790615 | 2731 | 2746 | CCAATGAGAATGCTTC | 38 | 31998 | 32013 | 2109 |
| 799192 | 2734 | 2749 | TTTCCAATGAGAATGC | 60 | 32001 | 32016 | 2110 |
| 799193 | 2738 | 2753 | TAAATTTCCAATGAGA | 43 | 32005 | 32020 | 2111 |
| 799194 | 2741 | 2756 | TGCTAAATTTCCAATG | 42 | 32008 | 32023 | 2112 |

TABLE 8-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 799195 | 2744 | 2759 | CAATGCTAAATTTCCA | 43 | 32011 | 32026 | 2113 |
| 790617 | 2747 | 2762 | CTACAATGCTAAATTT | 0 | 32014 | 32029 | 2114 |
| 799196 | 2750 | 2765 | GCACTACAATGCTAAA | 47 | 32017 | 32032 | 2115 |
| 772692 | 2753 | 2768 | AAAGCACTACAATGCT | 19 | 32020 | 32035 | 2116 |
| 790620 | 2794 | 2809 | TAATAAATCTCAGGTT | 30 | 32061 | 32076 | 2117 |
| 772700 | 2797 | 2812 | CTTTAATAAATCTCAG | 24 | 32064 | 32079 | 2118 |
| 799206 | 2848 | 2863 | TATATTTACAAGTAAT | 0 | 32115 | 32130 | 2119 |
| 799207 | 2851 | 2866 | CTTTATATTTACAAGT | 0 | 32118 | 32133 | 2120 |
| 772702 | 2854 | 2869 | CGTCTTTATATTTACA | 23 | 32121 | 32136 | 2121 |
| 799208 | 2868 | 2883 | TGATGCTTATAAAACG | 15 | 32135 | 32150 | 2122 |
| 799209 | 2871 | 2886 | TAATGATGCTTATAAA | 14 | 32138 | 32153 | 2123 |
| 799210 | 2875 | 2890 | TAAATAATGATGCTTA | 10 | 32142 | 32157 | 2124 |
| 799211 | 2878 | 2893 | ACATAAATAATGATGC | 0 | 32145 | 32160 | 2125 |
| 799212 | 2896 | 2911 | TTATACACATTGCACA | 35 | 32163 | 32178 | 2126 |
| 799219 | 2956 | 2971 | TGGCATTTGTTATTTG | 0 | 32223 | 32238 | 2127 |
| 799220 | 2960 | 2975 | AATTTGGCATTTGTTA | 0 | 32227 | 32242 | 2128 |
| 799221 | 2963 | 2978 | TTTAATTTGGCATTTG | 0 | 32230 | 32245 | 2129 |
| 799222 | 2967 | 2982 | CTTTTTTAATTTGGCA | 0 | 32234 | 32249 | 2130 |
| 799223 | 2980 | 2995 | ATCTTGTGTTTATCTT | 0 | 32247 | 32262 | 2131 |
| 799224 | 2983 | 2998 | CCAATCTTGTGTTTAT | 3 | 32250 | 32265 | 2132 |
| 799225 | 2986 | 3001 | ACACCAATCTTGTGTT | 4 | 32253 | 32268 | 2133 |
| 799226 | 2989 | 3004 | AAAACACCAATCTTGT | 15 | 32256 | 32271 | 2134 |
| 799227 | 2993 | 3008 | GAAAAAAACACCAATC | 2 | 32260 | 32275 | 2135 |
| 799228 | 2997 | 3012 | CATAGAAAAAAACACC | 4 | 32264 | 32279 | 2136 |
| 799236 | 3037 | 3052 | TAAACTCCTTTAGAAA | 45 | 32304 | 32319 | 2137 |
| 799237 | 3040 | 3055 | ACATAAACTCCTTTAG | 9 | 32307 | 32322 | 2138 |
| 790630 | 3043 | 3058 | GGAACATAAACTCCTT | 0 | 32310 | 32325 | 2139 |
| 799238 | 3046 | 3061 | AATGGAACATAAACTC | 17 | 32313 | 32328 | 2140 |
| 790631 | 3050 | 3065 | GTTTAATGGAACATAA | 0 | 32317 | 32332 | 2141 |

TABLE 9

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 772535 | 215 | 230 | CCGCACACCATGAAGA | 29 | 1710 | 1725 | 2142 |
| 772540 | 261 | 276 | AGGCGAGGAGAAAAGT | 10 | 1756 | 1771 | 2143 |
| 772551 | 550 | 565 | TTCAGATCCGCCTCGG | 39 | 2045 | 2060 | 2144 |
| 772552 | 555 | 570 | GCGCCTTCAGATCCGC | 34 | 2050 | 2065 | 2145 |
| 772553 | 576 | 591 | TCTTGAGCACCGAGTG | 59 | 2071 | 2086 | 2146 |
| 772567 | 794 | 809 | GACTTCCGAGGAATGC | 58 | 2289 | 2304 | 2147 |
| 772568 | 802 | 817 | AGCCTCTTGACTTCCG | 45 | 2297 | 2312 | 700 |
| 772571 | 823 | 838 | CCGTAAGATTCACAGC | 50 | 2318 | 2333 | 2148 |
| 772578 | 915 | 930 | GGTATCTGGAGTAAGG | 63 | 3784 | 3799 | 2149 |
| 772582 | 1014 | 1029 | CTGAAAGCCCCCCAGG | 34 | 9711 | 9726 | 2150 |
| 772584 | 1026 | 1041 | GAAGTTGGGAATCTGA | 4 | N/A | N/A | 2151 |
| 772589 | 1047 | 1062 | ACCGATCCCCAGGCTC | 9 | 30314 | 30329 | 2152 |
| 772591 | 1053 | 1068 | AGTGTGACCGATCCCC | 60 | 30320 | 30335 | 2153 |
| 772592 | 1057 | 1072 | CACCAGTGTGACCGAT | 24 | 30324 | 30339 | 2154 |
| 772593 | 1060 | 1075 | ACGCACCAGTGTGACC | 42 | 30327 | 30342 | 2155 |
| 772595 | 1063 | 1078 | ACCACGCACCAGTGTG | 2 | 30330 | 30345 | 2156 |
| 772604 | 1154 | 1169 | ATTCCCCTGAGGTAGA | 48 | 30421 | 30436 | 2157 |
| 772611 | 1169 | 1184 | TCCGAGGCAAAAGCCA | 14 | 30436 | 30451 | 2158 |
| 772614 | 1194 | 1209 | GACTCTTGTTGTCCGA | 43 | 30461 | 30476 | 2159 |
| 772623 | 1326 | 1341 | AGTCCGGGTTGTCCAG | 42 | 30593 | 30608 | 2160 |
| 772635 | 1468 | 1483 | AAGCTGATCTGCACGG | 43 | 30735 | 30750 | 2161 |
| 772687 | 2701 | 2716 | ACCTTTGTAGTTAGAA | 46 | 31968 | 31983 | 2162 |
| 772711 | 2988 | 3003 | AAACACCAATCTTGTG | 0 | 32255 | 32270 | 2163 |
| 772713 | 3005 | 3020 | ATAACACCCATAGAAA | 24 | 32272 | 32287 | 2164 |
| 772714 | 3010 | 3025 | AGGTGATAACACCCAT | 0 | 32277 | 32292 | 2165 |
| 772715 | 3014 | 3029 | AGCTAGGTGATAACAC | 0 | 32281 | 32296 | 2166 |
| 772732 | N/A | N/A | GATATTAGCTGTCAG | 58 | 3610 | 3625 | 2167 |
| 772733 | N/A | N/A | GGTGATTGCCTTGATA | 39 | 3622 | 3637 | 2168 |
| 772734 | N/A | N/A | AGGCAGGGCCGCGAGG | 16 | 3639 | 3654 | 2169 |
| 772735 | N/A | N/A | AACTGTTTGTCTTAGC | 52 | 3667 | 3682 | 2170 |
| 772738 | N/A | N/A | ACCAGTTGGTTTGAGA | 16 | 3810 | 3825 | 2171 |
| 772739 | N/A | N/A | TACTCACCAGTTGGTT | 0 | 3815 | 3830 | 2172 |
| 772762 | N/A | N/A | ATTTTGCTACCTAATG | 11 | 5481 | 5496 | 2173 |
| 772765 | N/A | N/A | GATTGGCAGGTTAATC | 35 | 5580 | 5595 | 2174 |
| 772808 | N/A | N/A | CCCCATTCATTAAGCC | 34 | 12507 | 12522 | 2175 |
| 772809 | N/A | N/A | CCTAAACTGAGCCCCA | 48 | 12518 | 12533 | 2176 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 772858 | N/A | N/A | AGTGTTCAACAATGCT | 62 | 18353 | 18368 | 2177 |
| 772929 | N/A | N/A | CGGAAGTCTTGTATTT | 37 | 29086 | 29101 | 2178 |
| 790463 | 206 | 221 | ATGAAGAAGTCGGGCG | 53 | 1701 | 1716 | 2179 |
| 790469 | 304 | 319 | CGGACGAGCGCAGATC | 41 | 1799 | 1814 | 2180 |
| 790471 | 333 | 348 | CGCCGGGCGCACGGCT | 4 | 1828 | 1843 | 2181 |
| 790484 | 761 | 776 | GAACACTTTGCACAGC | 62 | 2256 | 2271 | 2182 |
| 790486 | 781 | 796 | TGCCTGAGATCCGGCC | 23 | 2276 | 2291 | 2183 |
| 790488 | 791 | 806 | TTCCGAGGAATGCCTG | 81 | 2286 | 2301 | 2184 |
| 790491 | 821 | 836 | GTAAGATTCACAGCAA | 56 | 2316 | 2331 | 2185 |
| 790498 | 887 | 902 | CTCTAGTTCGCAGAGT | 11 | N/A | N/A | 2186 |
| 790508 | 1064 | 1079 | CACCACGCACCAGTGT | 0 | 30331 | 30346 | 2187 |
| 790516 | 1286 | 1301 | GTAACTGCTGCGGTTG | 45 | 30553 | 30568 | 2188 |
| 790519 | 1330 | 1345 | CTGGAGTCCGGGTTGT | 8 | 30597 | 30612 | 2189 |
| 790521 | 1401 | 1416 | GGCTGTACGCCTTCTC | 19 | 30668 | 30683 | 2190 |
| 790529 | 1467 | 1482 | AGCTGATCTGCACGGT | 65 | 30734 | 30749 | 2191 |
| 790537 | 1614 | 1629 | AGCAGCAAAGTAGTTT | 27 | 30881 | 30896 | 2192 |
| 790604 | 2625 | 2640 | TACGAGTGTATGAGTT | 30 | 31892 | 31907 | 2193 |
| 790605 | 2629 | 2644 | ATCATACGAGTGTATG | 32 | 31896 | 31911 | 2194 |
| 790609 | 2668 | 2683 | GTCTAAACATGCTCAT | 40 | 31935 | 31950 | 2195 |
| 790611 | 2680 | 2695 | GCTTATGTTAAAGTCT | 59 | 31947 | 31962 | 2196 |
| 790612 | 2704 | 2719 | TAAACCTTTGTAGTTA | 64 | 31971 | 31986 | 2197 |
| 790615 | 2731 | 2746 | CCAATGAGAATGCTTC | 40 | 31998 | 32013 | 2109 |
| 790616 | 2739 | 2754 | CTAAATTTCCAATGAG | 66 | 32006 | 32021 | 2198 |
| 790618 | 2751 | 2766 | AGCACTACAATGCTAA | 24 | 32018 | 32033 | 2199 |
| 790637 | N/A | N/A | ACCTAGTTCGCAGAGT | 0 | 2382 | 2397 | 2200 |
| 790647 | N/A | N/A | CGCGAGGCGGTGATTG | 24 | 3630 | 3645 | 2201 |
| 790652 | N/A | N/A | CACCAGTTGGTTTGAG | 25 | 3811 | 3826 | 2202 |
| 790659 | N/A | N/A | TGCCAGTCTCAAATGG | 27 | 4459 | 4474 | 2203 |
| 790666 | N/A | N/A | TAATTTATGACAACGC | 72 | 4866 | 4881 | 2204 |
| 790674 | N/A | N/A | TGCTACCTAATGTCAA | 40 | 5477 | 5492 | 2205 |
| 790678 | N/A | N/A | TCCTATTGGCTGATCT | 46 | 5561 | 5576 | 2206 |
| 790679 | N/A | N/A | AGGTTAATCACTTCCT | 13 | 5573 | 5588 | 2207 |
| 790693 | N/A | N/A | CAAAGTATACCTGTTC | 45 | 7676 | 7691 | 2208 |
| 790696 | N/A | N/A | CAAAGGTAAGCCAGCT | 41 | 7810 | 7825 | 2209 |
| 790697 | N/A | N/A | ATTCAGGGTGTCAGCC | 59 | 7836 | 7851 | 2210 |
| 790701 | N/A | N/A | GGATACACTTAATCAA | 57 | 8125 | 8140 | 2211 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 790732 | N/A | N/A | GCTTATTTCATGTGGT | 69 | 11190 | 11205 | 2212 |
| 790736 | N/A | N/A | TCAAACTTTGAAGCCT | 60 | 11988 | 12003 | 2213 |
| 790741 | N/A | N/A | ATTAAGCCCGCTCTCA | 30 | 12499 | 12514 | 2214 |
| 790747 | N/A | N/A | GTACAATCTCCTGGAA | 8 | 12941 | 12956 | 2215 |
| 790754 | N/A | N/A | CTAAGCTACTTGGTTT | 38 | 14094 | 14109 | 2216 |
| 790775 | N/A | N/A | TACAAGGTGAAAGTTA | 7 | 17280 | 17295 | 2217 |
| 790791 | N/A | N/A | GGGCACACCACCTGCC | 7 | 18421 | 18436 | 2218 |
| 790855 | N/A | N/A | ACCTTTTCCGGTATTT | 40 | 26989 | 27004 | 2219 |
| 790871 | N/A | N/A | TGTTAGGACCTGGGAA | 39 | 28757 | 28772 | 2220 |
| 790874 | N/A | N/A | CCGGAAGTCTTGTATT | 0 | 29087 | 29102 | 2221 |
| 798764 | 757 | 772 | ACTTTGCACAGCAGGA | 75 | 2252 | 2267 | 694 |
| 798781 | 822 | 837 | CGTAAGATTCACAGCA | 69 | 2317 | 2332 | 1456 |
| 799143 | 2562 | 2577 | TGGGTTATGACGGACC | 61 | 31829 | 31844 | 1320 |
| 799144 | 2563 | 2578 | TTGGGTTATGACGGAC | 72 | 31830 | 31845 | 1321 |
| 799184 | 2702 | 2717 | AACCTTTGTAGTTAGA | 48 | 31969 | 31984 | 1341 |
| 799396 | N/A | N/A | TGTTACAAATACAGAG | 66 | 5078 | 5093 | 1516 |
| 799566 | N/A | N/A | GAGTAAACAATACCCT | 89 | 10898 | 10913 | 1629 |
| 799572 | N/A | N/A | ACCATCTAACAACATC | 55 | 11125 | 11140 | 1635 |
| 799583 | N/A | N/A | AAGACAAACCTTCCGA | 74 | 11237 | 11252 | 1637 |
| 800109 | N/A | N/A | ACAGCCACAAGTCACA | 88 | 6284 | 6299 | 783 |
| 800768 | 116 | 131 | GCGCTCCGTGGCATGC | 18 | 1611 | 1626 | 2222 |
| 800769 | 171 | 186 | GCAGGCGACAGCAGCA | 49 | 1666 | 1681 | 2223 |
| 800771 | 387 | 402 | CCCGCAGCTCGCCTCC | 46 | 1882 | 1897 | 2224 |
| 800776 | 650 | 665 | GAGGCACGCGGTGCGC | 36 | 2145 | 2160 | 2225 |
| 800786 | 1058 | 1073 | GCACCAGTGTGACCGA | 0 | 30325 | 30340 | 2226 |
| 800787 | 1105 | 1120 | CAGTAGAGCCTCCCCA | 38 | 30372 | 30387 | 2227 |
| 800793 | 1195 | 1210 | TGACTCTTGTTGTCCG | 53 | 30462 | 30477 | 2228 |
| 800795 | 1285 | 1300 | TAACTGCTGCGGTTGT | 12 | 30552 | 30567 | 2229 |
| 800798 | 1331 | 1346 | CCTGGAGTCCGGGTTG | 36 | 30598 | 30613 | 2230 |
| 800821 | 2740 | 2755 | GCTAAATTTCCAATGA | 56 | 32007 | 32022 | 2231 |
| 800837 | 2703 | 2718 | AAACCTTTGTAGTTAG | 41 | 31970 | 31985 | 2232 |
| 800843 | N/A | N/A | TCGGCCACACACCTCA | 32 | 2777 | 2792 | 2233 |
| 800858 | N/A | N/A | AGCCCAACTGTTTGTC | 40 | 3672 | 3687 | 2234 |
| 800861 | N/A | N/A | CCAGTTGGTTTGAGAA | 32 | 3809 | 3824 | 2235 |
| 800883 | N/A | N/A | ACCATTTATCTGGTGT | 50 | 5039 | 5054 | 2236 |
| 800998 | N/A | N/A | CCCGCTCTCAGCCAGG | 39 | 12493 | 12508 | 2237 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 800999 | N/A | N/A | CATTCATTAAGCCCGC | 54 | 12504 | 12519 | 2238 |
| 801003 | N/A | N/A | GAATCAAGCCCTGGCT | 38 | 12557 | 12572 | 2239 |
| 801040 | N/A | N/A | GTCATGAAAGATTCTT | 72 | 17588 | 17603 | 2240 |
| 801051 | N/A | N/A | GTGTTCAACAATGCTT | 68 | 18352 | 18367 | 2241 |
| 801128 | N/A | N/A | AGTATCCATCAACTGC | 48 | 28270 | 28285 | 2242 |
| 801132 | N/A | N/A | GGTGACTCATCAGGCA | 55 | 28303 | 28318 | 2243 |
| 801138 | N/A | N/A | GTTAGGACCTGGGAAC | 6 | 28756 | 28771 | 2244 |
| 801145 | N/A | N/A | ACGCTGTGGTTTGTGG | 0 | 29117 | 29132 | 2245 |
| 829715 | 95 | 110 | TCTCCCGGAGGCCGGG | 40 | 1590 | 1605 | 2246 |
| 829716 | 96 | 111 | GTCTCCCGGAGGCCGG | 10 | 1591 | 1606 | 2247 |
| 829717 | 97 | 112 | AGTCTCCCGGAGGCCG | 28 | 1592 | 1607 | 2248 |
| 829718 | 99 | 114 | CCAGTCTCCCGGAGGC | 15 | 1594 | 1609 | 2249 |
| 829719 | 100 | 115 | GCCAGTCTCCCGGAGG | 15 | 1595 | 1610 | 2250 |
| 829720 | 102 | 117 | GCGCCAGTCTCCCGGA | 14 | 1597 | 1612 | 2251 |
| 829721 | 103 | 118 | TGCGCCAGTCTCCCGG | 33 | 1598 | 1613 | 2252 |
| 829722 | 104 | 119 | ATGCGCCAGTCTCCCG | 38 | 1599 | 1614 | 2253 |
| 829723 | 106 | 121 | GCATGCGCCAGTCTCC | 54 | 1601 | 1616 | 2254 |
| 829724 | 107 | 122 | GGCATGCGCCAGTCTC | 54 | 1602 | 1617 | 2255 |
| 829725 | 111 | 126 | CCGTGGCATGCGCCAG | 41 | 1606 | 1621 | 2256 |
| 829726 | 113 | 128 | CTCCGTGGCATGCGCC | 41 | 1608 | 1623 | 2257 |
| 829727 | 114 | 129 | GCTCCGTGGCATGCGC | 35 | 1609 | 1624 | 2258 |
| 829728 | 174 | 189 | GGCGCAGGCGACAGCA | 44 | 1669 | 1684 | 2259 |
| 829729 | 175 | 190 | AGGCGCAGGCGACAGC | 66 | 1670 | 1685 | 2260 |
| 829730 | 177 | 192 | GCAGGCGCAGGCGACA | 23 | 1672 | 1687 | 2261 |
| 829731 | 178 | 193 | AGCAGGCGCAGGCGAC | 50 | 1673 | 1688 | 2262 |
| 829732 | 207 | 222 | CATGAAGAAGTCGGGC | 40 | 1702 | 1717 | 2263 |
| 829733 | 209 | 224 | ACCATGAAGAAGTCGG | 54 | 1704 | 1719 | 2264 |
| 829734 | 216 | 231 | TCCGCACACCATGAAG | 71 | 1711 | 1726 | 2265 |
| 829735 | 218 | 233 | CCTCCGCACACCATGA | 61 | 1713 | 1728 | 2266 |
| 829736 | 231 | 246 | GGAGCGAACATGACCT | 41 | 1726 | 1741 | 2267 |
| 829737 | 232 | 247 | AGGAGCGAACATGACC | 52 | 1727 | 1742 | 2268 |
| 829738 | 234 | 249 | TAAGGAGCGAACATGA | 49 | 1729 | 1744 | 2269 |
| 829739 | 237 | 252 | TGCTAAGGAGCGAACA | 44 | 1732 | 1747 | 2270 |
| 829740 | 238 | 253 | CTGCTAAGGAGCGAAC | 52 | 1733 | 1748 | 2271 |
| 829741 | 305 | 320 | CCGGACGAGCGCAGAT | 32 | 1800 | 1815 | 2272 |
| 829742 | 307 | 322 | CGCCGGACGAGCGCAG | 43 | 1802 | 1817 | 2273 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829743 | 308 | 323 | ACGCCGGACGAGCGCA | 25 | 1803 | 1818 | 2274 |
| 829744 | 323 | 338 | ACGGCTCCTCCAGAGA | 39 | 1818 | 1833 | 2275 |
| 829745 | 330 | 345 | CGGGCGCACGGCTCCT | 19 | 1825 | 1840 | 2276 |
| 829746 | 331 | 346 | CCGGGCGCACGGCTCC | 46 | 1826 | 1841 | 2277 |
| 829747 | 337 | 352 | TCGCCGCCGGGCGCAC | 16 | 1832 | 1847 | 2278 |
| 829748 | 338 | 353 | CTCGCCGCCGGGCGCA | 43 | 1833 | 1848 | 2279 |
| 829749 | 340 | 355 | TCCTCGCCGCCGGGCG | 26 | 1835 | 1850 | 2280 |
| 829750 | 342 | 357 | CGTCCTCGCCGCCGGG | 33 | 1837 | 1852 | 2281 |
| 829751 | 384 | 399 | GCAGCTCGCCTCCTCC | 40 | 1879 | 1894 | 2282 |
| 829752 | 386 | 401 | CCGCAGCTCGCCTCCT | 27 | 1881 | 1896 | 2283 |
| 829753 | 389 | 404 | TCCCCGCAGCTCGCCT | 29 | 1884 | 1899 | 2284 |
| 829754 | 391 | 406 | TCTCCCCGCAGCTCGC | 49 | 1886 | 1901 | 2285 |
| 829755 | 392 | 407 | TTCTCCCCGCAGCTCG | 52 | 1887 | 1902 | 2286 |
| 829756 | 402 | 417 | CCGTCGCCCCTTCTCC | 42 | 1897 | 1912 | 2287 |
| 829757 | 424 | 439 | CCGGCCCCATGCGCTC | 15 | 1919 | 1934 | 2288 |
| 829758 | 426 | 441 | CACCGGCCCCATGCGC | 24 | 1921 | 1936 | 2289 |
| 829759 | 430 | 445 | CCGCCACCGGCCCCAT | 51 | 1925 | 1940 | 2290 |
| 829760 | 468 | 483 | CCGCCTTGCCCAGGCA | 3 | 1963 | 1978 | 2291 |
| 829761 | 549 | 564 | TCAGATCCGCCTCGGC | 21 | 2044 | 2059 | 2292 |
| 829762 | 552 | 567 | CCTTCAGATCCGCCTC | 67 | 2047 | 2062 | 2293 |
| 829763 | 579 | 594 | GTTTCTTGAGCACCGA | 65 | 2074 | 2089 | 2294 |
| 829764 | 590 | 605 | CCGCTCCTTCAGTTTC | 44 | 2085 | 2100 | 2295 |
| 829765 | 591 | 606 | GCCGCTCCTTCAGTTT | 28 | 2086 | 2101 | 2296 |
| 829766 | 593 | 608 | CTGCCGCTCCTTCAGT | 32 | 2088 | 2103 | 2297 |
| 829767 | 651 | 666 | GGAGGCACGCGGTGCG | 66 | 2146 | 2161 | 2298 |
| 829768 | 654 | 669 | GCAGGAGGCACGCGGT | 41 | 2149 | 2164 | 2299 |
| 829769 | 656 | 671 | CAGCAGGAGGCACGCG | 46 | 2151 | 2166 | 2300 |
| 829770 | 673 | 688 | CAGTCCAGGCGGCCGG | 42 | 2168 | 2183 | 2301 |
| 829771 | 674 | 689 | GCAGTCCAGGCGGCCG | 22 | 2169 | 2184 | 2302 |
| 829772 | 729 | 744 | AGGACGAGGGCGGCTG | 52 | 2224 | 2239 | 2303 |
| 829773 | 731 | 746 | GTAGGACGAGGGCGGC | 50 | 2226 | 2241 | 2304 |
| 829774 | 732 | 747 | AGTAGGACGAGGGCGG | 22 | 2227 | 2242 | 2305 |
| 829775 | 734 | 749 | CGAGTAGGACGAGGGC | 59 | 2229 | 2244 | 2306 |
| 829776 | 735 | 750 | GCGAGTAGGACGAGGG | 64 | 2230 | 2245 | 2307 |
| 829777 | 737 | 752 | GAGCGAGTAGGACGAG | 37 | 2232 | 2247 | 2308 |
| 829778 | 738 | 753 | GGAGCGAGTAGGACGA | 46 | 2233 | 2248 | 2309 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829779 | 739 | 754 | GGGAGCGAGTAGGACG | 58 | 2234 | 2249 | 2310 |
| 829780 | 770 | 785 | CGGCCACCTGAACACT | 37 | 2265 | 2280 | 2311 |
| 829781 | 771 | 786 | CCGGCCACCTGAACAC | 31 | 2266 | 2281 | 2312 |
| 829782 | 773 | 788 | ATCCGGCCACCTGAAC | 36 | 2268 | 2283 | 2313 |
| 829783 | 774 | 789 | GATCCGGCCACCTGAA | 52 | 2269 | 2284 | 2314 |
| 829784 | 775 | 790 | AGATCCGGCCACCTGA | 32 | 2270 | 2285 | 2315 |
| 829785 | 782 | 797 | ATGCCTGAGATCCGGC | 27 | 2277 | 2292 | 2316 |
| 829786 | 784 | 799 | GAATGCCTGAGATCCG | 56 | 2279 | 2294 | 2317 |
| 829787 | 785 | 800 | GGAATGCCTGAGATCC | 30 | 2280 | 2295 | 2318 |
| 829788 | 790 | 805 | TCCGAGGAATGCCTGA | 41 | 2285 | 2300 | 2319 |
| 829789 | 793 | 808 | ACTTCCGAGGAATGCC | 42 | 2288 | 2303 | 2320 |
| 829790 | 824 | 839 | CCCGTAAGATTCACAG | 51 | 2319 | 2334 | 2321 |
| 829791 | 826 | 841 | TTCCCGTAAGATTCAC | 38 | 2321 | 2336 | 2322 |
| 829792 | 827 | 842 | CTTCCCGTAAGATTCA | 39 | 2322 | 2337 | 2323 |
| 829793 | 828 | 843 | TCTTCCCGTAAGATTC | 41 | 2323 | 2338 | 2324 |
| 829794 | 830 | 845 | GATCTTCCCGTAAGAT | 24 | 2325 | 2340 | 2325 |
| 829795 | 831 | 846 | TGATCTTCCCGTAAGA | 34 | 2326 | 2341 | 2326 |
| 829796 | 832 | 847 | TTGATCTTCCCGTAAG | 27 | 2327 | 2342 | 2327 |
| 829797 | 834 | 849 | GGTTGATCTTCCCGTA | 54 | 2329 | 2344 | 2328 |
| 829798 | 835 | 850 | GGGTTGATCTTCCCGT | 26 | 2330 | 2345 | 2329 |
| 829799 | 872 | 887 | TCGGCTAAGGTGATGG | 51 | 2367 | 2382 | 2330 |
| 829800 | 873 | 888 | GTCGGCTAAGGTGATG | 30 | 2368 | 2383 | 2331 |
| 829801 | 874 | 889 | AGTCGGCTAAGGTGAT | 8 | 2369 | 2384 | 2332 |
| 829802 | 881 | 896 | TTCGCAGAGTCGGCTA | 28 | 2376 | 2391 | 2333 |
| 829803 | 883 | 898 | AGTTCGCAGAGTCGGC | 35 | 2378 | 2393 | 2334 |
| 829804 | 884 | 899 | TAGTTCGCAGAGTCGG | 39 | 2379 | 2394 | 2335 |
| 829805 | 886 | 901 | TCTAGTTCGCAGAGTC | 37 | N/A | N/A | 2336 |
| 829806 | 889 | 904 | GACTCTAGTTCGCAGA | 41 | N/A | N/A | 2337 |
| 829807 | 890 | 905 | AGACTCTAGTTCGCAG | 41 | N/A | N/A | 2338 |
| 829808 | 892 | 907 | GGAGACTCTAGTTCGC | 53 | N/A | N/A | 2339 |
| 829809 | 893 | 908 | GGGAGACTCTAGTTCG | 51 | N/A | N/A | 2340 |
| 829810 | 919 | 934 | ATCGGGTATCTGGAGT | 29 | 3788 | 3803 | 2341 |
| 829811 | 922 | 937 | TCCATCGGGTATCTGG | 0 | 3791 | 3806 | 2342 |
| 829814 | 944 | 959 | GTCTGCAGTTGGTTTG | 94 | N/A | N/A | 2343 |
| 829822 | 977 | 992 | TGTTTCAGCGGAGGAA | 43 | 9674 | 9689 | 2344 |
| 829829 | 1015 | 1030 | TCTGAAAGCCCCCCAG | 11 | N/A | N/A | 2345 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829830 | 1017 | 1032 | AATCTGAAAGCCCCCC | 36 | N/A | N/A | 2346 |
| 829831 | 1048 | 1063 | GACCGATCCCCAGGCT | 9 | 30315 | 30330 | 2347 |
| 829832 | 1049 | 1064 | TGACCGATCCCCAGGC | 51 | 30316 | 30331 | 2348 |
| 829833 | 1050 | 1065 | GTGACCGATCCCCAGG | 0 | 30317 | 30332 | 2349 |
| 829834 | 1052 | 1067 | GTGTGACCGATCCCCA | 29 | 30319 | 30334 | 2350 |
| 829835 | 1054 | 1069 | CAGTGTGACCGATCCC | 52 | 30321 | 30336 | 2351 |
| 829836 | 1055 | 1070 | CCAGTGTGACCGATCC | 48 | 30322 | 30337 | 2352 |
| 829837 | 1073 | 1088 | CCAGTATGCCACCACG | 16 | 30340 | 30355 | 2353 |
| 829838 | 1074 | 1089 | CCCAGTATGCCACCAC | 28 | 30341 | 30356 | 2354 |
| 829839 | 1108 | 1123 | ACACAGTAGAGCCTCC | 8 | 30375 | 30390 | 2355 |
| 829840 | 1110 | 1125 | GGACACAGTAGAGCCT | 0 | 30377 | 30392 | 2356 |
| 829841 | 1111 | 1126 | TGGACACAGTAGAGCC | 50 | 30378 | 30393 | 2357 |
| 829842 | 1168 | 1183 | CCGAGGCAAAAGCCAT | 26 | 30435 | 30450 | 2358 |
| 829843 | 1180 | 1195 | GAATTGAGCTGTCCGA | 49 | 30447 | 30462 | 2359 |
| 829844 | 1181 | 1196 | CGAATTGAGCTGTCCG | 49 | 30448 | 30463 | 2360 |
| 829845 | 1183 | 1198 | TCCGAATTGAGCTGTC | 40 | 30450 | 30465 | 2361 |
| 829846 | 1184 | 1199 | GTCCGAATTGAGCTGT | 29 | 30451 | 30466 | 2362 |
| 829847 | 1185 | 1200 | TGTCCGAATTGAGCTG | 64 | 30452 | 30467 | 2363 |
| 829848 | 1186 | 1201 | TTGTCCGAATTGAGCT | 47 | 30453 | 30468 | 2364 |
| 829849 | 1188 | 1203 | TGTTGTCCGAATTGAG | 49 | 30455 | 30470 | 2365 |
| 829850 | 1189 | 1204 | TTGTTGTCCGAATTGA | 36 | 30456 | 30471 | 2366 |
| 829851 | 1190 | 1205 | CTTGTTGTCCGAATTG | 31 | 30457 | 30472 | 2367 |
| 829852 | 1191 | 1206 | TCTTGTTGTCCGAATT | 33 | 30458 | 30473 | 2368 |
| 829853 | 1193 | 1208 | ACTCTTGTTGTCCGAA | 42 | 30460 | 30475 | 2369 |
| 829854 | 1197 | 1212 | GCTGACTCTTGTTGTC | 25 | 30464 | 30479 | 2370 |
| 829855 | 1198 | 1213 | AGCTGACTCTTGTTGT | 0 | 30465 | 30480 | 2371 |
| 829856 | 1201 | 1216 | ACCAGCTGACTCTTGT | 41 | 30468 | 30483 | 2372 |
| 829857 | 1204 | 1219 | TGCACCAGCTGACTCT | 31 | 30471 | 30486 | 2373 |
| 829858 | 1218 | 1233 | TGCTCCGCACCTTCTG | 59 | 30485 | 30500 | 2374 |
| 829859 | 1221 | 1236 | TTTTGCTCCGCACCTT | 39 | 30488 | 30503 | 2375 |
| 829860 | 1243 | 1258 | GTCAGCTGGATGCCGC | 31 | 30510 | 30525 | 2376 |
| 829861 | 1258 | 1273 | CCATCCACCTCCCGCG | 35 | 30525 | 30540 | 2377 |
| 829862 | 1282 | 1297 | CTGCTGCGGTTGTACA | 22 | 30549 | 30564 | 2378 |
| 829863 | 1283 | 1298 | ACTGCTGCGGTTGTAC | 31 | 30550 | 30565 | 2379 |
| 829864 | 1288 | 1303 | GGGTAACTGCTGCGGT | 68 | 30555 | 30570 | 2380 |
| 829865 | 1307 | 1322 | GGCGGACTTGATGAAG | 30 | 30574 | 30589 | 2381 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829866 | 1309 | 1324 | GTGGCGGACTTGATGA | 10 | 30576 | 30591 | 2382 |
| 829867 | 1310 | 1325 | TGTGGCGGACTTGATG | 22 | 30577 | 30592 | 2383 |
| 829868 | 1312 | 1327 | AGTGTGGCGGACTTGA | 52 | 30579 | 30594 | 2384 |
| 829869 | 1313 | 1328 | CAGTGTGGCGGACTTG | 37 | 30580 | 30595 | 2385 |
| 829870 | 1314 | 1329 | CCAGTGTGGCGGACTT | 19 | 30581 | 30596 | 2386 |
| 829871 | 1316 | 1331 | GTCCAGTGTGGCGGAC | 1 | 30583 | 30598 | 2387 |
| 829872 | 1317 | 1332 | TGTCCAGTGTGGCGGA | 50 | 30584 | 30599 | 2388 |
| 829873 | 1318 | 1333 | TTGTCCAGTGTGGCGG | 52 | 30585 | 30600 | 2389 |
| 829874 | 1319 | 1334 | GTTGTCCAGTGTGGCG | 43 | 30586 | 30601 | 2390 |
| 829875 | 1322 | 1337 | CGGGTTGTCCAGTGTG | 52 | 30589 | 30604 | 2391 |
| 829876 | 1323 | 1338 | CCGGGTTGTCCAGTGT | 30 | 30590 | 30605 | 2392 |
| 829877 | 1324 | 1339 | TCCGGGTTGTCCAGTG | 42 | 30591 | 30606 | 2393 |
| 829878 | 1327 | 1342 | GAGTCCGGGTTGTCCA | 18 | 30594 | 30609 | 2394 |
| 829879 | 1329 | 1344 | TGGAGTCCGGGTTGTC | 29 | 30596 | 30611 | 2395 |
| 829880 | 1332 | 1347 | TCCTGGAGTCCGGGTT | 32 | 30599 | 30614 | 2396 |
| 829881 | 1334 | 1349 | CGTCCTGGAGTCCGGG | 39 | 30601 | 30616 | 2397 |
| 829882 | 1402 | 1417 | AGGCTGTACGCCTTCT | 3 | 30669 | 30684 | 2398 |
| 829883 | 1403 | 1418 | CAGGCTGTACGCCTTC | 0 | 30670 | 30685 | 2399 |
| 829884 | 1405 | 1420 | TGCAGGCTGTACGCCT | 24 | 30672 | 30687 | 2400 |
| 829885 | 1409 | 1424 | CCGCTGCAGGCTGTAC | 31 | 30676 | 30691 | 2401 |
| 829886 | 1421 | 1436 | GTGGTCATTGGGCCGC | 6 | 30688 | 30703 | 2402 |
| 829887 | 1422 | 1437 | CGTGGTCATTGGGCCG | 47 | 30689 | 30704 | 2403 |
| 829888 | 1444 | 1459 | GTCCACGGCTGCTGCA | 47 | 30711 | 30726 | 2404 |
| 829889 | 1445 | 1460 | CGTCCACGGCTGCTGC | 48 | 30712 | 30727 | 2405 |
| 829890 | 1450 | 1465 | AAGCCCGTCCACGGCT | 0 | 30717 | 30732 | 2406 |
| 829891 | 1462 | 1477 | ATCTGCACGGTAAAGC | 25 | 30729 | 30744 | 2407 |
| 829892 | 1463 | 1478 | GATCTGCACGGTAAAG | 32 | 30730 | 30745 | 2408 |
| 829893 | 1464 | 1479 | TGATCTGCACGGTAAA | 14 | 30731 | 30746 | 2409 |
| 829894 | 1466 | 1481 | GCTGATCTGCACGGTA | 41 | 30733 | 30748 | 2410 |
| 829895 | 1473 | 1488 | TCACAAAGCTGATCTG | 37 | 30740 | 30755 | 2411 |
| 829896 | 1498 | 1513 | CGGGTGTAGCACTGGC | 44 | 30765 | 30780 | 2412 |
| 829897 | 1499 | 1514 | GCGGGTGTAGCACTGG | 40 | 30766 | 30781 | 2413 |
| 829898 | 1501 | 1516 | TGGCGGGTGTAGCACT | 31 | 30768 | 30783 | 2414 |
| 829899 | 1521 | 1536 | ACGGGCAGCTGCTGAT | 20 | 30788 | 30803 | 2415 |
| 829900 | 1522 | 1537 | CACGGGCAGCTGCTGA | 0 | 30789 | 30804 | 2416 |
| 829901 | 1524 | 1539 | AGCACGGGCAGCTGCT | 10 | 30791 | 30806 | 2417 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829902 | 1525 | 1540 | CAGCACGGGCAGCTGC | 0 | 30792 | 30807 | 2418 |
| 829903 | 1546 | 1561 | CTGTTGAAGATGACCT | 25 | 30813 | 30828 | 2419 |
| 829904 | 1547 | 1562 | GCTGTTGAAGATGACC | 21 | 30814 | 30829 | 2420 |
| 829905 | 1549 | 1564 | CGGCTGTTGAAGATGA | 20 | 30816 | 30831 | 2421 |
| 829906 | 1550 | 1565 | CCGGCTGTTGAAGATG | 0 | 30817 | 30832 | 2422 |
| 829907 | 1551 | 1566 | ACCGGCTGTTGAAGAT | 23 | 30818 | 30833 | 2423 |
| 829908 | 1553 | 1568 | CTACCGGCTGTTGAAG | 1 | 30820 | 30835 | 2424 |
| 829909 | 1556 | 1571 | CGGCTACCGGCTGTTG | 34 | 30823 | 30838 | 2425 |
| 829910 | 1653 | 1668 | GAGTTTGCATGAAAAG | 49 | 30920 | 30935 | 2426 |
| 829911 | 1661 | 1676 | CGACCAAAGAGTTTGC | 52 | 30928 | 30943 | 2427 |
| 829912 | 1663 | 1678 | AACGACCAAAGAGTTT | 24 | 30930 | 30945 | 2428 |
| 829913 | 2565 | 2580 | CCTTGGGTTATGACGG | 40 | 31832 | 31847 | 2429 |
| 829914 | 2566 | 2581 | ACCTTGGGTTATGACG | 35 | 31833 | 31848 | 2430 |
| 829915 | 2569 | 2584 | GGTACCTTGGGTTATG | 22 | 31836 | 31851 | 2431 |
| 829916 | 2594 | 2609 | GAAGAGTTAGGTGTCA | 33 | 31861 | 31876 | 2432 |
| 829917 | 2621 | 2636 | AGTGTATGAGTTGTAG | 45 | 31888 | 31903 | 2433 |
| 829918 | 2622 | 2637 | GAGTGTATGAGTTGTA | 53 | 31889 | 31904 | 2434 |
| 829919 | 2623 | 2638 | CGAGTGTATGAGTTGT | 47 | 31890 | 31905 | 2435 |
| 829920 | 2626 | 2641 | ATACGAGTGTATGAGT | 30 | 31893 | 31908 | 2436 |
| 829921 | 2628 | 2643 | TCATACGAGTGTATGA | 10 | 31895 | 31910 | 2437 |
| 829922 | 2631 | 2646 | GTATCATACGAGTGTA | 56 | 31898 | 31913 | 2438 |
| 829923 | 2632 | 2647 | AGTATCATACGAGTGT | 54 | 31899 | 31914 | 2439 |
| 829924 | 2657 | 2672 | CTCATTGAGCTAAGAA | 25 | 31924 | 31939 | 2440 |
| 829925 | 2660 | 2675 | ATGCTCATTGAGCTAA | 37 | 31927 | 31942 | 2441 |
| 829926 | 2661 | 2676 | CATGCTCATTGAGCTA | 24 | 31928 | 31943 | 2442 |
| 829927 | 2670 | 2685 | AAGTCTAAACATGCTC | 64 | 31937 | 31952 | 2443 |
| 829928 | 2749 | 2764 | CACTACAATGCTAAAT | 26 | 32016 | 32031 | 2444 |
| 829929 | 2984 | 2999 | ACCAATCTTGTGTTTA | 19 | 32251 | 32266 | 2445 |
| 829930 | 2985 | 3000 | CACCAATCTTGTGTTT | 0 | 32252 | 32267 | 2446 |
| 829931 | 2987 | 3002 | AACACCAATCTTGTGT | 0 | 32254 | 32269 | 2447 |
| 829932 | 3007 | 3022 | TGATAACACCCATAGA | 41 | 32274 | 32289 | 2448 |
| 829933 | 3008 | 3023 | GTGATAACACCCATAG | 38 | 32275 | 32290 | 2449 |
| 829934 | 3011 | 3026 | TAGGTGATAACACCCA | 26 | 32278 | 32293 | 2450 |
| 829935 | 3012 | 3027 | CTAGGTGATAACACCC | 0 | 32279 | 32294 | 2451 |
| 829936 | 3015 | 3030 | CAGCTAGGTGATAACA | 14 | 32282 | 32297 | 2452 |
| 829937 | 3017 | 3032 | TTCAGCTAGGTGATAA | 0 | 32284 | 32299 | 2453 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829938 | 3018 | 3033 | ATTCAGCTAGGTGATA | 17 | 32285 | 32300 | 2454 |
| 829939 | 3020 | 3035 | ACATTCAGCTAGGTGA | 34 | 32287 | 32302 | 2455 |
| 829944 | N/A | N/A | CCAGTTAATCATTACT | 23 | 9421 | 9436 | 2456 |
| 829945 | N/A | N/A | GCCAGTTAATCATTAC | 31 | 9422 | 9437 | 2457 |
| 829946 | N/A | N/A | GCAGCCAGTTAATCAT | 44 | 9425 | 9440 | 2458 |
| 829947 | N/A | N/A | GGGCAGCCAGTTAATC | 31 | 9427 | 9442 | 2459 |
| 829948 | N/A | N/A | CGGGCAGCCAGTTAAT | 43 | 9428 | 9443 | 2460 |
| 829949 | N/A | N/A | CCGGGCAGCCAGTTAA | 19 | 9429 | 9444 | 2461 |
| 829950 | N/A | N/A | TCCGGGCAGCCAGTTA | 43 | 9430 | 9445 | 2462 |
| 829951 | N/A | N/A | GCTCCGGGCAGCCAGT | 10 | 9432 | 9447 | 2463 |
| 829952 | N/A | N/A | ACCCGTCTGGGCTCCG | 2 | 9442 | 9457 | 2464 |
| 829953 | N/A | N/A | GTCACCCGTCTGGGCT | 34 | 9445 | 9460 | 2465 |
| 829954 | N/A | N/A | TTGTCACCCGTCTGGG | 53 | 9447 | 9462 | 2466 |
| 829955 | N A | N/A | CTTGTCACCCGTCTGG | 52 | 9448 | 9463 | 2467 |
| 829956 | N/A | N/A | CCTTGTCACCCGTCTG | 66 | 9449 | 9464 | 2468 |
| 829957 | N/A | N/A | CACCTTGTCACCCGTC | 41 | 9451 | 9466 | 2469 |
| 829958 | N/A | N/A | GCACCTTGTCACCCGT | 51 | 9452 | 9467 | 2470 |
| 829959 | N/A | N/A | TTATTAATGGTCTGCT | 12 | 9501 | 9516 | 2471 |
| 829960 | N/A | N/A | ATTATTAATGGTCTGC | 17 | 9502 | 9517 | 2472 |
| 829961 | N/A | N/A | TGATTATTAATGGTCT | 14 | 9504 | 9519 | 2473 |
| 829962 | N/A | N/A | CTGATTATTAATGGTC | 19 | 9505 | 9520 | 2474 |
| 829963 | N/A | N/A | CCTAGTTCGCAGAGTC | 46 | 2381 | 2396 | 2475 |
| 829964 | N/A | N/A | CACCTAGTTCGCAGAG | 3 | 2383 | 2398 | 2476 |
| 829965 | N/A | N/A | CTCACCTAGTTCGCAG | 0 | 2385 | 2400 | 2477 |
| 829966 | N/A | N/A | TTCCCAGGAGGGTATG | 0 | 2545 | 2560 | 2478 |
| 829967 | N/A | N/A | CCCCCAGGGAATGCCC | 0 | 2606 | 2621 | 2479 |
| 829968 | N/A | N/A | AACCCCCAGGGAATGC | 30 | 2608 | 2623 | 2480 |
| 829969 | N/A | N/A | GAACCCCCAGGGAATG | 17 | 2609 | 2624 | 2481 |
| 829970 | N/A | N/A | TGGAAGGGAACCCCCA | 0 | 2616 | 2631 | 2482 |
| 829971 | N/A | N/A | GCCACACACCTCAACG | 20 | 2774 | 2789 | 2483 |
| 829972 | N/A | N/A | CTCGGCCACACACCTC | 22 | 2778 | 2793 | 2484 |
| 829973 | N/A | N/A | AAGAGGCCGCCTGGCG | 17 | 3586 | 3601 | 2485 |
| 829974 | N/A | N/A | AAAAGAGGCCGCCTGG | 27 | 3588 | 3603 | 2486 |
| 829975 | N/A | N/A | CAAAAGAGGCCGCCTG | 32 | 3589 | 3604 | 2487 |
| 829976 | N/A | N/A | ACAAAAGAGGCCGCCT | 10 | 3590 | 3605 | 2488 |
| 829977 | N/A | N/A | TAGCTGTCAGATAAAC | 35 | 3604 | 3619 | 2489 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 829978 | N/A | N/A | ATATTTAGCTGTCAGA | 50 | 3609 | 3624 | 2490 |
| 829979 | N/A | N/A | TGATATTTAGCTGTCA | 49 | 3611 | 3626 | 2491 |
| 829980 | N/A | N/A | TTGATATTTAGCTGTC | 56 | 3612 | 3627 | 2492 |
| 829981 | N/A | N/A | GTGATTGCCTTGATAT | 14 | 3621 | 3636 | 2493 |
| 829982 | N/A | N/A | CGGTGATTGCCTTGAT | 44 | 3623 | 3638 | 2494 |
| 829983 | N/A | N/A | GGCGGTGATTGCCTTG | 43 | 3625 | 3640 | 2495 |
| 829984 | N/A | N/A | AGGCGGTGATTGCCTT | 0 | 3626 | 3641 | 2496 |
| 829985 | N/A | N/A | GAGGCGGTGATTGCCT | 16 | 3627 | 3642 | 2497 |
| 829986 | N/A | N/A | CGAGGCGGTGATTGCC | 28 | 3628 | 3643 | 2498 |
| 829987 | N/A | N/A | CCGCGAGGCGGTGATT | 6 | 3631 | 3646 | 2499 |
| 829988 | N/A | N/A | GCCGCGAGGCGGTGAT | 27 | 3632 | 3647 | 2500 |
| 829989 | N/A | N/A | GGCCGCGAGGCGGTGA | 2 | 3633 | 3648 | 2501 |
| 829990 | N/A | N/A | GGGCCGCGAGGCGGTG | 35 | 3634 | 3649 | 2502 |
| 829991 | N/A | N/A | AGGGCCGCGAGGCGGT | 26 | 3635 | 3650 | 2503 |
| 829992 | N/A | N/A | GCAGGGCCGCGAGGCG | 10 | 3637 | 3652 | 2504 |
| 829993 | N/A | N/A | GGCAGGGCCGCGAGGC | 26 | 3638 | 3653 | 2505 |
| 829994 | N/A | N/A | GGAGGCAGGGCCGCGA | 68 | 3641 | 3656 | 2506 |
| 829995 | N/A | N/A | TGGAGGCAGGGCCGCG | 78 | 3642 | 3657 | 2507 |
| 829996 | N/A | N/A | TTTGTCTTAGCTGTGG | 54 | 3662 | 3677 | 2508 |
| 829997 | N/A | N/A | GTTTGTCTTAGCTGTG | 21 | 3663 | 3678 | 2509 |
| 829998 | N/A | N/A | TGTTTGTCTTAGCTGT | 34 | 3664 | 3679 | 2510 |
| 829999 | N/A | N/A | CTGTTTGTCTTAGCTG | 46 | 3665 | 3680 | 2511 |
| 830000 | N/A | N/A | ACTGTTTGTCTTAGCT | 51 | 3666 | 3681 | 2512 |
| 830001 | N/A | N/A | GCCCAACTGTTTGTCT | 24 | 3671 | 3686 | 2513 |
| 830002 | N/A | N/A | TAGCCCAACTGTTTGT | 43 | 3673 | 3688 | 2514 |
| 830003 | N/A | N/A | GGCATTCTTTTAGCCC | 0 | 3683 | 3698 | 2515 |
| 830004 | N/A | N/A | TAAAGGCCCAGCCATG | 24 | 3729 | 3744 | 2516 |
| 830005 | N/A | N/A | CTCACCAGTTGGTTTG | 13 | 3813 | 3828 | 2517 |
| 830006 | N/A | N/A | ACTCACCAGTTGGTTT | 0 | 3814 | 3829 | 2518 |
| 830007 | N/A | N/A | CTACTCACCAGTTGGT | 0 | 3816 | 3831 | 2519 |
| 830008 | N/A | N/A | TAGAGGCTCTATTTCT | 0 | 3865 | 3880 | 2520 |
| 830009 | N/A | N/A | GTGTTAAAGCTGAGCC | 52 | 4073 | 4088 | 2521 |
| 830010 | N/A | N/A | GTCTCAAATGGGCTTC | 68 | 4454 | 4469 | 2522 |
| 830011 | N/A | N/A | CCAGTCTCAAATGGGC | 25 | 4457 | 4472 | 2523 |
| 830012 | N/A | N/A | GCCAGTCTCAAATGGG | 37 | 4458 | 4473 | 2524 |
| 830013 | N/A | N/A | GTGCCAGTCTCAAATG | 55 | 4460 | 4475 | 2525 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 830014 | N/A | N/A | GGTGCCAGTCTCAAAT | 22 | 4461 | 4476 | 2526 |
| 830015 | N/A | N/A | GCTGGTGCCAGTCTCA | 56 | 4464 | 4479 | 2527 |
| 830016 | N/A | N/A | GGTGCCCAACCCTTCA | 32 | 4762 | 4777 | 2528 |
| 830017 | N/A | N/A | AGGCGGAAGGACTTGC | 30 | 4797 | 4812 | 2529 |
| 830018 | N/A | N/A | CCCAACAGCCAAAACG | 10 | 4817 | 4832 | 2530 |
| 830019 | N/A | N/A | AGGCCCAACAGCCAAA | 16 | 4820 | 4835 | 2531 |
| 830020 | N/A | N/A | GAAAGGCCCAACAGCC | 23 | 4823 | 4838 | 2532 |
| 830021 | N/A | N/A | GGGAAAGGCCCAACAG | 42 | 4825 | 4840 | 2533 |
| 830022 | N/A | N/A | GGCTGCAGAGTATGGG | 59 | 4909 | 4924 | 2534 |
| 830023 | N/A | N/A | TCACATGCTTTGCGGG | 57 | 5001 | 5016 | 2535 |
| 830024 | N/A | N/A | TGTAAATCGAAAGCAA | 40 | 5021 | 5036 | 2536 |
| 830025 | N/A | N/A | TTTGTAAATCGAAAGC | 62 | 5023 | 5038 | 2537 |
| 830026 | N/A | N/A | TTTTGTAAATCGAAAG | 0 | 5024 | 5039 | 2538 |
| 830027 | N/A | N/A | AACCATTTATCTGGTG | 23 | 5040 | 5055 | 2539 |
| 830028 | N/A | N/A | CAGTCAAGTTACAGTC | 75 | 5131 | 5146 | 2540 |
| 830029 | N/A | N/A | TCACTCCACTCACCGA | 56 | 5439 | 5454 | 2541 |
| 830030 | N/A | N/A | ACCTAATGTCAACACT | 36 | 5473 | 5488 | 2542 |
| 830031 | N/A | N/A | TACCTAATGTCAACAC | 44 | 5474 | 5489 | 2543 |
| 830032 | N/A | N/A | GCTACCTAATGTCAAC | 35 | 5476 | 5491 | 2544 |
| 830033 | N/A | N/A | TCCCCCTTGGAAATGG | 28 | 5533 | 5548 | 2545 |
| 830034 | N/A | N/A | GGCTGATCTGGAGAAC | 30 | 5554 | 5569 | 2546 |
| 830035 | N/A | N/A | ATTGGCTGATCTGGAG | 48 | 5557 | 5572 | 2547 |
| 830036 | N/A | N/A | TATTGGCTGATCTGGA | 52 | 5558 | 5573 | 2548 |
| 830037 | N/A | N/A | CTATTGGCTGATCTGG | 67 | 5559 | 5574 | 2549 |
| 830038 | N/A | N/A | CCTATTGGCTGATCTG | 50 | 5560 | 5575 | 2550 |
| 830039 | N/A | N/A | TTCCTATTGGCTGATC | 51 | 5562 | 5577 | 2551 |
| 830040 | N/A | N/A | CACTTCCTATTGGCTG | 44 | 5565 | 5580 | 2552 |
| 830041 | N/A | N/A | TCACTTCCTATTGGCT | 56 | 5566 | 5581 | 2553 |
| 830042 | N/A | N/A | CAGGTTAATCACTTCC | 64 | 5574 | 5589 | 2554 |
| 830043 | N/A | N/A | TTGGCAGGTTAATCAC | 45 | 5578 | 5593 | 2555 |
| 830044 | N/A | N/A | CGATTGGCAGGTTAAT | 60 | 5581 | 5596 | 2556 |
| 830045 | N/A | N/A | CCGATTGGCAGGTTAA | 47 | 5582 | 5597 | 2557 |
| 830046 | N/A | N/A | TCCGATTGGCAGGTTA | 60 | 5583 | 5598 | 2558 |
| 830047 | N/A | N/A | TTCCGATTGGCAGGTT | 42 | 5584 | 5599 | 2559 |
| 830048 | N/A | N/A | TTTCCGATTGGCAGGT | 57 | 5585 | 5600 | 2560 |
| 830049 | N/A | N/A | GTTTCCGATTGGCAGG | 43 | 5586 | 5601 | 2561 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 830050 | N/A | N/A | AGTTTCCGATTGGCAG | 39 | 5587 | 5602 | 2562 |
| 830051 | N/A | N/A | TAGTTTCCGATTGGCA | 84 | 5588 | 5603 | 2563 |
| 830052 | N/A | N/A | GAGTAACCAGCTGTCT | 35 | 5604 | 5619 | 2564 |
| 830053 | N/A | N/A | GGGTGAGTAACCAGCT | 68 | 5608 | 5623 | 2565 |
| 830054 | N/A | N/A | TGGGTGAGTAACCAGC | 48 | 5609 | 5624 | 2566 |
| 830055 | N/A | N/A | TTGGGTGAGTAACCAG | 57 | 5610 | 5625 | 2567 |
| 830056 | N/A | N/A | GTTTTGGGTGAGTAAC | 40 | 5613 | 5628 | 2568 |
| 830057 | N/A | N/A | CGTTTTGGGTGAGTAA | 42 | 5614 | 5629 | 2569 |
| 830058 | N/A | N/A | GGTAGGCACATCATCA | 22 | 6687 | 6702 | 2570 |
| 830059 | N/A | N/A | GGGCCACCCAGTGAGC | 22 | 7617 | 7632 | 2571 |
| 830060 | N/A | N/A | TACCACCCCTGTGAAG | 8 | 7695 | 7710 | 2572 |
| 830061 | N/A | N/A | CTACCACCCCTGTGAA | 4 | 7696 | 7711 | 2573 |
| 830062 | N/A | N/A | CCTACCACCCCTGTGA | 17 | 7697 | 7712 | 2574 |
| 830063 | N/A | N/A | TCCCTACCACCCCTGT | 37 | 7699 | 7714 | 2575 |
| 830064 | N/A | N/A | ATGGTGCTCTGCCCTT | 29 | 7763 | 7778 | 2576 |
| 830065 | N/A | N/A | AATGGTGCTCTGCCCT | 43 | 7764 | 7779 | 2577 |
| 830066 | N/A | N/A | AAATGGTGCTCTGCCC | 37 | 7765 | 7780 | 2578 |
| 830067 | N/A | N/A | GAAATGGTGCTCTGCC | 63 | 7766 | 7781 | 2579 |
| 830068 | N/A | N/A | GTGAAATGGTGCTCTG | 39 | 7768 | 7783 | 2580 |
| 830069 | N/A | N/A | AAGGTAAGCCAGCTCC | 51 | 7808 | 7823 | 2581 |
| 830070 | N/A | N/A | AAAGGTAAGCCAGCTC | 44 | 7809 | 7824 | 2582 |
| 830071 | N/A | N/A | TCAAAGGTAAGCCAGC | 45 | 7811 | 7826 | 2583 |
| 830072 | N/A | N/A | ATCAAAGGTAAGCCAG | 28 | 7812 | 7827 | 2584 |
| 830073 | N/A | N/A | TCAGATCAAAGGTAAG | 41 | 7816 | 7831 | 2585 |
| 830074 | N/A | N/A | CTCAGATCAAAGGTAA | 43 | 7817 | 7832 | 2586 |
| 830075 | N/A | N/A | TCAGGGTGTCAGCCCA | 39 | 7834 | 7849 | 2587 |
| 830076 | N/A | N/A | CACATTCAGGGTGTCA | 43 | 7839 | 7854 | 2588 |
| 830077 | N/A | N/A | CCACATTCAGGGTGTC | 37 | 7840 | 7855 | 2589 |
| 830078 | N/A | N/A | ACCACATTCAGGGTGT | 0 | 7841 | 7856 | 2590 |
| 830079 | N/A | N/A | ATACCCTGCACTTTCT | 22 | 8058 | 8073 | 2591 |
| 830080 | N/A | N/A | TATACCCTGCACTTTC | 32 | 8059 | 8074 | 2592 |
| 830081 | N/A | N/A | GTGTATACCCTGCACT | 0 | 8062 | 8077 | 2593 |
| 830082 | N/A | N/A | GGTGTATACCCTGCAC | 34 | 8063 | 8078 | 2594 |
| 830083 | N/A | N/A | ATGGTGTATACCCTGC | 54 | 8065 | 8080 | 2595 |
| 830084 | N/A | N/A | GATACACTTAATCAAA | 26 | 8124 | 8139 | 2596 |
| 830085 | N/A | N/A | CAGGATACACTTAATC | 27 | 8127 | 8142 | 2597 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 830086 | N/A | N/A | TTTACAGGATACACTT | 40 | 8131 | 8146 | 2598 |
| 830087 | N/A | N/A | TTTTACAGGATACACT | 35 | 8132 | 8147 | 2599 |
| 830088 | N/A | N/A | GTTTTACAGGATACAC | 52 | 8133 | 8148 | 2600 |
| 830089 | N/A | N/A | AAGACCCTGTAAGCTT | 9 | 8657 | 8672 | 2601 |
| 830090 | N/A | N/A | ATACACAAGACCCTGT | 10 | 8663 | 8678 | 2602 |
| 830091 | N/A | N/A | AATACACAAGACCCTG | 37 | 8664 | 8679 | 2603 |
| 830092 | N/A | N/A | ATTAGTCCCATGAAAC | 43 | 8683 | 8698 | 2604 |
| 830093 | N/A | N/A | CTCATTAGTCCCATGA | 5 | 8686 | 8701 | 2605 |
| 830094 | N/A | N/A | TCTTACCTGAAAGCCC | 30 | 9717 | 9732 | 2606 |
| 830095 | N/A | N/A | TGAGTAAACAATACCC | 73 | 10899 | 10914 | 2607 |
| 830096 | N/A | N/A | AACAACATCCTGAGCG | 44 | 11118 | 11133 | 2608 |
| 830097 | N/A | N/A | CCATCTAACAACATCC | 68 | 11124 | 11139 | 2609 |
| 830098 | N/A | N/A | AGACAAACCTTCCGAA | 37 | 11236 | 11251 | 2610 |
| 830099 | N/A | N/A | GCCTTTGGAATTAGTA | 79 | 11976 | 11991 | 2611 |
| 830100 | N/A | N/A | GGAGCTCAAACTTTGA | 61 | 11993 | 12008 | 2612 |
| 830101 | N/A | N/A | GCCCGCTCTCAGCCAG | 46 | 12494 | 12509 | 2613 |
| 830102 | N/A | N/A | AGCCCGCTCTCAGCCA | 43 | 12495 | 12510 | 2614 |
| 830103 | N/A | N/A | AAGCCCGCTCTCAGCC | 39 | 12496 | 12511 | 2615 |
| 830104 | N/A | N/A | TAAGCCCGCTCTCAGC | 28 | 12497 | 12512 | 2616 |
| 830105 | N/A | N/A | TTAAGCCCGCTCTCAG | 48 | 12498 | 12513 | 2617 |
| 830106 | N/A | N/A | CATTAAGCCCGCTCTC | 33 | 12500 | 12515 | 2618 |
| 830107 | N/A | N/A | TCATTAAGCCCGCTCT | 50 | 12501 | 12516 | 2619 |
| 830108 | N/A | N/A | TTCATTAAGCCCGCTC | 54 | 12502 | 12517 | 2620 |
| 830109 | N/A | N/A | ATTCATTAAGCCCGCT | 44 | 12503 | 12518 | 2621 |
| 830110 | N/A | N/A | CCATTCATTAAGCCCG | 36 | 12505 | 12520 | 2622 |
| 830111 | N/A | N/A | CCCATTCATTAAGCCC | 38 | 12506 | 12521 | 2623 |
| 830112 | N/A | N/A | GCCCCATTCATTAAGC | 23 | 12508 | 12523 | 2624 |
| 830113 | N/A | N/A | AGCCCCATTCATTAAG | 36 | 12509 | 12524 | 2625 |
| 830114 | N/A | N/A | GAGCCCCATTCATTAA | 22 | 12510 | 12525 | 2626 |
| 830115 | N/A | N/A | ACCCTAAACTGAGCCC | 9 | 12520 | 12535 | 2627 |
| 830116 | N/A | N/A | CACCCTAAACTGAGCC | 11 | 12521 | 12536 | 2628 |
| 830117 | N/A | N/A | CCACCCTAAACTGAGC | 5 | 12522 | 12537 | 2629 |
| 830118 | N/A | N/A | TCCCACCCTAAACTGA | 0 | 12524 | 12539 | 2630 |
| 830119 | N/A | N/A | CCGACCTTCCTCCCAC | 24 | 12534 | 12549 | 2631 |
| 830120 | N/A | N/A | GCCGACCTTCCTCCCA | 27 | 12535 | 12550 | 2632 |
| 830121 | N/A | N/A | AGAATCAAGCCCTGGC | 69 | 12558 | 12573 | 2633 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 830122 | N/A | N/A | GAGAATCAAGCCCTGG | 57 | 12559 | 12574 | 2634 |
| 830123 | N/A | N/A | GGCACCACATTTTCAC | 44 | 12612 | 12627 | 2635 |
| 830124 | N/A | N/A | CCGAGGCACCACATTT | 27 | 12616 | 12631 | 2636 |
| 830125 | N/A | N/A | TCCGAGGCACCACATT | 46 | 12617 | 12632 | 2637 |
| 830126 | N/A | N/A | CTCCGAGGCACCACAT | 34 | 12618 | 12633 | 2638 |
| 830127 | N/A | N/A | CCTCCGAGGCACCACA | 62 | 12619 | 12634 | 2639 |
| 830128 | N/A | N/A | ACCTCCGAGGCACCAC | 87 | 12620 | 12635 | 2640 |
| 830129 | N/A | N/A | CACCTCCGAGGCACCA | 41 | 12621 | 12636 | 2641 |
| 830130 | N/A | N/A | CCACCTCCGAGGCACC | 32 | 12622 | 12637 | 2642 |
| 830131 | N/A | N/A | CCCACCTCCGAGGCAC | 68 | 12623 | 12638 | 2643 |
| 830132 | N/A | N/A | TACCCGCCCACTCCCC | 8 | 12739 | 12754 | 2644 |
| 830133 | N/A | N/A | ACAATCTCCTGGAAGC | 26 | 12939 | 12954 | 2645 |
| 830134 | N/A | N/A | AGTACAATCTCCTGGA | 61 | 12942 | 12957 | 2646 |
| 830135 | N/A | N/A | AAGTACAATCTCCTGG | 64 | 12943 | 12958 | 2647 |
| 830136 | N/A | N/A | GAAAGTACAATCTCCT | 64 | 12945 | 12960 | 2648 |
| 830137 | N/A | N/A | ATGAAAGTACAATCTC | 68 | 12947 | 12962 | 2649 |
| 830138 | N/A | N/A | GGAGTTGCATGCCTTT | 71 | 13287 | 13302 | 2650 |
| 830139 | N/A | N/A | TGGAGTTGCATGCCTT | 45 | 13288 | 13303 | 2651 |
| 830140 | N/A | N/A | TCCTAAGCTACTTGGT | 12 | 14096 | 14111 | 2652 |
| 830141 | N/A | N/A | GGCATTAGAGACCTCA | 58 | 14286 | 14301 | 2653 |
| 830142 | N/A | N/A | TGTGCACCAGGTGAGC | 60 | 14548 | 14563 | 2654 |
| 830143 | N/A | N/A | GGTGTGCACCAGGTGA | 62 | 14550 | 14565 | 2655 |
| 830144 | N/A | N/A | GGGTGTGCACCAGGTG | 66 | 14551 | 14566 | 2656 |
| 830145 | N/A | N/A | TGGGTGTGCACCAGGT | 47 | 14552 | 14567 | 2657 |
| 830146 | N/A | N/A | TGGTCTTCACCAGGGT | 62 | 14569 | 14584 | 2658 |
| 830147 | N/A | N/A | GACTGGTCTTCACCAG | 0 | 14572 | 14587 | 2659 |
| 830148 | N/A | N/A | GGACTGGTCTTCACCA | 19 | 14573 | 14588 | 2660 |
| 830149 | N/A | N/A | AGGACTGGTCTTCACC | 47 | 14574 | 14589 | 2661 |
| 830150 | N/A | N/A | CAGTGGTGACCTCCCT | 51 | 16793 | 16808 | 2662 |
| 830151 | N/A | N/A | GCCAGTGGTGACCTCC | 45 | 16795 | 16810 | 2663 |
| 830152 | N/A | N/A | CCCGGAGAGGAAGCCT | 23 | 16878 | 16893 | 2664 |
| 830153 | N/A | N/A | GCCTCAGCAGTTAATA | 21 | 16915 | 16930 | 2665 |
| 830154 | N/A | N/A | GTGCCTCAGCAGTTAA | 48 | 16917 | 16932 | 2666 |
| 830155 | N/A | N/A | TGTGCCTCAGCAGTTA | 38 | 16918 | 16933 | 2667 |
| 830156 | N/A | N/A | CTGTGCCTCAGCAGTT | 48 | 16919 | 16934 | 2668 |
| 830157 | N/A | N/A | GAACTGTGCCTCAGCA | 70 | 16922 | 16937 | 2669 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 830158 | N/A | N/A | AATTGAGAACTGTGCC | 43 | 16928 | 16943 | 2670 |
| 830159 | N/A | N/A | CCACTAAATTGAGAAC | 42 | 16934 | 16949 | 2671 |
| 830160 | N/A | N/A | TGGTGTGTTAACCACT | 54 | 16945 | 16960 | 2672 |
| 830161 | N/A | N/A | AGGTGAAAGTTATCAC | 13 | 17276 | 17291 | 2673 |
| 830162 | N/A | N/A | ACAAGGTGAAAGTTAT | 20 | 17279 | 17294 | 2674 |
| 830163 | N/A | N/A | CAACTGAAGGTGACCC | 60 | 17537 | 17552 | 2675 |
| 830164 | N/A | N/A | GCTGCTTGGCCTTACC | 38 | 17627 | 17642 | 2676 |
| 830165 | N/A | N/A | ACAGCTGTACCAGGGC | 58 | 17978 | 17993 | 2677 |
| 830166 | N/A | N/A | CACAGCTGTACCAGGG | 48 | 17979 | 17994 | 2678 |
| 830167 | N/A | N/A | TTTACACACCCCAGGG | 39 | 18337 | 18352 | 2679 |
| 830168 | N/A | N/A | ATGCTTTTACACACCC | 81 | 18342 | 18357 | 2680 |
| 830169 | N/A | N/A | CTCTGTTTGGACAAGT | 58 | 18380 | 18395 | 2681 |
| 830170 | N/A | N/A | GCTCTGTTTGGACAAG | 60 | 18381 | 18396 | 2682 |
| 830171 | N/A | N/A | TGCTCTGTTTGGACAA | 26 | 18382 | 18397 | 2683 |
| 830172 | N/A | N/A | CTGCTCTGTTTGGACA | 27 | 18383 | 18398 | 2684 |
| 830173 | N/A | N/A | AGAGGTGTTTCCAAGG | 48 | 18462 | 18477 | 2685 |
| 830174 | N/A | N/A | GAGAGGTGTTTCCAAG | 49 | 18463 | 18478 | 2686 |
| 830175 | N/A | N/A | TCTCAACAGACCACAC | 44 | 19025 | 19040 | 2687 |
| 830176 | N/A | N/A | ATTCTCAACAGACCAC | 61 | 19027 | 19042 | 2688 |
| 830177 | N/A | N/A | CAGCCCTTTCACCCCT | 40 | 21885 | 21900 | 2689 |
| 830178 | N/A | N/A | ACGACAGCCTGGAGAC | 32 | 21991 | 22006 | 2690 |
| 830179 | N/A | N/A | TTTACTGCATTCCGGC | 51 | 22180 | 22195 | 2691 |
| 830180 | N/A | N/A | CGTGTACCCAGCTGCC | 62 | 23221 | 23236 | 2692 |
| 830181 | N/A | N/A | GCGGCTTCCTGTGCCC | 10 | 23262 | 23277 | 2693 |
| 830182 | N/A | N/A | GTGTCCTTCAGAACAC | 0 | 24168 | 24183 | 2694 |
| 830183 | N/A | N/A | CGGTTGCCTCATCCTG | 47 | 25436 | 25451 | 2695 |
| 830184 | N/A | N/A | ACGGTTGCCTCATCCT | 48 | 25437 | 25452 | 2696 |
| 830185 | N/A | N/A | GCCACCAACGGTTGCC | 27 | 25444 | 25459 | 2697 |
| 830186 | N/A | N/A | AGGTCCAGGGTCCTCC | 50 | 25477 | 25492 | 2698 |
| 830187 | N/A | N/A | ATTACCCTGCTCATGA | 31 | 26595 | 26610 | 2699 |
| 830188 | N/A | N/A | CCACTTAGCAAGGAGC | 50 | 26638 | 26653 | 2700 |
| 830189 | N/A | N/A | TTGGAGCAACACCAGA | 49 | 26813 | 26828 | 2701 |
| 830190 | N/A | N/A | TAATCAGATGCCTGCT | 39 | 26865 | 26880 | 2702 |
| 830191 | N/A | N/A | CTAATCAGATGCCTGC | 47 | 26866 | 26881 | 2703 |
| 830192 | N/A | N/A | ACTAATCAGATGCCTG | 41 | 26867 | 26882 | 2704 |
| 830193 | N/A | N/A | CTTTTCCGGTATTTTC | 35 | 26987 | 27002 | 2705 |

TABLE 9-continued

Inhibition of SMAD7 mRNA expression by 3-10-3 cEt gapmers targeting SEQ ID NO: 1 and 2

| IONIS NO. | SEQ ID: 1 Start Site | SEQ ID: 1 Stop Site | Sequence | % Inhibition | SEQ ID: 2 Start Site | SEQ ID 2: Stop Site | SEQ ID NO. |
|---|---|---|---|---|---|---|---|
| 830194 | N/A | N/A | CCTTTTCCGGTATTTT | 49 | 26988 | 27003 | 2706 |
| 830195 | N/A | N/A | AACCTTTTCCGGTATT | 35 | 26990 | 27005 | 2707 |
| 830196 | N/A | N/A | TTAATGGCCCAGCCCA | 31 | 27613 | 27628 | 2708 |
| 830197 | N/A | N/A | GTTAATGGCCCAGCCC | 31 | 27614 | 27629 | 2709 |
| 830198 | N/A | N/A | AGGCTACACCAAAGAC | 30 | 28194 | 28209 | 2710 |
| 830199 | N/A | N/A | AAGGCTACACCAAAGA | 37 | 28195 | 28210 | 2711 |
| 830200 | N/A | N/A | GAAGGCTACACCAAAG | 33 | 28196 | 28211 | 2712 |
| 830201 | N/A | N/A | CTGAAGGCTACACCAA | 37 | 28198 | 28213 | 2713 |
| 830202 | N/A | N/A | TCTGAAGGCTACACCA | 50 | 28199 | 28214 | 2714 |
| 830203 | N/A | N/A | GCTCTGAAGGCTACAC | 40 | 28201 | 28216 | 2715 |
| 830204 | N/A | N/A | GTATCCATCAACTGCT | 59 | 28269 | 28284 | 2716 |
| 830205 | N/A | N/A | GACTCATCAGGCATTC | 26 | 28300 | 28315 | 2717 |
| 830206 | N/A | N/A | TGACTCATCAGGCATT | 51 | 28301 | 28316 | 2718 |
| 830207 | N/A | N/A | AGGTGACTCATCAGGC | 80 | 28304 | 28319 | 2719 |
| 830208 | N/A | N/A | AAGGTGACTCATCAGG | 57 | 28305 | 28320 | 2720 |
| 830209 | N/A | N/A | ACCGGAAGTCTTGTAT | 31 | 29088 | 29103 | 2721 |
| 830210 | N/A | N/A | GACCGGAAGTCTTGTA | 29 | 29089 | 29104 | 2722 |
| 830211 | N/A | N/A | AGACCGGAAGTCTTGT | 30 | 29090 | 29105 | 2723 |
| 830212 | N/A | N/A | GCAGGGTGGAGACCGG | 43 | 29099 | 29114 | 2724 |

TABLE 10

Inhibition of SMAD7 mRNA expression by 3-10-3 cEt gapmers targeting SEQ ID NO: 3 and 4

| ION NO. | SEQ ID: 3 Start Site | SEQ ID: 3 Stop Site | Sequence | % Inhibition | SEQ ID: 4 Start Site | SEQ ID 4: Stop Site | SEQ ID NO. |
|---|---|---|---|---|---|---|---|
| 790634 | 942 | 957 | AGTCAGTTGGTTTGAG | 0 | N/A | N/A | 2725 |
| 790635 | 946 | 961 | GGACAGTCAGTTGGTT | 40 | N/A | N/A | 2726 |
| 790636 | 953 | 968 | AGCATCTGGACAGTCA | 95 | N/A | N/A | 2727 |
| 799239 | 940 | 955 | TCAGTTGGTTTGAGAA | 16 | N/A | N/A | 2728 |
| 799240 | 950 | 965 | ATCTGGACAGTCAGTT | 45 | N/A | N/A | 2729 |
| 799268 | N/A | N/A | TCCAGTTCGGCCTTCC | 24 | 91 | 106 | 2730 |
| 799269 | N/A | N/A | AGACTCCAGTTCGGCC | 20 | 95 | 110 | 2731 |
| 829940 | 941 | 956 | GTCAGTTGGTTTGAGA | 14 | N/A | N/A | 2732 |
| 829941 | 943 | 958 | CAGTCAGTTGGTTTGA | 8 | N/A | N/A | 2733 |

TABLE 10-continued

Inhibition of SMAD7 mRNA expression by 3-10-3 cEt gapmers targeting SEQ ID NO: 3 and 4

| ION NO. | SEQ ID: 3 Start Site | SEQ ID: 3 Stop Site | Sequence | % Inhibition | SEQ ID: 4 Start Site | SEQ ID 4: Stop Site | SEQ ID NO. |
|---|---|---|---|---|---|---|---|
| 829942 | 952 | 967 | GCATCTGGACAGTCAG | 92 | N/A | N/A | 2734 |
| 829943 | N/A | N/A | GGGAGACTCCAGTTCG | 43 | 98 | 113 | 2735 |

Example 3: Dose-Dependent Antisense-Mediated Inhibition of Human SMAD7 mRNA Expression in Hep3B Cells Antisense oligonucleotides from the studies described above exhibiting significant in vitro inhibition of SMAD7 mRNA expression were selected and tested at various doses in Hep3B cells. The antisense oligonucleotides were tested in a series of experiments that had similar culture conditions as described below.

Study 1

Cells were plated at a density of 20,000 cells per well and transfected using electroporation with 0.31 μM, 1.25 μM, 5.00 μM, or 20.00 μM concentrations of antisense oligonucleotide, as specified in the Tables below. ION 483663 was included in the assays for comparison. After a treatment period of approximately 16 hours, RNA was isolated from the cells and SMAD7 mRNA levels were measured by quantitative real-time PCR. Primer probe set RTS5062 was used to measure human SMAD7 mRNA levels. SMAD7 mRNA levels were adjusted according to total RNA content, as measured by RIBOGREEN®. Results are presented as percent inhibition of SMAD7 mRNA expression, relative to untreated control cells.

The half maximal inhibitory concentration ($IC_{50}$) of each oligonucleotide is also presented. SMAD7 mRNA levels were significantly reduced in a dose-dependent manner in antisense oligonucleotide treated cells.

TABLE 11

% inhibition of SMAD7 mRNA expression

| ION No | 312.5 nM | 1250.0 nM | 5000.0 nM | 20000.0 nM | $IC_{50}$ (μM) |
|---|---|---|---|---|---|
| 278478 | 0 | 9 | 19 | 22 | >20 |
| 483663 | 0 | 0 | 14 | 27 | >20 |
| 771345 | 6 | 19 | 49 | 69 | 6 |
| 771386 | 9 | 3 | 25 | 60 | 19 |
| 771387 | 8 | 13 | 28 | 70 | 10 |
| 771390 | 0 | 12 | 26 | 51 | >20 |
| 771397 | 0 | 0 | 41 | 51 | 15 |
| 771399 | 0 | 6 | 26 | 53 | >20 |
| 771403 | 5 | 4 | 25 | 35 | >20 |
| 771407 | 17 | 0 | 30 | 46 | >20 |
| 771414 | 0 | 2 | 43 | 33 | >20 |
| 771416 | 0 | 3 | 19 | 35 | >20 |
| 771418 | 3 | 0 | 0 | 0 | 6 |
| 771439 | 0 | 24 | 49 | 55 | 9 |
| 771441 | 0 | 5 | 45 | 64 | 9 |
| 771444 | 0 | 0 | 9 | 29 | >20 |
| 771461 | 0 | 2 | 11 | 39 | >20 |
| 771464 | 11 | 8 | 21 | 50 | >20 |
| 771474 | 3 | 4 | 21 | 52 | 17 |
| 771479 | 0 | 8 | 49 | 74 | 7 |
| 771487 | 4 | 0 | 7 | 26 | >20 |

TABLE 11-continued

% inhibition of SMAD7 mRNA expression

| ION No | 312.5 nM | 1250.0 nM | 5000.0 nM | 20000.0 nM | $IC_{50}$ (μM) |
|---|---|---|---|---|---|
| 771492 | 0 | 5 | 32 | 50 | >20 |
| 771506 | 54 | 1 | 5 | 44 | >20 |
| 771509 | 0 | 0 | 13 | 47 | >20 |
| 771539 | 0 | 13 | 7 | 26 | >20 |
| 771552 | 2 | 25 | 20 | 45 | >20 |
| 771555 | 16 | 4 | 4 | 18 | >20 |
| 771556 | 1 | 0 | 9 | 33 | >20 |
| 771570 | 0 | 0 | 43 | 48 | >20 |
| 771572 | 0 | 10 | 38 | 13 | >20 |
| 771573 | 0 | 5 | 24 | 56 | 18 |
| 771574 | 0 | 5 | 36 | 58 | 13 |
| 771576 | 9 | 24 | 55 | 75 | 4 |
| 771579 | 0 | 0 | 46 | 68 | 9 |
| 771581 | 0 | 0 | 9 | 65 | 19 |
| 771583 | 0 | 15 | 36 | 59 | 10 |
| 771610 | 0 | 0 | 37 | 38 | >20 |
| 771611 | 18 | 21 | 47 | 59 | 9 |
| 771632 | 6 | 6 | 46 | 64 | 9 |
| 771634 | 0 | 3 | 40 | 36 | >20 |
| 771636 | 16 | 11 | 33 | 52 | >20 |
| 771636 | 0 | 15 | 33 | 31 | >20 |
| 771636 | 0 | 3 | 34 | 50 | 16 |
| 771636 | 8 | 7 | 27 | 42 | >20 |
| 771636 | 0 | 0 | 2 | 0 | >20 |
| 771641 | 3 | 16 | 24 | 50 | >20 |
| 771661 | 0 | 0 | 6 | 28 | >20 |
| 771663 | 10 | 24 | 43 | 56 | 11 |
| 771670 | 0 | 0 | 21 | 47 | >20 |
| 771671 | 0 | 9 | 27 | 49 | >20 |
| 771691 | 4 | 13 | 33 | 62 | 12 |
| 771699 | 0 | 24 | 48 | 68 | 6 |
| 771704 | 14 | 19 | 30 | 54 | >20 |
| 771705 | 0 | 0 | 0 | 9 | 9 |
| 771711 | 17 | 25 | 27 | 59 | 18 |
| 771715 | 7 | 18 | 42 | 49 | 17 |
| 771717 | 2 | 0 | 0 | 30 | >20 |
| 771732 | 35 | 24 | 39 | 58 | 15 |
| 771733 | 0 | 0 | 26 | 61 | 16 |
| 771734 | 0 | 0 | 30 | 53 | >20 |
| 771737 | 0 | 2 | 0 | 16 | 9 |
| 771742 | 0 | 0 | 0 | 23 | >20 |
| 771762 | 0 | 0 | 38 | 67 | >20 |
| 771769 | 10 | 0 | 3 | 53 | >20 |
| 771770 | 0 | 11 | 27 | 51 | >20 |
| 771773 | 0 | 0 | 0 | 42 | >20 |
| 771776 | 10 | 13 | 36 | 67 | 9 |
| 771777 | 0 | 0 | 27 | 50 | 8 |
| 771778 | 48 | 0 | 37 | 55 | >20 |
| 771782 | 0 | 9 | 27 | 38 | >20 |
| 771786 | 2 | 0 | 53 | 40 | >20 |
| 771788 | 1 | 0 | 0 | 0 | >20 |
| 771793 | 16 | 33 | 38 | 57 | 12 |
| 771794 | 0 | 0 | 27 | 41 | >20 |
| 771795 | 9 | 22 | 51 | 58 | 8 |
| 771797 | 1 | 0 | 15 | 35 | >20 |
| 771799 | 0 | 8 | 28 | 48 | >20 |
| 771808 | 10 | 0 | 23 | 66 | 16 |

TABLE 11-continued

% inhibition of SMAD7 mRNA expression

| ION No | 312.5 nM | 1250.0 nM | 5000.0 nM | 20000.0 nM | IC$_{50}$ (µM) |
|---|---|---|---|---|---|
| 771815 | 0 | 0 | 22 | 46 | >20 |
| 771820 | 3 | 3 | 7 | 7 | >20 |
| 771821 | 0 | 9 | 27 | 46 | >20 |
| 771822 | 0 | 0 | 30 | 45 | >20 |
| 771825 | 15 | 29 | 17 | 66 | 15 |
| 771831 | 0 | 13 | 32 | 51 | 16 |
| 771836 | 6 | 25 | 22 | 41 | >20 |
| 771838 | 0 | 24 | 26 | 43 | >20 |
| 771849 | 25 | 0 | 10 | 35 | >20 |
| 771850 | 0 | 8 | 20 | 44 | >20 |
| 771869 | 10 | 0 | 24 | 43 | >20 |
| 771885 | 0 | 4 | 20 | 45 | >20 |
| 771891 | 0 | 0 | 10 | 33 | >20 |
| 771900 | 0 | 11 | 8 | 29 | >20 |
| 771902 | 0 | 17 | 29 | 59 | 13 |
| 771937 | 0 | 0 | 4 | 41 | >20 |
| 771944 | 0 | 34 | 35 | 48 | >20 |

Study 2

Cells were plated at a density of 20,000 cells per well and transfected using electroporation with 0.74 µM, 2.22 µM, 6.67 µM, or 20.00 µM concentrations of antisense oligonucleotide, as specified in the Tables below. After a treatment period of approximately 16 hours, RNA was isolated from the cells and SMAD7 mRNA levels were measured by quantitative real-time PCR. Primer probe set RTS5062 was used to measure human SMAD7 mRNA levels. SMAD7 mRNA levels were adjusted according to total RNA content, as measured by RIBOGREEN®. Results are presented as percent inhibition of SMAD7 mRNA expression, relative to untreated control cells.

The half maximal inhibitory concentration (IC$_{50}$) of each oligonucleotide is also presented. SMAD7 mRNA levels were significantly reduced in a dose-dependent manner in antisense oligonucleotide treated cells.

TABLE 12

% inhibition of SMAD7 mRNA expression

| ION No | 740 nM | 2220 nM | 6670.0 nM | 20000.0 nM | IC$_{50}$ (µM) |
|---|---|---|---|---|---|
| 771576 | 0 | 23 | 23 | 22 | >20 |
| 772553 | 36 | 45 | 71 | 89 | 2 |
| 772560 | 0 | 32 | 57 | 82 | 5 |
| 772568 | 41 | 62 | 58 | 79 | 1 |
| 772578 | 54 | 44 | 70 | 86 | 1 |
| 772732 | 27 | 60 | 63 | 68 | 3 |
| 772842 | 3 | 23 | 65 | 72 | 6 |
| 772858 | 7 | 26 | 29 | 51 | >20 |
| 790476 | 8 | 38 | 63 | 69 | 5 |
| 790488 | 12 | 34 | 46 | 67 | 7 |
| 790614 | 0 | 29 | 45 | 54 | 11 |
| 790616 | 0 | 8 | 26 | 65 | 13 |
| 790636 | 89 | 93 | 95 | 99 | <0.7 |
| 790666 | 13 | 49 | 54 | 74 | 4 |
| 790732 | 70 | 78 | 88 | 93 | 2 |
| 790736 | 32 | 56 | 68 | 74 | >20 |
| 798662 | 0 | 28 | 22 | 25 | >20 |
| 798686 | 0 | 0 | 2 | 33 | 5 |
| 798687 | 27 | 42 | 60 | 61 | 7 |
| 798696 | 0 | 33 | 58 | 66 | <0.7 |
| 798733 | 58 | 84 | 88 | 95 | 4 |
| 798764 | 19 | 31 | 57 | 93 | 1 |
| 798764 | 42 | 64 | 72 | 87 | 5 |
| 798764 | 29 | 41 | 54 | 65 | 1 |
| 798764 | 43 | 47 | 72 | 83 | 2 |
| 798781 | 46 | 64 | 81 | 87 | 2 |
| 798823 | 27 | 27 | 63 | 70 | >20 |
| 798824 | 0 | 0 | 7 | 42 | 4 |
| 798931 | 0 | 43 | 72 | 83 | 7 |
| 798954 | 4 | 27 | 49 | 70 | >20 |
| 798987 | 0 | 0 | 8 | 47 | 4 |
| 799067 | 5 | 55 | 63 | 78 | 9 |
| 799070 | 0 | 44 | 42 | 60 | 4 |
| 799089 | 12 | 40 | 61 | 76 | 7 |
| 799118 | 0 | 16 | 50 | 75 | <0.7 |
| 799143 | 87 | 93 | 95 | 96 | 2 |
| 799144 | 32 | 50 | 67 | 83 | 2 |
| 799144 | 40 | 57 | 60 | 87 | 1 |
| 799159 | 43 | 55 | 78 | 90 | 19 |
| 799168 | 15 | 13 | 36 | 54 | 5 |
| 799312 | 23 | 46 | 49 | 69 | 4 |
| 799318 | 12 | 40 | 70 | 75 | 11 |
| 799321 | 0 | 5 | 36 | 67 | <0.7 |
| 799322 | 89 | 90 | 96 | 96 | 2 |
| 799364 | 39 | 54 | 67 | 88 | 3 |
| 799365 | 11 | 39 | 73 | 94 | 4 |
| 799366 | 18 | 39 | 64 | 76 | 8 |
| 799369 | 1 | 10 | 46 | 74 | 6 |
| 799382 | 0 | 36 | 56 | 75 | 3 |
| 799396 | 22 | 52 | 72 | 78 | 4 |
| 799396 | 10 | 38 | 70 | 85 | >20 |
| 799402 | 0 | 3 | 13 | 50 | 10 |
| 799404 | 15 | 39 | 42 | 59 | 2 |
| 799406 | 30 | 51 | 77 | 84 | 3 |
| 799410 | 26 | 42 | 64 | 74 | 2 |
| 799412 | 35 | 51 | 67 | 65 | 4 |
| 799429 | 24 | 50 | 60 | 63 | 7 |
| 799467 | 4 | 27 | 65 | 57 | >20 |
| 799471 | 0 | 9 | 14 | 46 | 5 |
| 799486 | 20 | 17 | 57 | 88 | 11 |
| 799496 | 3 | 12 | 34 | 69 | 3 |
| 799509 | 21 | 54 | 69 | 87 | 12 |
| 799511 | 0 | 0 | 35 | 65 | 3 |
| 799534 | 16 | 60 | 51 | 86 | 1 |
| 799540 | 41 | 60 | 63 | 73 | 5 |
| 799543 | 13 | 26 | 61 | 75 | 5 |
| 799544 | 19 | 38 | 54 | 73 | 4 |
| 799556 | 0 | 50 | 71 | 71 | 2 |
| 799563 | 32 | 57 | 85 | 88 | 5 |
| 799564 | 13 | 41 | 60 | 73 | 3 |
| 799565 | 23 | 49 | 67 | 86 | 11 |
| 799566 | 0 | 32 | 63 | 44 | 2 |
| 799566 | 10 | 64 | 82 | 98 | 1 |
| 799568 | 49 | 58 | 84 | 92 | 6 |
| 799572 | 0 | 35 | 62 | 66 | 1 |
| 799577 | 35 | 64 | 75 | 86 | 2 |
| 799583 | 26 | 61 | 73 | 65 | 3 |
| 799583 | 31 | 46 | 59 | 83 | 3 |
| 799589 | 15 | 58 | 77 | 82 | 4 |
| 799596 | 14 | 35 | 66 | 83 | 5 |
| 799605 | 18 | 46 | 51 | 75 | 8 |
| 799607 | 5 | 12 | 46 | 76 | 2 |
| 799608 | 35 | 56 | 70 | 76 | 3 |
| 799624 | 2 | 50 | 77 | 89 | 6 |
| 799631 | 0 | 25 | 49 | 88 | 3 |
| 799663 | 19 | 43 | 61 | 89 | >20 |
| 799667 | 8 | 8 | 17 | 47 | 9 |
| 799668 | 15 | 17 | 39 | 72 | 1 |
| 799669 | 47 | 72 | 82 | 95 | 3 |
| 799671 | 22 | 56 | 71 | 74 | 2 |
| 799673 | 29 | 66 | 74 | 86 | 4 |
| 799674 | 16 | 35 | 64 | 91 | 14 |
| 799686 | 18 | 35 | 36 | 56 | 2 |
| 799689 | 34 | 49 | 65 | 73 | 5 |
| 799708 | 15 | 35 | 52 | 79 | 11 |
| 799709 | 0 | 27 | 36 | 62 | 7 |
| 799711 | 36 | 47 | 51 | 54 | 5 |
| 799712 | 27 | 45 | 55 | 63 | 3 |
| 799718 | 23 | 52 | 66 | 72 | 4 |
| 799722 | 17 | 38 | 53 | 82 | 5 |
| 799734 | 8 | 44 | 64 | 67 | 8 |
| 799743 | 0 | 43 | 44 | 64 | 5 |
| 799751 | 11 | 35 | 69 | 65 | 10 |

TABLE 12-continued

% inhibition of SMAD7 mRNA expression

| ION No | 740 nM | 2220 nM | 6670.0 nM | 20000.0 nM | IC$_{50}$ (µM) |
|---|---|---|---|---|---|
| 799753 | 0 | 33 | 32 | 66 | 4 |
| 799755 | 13 | 44 | 66 | 75 | 6 |
| 799759 | 22 | 44 | 45 | 66 | 2 |
| 799781 | 23 | 75 | 72 | 92 | >20 |
| 799787 | 0 | 9 | 35 | 41 | 18 |
| 799791 | 11 | 4 | 29 | 60 | 6 |
| 799808 | 8 | 33 | 52 | 73 | 10 |
| 799851 | 15 | 36 | 46 | 57 | 2 |
| 799854 | 21 | 56 | 80 | 79 | 5 |
| 799858 | 18 | 43 | 48 | 71 | 2 |
| 799878 | 35 | 64 | 68 | 84 | 17 |
| 799904 | 3 | 9 | 23 | 62 | 8 |
| 799921 | 10 | 35 | 55 | 58 | 11 |
| 799964 | 4 | 15 | 46 | 61 | >20 |
| 799967 | 0 | 0 | 0 | 20 | 9 |
| 799980 | 22 | 22 | 51 | 61 | 13 |
| 800010 | 33 | 13 | 47 | 59 | 6 |
| 800025 | 0 | 42 | 55 | 74 | 6 |
| 800031 | 10 | 39 | 57 | 69 | 8 |
| 800048 | 0 | 31 | 58 | 58 | 4 |
| 800066 | 7 | 42 | 62 | 82 | 9 |
| 800109 | 0 | 10 | 41 | 71 | 1 |
| 800109 | 37 | 64 | 77 | 67 | 1 |
| 800109 | 44 | 57 | 75 | 93 | 1 |
| 800109 | 33 | 62 | 83 | 71 | 1 |
| 800109 | 53 | 69 | 85 | 97 | 1 |
| 801040 | 52 | 55 | 60 | 95 | 1 |
| 801051 | 52 | 62 | 76 | 88 | 4 |
| 829734 | 20 | 40 | 69 | 68 | 4 |
| 829762 | 27 | 41 | 59 | 78 | >20 |
| 829767 | 5 | 6 | 36 | 49 | 3 |
| 829776 | 26 | 40 | 66 | 81 | 5 |
| 829864 | 0 | 33 | 67 | 76 | 1 |
| 829942 | 44 | 70 | 84 | 94 | <0.7 |
| 829956 | 65 | 82 | 89 | 95 | 1 |
| 829980 | 52 | 63 | 79 | 92 | 3 |
| 829994 | 25 | 54 | 69 | 80 | 1 |
| 829995 | 36 | 74 | 76 | 84 | 8 |
| 830010 | 0 | 12 | 52 | 72 | 1 |
| 830025 | 42 | 58 | 72 | 88 | <0.7 |
| 830028 | 54 | 70 | 85 | 93 | 3 |
| 830037 | 30 | 56 | 70 | 87 | 3 |
| 830044 | 47 | 61 | 80 | 93 | 10 |
| 830051 | 0 | 18 | 42 | 67 | 2 |
| 830053 | 29 | 56 | 79 | 87 | 2 |
| 830067 | 23 | 59 | 80 | 88 | 10 |
| 830095 | 3 | 37 | 42 | 60 | 2 |
| 830097 | 29 | 60 | 78 | 86 | 1 |
| 830099 | 42 | 56 | 70 | 92 | 10 |
| 830100 | 3 | 8 | 38 | 69 | 2 |
| 830121 | 37 | 48 | 69 | 85 | <0.7 |
|  | 54 | 63 | 79 | 86 |  |
| 830122 | 28 | 54 | 66 | 74 | 3 |
| 830128 | 20 | 55 | 74 | 85 | 3 |
| 830131 | 34 | 48 | 51 | 61 | 5 |
| 830135 | 16 | 44 | 56 | 71 | 5 |
| 830137 | 19 | 46 | 63 | 84 | 3 |
| 830138 | 0 | 40 | 61 | 87 | 5 |
| 830142 | 13 | 37 | 32 | 49 | >20 |
| 830144 | 47 | 68 | 85 | 96 | 1 |
| 830157 | 24 | 50 | 73 | 81 | 3 |
| 830163 | 33 | 49 | 73 | 84 | 2 |
| 830168 | 31 | 46 | 65 | 73 | 3 |
| 830170 | 1 | 39 | 54 | 67 | 6 |
| 830180 | 21 | 39 | 43 | 64 | 8 |
| 830207 | 49 | 74 | 85 | 93 | 1 |
| 830208 | 38 | 70 | 79 | 90 | 1 |

Example 4: Dose-Dependent Antisense-Mediated Inhibition of Human SMAD7 mRNA Expression in Hep3B Cells The efficacy of select gapmers from the studies described above exhibiting significant in vitro inhibition of SMAD7 mRNA were compared with ION 28453.

Cells were plated at a density of 20,000 cells per well and transfected using electroporation with 0.25 µM, 0.74 µM, 2.22 µM, 6.67 µM, or 20.00 µM concentrations of antisense oligonucleotide, as specified in the Tables below. After a treatment period of approximately 16 hours, RNA was isolated from the cells and SMAD7 mRNA levels were measured by quantitative real-time PCR. Primer probe set RTS5062 was used to measure human SMAD7 mRNA levels. SMAD7 mRNA levels were adjusted according to total RNA content, as measured by RIBOGREEN®. Results are presented as percent inhibition of SMAD7 mRNa expression, relative to untreated control cells.

The half maximal inhibitory concentration (IC$_{50}$) of each oligonucleotide is also presented. SMAD7 mRNA levels were significantly reduced in a dose-dependent manner in antisense oligonucleotide treated cells. Several newly designed antisense oligonucleotides had greater potency than the previously disclosed lead compound, ION 28453.

TABLE 13

% inhibition of SMAD7 mRNA expression

| ION No | 0.25 µM | 0.74 µM | 2.22 µM | 6.67 µM | 20.00 µM | IC$_{50}$ (µM) |
|---|---|---|---|---|---|---|
| 28453 | 0 | 0 | 0 | 2 | 24 | >20 |
| 772568 | 14 | 0 | 25 | 47 | 61 | 9 |
| 798781 | 12 | 38 | 66 | 66 | 87 | 2 |
| 799184 | 0 | 10 | 18 | 51 | 78 | 6 |
| 800821 | 14 | 30 | 35 | 58 | 79 | 4 |
| 800966 | 0 | 0 | 0 | 0 | 0 | >20 |
| 801040 | 31 | 44 | 67 | 63 | 91 | 1 |
| 801051 | 0 | 10 | 34 | 62 | 83 | 4 |
| 823480 | 8 | 0 | 0 | 16 | 26 | >20 |
| 823481 | 11 | 10 | 10 | 32 | 47 | >20 |
| 823486 | 4 | 0 | 0 | 22 | 40 | >20 |
| 823500 | 0 | 0 | 0 | 0 | 0 | >20 |
| 823501 | 0 | 0 | 0 | 9 | 23 | >20 |
| 823667 | 0 | 0 | 2 | 31 | 55 | 18 |
| 823502 | 0 | 0 | 7 | 26 | 41 | >20 |
| 823694 | 0 | 0 | 0 | 0 | 0 | >20 |
| 823503 | 3 | 8 | 8 | 28 | 49 | >20 |
| 772568 | 0 | 0 | 22 | 36 | 61 | 13 |
| 823520 | 0 | 0 | 0 | 3 | 38 | >20 |
| 823525 | 0 | 0 | 0 | 0 | 27 | >20 |
| 823531 | 0 | 0 | 0 | 3 | 23 | >20 |
| 823532 | 1 | 1 | 18 | 42 | 59 | 13 |
| 823584 | 0 | 0 | 14 | 26 | 40 | >20 |

Example 5: Confirmation of Dose-Dependent Antisense-Mediated Inhibition of Human SMAD7 mRNA Expression in A431 Cells The efficacy of select gapmers from the studies described above exhibiting significant in vitro inhibition of SMAD7 mRNA were compared with ION 736697 which has the same sequence and chemistry as GED-0301 (Mongersen) disclosed in WO/2013/037970.

ION 736697 was designed as a uniform deoxy oligonucleotide with sequence GTCGCCCCTTCTCCCCGCAGC (designated herein as SEQ ID NO: 2736), and chemistry Gds Tds mCds Gds Cds Cds Cds Cds Tds Tds Cds Tds Cds Cds Cds mCds Gds Cds Ads Gds Cd, wherein 'd' is deoxy, 's' is phosphorothioate internucleoside linkage, 'mC' is 5-methylcytosine, and 'C', 'T', 'G', and 'A' are the notations of the four nucleobases.

The newly designed compounds disclosed herein are cEt-modified antisense oligonucleotides. Compared with first generation uniform phosphorothioate DNA antisense oligonucleotides, such as ION 736697, cEt-modified antisense oligonucleotides are known to exhibit higher stability leading to increased tissue resident time and uptake, as well as enhanced binding to the target RNA, resulting in increased potency and efficacy. The studies described below show a comparison of select cEt-modified gapmers and ION0736697/Mongersen.

Study 1

A431 cells were plated in collagen I-coated 96-well plates in DMEM with 10% penicillin-streptomycin. Immediately after plating, 0.08 µM, 0.25 µM, 0.74 µM, 2.22 µM, 6.67 µM, or 20.00 µM concentrations of antisense oligonucleotide were added. The plates were shaken briefly before incubating at 37° C. and 10% $CO_2$. After a treatment period of approximately 48 hours, the cells were washed and lyzed and RNA on 384-well Pall plates with DNase I treatment. SMAD7 mRNA levels were measured by quantitative real-time PCR. Primer probe set RTS5062 was used to measure human SMAD7 mRNA levels. SMAD7 mRNA levels were adjusted according to total RNA content, as measured by RIBOGREEN®. Results are presented as percent inhibition of SMAD7 mRNA expression, relative to untreated control cells.

SMAD7 mRNA levels were significantly reduced in a dose-dependent manner in antisense oligonucleotide treated cells. All Ionis oligonucleotides had greater potency than ION 736697/Mongersen. Specifically, both ION 830025 and ION 798781 were more efficacious than ION 736697/Mongersen.

TABLE 14

% inhibition of SMAD7 mRNA expression

| ION No | 0.08 µM | 0.25 µM | 0.74 µM | 2.22 µM | 6.67 µM | 20.00 µM | $IC_{50}$ (µM) |
|---|---|---|---|---|---|---|---|
| 736697 | 14 | 20 | 24 | 13 | 34 | 37 | >20 |
| 790615 | 14 | 43 | 55 | 63 | 70 | 75 | 0.7 |
| 798781 | 23 | 34 | 41 | 41 | 57 | 62 | 3.6 |
| 830025 | 16 | 30 | 22 | 41 | 54 | 67 | 4.7 |
| 830037 | 10 | 31 | 29 | 42 | 61 | 67 | 3.4 |
| 830121 | 11 | 18 | 27 | 21 | 35 | 44 | >20 |

Study 2

Many of the Ionis designed oligonucleotides as well as ION 736697/Mongersen are complementary to mouse Smad7 mRNA. To evaluate the potency of the oligonucleotides in murine cells, bEND cells were transfected using electroporation with 0.25 µM, 0.74 µM, 2.22 µM, 6.67 µM, or 20.00 µM concentrations of antisense oligonucleotide. After a treatment period of approximately 16 hours, the cells were washed and lyzed and RNA on 384-well Pall plates with DNase I treatment. Smad7 mRNA levels were measured by quantitative real-time PCR. Primer probe set RTS1114 (forward sequence CCATCAAGGCTTTTGACTATGAGA, designated herein as SEQ ID NO: 8; reverse sequence CCATGGTTGCTGCATGAACT, designated herein as SEQ ID NO: 9; probe sequence CTACAGCCTGCAGCGGCCCAA, designated herein as SEQ ID NO: 10) was used to measure murine Smad7 mRNA levels. Smad7 mRNA levels were adjusted according to total RNA content, as measured by RIBOGREEN®. Results are presented as percent inhibition of Smad7 mRNA expression, relative to untreated control cells.

SMAD7 mRNA levels were significantly reduced in a dose-dependent manner in antisense oligonucleotide treated cells. Many of the Ionis oligonucleotides had greater potency than ION 736697/Mongersen. Specifically, both ION 830025 and ION 798781 were more potent than ION 736697/Mongersen.

TABLE 15

% inhibition of SMAD7 mRNA expression

| ION No | 0.25 µM | 0.74 µM | 2.22 µM | 6.67 µM | 20.00 µM | $IC_{50}$ (µM) |
|---|---|---|---|---|---|---|
| 736697 | 1 | 1 | 0 | 0 | 0 | >20 |
| 790615 | 7 | 18 | 37 | 47 | 64 | 7.3 |
| 798781 | 0 | 0 | 20 | 33 | 51 | 19.8 |
| 830025 | 15 | 27 | 51 | 67 | 77 | 2.7 |
| 830037 | 0 | 6 | 1 | 0 | 0 | >20 |
| 830121 | 0 | 6 | 12 | 17 | 20 | >20 |

Example 6: Tolerability of 3-10-3 (S)-cEt Gapmers Targeting Human SMAD7 mRNA after Subcutaneous Administration in CD-1 Mice CD-1® mice (Charles River, Mass.) are a multipurpose mice model, frequently utilized for safety and efficacy testing. The mice were treated with Ionis human SMAD7 antisense oligonucleotides selected from studies described above and evaluated.

Treatment

Groups of 8-9 week old male CD-1 mice were injected subcutaneously twice a week for 7 weeks with 50 mg/kg of Ionis oligonucleotides (100 mg/kg/week dose). Each group contained 4 mice. One group of male CD-1 mice was injected subcutaneously twice a week for 7 weeks with PBS. Plasma was collected for analysis on day 28. Mice were euthanized 48 hours after the last dose, and organs and plasma were harvested for further analysis.

Plasma Chemistry Markers

To evaluate the effect of Ionis oligonucleotides on liver and kidney function, plasma levels of transaminases, albumin, and BUN were measured using an automated clinical chemistry analyzer (Olympus AU480 analyzer). The results are presented in the table below. Ionis SMAD7 oligonucleotides that caused changes in the levels of any of the liver or kidney function markers outside the expected range for antisense oligonucleotides were excluded in further studies.

TABLE 16

Plasma chemistry markers in CD-1 mice plasma at day 46

|  | ALT (IU/L) | AST (IU/L) | Albumin (g/dL) | BUN (mg/dL) |
|---|---|---|---|---|
| PBS | 31 | 62 | 2.4 | 23 |
| 790615 | 65 | 97 | 2.2 | 22 |
| 798781 | 40 | 66 | 2.2 | 26 |
| 799144 | 253 | 170 | 2.7 | 21 |
| 829994 | 65 | 90 | 2.9 | 25 |
| 830025 | 208 | 263 | 2.5 | 25 |
| 830027 | 40 | 104 | 2.5 | 23 |
| 830121 | 198 | 151 | 1.9 | 21 |

Organ Weights

Kidney, liver, and spleen weights were measured at the end of the study, and are presented in the table below. Ionis SMAD7 oligonucleotides that caused any changes in organ weights outside the expected range for antisense oligonucleotides were excluded from further studies.

TABLE 17

Organ weights (g)

|  | Kidneys | Liver | Spleen |
|---|---|---|---|
| PBS | 0.6 | 2.2 | 0.2 |
| 790615 | 0.6 | 2.0 | 0.2 |
| 798781 | 0.6 | 2.3 | 0.1 |
| 799144 | 0.6 | 2.3 | 0.1 |
| 829994 | 0.7 | 2.6 | 0.3 |
| 830025 | 0.6 | 2.2 | 0.2 |
| 830027 | 0.6 | 2.6 | 0.2 |
| 830121 | 0.6 | 2.4 | 0.2 |

Hematology Assays

Blood obtained from all mouse groups was measured by an ADVIA2120i hematology analyzer (Siemens, USA) for measurements of the various blood cells, as well as other hematology markers. The results are presented in the tables below. None of the Ionis SMAD7 oligonucleotides caused changes in the levels of any of the hematology markers outside the expected range for antisense oligonucleotides. 'n.d.' indicates that the number was below detection levels.

TABLE 18

Hematology markers in CD-1 mice

|  | RBC ($10^6$/L) | Hemoglobin (g/dL) | Hematocrit (%) | MCV (fL) | MCH (pg) | MCHC (g/dL) | platelets ($10^3$/μL) |
|---|---|---|---|---|---|---|---|
| PBS | 9.2 | 14.7 | 44.9 | 49.0 | 16.0 | 32.8 | 1223.5 |
| 790615 | 10.3 | 15.2 | 46.2 | 44.8 | 14.7 | 32.8 | 1055.8 |
| 798781 | 9.3 | 13.8 | 42.3 | 45.8 | 14.9 | 32.6 | 867.3 |
| 799144 | 9.5 | 14.3 | 43.1 | 45.8 | 15.2 | 33.2 | 614.0 |
| 829994 | 7.7 | 12.0 | 36.6 | 47.3 | 15.5 | 32.7 | 841.3 |
| 830025 | 8.0 | 12.5 | 38.7 | 48.8 | 15.7 | 32.3 | 805.0 |
| 830027 | 9.7 | 14.7 | 44.7 | 46.3 | 15.1 | 32.9 | 1141.8 |
| 830121 | 8.9 | 13.6 | 40.4 | 45.5 | 15.3 | 33.6 | 765.0 |

TABLE 19

Blood cells in CD-1 mice

|  | Reticulocytes (%) | Neutrophils (%) | Lymphocytes (%) | Eosinophils ($10^3$/μL) | Monocytes ($10^3$/μL) | Basophils ($10^3$/μL) | WBC ($10^3$/μL) |
|---|---|---|---|---|---|---|---|
| PBS | 3.6 | 23.0 | 70.2 | 2.2 | 4.3 | 0.2 | 7.7 |
| 790615 | 3.5 | 9.7 | 82.8 | 2.5 | 5.0 | 0.1 | 10.5 |
| 798781 | 3.3 | 18.8 | 73.7 | 2.4 | 5.2 | n.d. | 4.9 |
| 799144 | 3.3 | 11.4 | 80.7 | 2.9 | 4.9 | 0.1 | 6.2 |
| 829994 | 3.7 | 16.4 | 79.4 | 1.3 | 3.0 | n.d. | 5.0 |
| 830025 | 3.3 | 9.3 | 83.2 | 3.8 | 3.2 | 0.6 | 4.8 |
| 830027 | 3.4 | 25.6 | 64.4 | 1.9 | 8.2 | n.d. | 8.6 |
| 830121 | 4.5 | 15.8 | 75.3 | 3.5 | 5.1 | 0.3 | 10.1 |

Oligonucleotide Concentration

Oligonucleotide concentrations in the liver and colon were analyzed using LC-MS/MS method. The data is presented in the Table below.

TABLE 20

| Oligonucleotide concentration (μg/g tissue) | | |
|---|---|---|
| ION No. | Liver | Colon |
| 830121 | 50 | 14 |
| 829994 | 45 | 11 |
| 830037 | 97 | 24 |
| 798781 | 312 | 63 |
| 790615 | 75 | 13 |
| 830025 | 77 | 39 |

Histopathology Evaluations

Liver, kidneys, duodenum, ileum, colon, heart, and lungs were collected from all animals and the intestinal tissues were flushed with 0.9% saline. The tissues were fixed in 10% neutral-buffered formalin, embedded in paraffin, sectioned and stained with hematoxylin and eosin.

Tissues collected from all groups were histologically unremarkable for all mice. Therefore, twice weekly subcutaneous injection of mice with any of the Ionis SMAD7 antisense oligonucleotides at 50 mg/kg for 7 weeks was not associated with any antisense oligonucleotide-related tissue alterations.

Pharmacology

The pharmacological activity of the Ionis oligonucleotides in mice was assessed by measuring mouse Smad7 mRNA expression in liver, kidney, duodenum, ileum, and colon at necropsy.

Tissue samples from all mice were analyzed for Smad7 mRNA expression using the primer probe set HTS7555 (forward sequence CTGACGCGGGAAGTGGAT, designated SEQ ID NO: 2737; reverse sequence TGGCGGACTTGATGAAGATG, designated SEQ ID NO: 2738; probe sequence TGTGGGTTTACAACCGCAGCAGTTACC, designated SEQ ID NO: 2739), which was normalized to mRNA levels of the housekeeping gene, GAPDH. One-way ANOVA with Dunnet's comparison test was used for statistical analysis. The results are presented in the Table below. Treatment with several antisense oligonucleotides, including ION 830025, resulted in significant Smad7 mRNA reduction in various tissues.

TABLE 21

% inhibition of Smad7 mRNA expression (compared to control)

| ION | Kidney | Liver |
|---|---|---|
| 790615 | 23 | 18 |
| 798781 | 18 | 28 |
| 799144 | 3 | 0 |
| 829994 | 73 | 58 |
| 830025 | 45 | 60 |
| 830037 | 7 | 24 |
| 830121 | 0 | 24 |

Example 7: Effect of 3-10-3 (S)-cEt Gapmers Targeting Human SMAD7 mRNA after Oral Administration in CD-1 Mice The objective of this study was to evaluate the tolerability and pharmacodynamics of select Ionis human SMAD7 antisense oligonucleotides in CD-1 mice following 4 weeks of treatment. The mice were administered oligonucleotides by oral gavage.

Treatment

Groups of 7-8 week old male CD-1 mice were given an oral gavage dose once daily for 4 weeks of 500 mg/kg of Ionis SMAD7 oligonucleotides. Each group contained 8 mice. One group of male CD-1 mice was administered saline by oral gavage daily. Mice were euthanized 48 hours after the last dose, and organs and plasma were harvested for further analysis.

Blood Chemistry Markers

To evaluate the effect of Ionis SMAD7 oligonucleotides on liver and kidney function, approximately 0.7 mL of blood samples were collected from the animals and put into tubes without anticoagulant for serum separation. The tubes were kept at room temperature for a minimum of 90 minutes and then centrifuged at 3000 rpm for 10 minutes at room temperature o obtain serum. Levels of transaminases, albumin, and BUN were measured using a Toshiba 200FR NEO chemistry analyzer (Toshiba Co., Japan). The results are presented in the table below. None of the Ionis SMAD7 oligonucleotides caused changes in the levels of any of the liver or kidney function markers outside the expected range for antisense oligonucleotides.

TABLE 22

Plasma chemistry markers in CD-1 mouse plasma at day 30

| | ALT (IU/L) | AST (IU/L) | Albumin (g/dL) | BUN (mg/dL) | Bilirubin (mg/dL) |
|---|---|---|---|---|---|
| PBS | 46 | 77 | 3.4 | 24 | 0.3 |
| 830121 | 45 | 75 | 3.3 | 24 | 0.2 |
| 829994 | 38 | 71 | 3.2 | 25 | 0.3 |
| 830037 | 62 | 94 | 3.3 | 26 | 0.3 |
| 798781 | 43 | 73 | 3.2 | 25 | 0.3 |
| 790615 | 41 | 77 | 3.3 | 22 | 0.3 |
| 830025 | 34 | 65 | 3.3 | 21 | 0.2 |

Body and Organ Weights

Final body weights were measured at the end of the study. There was no significant difference in the body weight of the mice treated with antisense oligonucleotide compared to the control.

Organ weights were also measured at the end of the study, and are presented in the table below. None of the Ionis SMAD7 oligonucleotides caused any changes in organ weights outside the expected range for antisense oligonucleotides.

TABLE 23

Body and organ weights (g)

| | Body | Heart | Kidneys | Spleen | Liver with gallbladder |
|---|---|---|---|---|---|
| PBS | 34 | 0.16 | 0.62 | 0.10 | 1.91 |
| 830121 | 34 | 0.17 | 0.61 | 0.10 | 1.92 |
| 829994 | 35 | 0.18 | 0.62 | 0.11 | 2.02 |
| 830037 | 35 | 0.17 | 0.69 | 0.10 | 1.93 |
| 798781 | 35 | 0.17 | 0.64 | 0.09 | 1.86 |
| 790615 | 35 | 0.17 | 0.64 | 0.11 | 1.88 |
| 830025 | 35 | 0.17 | 0.71 | 0.10 | 1.88 |

Hematology Assays

Blood obtained from all mouse groups was measured by an ADVIA2120i hematology analyzer (Siemens, USA) for measurements of the various blood cells, as well as other hematology markers. The results are presented in the tables below. None of the Ionis SMAD7 oligonucleotides caused changes in the levels of any of the hematology markers outside the expected range for antisense oligonucleotides.

TABLE 24

Hematology markers in CD-1 mice

| | RBC ($10^6$/L) | Hemoglobin (g/dL) | Hematocrit (%) | MCV (fL) | MCH (pg) | MCHC (g/dL) | platelets ($10^3$/µL) |
|---|---|---|---|---|---|---|---|
| PBS | 10.0 | 15.0 | 52.0 | 52.0 | 15.0 | 28.9 | 1108 |
| 830121 | 10.0 | 15.1 | 51.8 | 51.6 | 15.0 | 29.1 | 1170 |
| 829994 | 10.1 | 15.2 | 51.5 | 51.2 | 15.1 | 29.5 | 1219 |
| 830037 | 10.1 | 15.4 | 53.4 | 53.2 | 15.4 | 28.9 | 1122 |
| 798781 | 10.1 | 15.2 | 52.0 | 51.7 | 15.1 | 29.1 | 1099 |
| 790615 | 10.1 | 15.2 | 52.2 | 51.6 | 15.0 | 29.1 | 1033 |
| 830025 | 10.1 | 15.0 | 52.4 | 52.3 | 14.9 | 28.5 | 1236 |

TABLE 25

Blood cells in CD-1 mice

| | Reticulocytes (%) | Neutrophils (%) | Lymphocytes (%) | Eosinophils ($10^3$/µL) | Monocytes ($10^3$/µL) | Basophils ($10^3$/µL) | Leucocytes ($10^3$/µL) | WBC ($10^3$/µL) |
|---|---|---|---|---|---|---|---|---|
| Saline | 3.1 | 12.7 | 81.7 | 0.09 | 0.10 | 0.01 | 0.03 | 4.5 |
| 830121 | 3.0 | 11.6 | 81.7 | 0.08 | 0.15 | 0.01 | 0.03 | 4.1 |
| 829994 | 3.0 | 14.0 | 80.4 | 0.09 | 0.10 | 0.01 | 0.03 | 4.1 |

TABLE 25-continued

Blood cells in CD-1 mice

| | Reticulocytes (%) | Neutrophils (%) | Lymphocytes (%) | Eosinophils ($10^3/\mu L$) | Monocytes ($10^3/\mu L$) | Basophils ($10^3/\mu L$) | Leucocytes ($10^3/\mu L$) | WBC ($10^3/\mu L$) |
|---|---|---|---|---|---|---|---|---|
| 830037 | 3.1 | 19.3 | 73.2 | 0.15 | 0.13 | 0.01 | 0.03 | 4.3 |
| 798781 | 3.0 | 18.0 | 74.0 | 0.26 | 0.18 | 0.02 | 0.04 | 5.7 |
| 790615 | 2.8 | 16.0 | 78.3 | 0.11 | 0.15 | 0.01 | 0.04 | 5.4 |
| 830025 | 3.2 | 17.5 | 77.6 | 0.08 | 0.12 | 0.01 | 0.03 | 4.7 |

Tissue and Organ Evaluation

Histopathology evaluations were performed on the mice treated with Ionis oligonucleotides to evaluate any tissue damage in the liver (with gallbladder), kidneys, heart, spleen, thymus, mesenteric lymph nodes, and different parts of the GI tract, including duodenum, ileum, and colon (proximal and distal). Tissues were collected and fixed in 10% neutral-buffered formalin, embedded in paraffin, sectioned, and stained with hematoxylin and eosin. All the tissues were histologically unremarkable in all mice.

Daily oral gavage of mice with ION 798781, ION 790615, and ION 830025 at a dose of 500 mg/kg for one month was not associated with any antisense oligonucleotide-related tissue alterations.

Oligonucleotide Concentrations

Oligonucleotide concentrations were detected in various tissues by LC-MS/MS analysis. The results are presented below. The greatest concentration was found in the kidney, followed by the colon.

TABLE 26

Oligonucleotide concentration (μg/g)

| | Colon | Duodenum | Ileum | Kidney | Liver |
|---|---|---|---|---|---|
| 830121 | 2.7 | 0.4 | 1.1 | 13.2 | 0.9 |
| 829994 | 5.7 | 0.8 | 4.0 | 9.8 | 1.3 |
| 830037 | 4.8 | 1.2 | 2.7 | 32.4 | 3.9 |
| 798781 | 4.4 | 0.7 | 2.9 | 45.2 | 2.9 |
| 790615 | 2.9 | 0.9 | 1.6 | 23.6 | 2.8 |
| 830025 | 3.6 | 0.7 | 1.9 | 21.5 | 2.3 |

Example 8: Effect of 3-10-3 (S)-cEt Gapmers Targeting Human SMAD7 after Subcutaneous Administration in Beagle Dogs The study was conducted to evaluate the tolerability and pharmacodynamics of human SMAD7 antisense oligonucleotides in beagle dogs. All the antisense oligonucleotides in this study are cross-reactive with dog SMAD7 mRNA.

Treatment

Groups of 24-25 week old male beagle dogs were injected subcutaneously with 30 mg/kg ION Ionis oligonucleotide. There were 4 animals per group. Dogs were injected every two days for the first week (day 1, 3, and 5) and once weekly thereafter (days 8, 15, 22, and 29). A control group of dogs received subcutaneous injections of PBS. Dogs were sacrificed on day 31 approximately 48 hours after the final dose and organs and plasma were harvested for further analysis.

Plasma Chemistry Markers

To evaluate the effect of Ionis SMAD7 oligonucleotides on liver and kidney function, plasma levels of transaminases, albumin, creatine and BUN were measured using an automated clinical chemistry analyzer (Toshiba 200FR Neo chemistry analyzer, Toshiba Co., Japan). The results are presented in the table below. Ionis SMAD7 oligonucleotides that caused changes in the levels of any of the liver or kidney function markers or other plasma chemistry markers outside the expected range for antisense oligonucleotides were excluded in further studies. Specifically, ION 830025 and ION 798781 were well tolerated.

TABLE 27

Plasma chemistry markers in beagle dogs plasma at day 31

| | ALT (IU/L) | AST (IU/L) | Albumin (g/dL) | BUN (mg/dL) | Creatine (mg/dL) | Bilirubin (mg/dL) |
|---|---|---|---|---|---|---|
| PBS | 27 | 40 | 3.0 | 17.1 | 0.7 | 0.2 |
| 830121 | 1454 | 383 | 3.0 | 20.0 | 0.9 | 2.6 |
| 829994 | 62 | 52 | 3.1 | 15.4 | 0.7 | 0.1 |
| 830037 | 3091 | 1132 | 3.7 | 21.2 | 1.0 | 0.8 |
| 798781 | 32 | 45 | 3.0 | 19.4 | 0.9 | 0.2 |
| 790615 | 38 | 41 | 3.4 | 15.7 | 0.8 | 0.2 |
| 830025 | 26 | 38 | 3.1 | 17.9 | 0.9 | 0.1 |

Body and Organ Weights

Body weights as well as kidney, spleen, liver (with gall bladder), mesenteric lymph node, heart, and thymus weights were measured at the end of the study. To control for changes in body weight, results are presented as the organ weight divided by total body weight and then normalized to this result for the PBS control group. Ionis SMAD7 oligonucleotides that caused any changes in organ weights outside the expected range for antisense oligonucleotides were excluded from further studies.

TABLE 28

Body and organ weights (g) in beagle dogs

| | Body | Kidney | Spleen | Liver | Mesenteric LN | Heart | Thymus |
|---|---|---|---|---|---|---|---|
| PBS | 7849 | 37.8 | 24.9 | 260.6 | 10.1 | 63.4 | 9.5 |
| 830121 | 6091 | 40.0 | 27.5 | 202.0 | 12.2 | 52.6 | 2.8 |
| 829994 | 7335 | 39.1 | 22.8 | 250.0 | 9.0 | 57.9 | 6.3 |
| 830037 | 6437 | 36.7 | 23.7 | 204.1 | 9.0 | 51.9 | 6.3 |
| 798781 | 6661 | 40.0 | 26.4 | 242.9 | 7.8 | 53.4 | 6.0 |
| 790615 | 7372 | 44.1 | 32.3 | 253.7 | 10.2 | 63.6 | 9.9 |
| 830025 | 7403 | 40.3 | 28.9 | 250.3 | 10.9 | 60.5 | 8.3 |

Hematology Assays

Blood samples were collected from the cephalic vein or saphenous vein of each animal. About 0.5 mL of blood samples was put into tubes containing the potassium salt of EDTA. Blood obtained from all dog groups was measured using an ADVIA2120i hematology analyzer for measurements of the various blood cells, as well as other hematology markers. The results are presented in the tables below. Ionis SMAD7 oligonucleotides that caused changes in the levels of any of the hematology markers outside the expected range for antisense oligonucleotides were excluded in further studies.

TABLE 29

Hematology markers in Beagle Dogs

|  | RBC (^6/L) | Hemo-globin (g/dL) | Hemat-ocrit (%) | MCV (fL) | MCH (pg) | MCHC (g/dL) | PLT (^3/μL) | WBC (^3/μL) |
| --- | --- | --- | --- | --- | --- | --- | --- | --- |
| PBS | 6.8 | 16.5 | 46 | 67 | 24.3 | 36.1 | 271 | 9.4 |
| 830121 | 8.5 | 18.5 | 56 | 66 | 21.7 | 32.9 | 249 | 8.2 |
| 829994 | 6.6 | 15.3 | 44 | 66 | 23.2 | 35.1 | 287 | 12.5 |
| 830037 | 8.0 | 17.5 | 52 | 66 | 22.1 | 33.6 | 280 | 8.5 |
| 798781 | 7.3 | 16.2 | 48 | 67 | 22.3 | 33.6 | 191 | 7.3 |
| 790615 | 6.6 | 14.5 | 45 | 68 | 21.9 | 32.5 | 242 | 7.1 |
| 830025 | 6.4 | 13.9 | 43 | 67 | 21.7 | 32.5 | 250 | 5.7 |

TABLE 30

Blood cells in Beagle Dogs

| ION No | Reticulocytes (%) | Neutrophils (%) | Lymphocytes (%) | Eosinophils (%) | Monocytes (%) | Basophils (%) |
| --- | --- | --- | --- | --- | --- | --- |
| PBS | 0.9 | 56 | 35 | 2.6 | 5.7 | 0.6 |
| 830121 | 0.5 | 59 | 30 | 2.5 | 7.7 | 0.8 |
| 829994 | 0.9 | 65 | 26 | 1.8 | 6.3 | 0.5 |
| 830037 | 0.3 | 57 | 32 | 2.6 | 8.0 | 0.7 |
| 798781 | 0.6 | 56 | 34 | 2.7 | 6.5 | 0.5 |
| 790615 | 0.7 | 53 | 36 | 2.6 | 7.9 | 0.5 |
| 830025 | 1.2 | 55 | 34 | 2.4 | 8.2 | 0.3 |

Oligonucleotide Concentration Analysis

Oligonucleotide concentrations of both ION 830025 and ION 798781 were detected in various tissues by LC-MS/MS analysis. The results are presented below, expressed as μg/g tissue. The data was collected 48 hours after the last dose.

TABLE 31

Full length oligonucleotide (μg/g)

|  | Liver | Duodenum | Ileum | Distal colon | Proximal colon | Kidney |
| --- | --- | --- | --- | --- | --- | --- |
| 830121 | 443 | 26 | 26 | 20 | 19 | 1468 |
| 829994 | 335 | 23 | 12 | 7 | 11 | 894 |
| 830037 | 521 | 55 | 67 | 46 | 86 | 894 |
| 798781 | 964 | 97 | 177 | 68 | 73 | 3300 |
| 790615 | 220 | 17 | 18 | 17 | 17 | 1156 |
| 830025 | 466 | 97 | 41 | 49 | 31 | 1470 |

Tissue and Organ Evaluation

Histopathology evaluations were performed on the dogs treated with Ionis oligonucleotides to evaluate any tissue damage in the liver (with gallbladder), kidneys, heart, spleen, thymus, mesenteric lymph nodes, and different parts of the GI tract, including duodenum, ileum, and colon (proximal and distal). Tissues were collected and fixed in 10% neutral-buffered formalin, embedded in paraffin, sectioned, and stained with hematoxylin and eosin. Antisense oligonucleotide-related lesions in treated dogs were generally within the typical spectrum expected for antisense oligonucleotides at high tissue concentrations.

Pharmacology

The pharmacological activity of the Ionis oligonucleotides in dogs was assessed by measuring dog SMAD7 mRNA expression in liver, kidney, duodenum, ileum, and colon at necropsy. All the human ASOs used are complementary to dog SMAD7 mRNA.

Tissue samples from all dogs were analyzed for SMAD7 mRNA expression using the primer probe set RTS34649 (forward sequence CCGATGGATTTTCTCAAACCA, designated SEQ ID NO: 2740; reverse sequence AATTCGTTCCCCCTGTTTCAG, designated SEQ ID NO: 2741; probe sequence ACTGTCCAGATGCTGTGCCTTCCTCC, designated SEQ ID NO: 2742), which was normalized to mRNA levels of the housekeeping gene, HPRT1. One-way ANOVA with Dunnet's comparison test was used for statistical analysis. The results are presented in the Table below.

TABLE 32

% inhibition of SMAD7 mRNA expression (compared to control)

| ION | Kidney | Liver | Duodenum | Ileum | Proximal colon | Distal colon |
| --- | --- | --- | --- | --- | --- | --- |
| 830121 | 39 | 0 | 55 | 0 | 20 | 21 |
| 829994 | 0 | 0 | 2 | 32 | 34 | 29 |
| 830037 | 40 | 0 | 33 | 22 | 50 | 22 |
| 798781 | 28 | 0 | 0 | 0 | 26 | 34 |
| 790615 | 37 | 9 | 35 | 0 | 41 | 31 |
| 830025 | 25 | 0 | 7 | 9 | 24 | 3 |

Example 9: Evaluation of 3-10-3 cEt Gapmers Targeting Human SMAD7 in Human PBMC Activation Assay Human peripheral blood mononuclear cells (PBMCs) can be stimulated by various means to produce specific cytokines. Ionis SMAD7 oligonucleotides were tested in an in vitro assay for potential immunostimulatory properties in an in vitro human peripheral blood mononuclear cell (PBMC) activation assay.

Treatment

Blood samples were collected from healthy human volunteers in heparinized vials and mixed well. Human PBMCs were isolated by gradient centrifugation using Ficoll-Histopaque. The cells were washed, counted and resuspended in medium. The PBMCs were plated in a 24-well culture plate and various concentrations of oligonucleotides were added to the media. An oligonucleotide historically known to promote an inflammatory response was used as a positive control, whereas an oligonucleotide known not to be pro-inflammatory was used as a negative control. ION 736697/Mongersen was also included in this assay. The supernatants were collected after 24 hours and analyzed for cytokine levels using MSD platform. The results are presented in the Table below and demonstrate that Ionis SMAD7 oligonucleotides have a more favorable profile than ION 736697/Mongersen in this PBMC assay. Specifically, ION 830025 elicited minimal cytokine and chemokine production which was similar or less than the negative control ASO.

TABLE 33

Levels of IL-10 (pg/ml)

|  | 0 μM | 0.0128 μM | 0.064 μM | 0.32 μM | 1.6 μM | 8 μM | 40 μM | 200 μM |
|---|---|---|---|---|---|---|---|---|
| (−) control | 0.9 | 1.1 | 1.9 | 2.8 | 1.8 | 1.3 | 1.4 | n.d. |
| 830121 | 1.2 | 2.0 | 1.3 | 1.3 | 3.1 | 3.7 | 2.2 | 1.4 |
| 830025 | 1.4 | 1.5 | 1.9 | 2.6 | 3.6 | 2.9 | 1.4 | 0.7 |
| 829994 | 2.0 | 2.0 | 1.8 | 1.8 | 5.2 | 8.0 | 4.3 | 3.8 |
| 830037 | 0.8 | 1.6 | 3.2 | 8.2 | 9.5 | 7.1 | 4.7 | 3.8 |
| 798781 | 1.1 | 2.2 | 2.0 | 2.3 | 3.9 | 2.9 | 1.4 | 0.6 |
| 790615 | 2.4 | 1.1 | 1.6 | 2.4 | 3.1 | 1.9 | 0.8 | 0.7 |
| 736697 | 1.2 | 2.1 | 3.1 | 3.5 | 2.2 | 4.2 | 4.7 | 4.0 |
| ION 736697/Mongersen | 1.2 | 2.1 | 3.1 | 3.5 | 2.2 | 4.2 | 4.7 | 4.0 |
| (+) control | 1.1 | 2.7 | 16.6 | 24.4 | 17.2 | 6.3 | 4.3 | 4.2 |

TABLE 34

Levels of IL-6 (pg/ml)

|  | 0 μM | 0.0128 μM | 0.064 μM | 0.32 μM | 1.6 μM | 8 μM | 40 μM | 200 μM |
|---|---|---|---|---|---|---|---|---|
| (−) control | 9.3 | 4.4 | 5.5 | 7.3 | 9.6 | 13.6 | 24.9 | n.d. |
| 830121 | 3.3 | 4.1 | 4.9 | 4.4 | 5.4 | 7.5 | 14.3 | 35.2 |
| 830025 | 3.8 | 3.1 | 3.8 | 5.0 | 12.9 | 17.8 | 19.5 | 30.6 |
| 829994 | 3.6 | 4.1 | 3.8 | 4.5 | 15.9 | 202.5 | 66.1 | 97.1 |
| 830037 | 3.4 | 3.8 | 9.8 | 26.7 | 38.6 | 38.4 | 58.7 | 71.2 |
| 798781 | 3.6 | 3.4 | 4.9 | 6.9 | 12.3 | 18.1 | 20.7 | 28.0 |
| 790615 | 4.2 | 3.7 | 3.8 | 6.5 | 9.0 | 10.0 | 11.0 | 22.9 |
| 736697 | 3.7 | 3.6 | 5.3 | 12.3 | 15.5 | 57.4 | 63.3 | 64.8 |
| ION 736697/Mongersen | 3.7 | 3.6 | 5.3 | 12.3 | 15.5 | 57.4 | 63.3 | 64.8 |
| (+) control | 3.7 | 8.7 | 85.1 | 122.7 | 124.5 | 91.7 | 98.4 | 89.5 |

TABLE 35

Levels of MCP-1 (pg/ml)

|  | 0 μM | 0.0128 μM | 0.064 μM | 0.32 μM | 1.6 μM | 8 μM | 40 μM | 200 μM |
|---|---|---|---|---|---|---|---|---|
| (−) control | 50.1 | 337.6 | 461.2 | 440.6 | 422.3 | 591.5 | 398.6 | n.d. |
| 830121 | 269.1 | 324.5 | 370.4 | 336.4 | 501.8 | 717.1 | 1225.2 | 411.0 |
| 830025 | 277.3 | 309.7 | 353.9 | 387.7 | 554.3 | 750.0 | 580.8 | 52.7 |
| 829994 | 262.5 | 299.8 | 379.8 | 489.7 | 1300.0 | 3370.0 | 1998.4 | 391.7 |
| 830037 | 222.3 | 369.4 | 557.1 | 1284.2 | 1085.9 | 1917.1 | 3414.8 | 2449.3 |
| 798781 | 289.2 | 332.9 | 387.0 | 483.1 | 597.2 | 582.7 | 565.8 | 61.3 |
| 790615 | 238.1 | 329.5 | 281.8 | 424.3 | 495.8 | 449.0 | 301.9 | 81.6 |
| 736697 | 268.5 | 297.6 | 385.9 | 681.3 | 693.9 | 2306.8 | 2974.9 | 622.8 |
| ION 736697/Mongersen | 268.5 | 297.6 | 385.9 | 681.3 | 693.9 | 2306.8 | 2974.9 | 622.8 |
| (+) control | 296.9 | 523.8 | 963.3 | 1623 | 1638.6 | 997.6 | 1775.1 | 516.8 |

TABLE 36

Levels of TNF-α (pg/ml)

|  | 0 μM | 0.0128 μM | 0.064 μM | 0.32 μM | 1.6 μM | 8 μM | 40 μM | 200 μM |
|---|---|---|---|---|---|---|---|---|
| (−) control | 2.1 | 2.5 | 3.3 | 3.5 | 4.1 | 6.6 | 7.9 | n.d. |
| 830121 | 3.2 | 3.0 | 3.5 | 3.1 | 3.6 | 4.8 | 9.4 | 14.2 |
| 830025 | 3.0 | 2.8 | 2.9 | 3.9 | 5.4 | 6.7 | 7.6 | 4.9 |
| 829994 | 2.8 | 2.5 | 2.9 | 3.0 | 8.0 | 63.2 | 32.3 | 28.6 |
| 830037 | 2.4 | 3.2 | 4.1 | 8.2 | 9.2 | 11.1 | 16.6 | 18.9 |
| 798781 | 3.1 | 2.6 | 3.3 | 3.8 | 5.1 | 6.5 | 6.3 | 4.0 |
| 790615 | 2.7 | 3.1 | 2.5 | 3.4 | 4.2 | 4.8 | 4.8 | 4.8 |
| 736697 | 2.8 | 2.8 | 3.5 | 5.5 | 6.8 | 13.6 | 28.1 | 43.7 |
| ION 736697/Mongersen | 2.8 | 2.8 | 3.5 | 5.5 | 6.8 | 13.6 | 28.1 | 43.7 |
| (+) control | 2.6 | 4.9 | 12.1 | 13.3 | 14.5 | 14.9 | 20.5 | 28.7 |

Example 10: Efficacy of 3-10-3 (S)-cEt Gapmers Targeting Human SMAD7 after Subcutaneous Administration in BALB/c Mice The objective of this study was to evaluate the efficacy of Ionis SMAD7 antisense oligonucleotides compared to ION 736697/Mongersen in BALB/c mice following 4 weeks of treatment. Both ION 830025 and ION 798781 are cross-reactive with mouse Smad7 mRNA.

Treatment

Groups of BALB/c mice were subcutaneously administered 50 mg/kg of Ionis SMAD7 oligonucleotides once a week for 4 weeks. Each group contained 4 mice. One group of mice was administered PBS once a week for 4 weeks. Mice were euthanized 24 hours after the last dose, and organs and plasma were harvested for further analysis.

RNA Analysis

To evaluate the efficacy of the oligonucleotides, murine Smad7 mRNA expression in the liver and the colon was measured. The results are presented below and demonstrate that all the Ionis SMAD7 oligonucleotides tested were more efficacious than the ION 736697/Mongersen in reducing mouse Smad7 mRNA expression in the liver and GI segments.

TABLE 37

| Mouse Smad7 mRNA expression (% inhibition) | | | | | |
|---|---|---|---|---|---|
| | Liver | Kidney | Duodenum | Ileum | Colon |
| ION 830025 | 46 | 5 | 26 | 14 | 32 |
| ION 790615 | 47 | 28 | 39 | 41 | 71 |
| ION 798781 | 36 | 11 | 27 | 22 | 41 |
| ION 736697/Mongersen | 6 | 9 | 0 | 0 | 3 |

Example 11: Efficacy of 3-10-3 (S)-cEt Gapmers Targeting Human SMAD7 after Oral Administration in BALB/c Mice The objective of this study was to evaluate the efficacy of Ionis SMAD7 antisense oligonucleotides in BALB/c mice following daily oral administration. The Ionis oligonucleotides are cross-reactive with mouse Smad7 mRNA.

Treatment

Groups of BALB/c mice were orally administered 500 mg/kg/day for 3 weeks of human Smad7 oligonucleotides, ION 790615, ION 798781, or ION 830025, or mouse Smad7 oligonucleotide, ION 772797 (a 3-10-3 cEt gapmer with phosphorothioate backbone and sequence AATGAACTGTATCTCC; designated herein as SEQ ID NO: 2743). One group of mice was orally administered PBS daily for 3 weeks. Each group contained 4 mice. Mice were euthanized 24 hours after the last dose, and organs and plasma were harvested for further analysis.

RNA Analysis

To evaluate the efficacy of the oligonucleotides, murine Smad7 mRNA expression in the liver, kidneys, duodenum, ileum, and colon was measured using primer probe set RTS1114. The results are presented below. The data demonstrate that ION 830025 was efficacious in reducing Smad7 mRNA expression.

TABLE 38

| Mouse Smad7 mRNA expression (% inhibition) | | | | | |
|---|---|---|---|---|---|
| | Liver | Kidney | Duodenum | Ileum | Colon |
| 772797 (mouse ASO) | 7 | 0 | 36 | 8 | 1 |
| 798781 (human ASO) | 0 | 12 | 47 | 0 | 0 |
| 790615 (human ASO) | 52 | 41 | 54 | 0 | 72 |
| 830025 (human ASO) | 25 | 31 | 51 | 0 | 39 |

Example 12: Effect of 3-10-3 (S)-cEt Gapmers Targeting Human SMAD7 after Oral Administration in Beagle Dogs The study was conducted to evaluate the tolerability and pharmacodynamics of select human SMAD7 antisense oligonucleotides in beagle dogs following 4 weeks of treatment. The dogs were administered oligonucleotides by oral gavage.

Treatment

Groups of 24-25 week old male beagle dogs were administered 200 mg Ionis human SMAD7 oligonucleotide by oral gavage once a week for 4 weeks. There were 4 animals per group. A control group of dogs received oral administration of distilled water. Dogs were sacrificed on day 30 approximately 48 hours after the final dose and organs and plasma were harvested for further analysis.

Plasma Chemistry Markers

To evaluate the effect of Ionis SMAD7 oligonucleotides on liver and kidney function, approximately 1.5 mL of blood samples were collected and put into tubes without anticoagulant for serum separation. The tubes were kept at room temperature for a minimum of 90 min and then centrifuged (approximately 3,000 rpm for 10 min) to obtain serum. Plasma levels of transaminases, albumin, bilirubin, and BUN were measured using an automated clinical chemistry analyzer (Toshiba 200FR Neo chemistry analyzer, Toshiba Co., Japan). The results are presented in the table below. The results indicate that Ionis SMAD7 oligonucleotides did not cause any changes in the levels of plasma chemistry markers outside the expected range for antisense oligonucleotides. Specifically, ION 830025 and ION 798781 were very well tolerated.

TABLE 39

| Plasma chemistry markers (% of control) in beagle dog plasma at day 30 | | | | | |
|---|---|---|---|---|---|
| | Albumin | ALT | AST | BUN | Bilirubin |
| Control | 100 | 100 | 100 | 100 | 100 |
| 830025 | 96 | 117 | 106 | 93 | 96 |
| 798781 | 101 | 115 | 114 | 104 | 114 |
| 790615 | 98 | 118 | 147 | 108 | 102 |

Organ Weights

The weights of liver, kidney, and spleen were measured after terminal sacrifice and the results are presented in the table below. The results indicate that Ionis SMAD7 oligonucleotides did not cause any changes in the organ weights outside the expected range for antisense oligonucleotides. Specifically, ION 830025 and ION 798781 were very well tolerated.

TABLE 40

Organ weights (% of control) in beagle dogs at day 30

|  | Liver | Kidney | Spleen |
|---|---|---|---|
| Control | 100 | 100 | 100 |
| 830025 | 79 | 99 | 87 |
| 798781 | 91 | 86 | 102 |
| 790615 | 85 | 94 | 106 |

Histopathology

Liver (with gall bladder), kidneys, spleen, heart, thymus, duodenum, ileum, colon (distal and proximal), stomach, mesenteric lymph nodes and gut-associated lymph nodes (GALT) were collected from all animals and the intestinal tissues were flushed with 0.9% saline. The tissues were fixed in 10% neutral-buffered formalin, embedded in paraffin, sectioned and stained with hematoxylin and eosin.

Tissues collected from control animals exhibited typical spontaneous background alterations common in dogs of this age. The dogs orally administered Ionis SMAD7 oligonucleotides had no oligonucleotide-related tissue alterations. Therefore, all three oligonucleotides were very well tolerated.

Pharmacokinetics

Canine tissue exposure following oral administration of the Ionis SMAD7 oligonucleotides was measured in various organs and intestinal tissues. The results are presented below. The data indicates that tissue accumulation was the greatest in the kidney, followed by the liver, duodenum, ileum, and proximal colon. Distal colon accumulation was detected in dogs administered ION 830025.

Plasma concentrations of Ionis oligonucleotides were also measured on Day 28 at various time points. The results are presented in the Table below. Both the oligonucleotides had comparable accumulation in the GI tract, with ION 798781 showing higher accumulation in the liver and kidneys.

TABLE 41

Oligonucleotide concentration in tissues (µg/g)

|  | ION 830025 | ION 798781 |
|---|---|---|
| Kidney | 48.1 | 108.1 |
| Liver | 7.8 | 12.9 |
| Duodenum | 0.8 | 0.6 |
| Ileum | 0.3 | 0.5 |
| Proximal colon | 0.2 | 0.1 |
| Distal colon | 0.1 | n.d. |

TABLE 42

Oligonucleotide concentration in the plasma on day 28 (ng/mL)

|  | 830025 | 798781 | 790615 |
|---|---|---|---|
| 2 hr | 13.6 | 18.7 | 16.7 |
| 4 hr | 3.8 | 5.4 | 4.8 |
| 8 hr | 1.7 | 3.6 | 0.5 |
| 24 hr | 0.0 | 0.4 | 0.0 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10517889B2). An electronic copy of the "Sequence Listing" will also be available from the USPTO upon request and payment of the fee set forth in 37 CFR 1.19(b)(3).

What is claimed:

1. A compound comprising a modified oligonucleotide 16 to 30 linked nucleosides in length, wherein the modified oligonucleotide has a nucleobase sequence comprising any one of SEQ ID NOs: 2537, 1456, or 2109, wherein the modified oligonucleotide comprises:
    a gap segment consisting of linked deoxynucleosides;
    a 5' wing segment consisting of linked nucleosides; and
    a 3' wing segment consisting of linked nucleosides;
    wherein the gap segment is positioned between the 5' wing segment and the 3' wing segment and wherein each nucleoside of each wing segment comprises a modified sugar.

2. The compound of claim 1, wherein the compound is single-stranded.

3. The compound of claim 1, wherein the compound is double-stranded.

4. The compound of claim 1, wherein the compound comprises ribonucleotides.

5. The compound of claim 1, wherein the compound comprises deoxyribonucleotides.

6. A compound comprising a modified oligonucleotide 16 linked nucleosides in length having a nucleobase sequence consisting of any one of SEQ ID NOs: 2537, 1456, or 2109, wherein the modified oligonucleotide comprises:
    a gap segment consisting of ten linked deoxynucleosides;
    a 5' wing segment consisting of three linked nucleosides; and
    a 3' wing segment consisting of three linked nucleosides;
    wherein the gap segment is positioned between the 5' wing segment and the 3' wing segment; wherein each nucleoside of the 5' wing segment and the 3' wing segment comprises a cEt sugar; wherein at least one internucleoside linkage is a phosphorothioate linkage; and wherein each cytosine is a 5-methylcytosine.

7. A compound comprising a modified oligonucleotide according to the following formula: Tks Tks Tks Gds Tds Ads Ads Ads Tds mCds Gds Ads Ads Aks Gks mCk (SEQ ID NO: 2537); wherein,
    A=an adenine,
    mC=a 5-methylcytosine
    G=a guanine,
    T=a thymine,
    k=a cEt modified sugar,
    d=a 2'-deoxynucleoside, and
    s=a phosphorothioate internucleoside linkage.

8. A compound according to the following formula:

(SEQ ID NO: 2537)

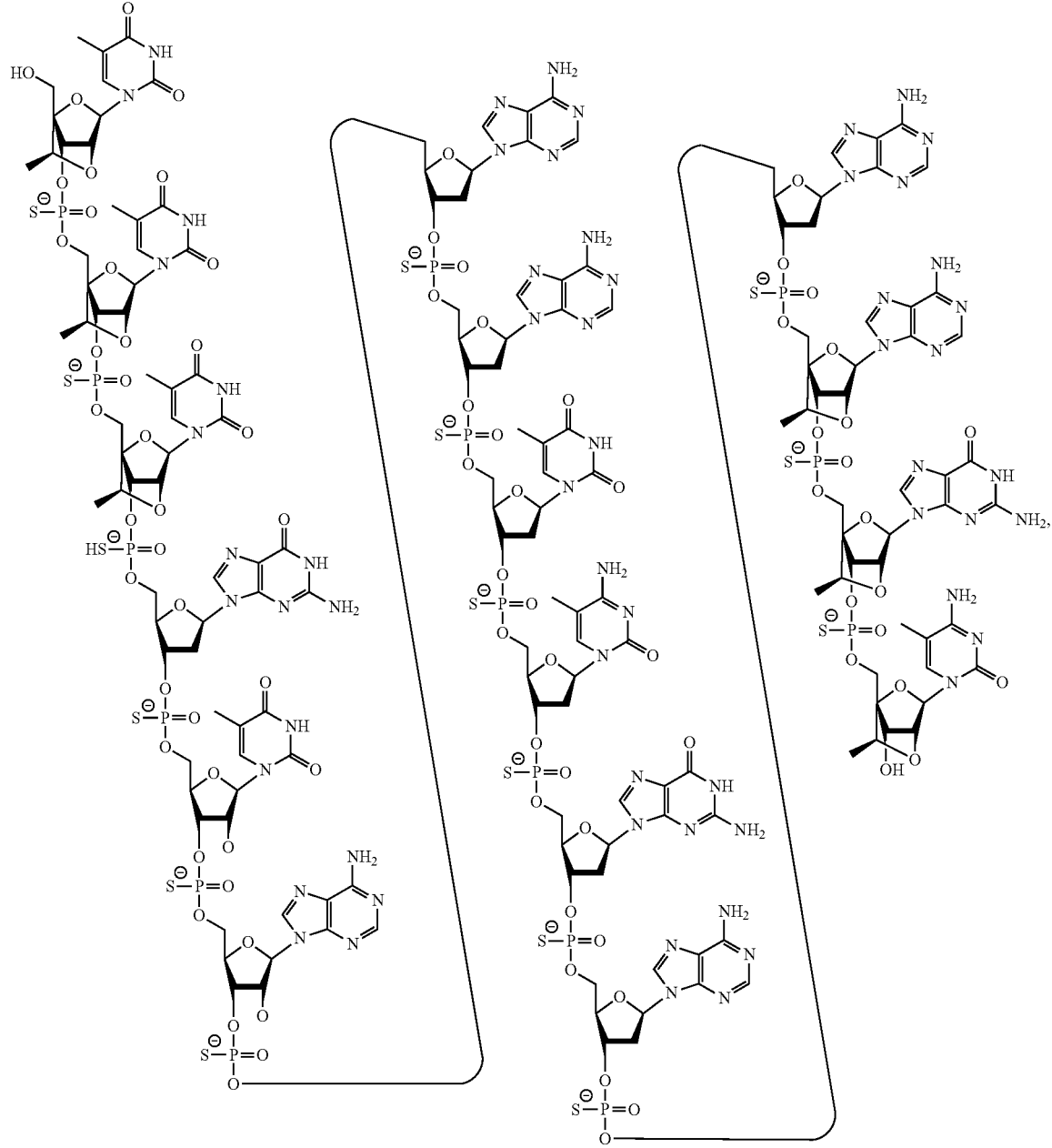

or a pharmaceutically acceptable salt thereof.

9. A modified oligonucleotide consisting of 16 linked nucleosides having the sequence of SEQ ID NO: 2537 and consisting of:
 a gap segment consisting of ten linked deoxynucleosides;
 a 5' wing segment consisting of three linked nucleosides; and
 a 3' wing segment consisting of three linked nucleosides;
 wherein the gap segment is positioned between the 5' wing segment and the 3' wing segment, wherein each nucleoside of each wing segment comprises a cEt sugar; wherein each internucleoside linkage is a phosphorothioate linkage; wherein each cytosine is a 5-methylcytosine.

10. The compound of claim 8, wherein the pharmaceutically acceptable salt is a sodium salt.

11. The compound of claim 8, wherein the pharmaceutically acceptable salt is a potassium salt.

12. A method of treating, preventing, or ameliorating a disease associated with SMAD7 in an individual comprising administering to the individual the compound of claim 8, thereby treating, preventing, or ameliorating the disease, wherein the disease is ulcerative colitis, Crohn's disease, inflammatory bowel disease, indeterminate colitis, familial adenomatous polyposis, intestinal GvHD, or cancer therapy-induced colitis.

13. The method of claim 12, wherein administering the compound inhibits, reduces, or improves inflammation in the gastrointestinal tract of the individual.

14. A method of inhibiting expression of SMAD7 in a cell comprising contacting the cell with the compound of claim 8, thereby inhibiting expression of SMAD7 in the cell, wherein the cell is in the gastrointestinal tract of an individual.

15. A method of reducing or inhibiting inflammation in the gastrointestinal tissues of an individual having, or at risk of having, a disease associated with SMAD7 comprising administering the compound of claim 8 to the individual, thereby reducing or inhibiting inflammation in the gastrointestinal tissues of the individual, wherein the individual has, or is at risk of having, ulcerative colitis, Crohn's disease, inflammatory bowel disease, indeterminate colitis, familial adenomatous polyposis, intestinal GvHD, or cancer therapy-induced colitis.

16. A method of treating, preventing, or ameliorating a disease associated with SMAD7 in an individual comprising administering to the individual the compound of claim 1, thereby treating, preventing, or ameliorating the disease, wherein the disease is ulcerative colitis, Crohn's disease, inflammatory bowel disease, indeterminate colitis, familial adenomatous polyposis, intestinal GvHD, or cancer therapy-induced colitis.

17. The method of claim 16, wherein administering the compound inhibits, reduces, or improves inflammation in the gastrointestinal tract of the individual.

18. A method of inhibiting expression of SMAD7 in a cell comprising contacting the cell with the compound of claim 1, thereby inhibiting expression of SMAD7 in the cell, wherein the cell is in the gastrointestinal tract of an individual.

19. A method of reducing or inhibiting inflammation in the gastrointestinal tissues of an individual having, or at risk of having, a disease associated with SMAD7 comprising administering the compound of claim 1 to the individual, thereby reducing or inhibiting inflammation in the gastrointestinal tissues of the individual, wherein the individual has, or is at risk of having, ulcerative colitis, Crohn's disease, inflammatory bowel disease, indeterminate colitis, familial adenomatous polyposis, intestinal GvHD, or cancer therapy-induced colitis.

20. A method of treating, preventing, or ameliorating a disease associated with SMAD7 in an individual comprising administering to the individual the compound of claim 6, thereby treating, preventing, or ameliorating the disease, wherein the disease is ulcerative colitis, Crohn's disease, inflammatory bowel disease, indeterminate colitis, familial adenomatous polyposis, intestinal GvHD, or cancer therapy-induced colitis.

21. The method of claim 20, wherein administering the compound inhibits, reduces, or improves inflammation in the gastrointestinal tract of the individual.

22. A method of inhibiting expression of SMAD7 in a cell comprising contacting the cell with the compound of claim 6, thereby inhibiting expression of SMAD7 in the cell, wherein the cell is in the gastrointestinal tract of an individual.

23. A method of reducing or inhibiting inflammation in the gastrointestinal tissues of an individual having, or at risk of having, a disease associated with SMAD7 comprising administering the compound of claim 6 to the individual, thereby reducing or inhibiting inflammation in the gastrointestinal tissues of the individual, wherein the individual has, or is at risk of having, ulcerative colitis, Crohn's disease, inflammatory bowel disease, indeterminate colitis, familial adenomatous polyposis, intestinal GvHD, or cancer therapy-induced colitis.

24. A composition comprising the compound of claim 8, and a pharmaceutically acceptable carrier.

25. A composition comprising the compound of claim 1, and a pharmaceutically acceptable carrier.

26. A composition comprising the compound of claim 6, and a pharmaceutically acceptable carrier.

* * * * *